US008846042B2

(12) United States Patent  (10) Patent No.: US 8,846,042 B2
Zhou  (45) Date of Patent: Sep. 30, 2014

(54) MULTI-SPECIFIC FAB FUSION PROTEINS AND METHODS OF USE

(75) Inventor: Hongxing Zhou, Bellevue, WA (US)

(73) Assignee: Fabion Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/473,017

(22) Filed: May 16, 2012

(65) Prior Publication Data

US 2012/0321626 A1  Dec. 20, 2012

Related U.S. Application Data

(60) Provisional application No. 61/486,690, filed on May 16, 2011.

(51) Int. Cl.
*A61K 39/395* (2006.01)
*C07K 16/46* (2006.01)
*C07K 16/28* (2006.01)
*C07K 14/705* (2006.01)
*C07K 16/30* (2006.01)

(52) U.S. Cl.
CPC ........... *C07K 14/705* (2013.01); *C07K 2319/00* (2013.01); *C07K 2317/31* (2013.01); *C07K 2317/55* (2013.01); *C07K 16/2809* (2013.01); *C07K 2319/74* (2013.01); *C07K 16/30* (2013.01)
USPC ..................................... 424/136.1; 530/387.3

(58) Field of Classification Search
None
See application file for complete search history.

(56) References Cited

U.S. PATENT DOCUMENTS

| 2005/0112694 | A1 | 5/2005 | Carter et al. | |
|---|---|---|---|---|
| 2007/0287170 | A1 | 12/2007 | Davis et al. | |
| 2009/0202433 | A1 | 8/2009 | Chang et al. | |
| 2010/0150918 | A1* | 6/2010 | Kufer et al. | ................. 424/133.1 |
| 2010/0183615 | A1 | 7/2010 | Kufer et al. | |

FOREIGN PATENT DOCUMENTS

| WO | WO94/09131 | * | 4/1994 |
|---|---|---|---|
| WO | WO 99/37791 | | 7/1999 |
| WO | WO 2004/106380 | | 12/2004 |
| WO | WO 2007/042261 | | 4/2007 |
| WO | WO2007/042261 | * | 4/2007 |
| WO | WO 2008/024188 | | 2/2008 |
| WO | WO 2008/119567 | | 10/2008 |
| WO | WO2009/068630 | * | 6/2009 |
| WO | WO 2009/149185 | | 12/2009 |
| WO | WO 2010/037836 | | 4/2010 |
| WO | WO 2010/037838 | | 4/2010 |

OTHER PUBLICATIONS

Adams, et al., "Avidity-Mediated Enhancement of In vivo Tumor Targeting by Single-Chain Fv Dimmers," *Clin. Cancer Res.* 12:1599-1605, 2006.

Alarcon et al., "The CD3-gamma and CD3-delta subunits of the T cell antigen receptor can be expressed within distinct functional TCR/CD3 complexes," *EMBO Journal*, 10, 4:903-912, 1991.

Alt et al., "Novel tetravalent and bispecific IgG-like antibody molecules combining single-chain diabodies with the immunoglobulin gammal Fc or CH3 region," *FEBS Letters*, 454:90-94 1999.

Anasetti et al., "Induction of specific Nonresponsiveness in Unprimed Human T Dells by Anti-CD3 Antibody and Alloantigen," *J. Exp. Med.*, 172:1691 1990.

Bargou, et al., "Tumor regression in cancer patients by very low doses of a T cell-engaging antibody," *Science*, 321 :974-7 2008.

Beverley, P.C., et al., "Distinctive functional characteristics of human "T" lymphocytes defined by E rosetting or a monoclonal anti-T cell antibody," *Eur. J. lmmunol.* 11:329-334 1981.

Carpenter et al., "A humanized non-FcR-binding anti-CD3 antibody, visilizumab, for treatment of steroid-refractory acute graft-versus-host disease," *Blood*, 99:2712-2719 2002.

Chames, et al., "Bispecific antibodies for cancer therapy: The light at the end of the tunnel?" *mAbs*, 1:6, 539-547 2009.

Chang, et al., "Molecular Advances in Pretargeting Radioimunotherapy with Bispecific Antibodies," *Mol Cancer Ther*, 1:553-563 2002.

Chetty R. et al., "CD3: structure, function, and role of immunostaining in clinical practice," *J Pathol.*, 173(4):303-307 1994.

Coloma and Morrison, "Design and production of novel tetravalent bispecific antibodies," *Nat. Biotechnol.* 15:159-63 1997.

Conrad, ML., et al., "TCR and CD3 Antibody Cross-Reactivity in 44 Species," *Cytometry* A 71(11):925-33 2007.

Davis, et al., "SEEDbodies: fusion proteins based on strand-exchange engineered domain (SEED) CH3 heterodimers in an Fc analogue platform for asymmetric binders or imunofusions and bispecific antibodies," *Protein Engineering, Design & Selection*, 23,4:195-202 2010.

Deyev and Lebedenko, "Multivalency: the hallmark of antibodies used for optimization of tumor targeting by design," *BioEssays*, 30:904-918 2008.

Dong, et al., "Stable IgG-like Bispecific Antibodies Directed Toward the Type I Insulin-like Growth Factor Receptor Demonstrate Enhanced Ligand Blockade and Anti-tumor Activity," *Journal of Biological Chemistry*, 286,6:4703-4717 2011.

(Continued)

*Primary Examiner* — Hong Sang
*Assistant Examiner* — Michael D Allen
(74) *Attorney, Agent, or Firm* — Cooley LLP

(57) ABSTRACT

The present disclosure relates generally to multi-specific Fab fusion proteins (MSFP) which comprise an antibody Fab fragment with both N-termini fused to a fusion moiety (fusion moiety A or B). MSFP containing the Fab fragment exhibit significantly reduced binding ability of the Fab fragment to the Fab target. Binding of the Fab to its target is restored when the MSFP is clustered on a cell surface by binding of the fusion moieties to their target. The reduced binding of the Fab to its target, especially when presented on a cell surface in its native state, absent fusion moiety binding provides advantages such as: reduced side effects and allows desirable pharmacological effects of selectivity and specificity in a controlled manner.

4 Claims, 24 Drawing Sheets

(56) References Cited

OTHER PUBLICATIONS

Grosse-Hovest, et al., "A recombinant bispecific single-chain antibody induces targeted, supra-agonistic CD28-stimulation and tumor cell killing," *Eur. J. Immunol.*, 33:1334-1340 2003.

Gunasekaran, K, et al., "Enhancing Antibody Fc Heterodimer Formation through Electrostatic Steering Effects: Applications to Bispecific Molecules and Monovalent IgG," *Journal of Biological Chemistry*, 285,25:19637-19646 2010.

Herold et al., "Activation of human T cells by FcR nonbinding anti-CD3 mAb, hOKT3gammal(Ala-Ala)," *J. Clin. Invest.*, 11:409-418, 2003.

Hirsch, et al., "Effects of in vivo administration of anti-T3 monoclonal antibody on T cell function in mice. I. Immunosuppression of transplantation responses," *J. Immunol.*, 140:3766-3772, 1988.

Holliger, et al., "'Diabodies': small bivalent and bispecific antibody fragments," *Proc Natl Acad Sci USA*, 90:6444-6448, 1993.

International Search Report for PCT/US2012/038177, dated Nov. 14, 2012.

Johnson, et al., "Effector Cell Recruitment with Novel Fv-based Dual-affinity Re-targeting Protein Leads to Potent Tumor Cytolysis and in Vivo B-cell Depletion," *J. Mol. Biol*, 399:436-449 2010.

Kipriyanov and Le Gall, "Recent advances in the generation of bispecific antibodies for tumor immunotherapy," *Curr. Opin. Drug Discov. Devel.* 7:233, 2004.

Kipriyanov, et al., "Bispecific tandem diabody for tumor therapy with improved antigen binding and pharmacokinetics," *J. Mol. Biol.*, 293:41-56, 1999.

Kontermann, "Recombinant bispecific antibodies for cancer therapy ," *Acta Pharmacol Sin.*, 26,1:1-9, 2005.

Liu, et al., "Efficient Inhibition of Human B-cell Lymphoma in SCID Mice by Synergistic Antitumor Effect of Human 4-1BB Ligand/anti-CD20 Fusion Proteins and Anti-CD3/anti-CD20 Diabodies," *J. Immunother*, 33:500-9, 2010.

Mabry, et al., "Engineering of stable bispecific antibodies targeting IL-17A and IL-23," *Protein Eng Des Sel.*, 23:115-127, 2010.

Mack, et al., "A small bispecific antibody construct expressed as a functional single-chain molecule with high tumor cell cytotoxic," *Proc. Natl. Acad. Sci., USA*. 92:7021-5, 1995.

Marvin and Zhu, "Recombinant approaches to IgG-like bispecific antibodies," Acta *Pharmacol. Sin.*, 26, 649-658, 2005.

Merchant, et al., "An efficient route to human bispecific IgG," *Nat Biotechnol.* 16: 677-81.

Michaelson, et al., "Anti-tumor activity of stability-engineered IgG-like bispecific antibodies targeting TRAIL-R2 and LTbetaR," *mAbs*, 1:2:128-141; 2009.

Miller, et al., "Stability engineering of scFvs for the development of bispecific and multivalent antibodies," *Protein Eng Des Sel.*, 23:549-557, 201 2010.

Muller and Kontermann, "Bispecific Antibodies for Cancer Immunotherapy: Current Perspectives," *Biodrugs*, 24:89-98, 2010.

Orcutt, et al., "A modular IgG-scFv bispecific antibody topology," *Protein Eng Des Sel.*, 23:221-228, 2010.

Ortho Multicenter Transplant Study Group "A randomized clinical trial of OKT3 monoclonal antibody for acute rejection of cadaveric renal transplants. Ortho Multicenter Transplant Study Group," *N. Engl. J. Med.*, 313:337, 1985.

Otz,et al., "A bispecific single-chain antibody that mediates target cell-restricted, supra-agonistic CD28 stimulation and killing of lymphoma cells," *Leukemia*, 23:71-77 2009.

Pessano, S., et al., "The T3/T cell receptor complex: antigenic distinction between the two 20-kd T3 (T3-delta and T3-epsilon) subunits," *The EMBO J.*, 4,2:337-344 1985.

Ridgway, JB., et al., "Knobs-into-holes' engineering of antibody CH3 domains for heavy chain heterodimerization," *Protein Engineering*, 9:617-621 1996.

Robinson, et al., "Targeting ErbB2 and ErbB3 with a bispecific single-chain Fv enhances targeting selectivity and induces a therapeutic effect in vitro," *British Journal of Cancer*, 99:1415-1425 2008.

Salmeron, et al., "A conformational epitope expressed upon association of CD3-epsilon with either CD3-delta or CD3-gamma is the main target for recognition by anti-CD3 monoclonal antibodies," *J. Immunol.*, 147:3047-3052 1991.

Schoonjans, R., et al., "Fab chains as an efficient heterodimerization scaffold for the production of recombinant bispecific and trispecific antibody derivatives" *Journal of Immunology*, 165:7050-7057 2000.

Schaefer, et al., "Immunoglobulin domain crossover as a generic approach for the production of bispecific IgG antibodies" *PNAS* 108:111870-92 2011.

Shen, et al., "Single variable domain-IgG fusion. A novel recombinant approach to Fc domain-containing bispecific antibodies," *J. Bioi. Chem.*, 281,16:10706-10714 2006.

Shen, et al., "Single variable domain antibody as a versatile building block for the construction of IgG-like bispecific antibodies," *J. Immunol. Methods*, 318:65-74 2007.

Staerz, et al., "Hybrid hybridoma producing a bispecific monoclonal antibody that can focus effector T-cell activity," *Proc Natl Acad Sci USA*, 83:1453-7 1986.

Willems et al.; CD3 X CD28 cross-interacting bispecific antibodies improve tumor cell dependent T-cell activation, *Cancer Immunol Immunother*, 54:1059-1071 2005.

Wu, et al., "Simultaneous targeting of multiple disease mediators by a dual-variable-domain immunoglobulin," *Nat. Biotechnol.*, 25:1290-7 2007.

Yang, et al., "A common pathway for T lymphocyte activation involving both the CD3-Ti complex and CD2 sheep erythrocyte receptor determinants," *J. Immunol.*, 137:1097-1100 1986.

Yoshino, N., et al., Upgrading of Flow Cytometric Analysis for Absolute Counts, Cytokines and Other Antigenic Molecules of Cynomolgus Monkeys (*Macaca fascicularis*) by Using Antigenic Molecules of Cynomolgus Monkeys (*Macaca fascicularis*) by Using Anti-Human Cross-Reactive Antibodies, *Exp. Anim.*, 49(2):97-110 2000.

Mertens, et al., "New Strategies in Polypeptide and Antibody Synthesis: An Overview," *Cancer Biotherapy & Radiopharmaceuticals*, 19:99-109, 2004.

International Preliminary Report on Patentability, for PCT/US2012/ 038177, mailed on Nov. 19, 2013. 7 pages.

\* cited by examiner

Humanized 1F3 Fabs bind to Jurkat cells (human T cell line expressing CD3) by FACS.

Figure 14: EpCAM x CD3 Fabs binding to Jurkat cells

EpCAM x CD3 FabE binding to human PBMCs

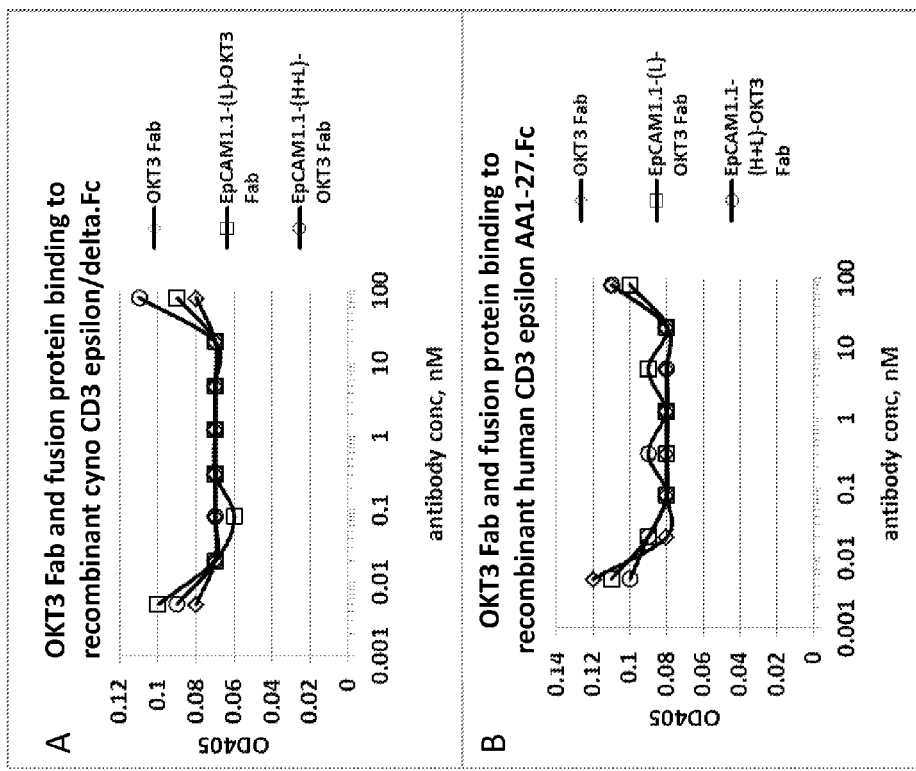
Figure 16: EpCAM1.1 x OKT3 MSFP binding to soluble CD3 related proteins

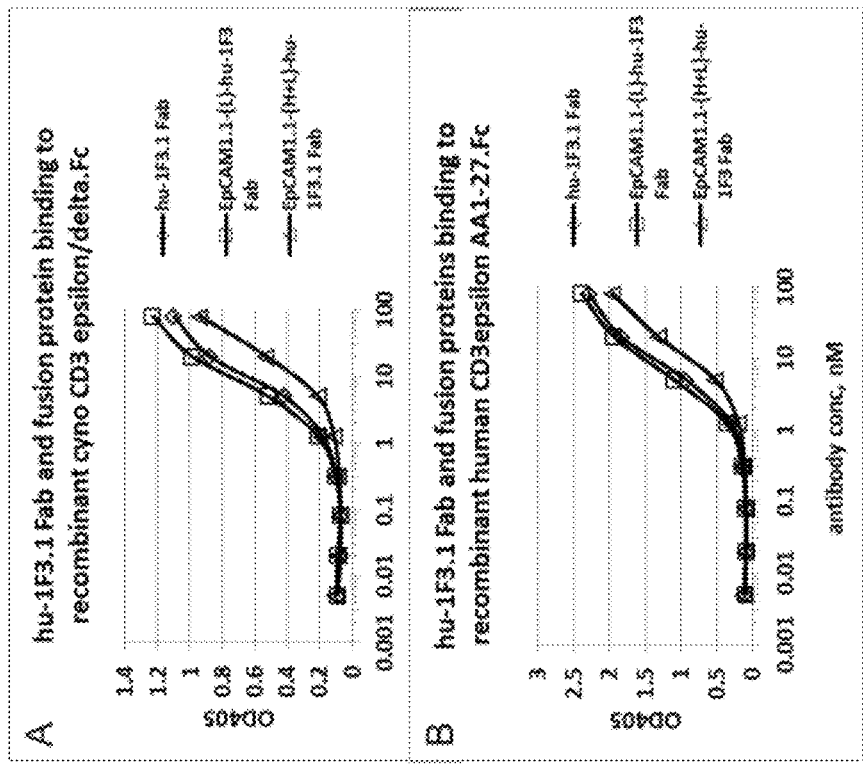
Figure 17: EpCAM1.1 x hu-1F3.1 MSFP binding to soluble CD3 related proteins

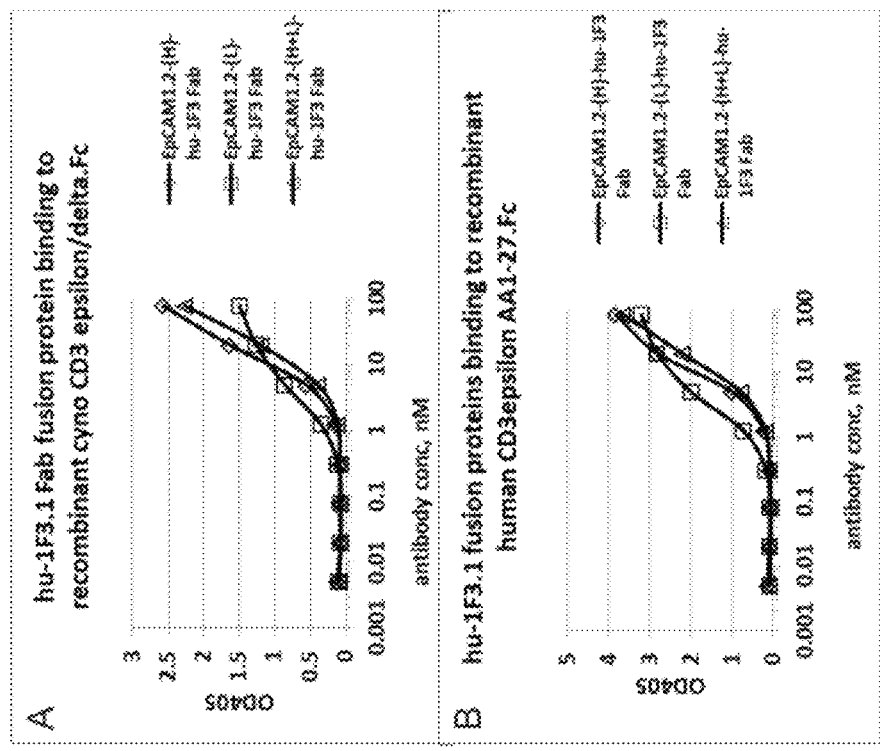
Figure 18: EpCAM1.2 x hu-1F3.1 MSFP binding to soluble CD3 related proteins

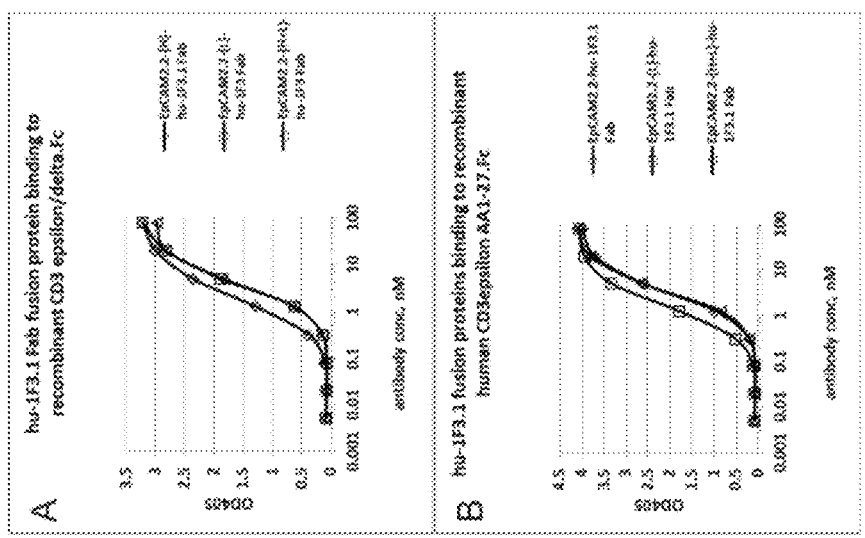
Figure 19: EpCAM2.2 x hu-1F3.1 MSFP binding to soluble CD3 related proteins

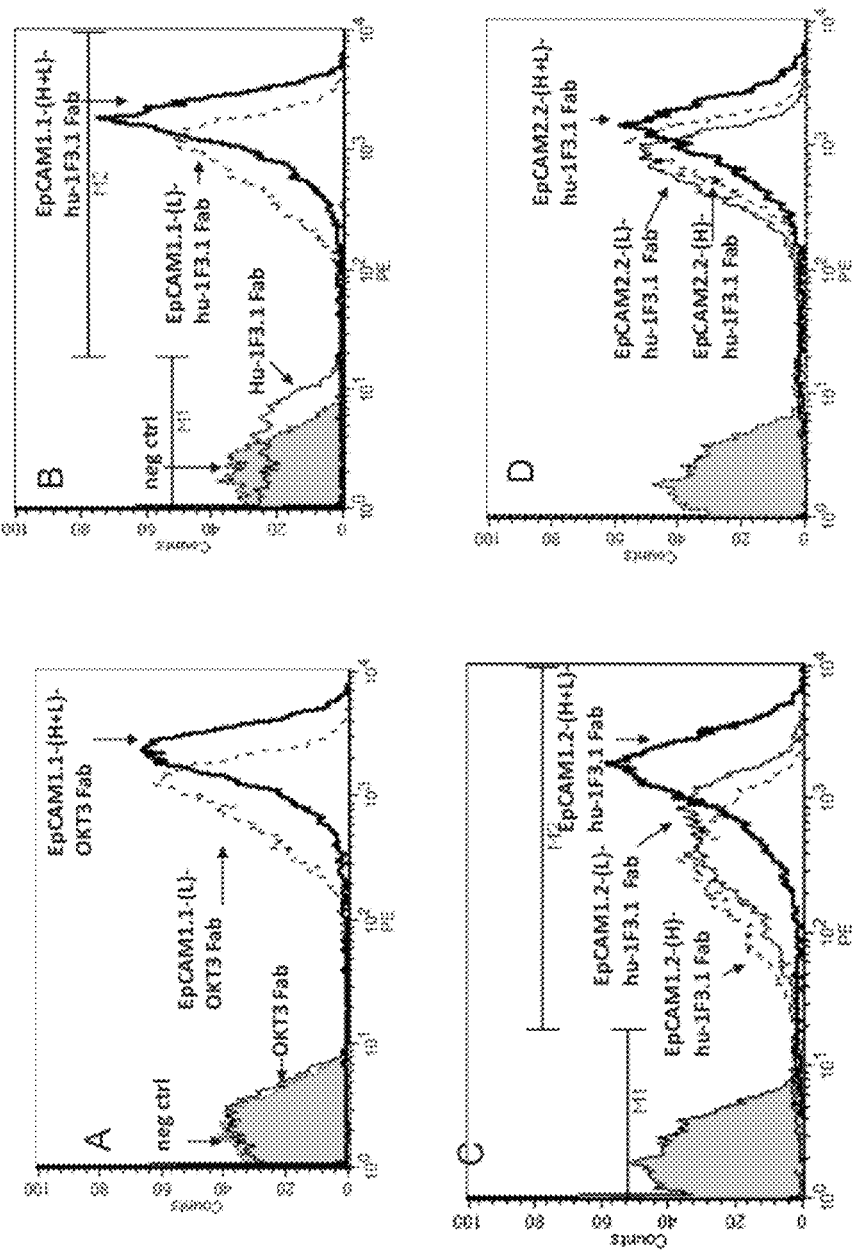
Figure 20: EpCAM x CD3 MSFP protein binding to EpCAM-expressing CHO cells

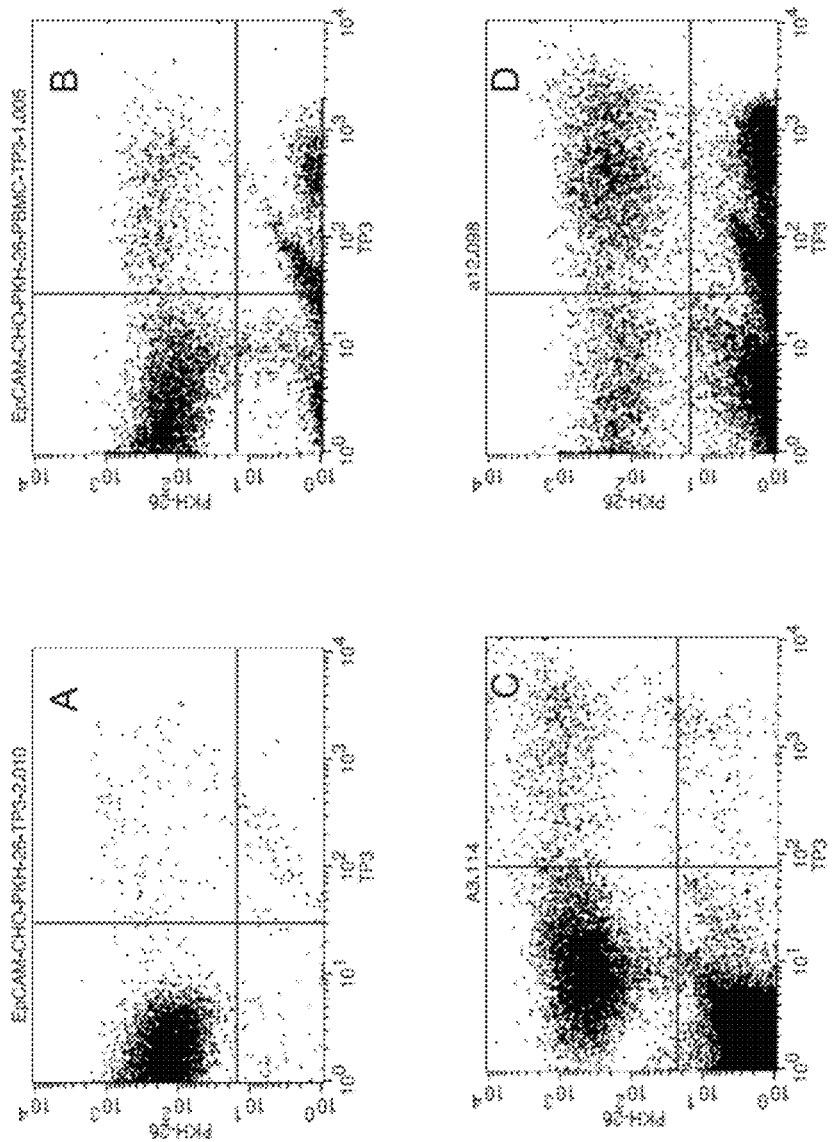
Figure 21: Cytotoxicity bioassay based on FACS analysis

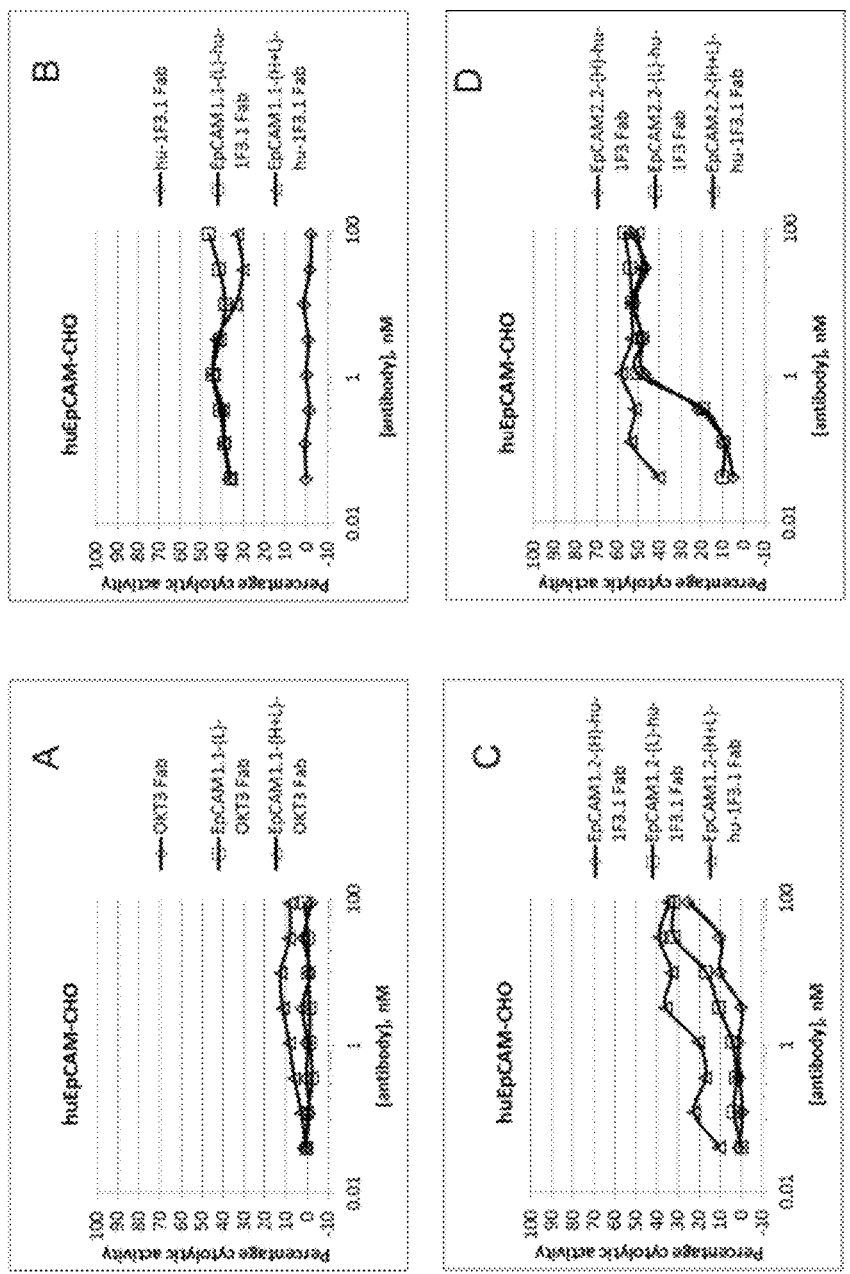
Figure 22: Redirected lysis of CHO cells expressing human-EpCAM by EpCAM-CD3 MSFP

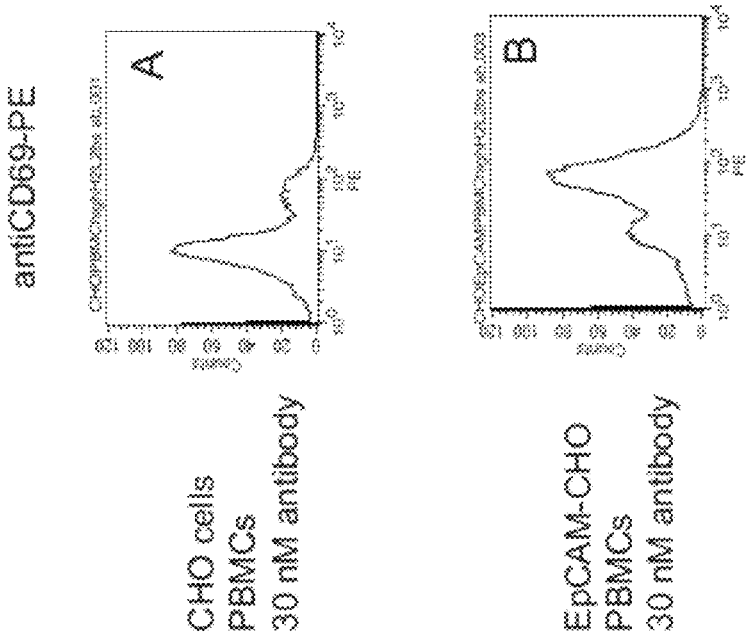
Figure 23: EpCAM2.2 x hu-1F3.1 bispecific Fabc activates T cells in a tumor target dependent manner

SEQUENCE LISTING

```
<160> NUMBER OF SEQ ID NOS: 150

<210> SEQ ID NO 1
<211> LENGTH: 1503
<212> TYPE: DNA
<213> ORGANISM: Homo sapiens

<400> SEQUENCE: 1
atggcgcccc cgcaggtcct cgcgttcggg cttctgcttg ccgcggcgac ggcgactttt      60
gccgcagctc aggaagaatg tgtctgtgaa aactacaagc tggccgtaaa ctgctttgtg     120
aataataatc gtcaatgcca gtgtacttca gttggtgcac aaaatactgt catttgctca     180
aagctggctg ccaaatgttt ggtgatgaag gcagaaatga atggctcaaa acttgggaga     240
agagcaaaac ctgaagggc cctccagaac aatgatgggc tttatgatcc tgactgcgat     300
gagagcgggc tctttaaggc caagcagtgc aacggcacct ccatgtgctg gtgtgtgaac     360
actgctgggg tcagaagaac agacaaggac actgaaataa cctgctctga gcgagtgaga     420
```

```
acctactgga tcatcattga actaaaacac aaagcaagag aaaaacctta tgatagtaaa    480
agtttgcgga ctgcacttca gaaggagatc acaacgcgtt atcaactgga tccaaaattt    540
atcacgagta ttttgtatga aataatgtt atcactattg atctggttca aaattcttct    600
caaaaactc agaatgatgt ggacatagct gatgtggctt attattttga aaaagatgtt    660
aaaggtgaat ccttgtttca ttctaagaaa atggacctga cagtaaatgg ggaacaactg    720
gatctggatc ctggtcaaac tttaatttat tatgttgatg aaaaagcacc tgaattctca    780
atgcagggtc taaaagcggc cgcagagccc aaatcttgtg acaaaactca cacatgccca    840
ccgtgcccag cacctgaact cctgggggga ccgtcagtct tcctcttccc cccaaaaccc    900
aaggacaccc tcatgatctc ccggacccct gaggtcacat gcgtggtggt ggacgtgagc    960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag    1200
gtgtacaccc tgcccccatc ccgggaggag atgaccaaga accaggtcag cctgacctgc    1260
ctggtcaaag gcttctatcc agcgacatc gccgtggagt gggagagcaa tgggcagccg    1320
gagaacaact acaagaccac gcctcccgtg ctggactccg acggctcctt cttcctctat    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaaa    1500
tga                                                                   1503

<210> SEQ ID NO 2
<211> LENGTH: 479
<212> TYPE: PRT
<213> ORGANISM: Homo sapiens

<400> SEQUENCE: 2

Ala Ala Gln Glu Glu Cys Val Cys Glu Asn Tyr Lys Leu Ala Val Asn
1               5                   10                  15

Cys Phe Val Asn Asn Asn Arg Gln Cys Gln Cys Thr Ser Val Gly Ala
            20                  25                  30

Gln Asn Thr Val Ile Cys Ser Lys Leu Ala Ala Lys Cys Leu Val Met
        35                  40                  45

Lys Ala Glu Met Asn Gly Ser Lys Leu Gly Arg Arg Ala Lys Pro Glu
    50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Met Cys Trp
                85                  90                  95

Cys Val Asn Thr Ala Gly Val Arg Arg Thr Asp Lys Asp Thr Glu Ile
            100                 105                 110

Thr Cys Ser Glu Arg Val Arg Thr Tyr Trp Ile Ile Glu Leu Lys
        115                 120                 125

His Lys Ala Arg Glu Lys Pro Tyr Asp Ser Lys Ser Leu Arg Thr Ala
    130                 135                 140

Leu Gln Lys Glu Ile Thr Thr Arg Tyr Gln Leu Asp Pro Lys Phe Ile
145                 150                 155                 160

Thr Ser Ile Leu Tyr Glu Asn Asn Val Ile Thr Ile Asp Leu Val Gln
                165                 170                 175
```

```
Asn Ser Ser Gln Lys Thr Gln Asn Asp Val Asp Ile Ala Asp Val Ala
            180                 185                 190

Tyr Tyr Phe Glu Lys Asp Val Lys Gly Glu Ser Leu Phe His Ser Lys
        195                 200                 205

Lys Met Asp Leu Thr Val Asn Gly Glu Gln Leu Asp Leu Asp Pro Gly
    210                 215                 220

Gln Thr Leu Ile Tyr Tyr Val Asp Glu Lys Ala Pro Glu Phe Ser Met
225                 230                 235                 240

Gln Gly Leu Lys Ala Ala Glu Pro Lys Ser Cys Asp Lys Thr His
                245                 250                 255

Thr Cys Pro Pro Cys Pro Ala Pro Glu Leu Leu Gly Gly Pro Ser Val
        260                 265                 270

Phe Leu Phe Pro Pro Lys Pro Lys Asp Thr Leu Met Ile Ser Arg Thr
    275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
        340                 345                 350

Cys Lys Val Ser Asn Lys Ala Leu Pro Ala Pro Ile Glu Lys Thr Ile
    355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 3
<211> LENGTH: 1503
<212> TYPE: DNA
<213> ORGANISM: Macaca fascicularis

<400> SEQUENCE: 3
atggcgcccc gcaggtcct cgcgttcggg cttctgcttg cggcggcgac tgcgagtttt      60
gccgcagctc agaaagaatg tgtctgtgaa aactacaagc tggccgtaaa ctgcttttg    120 aatgacaatg tcaatgcca gtgtacttcg attggtgcac aaaatactgt cctttgctca    180
aagctggctg ccaaatgttt ggtgatgaag cagaaatga acggctcaaa acttgggaga    240
agagcgaaac ctgaaggggc tctccagaac aatgatggcc tttacgatcc tgactgcgat    300
gagagcgggc tctttaaggc caagcagtgc aacggcacct ccacgtgctg gtgtgtgaac    360
actgctgggg tcagaagaac tgacaaggac actgaaaataa cctgctctga gcagtgaga    420
```

```
acctactgga tcatcattga attaaaacac aaagcaagag aaaaacctta tgatgttcaa    480
agtttgcgga ctgcacttga ggaggcgatc aaaacgcgtt atcaactgga tccaaaattt    540
atcacaaata ttttgtatga ggataatgtt atcactattg atctggttca aaattcttct    600
cagaaaactc agaatgatgt ggacatagct gatgtggctt attatttga aaaagatgtt     660
aaaggtgaat ccttgtttca ttctaagaaa atggacctga gagtaaatgg ggaacaactg    720
gatctggatc ctggtcaaac tttaatttat tatgtcgatg aaaaagcacc tgaattctca    780
atgcagggtc taaaagcggc cgcagagccc aaatcttgtg acaaaactca cacatgccca    840
ccgtgcccag cacctgaact cctgggggga ccgtcagtct tcctcttccc cccaaaaccc    900
aaggacaccc tcatgatctc ccggacccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg agaaccacag    1200
gtgtacaccc tgcccccatc ccgggaggag atgaccaaga accaggtcag cctgacctgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctat   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaaa   1500
tga                                                                 1503

<210> SEQ ID NO 4
<211> LENGTH: 479
<212> TYPE: PRT
<213> ORGANISM: Macaca fascicularis

<400> SEQUENCE: 4

Ala Ala Gln Lys Glu Cys Val Cys Glu Asn Tyr Lys Leu Ala Val Asn
1               5                   10                  15

Cys Phe Leu Asn Asp Asn Gly Gln Cys Gln Cys Thr Ser Ile Gly Ala
            20                  25                  30

Gln Asn Thr Val Leu Cys Ser Lys Leu Ala Ala Lys Cys Leu Val Met
        35                  40                  45

Lys Ala Glu Met Asn Gly Ser Lys Leu Gly Arg Arg Ala Lys Pro Glu
    50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Thr Cys Trp
                85                  90                  95

Cys Val Asn Thr Ala Gly Val Arg Arg Thr Asp Lys Asp Thr Glu Ile
            100                 105                 110

Thr Cys Ser Glu Arg Val Arg Thr Tyr Trp Ile Ile Glu Leu Lys
        115                 120                 125

His Lys Ala Arg Glu Lys Pro Tyr Asp Val Gln Ser Leu Arg Thr Ala
    130                 135                 140

Leu Glu Glu Ala Ile Lys Thr Arg Tyr Gln Leu Asp Pro Lys Phe Ile
145                 150                 155                 160

Thr Asn Ile Leu Tyr Glu Asp Asn Val Ile Thr Ile Asp Leu Val Gln
                165                 170                 175
```

```
Asn Ser Ser Gln Lys Thr Gln Asn Asp Val Asp Ile Ala Asp Val Ala
            180                 185                 190
Tyr Tyr Phe Glu Lys Asp Val Lys Gly Glu Ser Leu Phe His Ser Lys
        195                 200                 205
Lys Met Asp Leu Arg Val Asn Gly Glu Gln Leu Asp Leu Asp Pro Gly
210                 215                 220
Gln Thr Leu Ile Tyr Tyr Val Asp Glu Lys Ala Pro Glu Phe Ser Met
225                 230                 235                 240
Gln Gly Leu Lys Ala Ala Ala Glu Pro Lys Ser Cys Asp Lys Thr His
            245                 250                 255
Thr Cys Pro Pro Cys Pro Ala Pro Glu Leu Leu Gly Gly Pro Ser Val
            260                 265                 270
Phe Leu Phe Pro Pro Lys Pro Lys Asp Thr Leu Met Ile Ser Arg Thr
        275                 280                 285
Pro Glu Val Thr Cys Val Val Val Asp Val Ser His Glu Asp Pro Glu
290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
            325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
        355                 360                 365
Ser Lys Ala Lys Gly Gln Pro Arg Glu Pro Gln Val Tyr Thr Leu Pro
370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
            405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
        435                 440                 445
Trp Gln Gln Gly Asn Val Phe Ser Cys Ser Val Met His Glu Ala Leu
450                 455                 460
His Asn His Tyr Thr Gln Lys Ser Leu Ser Leu Ser Pro Gly Lys
465                 470                 475

<210> SEQ ID NO 5
<211> LENGTH: 945
<212> TYPE: DNA
<213> ORGANISM: Homo sapiens

<400> SEQUENCE: 5
atggcgcccc cgcaggtcct cgcgttcggg cttctgcttg ccgcggcgac ggcgactttt      60
gccgcagctc aggaagaatg tgtctgtgaa aactacaagc tggccgtaaa ctgctttgtg     120
aataataatc gtcaatgcca gtgtacttca gttggtgcac aaaatactgt catttgctca     180
aagctggctg ccaaatgttt ggtgatgaag cagaaatgaa tggctcaaa acttgggaga      240 agagcaaaac ctgaaggggc cctccagaac aatgatgggc tttatgatcc tgactgcgat     300
gagagcgggc tctttaaggc caagcagtgc aacggcacct ccatgtgctg gtgtgtgaac     360
actgctgggg tcagaagaac agacaaggac actgaaaataa cctgctctga gcgagtgaga     420
```

```
acctactgga tcatcattga actaaaacac aaagcaagag aaaaacctta tgatagtaaa    480
agtttgcgga ctgcacttca gaaggagatc acaacgcgtt atcaactgga tccaaaattt    540
atcacgagta ttttgtatga gaataatgtt atcactattg atctggttca aaattcttct    600
caaaaaactc agaatgatgt ggacatagct gatgtggctt attattttga aaaagatgtt    660
aaaggtgaat ccttgtttca ttctaagaaa atggacctga cagtaaatgg ggaacaactg    720
gatctggatc ctggtcaaac tttaatttat tatgttgatg aaaaagcacc tgaattctca    780
atgcagggtc taaaagctgg tgttattgct gttattgtgg ttgtggtgat agcagttgtt    840
gctggaattg ttgtgctggt tatttccaga agaagagaa tggcaaagta tgagaaggcc    900
gagatcaagg agatgggtga gatgcatagg gaactcaatg cataa               945
```

<210> SEQ ID NO 6
<211> LENGTH: 293
<212> TYPE: PRT
<213> ORGANISM: Homo sapiens

<400> SEQUENCE: 6

```
Ala Ala Gln Glu Glu Cys Val Cys Glu Asn Tyr Lys Leu Ala Val Asn
1               5                   10                  15

Cys Phe Val Asn Asn Asn Arg Gln Cys Gln Cys Thr Ser Val Gly Ala
                20                  25                  30

Gln Asn Thr Val Ile Cys Ser Lys Leu Ala Ala Lys Cys Leu Val Met
            35                  40                  45

Lys Ala Glu Met Asn Gly Ser Lys Leu Gly Arg Arg Ala Lys Pro Glu
        50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Met Cys Trp
                85                  90                  95

Cys Val Asn Thr Ala Gly Val Arg Arg Thr Asp Lys Asp Thr Glu Ile
                100                 105                 110

Thr Cys Ser Glu Arg Val Arg Thr Tyr Trp Ile Ile Ile Glu Leu Lys
            115                 120                 125

His Lys Ala Arg Glu Lys Pro Tyr Asp Ser Lys Ser Leu Arg Thr Ala
        130                 135                 140

Leu Gln Lys Glu Ile Thr Thr Arg Tyr Gln Leu Asp Pro Lys Phe Ile
145                 150                 155                 160

Thr Ser Ile Leu Tyr Glu Asn Asn Val Ile Thr Ile Asp Leu Val Gln
                165                 170                 175

Asn Ser Ser Gln Lys Thr Gln Asn Asp Val Asp Ile Ala Asp Val Ala
                180                 185                 190

Tyr Tyr Phe Glu Lys Asp Val Lys Gly Glu Ser Leu Phe His Ser Lys
            195                 200                 205

Lys Met Asp Leu Thr Val Asn Gly Glu Gln Leu Asp Leu Asp Pro Gly
        210                 215                 220

Gln Thr Leu Ile Tyr Tyr Val Asp Glu Lys Ala Pro Glu Phe Ser Met
225                 230                 235                 240

Gln Gly Leu Lys Ala Gly Val Ile Ala Val Ile Val Val Val Val Ile
                245                 250                 255

Ala Val Val Ala Gly Ile Val Val Leu Val Ile Ser Arg Lys Lys Arg
                260                 265                 270

Met Ala Lys Tyr Glu Lys Ala Glu Ile Lys Glu Met Gly Glu Met His
            275                 280                 285
```

Arg Glu Leu Asn Ala
    290

<210> SEQ ID NO 7
<211> LENGTH: 945
<212> TYPE: DNA
<213> ORGANISM: Macaca fascicularis

<400> SEQUENCE: 7

```
atggcgcccc cgcaggtcct cgcgttcggg cttctgcttg cggcggcgac tgcgagtttt     60
gccgcagctc agaaagaatg tgtctgtgaa aactacaagc tggccgtaaa ctgcttttg    120
aatgacaatg gtcaatgcca gtgtacttcg attggtgcac aaaatactgt cctttgctca   180
aagctggctg ccaaatgttt ggtgatgaag gcagaaatga acggctcaaa acttgggaga   240
agagcgaaac ctgaaggggc tctccagaac aatgatggcc tttacgatcc tgactgcgat   300
gagagcgggc tctttaaggc caagcagtgc aacggcacct ccacgtgctg gtgtgtgaac   360
actgctgggg tcagaagaac tgacaaggac actgaaataa cctgctctga gcagtgagaa   420
acctactgga tcatcattga attaaaacac aaagcaagag aaaaacctta tgatgttcaa   480
agtttgcgga ctgcacttga ggaggcgatc aaaacgcgtt atcaactgga tccaaaattt   540
atcacaaata ttttgtatga ggataatgtt atcactattg atctggttca aaattcttct   600
cagaaaactc agaatgatgt ggacatagct gatgtggctt attattttga aaaagatgtt   660
aaaggtgaat ccttgtttca ttctaagaaa atggacctga gtaaatgg ggaacaactg      720
gatctggatc ctggtcaaac tttaatttat tatgtcgatg aaaaagcacc tgaattctca   780
atgcagggtc taaaagctgg tgttattgct gttattgtgg ttgtggtgat agcagttgtt   840
gctggaattg ttgtgctggt tatttccaga aagaagagaa tggcaaagta tgagaaggcc   900
gagatcaagg agatgggtga gatgcatagg gaactcaatg cataa                    945
```

<210> SEQ ID NO 8
<211> LENGTH: 293
<212> TYPE: PRT
<213> ORGANISM: Macaca fascicularis

<400> SEQUENCE: 8

Ala Ala Gln Lys Glu Cys Val Cys Glu Asn Tyr Lys Leu Ala Val Asn
1               5                   10                  15

Cys Phe Leu Asn Asp Asn Gly Gln Cys Gln Cys Thr Ser Ile Gly Ala
            20                  25                  30

Gln Asn Thr Val Leu Cys Ser Lys Leu Ala Ala Lys Cys Leu Val Met
        35                  40                  45

Lys Ala Glu Met Asn Gly Ser Lys Leu Gly Arg Arg Ala Lys Pro Glu
    50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Thr Cys Trp
                85                  90                  95

Cys Val Asn Thr Ala Gly Val Arg Arg Thr Asp Lys Asp Thr Glu Ile
            100                 105                 110

Thr Cys Ser Glu Arg Val Arg Thr Tyr Trp Ile Ile Ile Glu Leu Lys
        115                 120                 125

His Lys Ala Arg Glu Lys Pro Tyr Asp Val Gln Ser Leu Arg Thr Ala
    130                 135                 140

Leu Glu Glu Ala Ile Lys Thr Arg Tyr Gln Leu Asp Pro Lys Phe Ile
145                 150                 155                 160

Thr Asn Ile Leu Tyr Glu Asp Asn Val Ile Thr Ile Asp Leu Val Gln
            165                 170                 175

Asn Ser Ser Gln Lys Thr Gln Asn Asp Val Asp Ile Ala Asp Val Ala
            180                 185                 190

Tyr Tyr Phe Glu Lys Asp Val Lys Gly Glu Ser Leu Phe His Ser Lys
        195                 200                 205

Lys Met Asp Leu Arg Val Asn Gly Glu Gln Leu Asp Leu Asp Pro Gly
210                 215                 220

Gln Thr Leu Ile Tyr Tyr Val Asp Glu Lys Ala Pro Glu Phe Ser Met
225                 230                 235                 240

Gln Gly Leu Lys Ala Gly Val Ile Ala Val Ile Val Val Val Val Ile
            245                 250                 255

Ala Val Val Ala Gly Ile Val Val Leu Val Ile Ser Arg Lys Lys Arg
            260                 265                 270

Met Ala Lys Tyr Glu Lys Ala Glu Ile Lys Glu Met Gly Glu Met His
        275                 280                 285

Arg Glu Leu Asn Ala
    290

<210> SEQ ID NO 9
<211> LENGTH: 999
<212> TYPE: DNA
<213> ORGANISM: Homo sapiens

<400> SEQUENCE: 9

```
caagatggta atgaagaaat gggtggtatt acacagacac catataaagt ctccatctct      60
ggaaccacag taatattgac atgccctcag tatcctggat ctgaaatact atggcaacac     120
aatgataaaa acataggcgg tgatgaggat gataaaaaca taggcagtga tgaggatcac     180
ctgtcactga aggaattttc agaattggag caaagtggtt attatgtctg ctaccccaga     240
ggaagcaaac cagaagatgc gaacttttat ctctacctga gggcaagagt ggcggccgca     300
gagcccaaat cttctgacaa aactcacaca tgcccaccgt gcccagcacc tgaactcctg     360
gggggaccgt cagtcttcct cttccccccaa aacccaagg acaccctcat gatctcccgg     420
accccctgagg tcacatgcgt ggtggtggac gtgagccacg aagaccctga ggtcaagttc     480
aactggtacg tggacggcgt ggaggtgcat aatgccaaga caaagccgcg ggaggagcag     540
tacaacagca cgtaccgtgt ggtcagcgtc ctcaccgtcc tgcaccagga ctggctgaat     600
ggcaaggagt acaagtgcaa ggtctccaac aaagccctcc cagcccccat cgagaaaacc     660
atctccaaag ccaaagggca gccccgagaa ccacaggtgt acaccctgcc cccatcccgg     720
gaggagatga ccaagaacca ggtcagcctg tggtgcctgg tcaaaggctt ctatcccagc     780
gacatcgccg tggagtggga gagcaatggg cagccggaga acaactacaa gaccacgcct     840
cccgtgctgg actccgacgg ctccttcttc ctctatagca agctcaccgt ggacaagagc     900
aggtggcagc aggggaacgt cttctcatgc tccgtgatgc atgaggctct gcacaaccac     960
tacacgcaga agagcctctc cctgtctccg ggtaaatga                            999
```

<210> SEQ ID NO 10
<211> LENGTH: 332
<212> TYPE: PRT
<213> ORGANISM: Homo sapiens

<400> SEQUENCE: 10

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Ala Ala Ala Glu Pro Lys Ser Ser Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Trp Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 11
<211> LENGTH: 972
<212> TYPE: DNA
<213> ORGANISM: Macaca fascicularis

<400> SEQUENCE: 11
caagatggta atgaagaaat gggtagtatt acacagacac catatcaagt ctccatctct     60
ggaaccacag taatactgac atgctctcag catcttggat ctgaagcaca atggcaacac    120
aatggtaaaa acaagaaga ttctggggat cggctgtttc tgccggaatt ttcagaaatg    180
gagcaaagtg gttattatgt ctgctacccc agaggaagca atccagagga cgcgagccat    240

```
catctctacc tgaaggcaag agtggcggcc gcagagccca aatcttctga caaaactcac    300
acatgcccac cgtgcccagc acctgaactc ctggggggac cgtcagtctt cctcttcccc    360
ccaaaaccca aggacaccct catgatctcc cggacccctg aggtcacatg cgtggtggtg    420
gacgtgagcc acgaagaccc tgaggtcaag ttcaactggt acgtggacgg cgtggaggtg    480
cataatgcca agacaaagcc gcgggaggag cagtacaaca gcacgtaccg tgtggtcagc    540
gtcctcaccg tcctgcacca ggactggctg aatggcaagg agtacaagtg caaggtctcc    600
aacaaagccc tcccagcccc catcgagaaa accatctcca aagccaaagg cagccccga    660 gaaccacagg tgtacaccct gcccccatcc cgggaggaga tgaccaagaa ccaggtcagc    720
ctgtggtgcc tggtcaaagg cttctatccc agcgacatcg ccgtggagtg ggagagcaat    780
gggcagccgg agaacaacta caagaccacg cctcccgtgc tggactccga cggctccttc    840
ttcctctata gcaagctcac cgtggacaag agcaggtggc agcagggaa cgtcttctca    900 tgctccgtga tgcatgaggc tctgcacaac cactacacgc agaagagcct ctccctgtct    960
ccgggtaaat ga                                                        972
```

<210> SEQ ID NO 12
<211> LENGTH: 323
<212> TYPE: PRT
<213> ORGANISM: Macaca fascicularis

<400> SEQUENCE: 12

```
Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Ala Ala Glu Pro Lys Ser Ser
                85                  90                  95

Asp Lys Thr His Thr Cys Pro Pro Cys Pro Ala Pro Glu Leu Leu Gly
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
    130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Arg Glu Glu Met Thr Lys Asn Gln Val Ser
225                 230                 235                 240
```

Leu Trp Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300

His Glu Ala Leu His Asn His Tyr Thr Gln Lys Ser Leu Ser Leu Ser
305                 310                 315                 320

Pro Gly Lys

<210> SEQ ID NO 13
<211> LENGTH: 921
<212> TYPE: DNA
<213> ORGANISM: Homo sapiens

<400> SEQUENCE: 13

```
ttcaagatac ctatagagga acttgaggac agagtgtttg tgaattgcaa taccagcatc    60
acatgggtag agggaacggt gggaacactg ctctcagaca ttacaagact ggacctggga   120
aaacgcatcc tggacccacg aggaatatat aggtgtaatg ggacagatat atacaaggac   180
aaagaatcta ccgtgcaagt tcattatcga atggcggccg cagagcccaa atcttctgac   240
aaaactcaca catgcccacc gtgcccagca cctgaactcc tggggggacc gtcagtcttc   300
ctcttccccc caaaacccaa ggacaccctc atgatctccc ggacccctga ggtcacatgc   360
gtggtggtgg acgtgagcca cgaagaccct gaggtcaagt tcaactggta cgtggacggc   420
gtggaggtgc ataatgccaa gacaaagccg cgggaggagc agtacaacag cacgtaccgt   480
gtggtcagcg tcctcaccgt cctgcaccag gactggctga atggcaagga gtacaagtgc   540
aaggtctcca acaaagccct cccagccccc atcgagaaaa ccatctccaa agccaaaggg   600
cagccccgag aaccacaggt gtacaccctg cccccatccc gggaggagat gaccaagaac   660
caggtcagcc tgagctgcgc agtcaaaggc ttctatccca gcgacatcgc cgtggagtgg   720
gagagcaatg ggcagccgga gaacaactac aagaccacgc ctcccgtgct ggactccgac   780
ggctccttct tcctcgtcag caagctcacc gtggacaaga gcaggtggca gcaggggaac   840
gtcttctcat gctccgtgat gcatgaggct ctgcacaacc actacacgca gaagagcctc   900
tccctgtctc cgggtaaatg a                                             921
```

<210> SEQ ID NO 14
<211> LENGTH: 306
<212> TYPE: PRT
<213> ORGANISM: Homo sapiens

<400> SEQUENCE: 14

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Ala Ala Ala Glu Pro Lys Ser Ser Asp

```
             65                  70                  75                  80
Lys Thr His Thr Cys Pro Pro Cys Pro Ala Pro Glu Leu Leu Gly Gly
                     85                  90                  95

Pro Ser Val Phe Leu Phe Pro Pro Lys Pro Lys Asp Thr Leu Met Ile
            100                 105                 110

Ser Arg Thr Pro Glu Val Thr Cys Val Val Val Asp Val Ser His Glu
        115                 120                 125

Asp Pro Glu Val Lys Phe Asn Trp Tyr Val Asp Gly Val Glu Val His
    130                 135                 140

Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Ala Leu Pro Ala Pro Ile Glu
            180                 185                 190

Lys Thr Ile Ser Lys Ala Lys Gly Gln Pro Arg Glu Pro Gln Val Tyr
        195                 200                 205

Thr Leu Pro Pro Ser Arg Glu Glu Met Thr Lys Asn Gln Val Ser Leu
    210                 215                 220

Ser Cys Ala Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Val Ser Lys Leu Thr Val Asp
            260                 265                 270

Lys Ser Arg Trp Gln Gln Gly Asn Val Phe Ser Cys Ser Val Met His
        275                 280                 285

Glu Ala Leu His Asn His Tyr Thr Gln Lys Ser Leu Ser Leu Ser Pro
    290                 295                 300

Gly Lys
305

<210> SEQ ID NO 15
<211> LENGTH: 921
<212> TYPE: DNA
<213> ORGANISM: Macaca fascicularis

<400> SEQUENCE: 15
ttcaagatac ctgtagagga acttgaggac agagtgtttg tgaaatgcaa taccagcgtc      60
acatgggtag agggaacggt gggaacactg ctcacaaata atacaagact ggacctggga     120
aaacgcatcc tggacccacg aggaatatat aggtgtaatg gacagatat atacaaggac      180 aaagaatctg ctgtgcaagt tcattatcga atggcggccg cagagcccaa atcttctgac     240
aaaactcaca catgcccacc gtgcccagca cctgaactcc tggggggacc gtcagtcttc     300
ctcttccccc caaaacccaa ggacaccctc atgatctccc ggacccctga ggtcacatgc     360
gtggtggtgg acgtgagcca cgaagaccct gaggtcaagt tcaactggta cgtggacggc     420
gtggaggtgc ataatgccaa gacaaagccg cgggaggagc agtacaacag cacgtaccgt     480
gtggtcagcg tcctcaccgt cctgcaccag gactggctga atggcaagga gtacaagtgc     540
aaggtctcca acaaagccct cccagccccc atcgagaaaa ccatctccaa agccaaaggg     600
cagccccgag aaccacaggt gtacaccctg cccccatccc gggaggagat gaccaagaac     660
caggtcagcc tgagctgcgc agtcaaaggc ttctatccca gcgacatcgc cgtggagtgg     720
```

```
gagagcaatg ggcagccgga gaacaactac aagaccacgc ctcccgtgct ggactccgac    780
ggctccttct tcctcgtcag caagctcacc gtggacaaga gcaggtggca gcagggaac     840 gtcttctcat gctccgtgat gcatgaggct ctgcacaacc actacacgca gaagagcctc    900
tccctgtctc cgggtaaatg a                                              921
```

```
<210> SEQ ID NO 16
<211> LENGTH: 306
<212> TYPE: PRT
<213> ORGANISM: Macaca fascicularis

<400> SEQUENCE: 16

Phe Lys Ile Pro Val Glu Glu Leu Glu Asp Arg Val Phe Val Lys Cys
 1               5                  10                  15

Asn Thr Ser Val Thr Trp Val Glu Gly Thr Val Gly Thr Leu Leu Thr
            20                  25                  30

Asn Asn Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Ala
    50                  55                  60

Val Gln Val His Tyr Arg Met Ala Ala Ala Glu Pro Lys Ser Ser Asp
65                  70                  75                  80

Lys Thr His Thr Cys Pro Pro Cys Pro Ala Pro Glu Leu Leu Gly Gly
                85                  90                  95

Pro Ser Val Phe Leu Phe Pro Pro Lys Pro Lys Asp Thr Leu Met Ile
           100                 105                 110

Ser Arg Thr Pro Glu Val Thr Cys Val Val Val Asp Val Ser His Glu
       115                 120                 125

Asp Pro Glu Val Lys Phe Asn Trp Tyr Val Asp Gly Val Glu Val His
   130                 135                 140

Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Ala Leu Pro Ala Pro Ile Glu
           180                 185                 190

Lys Thr Ile Ser Lys Ala Lys Gly Gln Pro Arg Glu Pro Gln Val Tyr
       195                 200                 205

Thr Leu Pro Pro Ser Arg Glu Glu Met Thr Lys Asn Gln Val Ser Leu
   210                 215                 220

Ser Cys Ala Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Val Ser Lys Leu Thr Val Asp
           260                 265                 270

Lys Ser Arg Trp Gln Gln Gly Asn Val Phe Ser Cys Ser Val Met His
       275                 280                 285

Glu Ala Leu His Asn His Tyr Thr Gln Lys Ser Leu Ser Leu Ser Pro
   290                 295                 300

Gly Lys
305

<210> SEQ ID NO 17
<211> LENGTH: 804
```

```
<212> TYPE: DNA
<213> ORGANISM: Homo sapiens

<400> SEQUENCE: 17
caagatggta atgaagaaat gggtggtatt acacagacac catataaagt ctccatctct      60
ggaaccacag taatattgac aggcggtggt gggagcgcgg ccgcagagcc caaatcttgt     120
gacaaaactc acacatgccc accgtgccca gcacctgaac tcctgggggg accgtcagtc     180
ttcctcttcc ccccaaaacc caaggacacc ctcatgatct cccggacccc tgaggtcaca     240
tgcgtggtgg tggacgtgag ccacgaagac cctgaggtca agttcaactg gtacgtggac     300
ggcgtggagg tgcataatgc caagacaaag ccgcgggagg agcagtacaa cagcacgtac     360
cgtgtggtca gcgtcctcac cgtcctgcac caggactggc tgaatggcaa ggagtacaag     420
tgcaaggtct ccaacaaagc cctcccagcc cccatcgaga aaaccatctc caaagccaaa     480
gggcagcccc gagaaccaca ggtgtacacc ctgcccccat cccgggagga tgaccaagaa     540
aaccaggtca gcctgacctg cctggtcaaa ggcttctatc ccagcgacat cgccgtggag     600
tgggagagca atgggcagcc ggagaacaac tacaagacca cgcctcccgt gctggactcc     660
gacggctcct tcttcctcta tagcaagctc accgtggaca agagcaggtg gcagcagggg     720
aacgtcttct catgctccgt gatgcatgag gctctgcaca accactacac gcagaagagc     780
ctctccctgt ctccgggtaa atga                                             804

<210> SEQ ID NO 18
<211> LENGTH: 267
<212> TYPE: PRT
<213> ORGANISM: Homo sapiens

<400> SEQUENCE: 18

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Gly Gly Ser
            20                  25                  30

Ala Ala Ala Glu Pro Lys Ser Cys Asp Lys Thr His Thr Cys Pro Pro
        35                  40                  45

Cys Pro Ala Pro Glu Leu Leu Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser His Glu Asp Pro Glu Val Lys Phe Asn
                85                  90                  95

Trp Tyr Val Asp Gly Val Glu Val His Asn Ala Lys Thr Lys Pro Arg
            100                 105                 110

Glu Glu Gln Tyr Asn Ser Thr Tyr Arg Val Val Ser Val Leu Thr Val
        115                 120                 125

Leu His Gln Asp Trp Leu Asn Gly Lys Glu Tyr Lys Cys Lys Val Ser
    130                 135                 140

Asn Lys Ala Leu Pro Ala Pro Ile Glu Lys Thr Ile Ser Lys Ala Lys
145                 150                 155                 160

Gly Gln Pro Arg Glu Pro Gln Val Tyr Thr Leu Pro Pro Ser Arg Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
        195                 200                 205
```

```
Asn Asn Tyr Lys Thr Thr Pro Pro Val Leu Asp Ser Asp Gly Ser Phe
        210                 215                 220

Phe Leu Tyr Ser Lys Leu Thr Val Asp Lys Ser Arg Trp Gln Gln Gly
225                 230                 235                 240

Asn Val Phe Ser Cys Ser Val Met His Glu Ala Leu His Asn His Tyr
                245                 250                 255

Thr Gln Lys Ser Leu Ser Leu Ser Pro Gly Lys
            260                 265
```

```
<210> SEQ ID NO 19
<211> LENGTH: 804
<212> TYPE: DNA
<213> ORGANISM: Homo sapiens

<400> SEQUENCE: 19
aaatatccaa cacagacaat tggtggtatg aagaaaatg gtgatcaagt ctccatctct       60
ggaaccacag taatattgac aggcggtggt gggagcgcgg ccgcagagcc caaatcttgt    120
gacaaaactc acacatgccc accgtgccca gcacctgaac tcctgggggg accgtcagtc    180
ttcctcttcc ccccaaaacc caaggacacc ctcatgatct cccggacccc tgaggtcaca    240
tgcgtggtgg tggacgtgag ccacgaagac cctgaggtca agttcaactg gtacgtggac    300
ggcgtggagg tgcataatgc caagacaaag ccgcgggagg agcagtacaa cagcacgtac    360
cgtgtggtca gcgtcctcac cgtcctgcac caggactggc tgaatggcaa ggagtacaag    420
tgcaaggtct ccaacaaagc cctcccagcc cccatcgaga aaaccatctc caaagccaaa    480
gggcagcccc gagaaccaca ggtgtacacc ctgcccccat cccgggagga gatgaccaag    540
aaccaggtca gcctgacctg cctggtcaaa ggcttctatc ccagcgacat cgccgtggag    600
tgggagagca atgggcagcc ggagaacaac tacaagacca cgcctcccgt gctggactcc    660
gacggctcct tcttcctcta tagcaagctc accgtggaca agagcaggtg gcagcagggg    720
aacgtcttct catgctccgt gatgcatgag gctctgcaca accactacac gcagaagagc    780
ctctccctgt ctccgggtaa atga                                           804
```

```
<210> SEQ ID NO 20
<211> LENGTH: 267
<212> TYPE: PRT
<213> ORGANISM: Homo sapiens

<400> SEQUENCE: 20

Lys Tyr Pro Thr Gln Thr Ile Gly Gly Met Glu Glu Asn Gly Asp Gln
1               5                   10                  15

Val Ser Ile Ser Gly Thr Thr Val Ile Leu Thr Gly Gly Gly Ser
            20                  25                  30

Ala Ala Ala Glu Pro Lys Ser Cys Asp Lys Thr His Thr Cys Pro Pro
            35                  40                  45

Cys Pro Ala Pro Glu Leu Leu Gly Gly Pro Ser Val Phe Leu Phe Pro
        50                  55                  60

Pro Lys Pro Lys Asp Thr Leu Met Ile Ser Arg Thr Pro Glu Val Thr
65                  70                  75                  80

Cys Val Val Val Asp Val Ser His Glu Asp Pro Glu Val Lys Phe Asn
                85                  90                  95

Trp Tyr Val Asp Gly Val Glu Val His Asn Ala Lys Thr Lys Pro Arg
            100                 105                 110

Glu Glu Gln Tyr Asn Ser Thr Tyr Arg Val Val Ser Val Leu Thr Val
```

```
                  115                 120                 125
Leu His Gln Asp Trp Leu Asn Gly Lys Glu Tyr Lys Cys Lys Val Ser
    130                 135                 140

Asn Lys Ala Leu Pro Ala Pro Ile Glu Lys Thr Ile Ser Lys Ala Lys
145                 150                 155                 160

Gly Gln Pro Arg Glu Pro Gln Val Tyr Thr Leu Pro Pro Ser Arg Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
        195                 200                 205

Asn Asn Tyr Lys Thr Thr Pro Pro Val Leu Asp Ser Asp Gly Ser Phe
210                 215                 220

Phe Leu Tyr Ser Lys Leu Thr Val Asp Lys Ser Arg Trp Gln Gln Gly
225                 230                 235                 240

Asn Val Phe Ser Cys Ser Val Met His Glu Ala Leu His Asn His Tyr
                245                 250                 255

Thr Gln Lys Ser Leu Ser Leu Ser Pro Gly Lys
            260                 265

<210> SEQ ID NO 21

<400> SEQUENCE: 21

000

<210> SEQ ID NO 22

<400> SEQUENCE: 22

000

<210> SEQ ID NO 23
<211> LENGTH: 5
<212> TYPE: PRT
<213> ORGANISM: Mus musculus

<400> SEQUENCE: 23

Thr Tyr Ala Met Asn
1               5

<210> SEQ ID NO 24
<211> LENGTH: 19
<212> TYPE: PRT
<213> ORGANISM: Mus musculus

<400> SEQUENCE: 24

Arg Ile Arg Ser Lys Tyr Asn Asn Tyr Ala Thr Tyr Tyr Ala Asp Ser
1               5                   10                  15

Val Lys Asp

<210> SEQ ID NO 25
<211> LENGTH: 14
<212> TYPE: PRT
<213> ORGANISM: Mus musculus

<400> SEQUENCE: 25

His Gly Asn Phe Gly Asn Ser Tyr Val Ser Trp Phe Ala Tyr
1               5                   10
```

```
<210> SEQ ID NO 26
<211> LENGTH: 14
<212> TYPE: PRT
<213> ORGANISM: Mus musculus

<400> SEQUENCE: 26

Arg Ser Ser Thr Gly Ala Val Thr Thr Ser Asn Tyr Ala Asn
1               5                   10

<210> SEQ ID NO 27
<211> LENGTH: 7
<212> TYPE: PRT
<213> ORGANISM: Mus musculus

<400> SEQUENCE: 27

Gly Thr Asn Lys Arg Ala Pro
1               5

<210> SEQ ID NO 28
<211> LENGTH: 9
<212> TYPE: PRT
<213> ORGANISM: Mus musculus

<400> SEQUENCE: 28

Ala Leu Trp Tyr Ser Asn Leu Trp Val
1               5

<210> SEQ ID NO 29
<211> LENGTH: 1650
<212> TYPE: DNA
<213> ORGANISM: Artificial Sequence
<220> FEATURE:
<223> OTHER INFORMATION: cDNA encoding  humanized IF3-IgGNC antibody
      sequence;

<400> SEQUENCE: 29
gaggtgcagc tggtggagtc tgggggaggc ttggtacagc ctgggggtc cctgagactc        60 tcctgtgcag cctctggatt cacctttagc acctacgcca tgaactgggt ccgccaggct      120
ccagggaagg ggctgagtg gtctcacgc ataagaagta aatataataa ttatgcaaca        180
tattatgccg attcagtgaa agaccggttc accatctcca gagacgattc caagaacacg      240
ctgtatctgc aaatgaacag cctgagagcc gaggacacgg ccgtatatta ctgtgcgaga      300
catgggaact tcgtaatag ctacgtttcc tggtttgctt actggggcca agggacaatg       360
gtcaccgtct cttcagctag caccaagggc ccatcggtct tccccctggc gccctgctcc      420
aggagcacct ccgagagcac agcggccctg ggctgcctgg tcaaggacta cttccccgaa      480
ccggtgacgg tgtcgtggaa ctcaggcgct ctgaccagcg gcgtgcacac cttcccagct      540
gtcctacagt cctcaggact ctactccctc agcagcgtgg tgaccgtgcc ctccagcaac      600
ttcggcaccc agacctacac ctgcaacgta gatcacaagc ccagcaacac caaggtggac      660
aagacagttg ctagcaccaa gggcccatcg gtcttccccc tggcgccctg ctccaggagc      720
acctccgaga gcacagcggc cctgggctgc ctggtcaagg actacttccc cgaaccggtg      780
acggtgtcgt ggaactcagg cgctctgacc agcggcgtgc acaccttccc agctgtccta      840
cagtcctcag gactctactc cctcagcagc gtggtgaccg tgcccccag caacttcggc       900 acccagacct acacctgcaa cgtagatcac aagcccagca acaccaaggt ggacaagaca      960
gttgagcgca aatgttgtgt cgagtgccca ccgtgcccag caccacctgt ggcaggaccg     1020
tcagtcttcc tcttcccccc aaaacccaag gacaccctca tgatctcccg gacccctgag     1080
```

```
gtcacgtgcg tggtggtgga cgtgagccac gaagacccg aggtccagtt caactggtac    1140
gtggacggcg tggaggtgca taatgccaag acaaagccac gggaggagca gttcaacagc    1200
acgttccgtg tggtcagcgt cctcaccgtt gtgcaccagg actggctgaa cggcaaggag    1260
tacaagtgca aggtctccaa caaaggcctc ccagccccca tcgagaaaac catctccaaa    1320
accaaagggc agccccgaga accacaggtg tacaccctgc ccccatcccg ggaggagatg    1380
accaagaacc aggtcagcct gacctgcctg gtcaaaggct tctacccag cgacatcgcc    1440 gtggagtggg agagcaatgg gcagccggag aacaactaca agaccacacc tcccatgctg    1500
gactccgacg gctccttctt cctctacagc aagctcaccg tggacaagag caggtggcag    1560
caggggaacg tcttctcatg ctccgtgatg catgaggctc tgcacaacca ctacacgcag    1620
aagagcctct ccctgtctcc gggtaaatga                                    1650
```

<210> SEQ ID NO 30
<211> LENGTH: 549
<212> TYPE: PRT
<213> ORGANISM: Artificial Sequence
<220> FEATURE:
<223> OTHER INFORMATION: Humanized IF3-IgGHC antibody sequence;

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Ala
    210                 215                 220

Ser Thr Lys Gly Pro Ser Val Phe Pro Leu Ala Pro Cys Ser Arg Ser
225                 230                 235                 240

Thr Ser Glu Ser Thr Ala Ala Leu Gly Cys Leu Val Lys Asp Tyr Phe
                245                 250                 255

Pro Glu Pro Val Thr Val Ser Trp Asn Ser Gly Ala Leu Thr Ser Gly
```

```
            260                 265                 270
Val His Thr Phe Pro Ala Val Leu Gln Ser Ser Gly Leu Tyr Ser Leu
            275                 280                 285

Ser Ser Val Val Thr Val Pro Ser Ser Asn Phe Gly Thr Gln Thr Tyr
            290                 295                 300

Thr Cys Asn Val Asp His Lys Pro Ser Asn Thr Lys Val Asp Lys Thr
305                 310                 315                 320

Val Glu Arg Lys Cys Cys Val Glu Cys Pro Pro Cys Pro Ala Pro Pro
                325                 330                 335

Val Ala Gly Pro Ser Val Phe Leu Phe Pro Pro Lys Pro Lys Asp Thr
            340                 345                 350

Leu Met Ile Ser Arg Thr Pro Glu Val Thr Cys Val Val Val Asp Val
            355                 360                 365

Ser His Glu Asp Pro Glu Val Gln Phe Asn Trp Tyr Val Asp Gly Val
            370                 375                 380

Glu Val His Asn Ala Lys Thr Lys Pro Arg Glu Glu Gln Phe Asn Ser
385                 390                 395                 400

Thr Phe Arg Val Val Ser Val Leu Thr Val Val His Gln Asp Trp Leu
                405                 410                 415

Asn Gly Lys Glu Tyr Lys Cys Lys Val Ser Asn Lys Gly Leu Pro Ala
            420                 425                 430

Pro Ile Glu Lys Thr Ile Ser Lys Thr Lys Gly Gln Pro Arg Glu Pro
            435                 440                 445

Gln Val Tyr Thr Leu Pro Pro Ser Arg Glu Glu Met Thr Lys Asn Gln
            450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
                485                 490                 495

Pro Pro Met Leu Asp Ser Asp Gly Ser Phe Phe Leu Tyr Ser Lys Leu
            500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
530                 535                 540

Leu Ser Pro Gly Lys
545

<210> SEQ ID NO 31
<211> LENGTH: 648
<212> TYPE: DNA
<213> ORGANISM: Artificial Sequence
<220> FEATURE:
<223> OTHER INFORMATION: cDNA encoding  humanized IF3-1LC antibody
      sequence;

<400> SEQUENCE: 31
caggctgtgg tgactcagga gccctcactg actgtgtccc caggagggac agtcactctc      60
acctgtcgct caagtactgg ggctgttaca actagtaact atgccaactg ggtccagcag     120
aaacctggac aagcacccag ggtctgatt ggtggtacca caagcgagc tccaggtacc      180 cctgcccggt tctcaggctc cctccttggg ggcaaagctg ccctgacact gtcaggtgtg     240
cagcctgagg acgaggctga gtattactgc gctctatggt acagcaacct ctgggtgttc     300
ggcggaggga ccaagctgac cgtcctaggc caaccgaaag cggcgccctc ggtcactctg     360
```

| | |
|---|---|
| ttcccgccct cctctgagga gcttcaagcc aacaaggcca cactggtgtg tctcataagt | 420 |
| gacttctacc cgggagccgt gacagtggcc tggaaggcag atagcagccc cgtcaaggcg | 480 |
| ggagtggaga ccaccacacc ctccaaacaa agcaacaaca agtacgcggc cagcagctat | 540 |
| ctgagcctga cgcctgagca gtggaagtcc cacagaagct acagctgcca ggtcacgcat | 600 |
| gaagggagca ccgtggagaa gacagtggcc cctacagaat gttcatag | 648 |

```
<210> SEQ ID NO 32
<211> LENGTH: 215
<212> TYPE: PRT
<213> ORGANISM: Artificial Sequence
<220> FEATURE:
<223> OTHER INFORMATION: Humanized IF3-1LC antibody sequence;

<400> SEQUENCE: 32

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 33
<211> LENGTH: 375
<212> TYPE: DNA
<213> ORGANISM: Artificial Sequence
<220> FEATURE:
<223> OTHER INFORMATION: cDNA encoding humanized IF3-1VH antibody
      sequence;

<400> SEQUENCE: 33
```

| | |
|---|---|
| gaggtgcagc tggtggagtc tgggggaggc ttggtacagc ctggggggtc cctgagactc | 60 |
| tcctgtgcag cctctggatt cacctttagc acctacgcca tgaactgggt ccgccaggct | 120 |
| ccagggaagg ggctggagtg ggtctcacgc ataagaagta aatataataa ttatgcaaca | 180 |

```
tattatgccg attcagtgaa agaccggttc accatctcca gagacgattc caagaacacg      240
ctgtatctgc aaatgaacag cctgagagcc gaggacacgg ccgtatatta ctgtgcgaga      300
catgggaact tcggtaatag ctacgtttcc tggtttgctt actggggcca aggacaatg      360 gtcaccgtct cttca                                                      375
```

```
<210> SEQ ID NO 34
<211> LENGTH: 125
<212> TYPE: PRT
<213> ORGANISM: Artificial Sequence
<220> FEATURE:
<223> OTHER INFORMATION: Humanized IF3-1VH antibody sequence;

<400> SEQUENCE: 34
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

```
<210> SEQ ID NO 35
<211> LENGTH: 708
<212> TYPE: DNA
<213> ORGANISM: Artificial Sequence
<220> FEATURE:
<223> OTHER INFORMATION: cDNA encoding  humanized IF3-1Fd antibody
      sequence;

<400> SEQUENCE: 35
gaggtgcagc tggtggagtc tgggggaggc ttggtacagc ctggggggtc cctgagactc      60
tcctgtgcag cctctggatt caccttagc acctacgcca tgaactgggt ccgccaggct     120
ccagggaagg ggctggagtg ggtctcacgc ataagaagta aatataataa ttatgcaaca    180
tattatgccg attcagtgaa agaccggttc accatctcca gagacgattc caagaacacg    240
ctgtatctgc aaatgaacag cctgagagcc gaggacacgg ccgtatatta ctgtgcgaga    300
catgggaact tcggtaatag ctacgtttcc tggtttgctt actggggcca aggacaatg    360 gtcaccgtct cttcagctag caccaagggc ccatcggtct tccccctggc gccctgctcc    420
aggagcacct ccgagagcac agcggccctg gctgcctgg tcaaggacta cttccccgaa    480
ccggtgacgg tgtcgtggaa ctcaggcgct ctgaccagcg gcgtgcacac cttcccagct    540
gtcctacagt cctcaggact ctactccctc agcagcgtgg tgaccgtgcc ctccagcaac    600
ttcggcaccc agacctacac ctgcaacgta gatcacaagc ccagcaacac caaggtggac    660
aagacagttg gtggcggggg ctcccatcat catcatcatc atcattag                 708
```

```
<210> SEQ ID NO 36
```

<211> LENGTH: 235
<212> TYPE: PRT
<213> ORGANISM: Artificial Sequence
<220> FEATURE:
<223> OTHER INFORMATION: Humanized IF3-1Fd antibody sequence;

<400> SEQUENCE: 36

```
Glu Val Gln Leu Val Glu Ser Gly Gly Gly Leu Val Gln Pro Gly
1               5                   10                  15
Ser Leu Arg Leu Ser Cys Ala Ala Ser Gly Phe Thr Phe Ser Thr Tyr
            20                  25                  30
Ala Met Asn Trp Val Arg Gln Ala Pro Gly Lys Gly Leu Glu Trp Val
        35                  40                  45
Ser Arg Ile Arg Ser Lys Tyr Asn Asn Tyr Ala Thr Tyr Tyr Ala Asp
    50                  55                  60
Ser Val Lys Asp Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg His Gly Asn Phe Gly Asn Ser Tyr Val Ser Trp Phe
            100                 105                 110
Ala Tyr Trp Gly Gln Gly Thr Met Val Thr Val Ser Ser Ala Ser Thr
        115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Asn Phe Gly Thr Gln Thr Tyr Thr Cys
        195                 200                 205
Asn Val Asp His Lys Pro Ser Asn Thr Lys Val Asp Lys Thr Val Gly
    210                 215                 220
Gly Gly Gly Ser His His His His His His
225                 230                 235
```

<210> SEQ ID NO 37
<211> LENGTH: 375
<212> TYPE: DNA
<213> ORGANISM: Artificial Sequence
<220> FEATURE:
<223> OTHER INFORMATION: cDNA encoding humanized IF3-2VH antibody sequence;

<400> SEQUENCE: 37

```
gaggtgcagc tggtggagtc tgggggaggc ttggtacagc ctgggggtc cctgagactc      60 tcctgtgcag cctctggatt cacctttaac acctacgcca tgaactgggt ccgccaggct    120
ccagggaagg ggctggagtg gtctcacgc ataagaagta aatataataa ttatgcaaca    180
tattatgccg attcagtgaa agaccggttc accatctcca gagacgattc caagaacacg    240
ctgtatctgc aaatgaacag cctgagagcc gaggacacgg ccgtatatta ctgtgcgaga    300
catgggaact tcggtaatag ctacgtttcc tggtttgctt actggggcca aggacaatg    360 gtcaccgtct cttca                                                    375
```

<210> SEQ ID NO 38
<211> LENGTH: 125
<212> TYPE: PRT
<213> ORGANISM: Artificial Sequence
<220> FEATURE:
<223> OTHER INFORMATION: Humanized IF3-2VH antibody sequence;

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125
```

<210> SEQ ID NO 39
<211> LENGTH: 708
<212> TYPE: DNA
<213> ORGANISM: Artificial Sequence
<220> FEATURE:
<223> OTHER INFORMATION: cDNA encoding humanized IF3-2Fd antibody
sequence;

<400> SEQUENCE: 39

```
gaggtgcagc tggtggagtc tgggggaggc ttggtacagc ctggggggtc cctgagactc      60
tcctgtgcag cctctggatt cacctttaac acctacgcca tgaactgggt ccgccaggct     120
ccagggaagg gctggagtg gtctcacgc ataagaagta aatataataa ttatgcaaca       180
tattatgccg attcagtgaa agaccggttc accatctcca gagacgattc aagaacacg      240
ctgtatctgc aaatgaacag cctgagagcc gaggacacgg ccgtatatta ctgtgcgaga     300
catgggaact tcggtaatag ctacgttccc tggtttgctt actggggcca agggacaatg    360
gtcaccgtct cttcagctag caccaagggc ccatcggtct tccccctggc gccctgctcc    420
aggagcacct ccgagagcac agcggccctg ggctgcctgg tcaaggacta cttccccgaa    480
ccggtgacgg tgtcgtggaa ctcaggcgct ctgaccagcg gcgtgcacac cttcccagct    540
gtcctacagt cctcaggact ctactccctc agcagcgtgg tgaccgtgcc ctccagcaac    600
ttcggcaccc agacctacac ctgcaacgta gatcacaagc ccagcaacac caaggtggac    660
aagacagttg gtggcggggg ctcccatcat catcatcatc atcattag                  708
```

<210> SEQ ID NO 40
<211> LENGTH: 235
<212> TYPE: PRT
<213> ORGANISM: Artificial Sequence
<220> FEATURE:
<223> OTHER INFORMATION: Humanized IF3-2Fd antibody sequence;

<400> SEQUENCE: 40

```
Glu Val Gln Leu Val Glu Ser Gly Gly Gly Leu Val Gln Pro Gly Gly
```

```
 1               5                  10                 15
Ser Leu Arg Leu Ser Cys Ala Ala Ser Gly Phe Thr Phe Asn Thr Tyr
             20                 25                 30

Ala Met Asn Trp Val Arg Gln Ala Pro Gly Lys Gly Leu Glu Trp Val
             35                 40                 45

Ser Arg Ile Arg Ser Lys Tyr Asn Asn Tyr Ala Thr Tyr Tyr Ala Asp
 50                 55                 60

Ser Val Lys Asp Arg Phe Thr Ile Ser Arg Asp Asp Ser Lys Asn Thr
 65                 70                 75                 80

Leu Tyr Leu Gln Met Asn Ser Leu Arg Ala Glu Asp Thr Ala Val Tyr
             85                 90                 95

Tyr Cys Ala Arg His Gly Asn Phe Gly Asn Ser Tyr Val Ser Trp Phe
            100                105                110

Ala Tyr Trp Gly Gln Gly Thr Met Val Thr Val Ser Ser Ala Ser Thr
            115                120                125

Lys Gly Pro Ser Val Phe Pro Leu Ala Pro Cys Ser Arg Ser Thr Ser
            130                135                140

Glu Ser Thr Ala Ala Leu Gly Cys Leu Val Lys Asp Tyr Phe Pro Glu
145                150                155                160

Pro Val Thr Val Ser Trp Asn Ser Gly Ala Leu Thr Ser Gly Val His
                165                170                175

Thr Phe Pro Ala Val Leu Gln Ser Ser Gly Leu Tyr Ser Leu Ser Ser
            180                185                190

Val Val Thr Val Pro Ser Ser Asn Phe Gly Thr Gln Thr Tyr Thr Cys
            195                200                205

Asn Val Asp His Lys Pro Ser Asn Thr Lys Val Asp Lys Thr Val Gly
            210                215                220

Gly Gly Gly Ser His His His His His His
225                230                235

<210> SEQ ID NO 41
<211> LENGTH: 375
<212> TYPE: DNA
<213> ORGANISM: Artificial Sequence
<220> FEATURE:
<223> OTHER INFORMATION: cDNA encoding  humanized IF3-3VH antibody
      sequence;

<400> SEQUENCE: 41
gaggtgcagc tggtggagtc tgggggaggc ttggtacagc ctgggggggtc cctgagactc        60 tcctgtgcag cctctggatt cacctttagc acctacgcca tgaactgggt ccgccaggct       120
ccagggaagg gctggagtg gtcgcacgc ataagaagta aatataataa ttatgcaaca         180
tattatgccg attcagtgaa agaccggttc accatctcca gagacgattc caagaacacg       240
ctgtatctgc aaatgaacag cctgagagcc gaggacacgg ccgtatatta ctgtgcgaga       300
catgggaact tcggtaatag ctacgtttcc tggtttgctt actggggcca aggacaatg        360 gtcaccgtct cttca                                                        375

<210> SEQ ID NO 42
<211> LENGTH: 125
<212> TYPE: PRT
<213> ORGANISM: Artificial Sequence
<220> FEATURE:
<223> OTHER INFORMATION: Humanized IF3-3VH antibody sequence;

<400> SEQUENCE: 42
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
            115                 120                 125
```

<210> SEQ ID NO 43
<211> LENGTH: 708
<212> TYPE: DNA
<213> ORGANISM: Artificial Sequence
<220> FEATURE:
<223> OTHER INFORMATION: cDNA encoding humanized IF3-3Fd antibody sequence;

<400> SEQUENCE: 43

```
gaggtgcagc tggtggagtc tgggggaggc ttggtacagc ctggggggtc cctgagactc      60
tcctgtgcag cctctggatt caccttagc acctacgcca tgaactgggt ccgccaggct     120
ccagggaagg gctggagtg gtcgcacgc ataagaagta atataataa ttatgcaaca       180
tattatgccg attcagtgaa agaccggttc accatctcca gagacgattc caagaacacg     240
ctgtatctgc aaatgaacag cctgagagcc gaggacacgg ccgtatatta ctgtgcgaga     300
catgggaact tcggtaatag ctacgttttcc tggttttgctt actggggcca agggacaatg   360
gtcaccgtct cttcagctag caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccagct     540
gtcctacagt cctcaggact ctactccctc agcagcgtgg tgaccgtgcc ctccagcaac     600
ttcggcaccc agacctacac ctgcaacgta gatcacaagc ccagcaacac caaggtggac     660
aagacagttg gtggcggggg ctcccatcat catcatcatc atcattag                  708
```

<210> SEQ ID NO 44
<211> LENGTH: 235
<212> TYPE: PRT
<213> ORGANISM: Artificial Sequence
<220> FEATURE:
<223> OTHER INFORMATION: Humanized IF3-3Fd antibody sequence;

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
```

```
                 50                  55                  60
Ser Val Lys Asp Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg His Gly Asn Phe Gly Asn Ser Tyr Val Ser Trp Phe
                100                 105                 110

Ala Tyr Trp Gly Gln Gly Thr Met Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Gly
    210                 215                 220

Gly Gly Gly Ser His His His His His His
225                 230                 235

<210> SEQ ID NO 45
<211> LENGTH: 375
<212> TYPE: DNA
<213> ORGANISM: Artificial Sequence
<220> FEATURE:
<223> OTHER INFORMATION: cDNA encoding humanized IF3-4VH antibody
      sequence;

<400> SEQUENCE: 45
gaggtgcagc tggtggagtc tgggggaggc ttggtacagc ctggggggtc cctgagactc      60
tcctgtgcag cctctggatt caccttagc acctacgcca tgaactgggt ccgccaggct     120
ccagggaagg ggctggagtg ggtcgcacgc ataagaagta aatataataa ttatgcaaca    180
tattatgccg attcagtgaa agaccggttc accatctcca gagacgattc caagaacacg    240
ctgtatctgc aaatgaacag cctgagagcc gaggacacgg ccgtatatta ctgtgtgaga    300
catgggaact tcggtaatag ctacgtttcc tggtttgctt actggggcca agggacaatg    360
gtcaccgtct cttca                                                     375

<210> SEQ ID NO 46
<211> LENGTH: 125
<212> TYPE: PRT
<213> ORGANISM: Artificial Sequence
<220> FEATURE:
<223> OTHER INFORMATION: Humanized IF3-4VH antibody sequence;

<400> SEQUENCE: 46

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
             35                  40                  45
```

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Met Val Thr Val Ser Ser
                115                 120                 125

<210> SEQ ID NO 47
<211> LENGTH: 708
<212> TYPE: DNA
<213> ORGANISM: Artificial Sequence
<220> FEATURE:
<223> OTHER INFORMATION: cDNA encoding humanized IF3-4Fd antibody
      sequence;

<400> SEQUENCE: 47
gaggtgcagc tggtggagtc tggggggaggc ttggtacagc ctgggggggtc cctgagactc        60
tcctgtgcag cctctggatt cacctttagc acctacgcca tgaactgggt ccgccaggct       120
ccagggaagg ggctggagtg ggtcgcacgc ataagaagta aatataataa ttatgcaaca       180
tattatgccg attcagtgaa agaccggttc accatctcca gagacgattc aagaacacg        240
ctgtatctgc aaatgaacag cctgagagcc gaggacacgg ccgtatatta ctgtgtgaga       300
catgggaact tcggtaatag ctacgtttcc tggtttgctt actggggcca agggacaatg       360
gtcaccgtct cttcagctag caccaagggc ccatcggtct tccccctggc gccctgctcc       420
aggagcacct ccgagagcac agcggccctg ggctgcctgg tcaaggacta cttccccgaa       480
ccggtgacgg tgtcgtggaa ctcaggcgct ctgaccagcg gcgtgcacac cttcccagct       540
gtcctacagt cctcaggact ctactccctc agcagcgtgg tgaccgtgcc ctccagcaac       600
ttcggcaccc agacctacac ctgcaacgta gatcacaagc ccagcaacac caaggtggac       660
aagacagttg gtggcggggg ctcccatcat catcatcatc atcattag                    708

<210> SEQ ID NO 48
<211> LENGTH: 235
<212> TYPE: PRT
<213> ORGANISM: Artificial Sequence
<220> FEATURE:
<223> OTHER INFORMATION: Humanized IF3-4Fd antibody sequence;

<400> SEQUENCE: 48

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe

```
                   100                 105                 110
Ala Tyr Trp Gly Gln Gly Thr Met Val Thr Val Ser Ser Ala Ser Thr
            115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Gly
            210                 215                 220

Gly Gly Gly Ser His His His His His His
225                 230                 235

<210> SEQ ID NO 49
<211> LENGTH: 375
<212> TYPE: DNA
<213> ORGANISM: Artificial Sequence
<220> FEATURE:
<223> OTHER INFORMATION: cDNA encoding  humanized IF3-5VH antibody
      sequence;

<400> SEQUENCE: 49
gaggtgcagc tggtggagtc tgggggaggc ttggtacagc ctggggggtc cctgagactc        60
tcctgtgcag cctctggatt cacctttaac acctacgcca tgaactgggt ccgccaggct       120
ccagggaagg ggctggagtg ggtcgcacgc ataagaagta aatataataa ttatgcaaca       180
tattatgccg attcagtgaa agaccggttc accatctcca gagacgattc caagaacacg       240
ctgtatctgc aaatgaacag cctgagagcc gaggacacgg ccgtatatta ctgtgtgaga       300
catgggaact tcggtaatag ctacgtttcc tggtttgctt actggggcca agggacaatg       360
gtcaccgtct cttca                                                       375

<210> SEQ ID NO 50
<211> LENGTH: 125
<212> TYPE: PRT
<213> ORGANISM: Artificial Sequence
<220> FEATURE:
<223> OTHER INFORMATION: Humanized IF3-5VH antibody sequence;

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 51
<211> LENGTH: 708
<212> TYPE: DNA
<213> ORGANISM: Artificial Sequence
<220> FEATURE:
<223> OTHER INFORMATION: cDNA encoding humanized IF3-5Fd antibody
      sequence;

<400> SEQUENCE: 51
gaggtgcagc tggtggagtc tgggggaggc ttggtacagc ctggggggtc cctgagactc      60
tcctgtgcag cctctggatt cacctttaac acctacgcca tgaactgggt ccgccaggct     120
ccagggaagg gctggagtg gtcgcacgc ataagaagta aatataataa ttatgcaaca      180
tattatgccg attcagtgaa agaccggttc accatctcca gagacgattc caagaacacg     240
ctgtatctgc aaatgaacag cctgagagcc gaggacacgg ccgtatatta ctgtgtgaga     300
catgggaact tcggtaatag ctacgtttcc tggtttgctt actggggcca agggacaatg     360
gtcaccgtct cttcagctag caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccagct     540
gtcctacagt cctcaggact ctactccctc agcagcgtgg tgaccgtgcc ctccagcaac     600
ttcggcaccc agacctacac ctgcaacgta gatcacaagc ccagcaacac caaggtggac     660
aagacagttg gtggcggggg ctcccatcat catcatcatc atcattag                  708

<210> SEQ ID NO 52
<211> LENGTH: 235
<212> TYPE: PRT
<213> ORGANISM: Artificial Sequence
<220> FEATURE:
<223> OTHER INFORMATION: Humanized IF3-5Fd antibody sequence;

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu

```
                145                 150                 155                 160
Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
                195                 200                 205

Asn Val Asp His Lys Pro Ser Asn Thr Lys Val Asp Lys Thr Val Gly
            210                 215                 220

Gly Gly Gly Ser His His His His His His
225                 230                 235

<210> SEQ ID NO 53
<211> LENGTH: 375
<212> TYPE: DNA
<213> ORGANISM: Artificial Sequence
<220> FEATURE:
<223> OTHER INFORMATION: cDNA encoding  humanized IF3-11VH antibody
      sequence;

<400> SEQUENCE: 53
gaggtgcagc tggtggagag cggcggcggc ctggtgcagc ccggcggcag cctgaagctg      60
agctgcgccg ccagcggctt caccttcagc acctacgcca tgaactgggt gcggcaggcc     120
agcggcaagg gcctggagtg ggtgggccgg atccggagca gtacaacaa ctacgccacc      180 tactacgccg acagcgtgaa ggaccggttc accatcagcc gggacgacag caagaacacc     240
gcctacctgc agatgaacag cctgaagacc gaggacaccg ccgtgtacta ctgcacccgg     300
cacggcaact tcggcaacag ctacgtgagc tggttcgcct actggggcca gggcaccctg     360
gtgaccgtga gcagc                                                      375

<210> SEQ ID NO 54
<211> LENGTH: 125
<212> TYPE: PRT
<213> ORGANISM: Artificial Sequence
<220> FEATURE:
<223> OTHER INFORMATION: Humanized IF3-11VH antibody sequence;

<400> SEQUENCE: 54

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 55
<211> LENGTH: 327
```

<212> TYPE: DNA
<213> ORGANISM: Artificial Sequence
<220> FEATURE:
<223> OTHER INFORMATION: cDNA encoding humanized IF3-1VL antibody
      sequence;

<400> SEQUENCE: 55

```
caggctgtgg tgactcagga gccctcactg actgtgtccc caggagggac agtcactctc    60
acctgtcgct caagtactgg ggctgttaca actagtaact atgccaactg ggtccagcag   120
aaacctggac aagcacccag gggtctgatt ggtggtacca acaagcgagc tccaggtacc   180
cctgcccggt tctcaggctc cctccttggg ggcaaagctg ccctgacact gtcaggtgtg   240
cagcctgagg acgaggctga gtattactgc gctctatggt acagcaacct ctgggtgttc   300
ggcggaggga ccaagctgac cgtccta                                       327
```

<210> SEQ ID NO 56
<211> LENGTH: 109
<212> TYPE: PRT
<213> ORGANISM: Artificial Sequence
<220> FEATURE:
<223> OTHER INFORMATION: Humanized IF3-1VL antibody sequence;

<400> SEQUENCE: 56

```
Gln Ala Val Val Thr Gln Glu Pro Ser Leu Thr Val Ser Pro Gly Gly
1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 57
<211> LENGTH: 327
<212> TYPE: DNA
<213> ORGANISM: Artificial Sequence
<220> FEATURE:
<223> OTHER INFORMATION: cDNA encoding humanized IF3-2VL antibody
      sequence;

<400> SEQUENCE: 57

```
caggctgtgg tgactcagga gccctcactg actgtgtccc caggagggac agtcactctc    60
acctgtcgct caagtactgg ggctgttaca actagtaact atgccaactg ggttccagcag  120
aaacctggac aagcacccag gggtctgatt ggtggtacca acaagcgagc tccagtcacc   180
cctgcccggt tctcaggctc cctccttggg ggcaaagctg ccctgacact gtcaggtgtg   240
cagcctgagg acgaggctga gtattactgc gctctatggt acagcaacct ctgggtgttc   300
ggcggaggga ccaagctgac cgtccta                                       327
```

<210> SEQ ID NO 58
<211> LENGTH: 109
<212> TYPE: PRT
<213> ORGANISM: Artificial Sequence

```
<220> FEATURE:
<223> OTHER INFORMATION: Humanized IF3-2VL antibody sequence;

<400> SEQUENCE: 58

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 59
<211> LENGTH: 648
<212> TYPE: DNA
<213> ORGANISM: Artificial Sequence
<220> FEATURE:
<223> OTHER INFORMATION: cDNA encoding humanized IF3-2LC antibody
      sequence;

<400> SEQUENCE: 59
caggctgtgg tgactcagga gccctcactg actgtgtccc caggagggac agtcactctc      60
acctgtcgct caagtactgg ggctgttaca actagtaact atgccaactg gttccagcag     120
aaacctggac aagcacccag gggtctgatt ggtggtacca acaagcgagc tccagtcacc     180
cctgcccggt tctcaggctc cctccttggg ggcaaagctg ccctgacact gtcaggtgtg     240
cagcctgagg acgaggctga gtattactgc gctctatggt acagcaacct ctgggtgttc     300
ggcggaggga ccaagctgac cgtcctaggc caaccgaaag cggcgccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat     540 ctgagcctga cgcctgagca gtggaagtcc cacagaagct acagctgcca ggtcacgcat     600
gaagggagca ccgtggagaa gacagtggcc cctacagaat gttcatag                 648

<210> SEQ ID NO 60
<211> LENGTH: 215
<212> TYPE: PRT
<213> ORGANISM: Artificial Sequence
<220> FEATURE:
<223> OTHER INFORMATION: Humanized IF3-2LC antibody sequence;

<400> SEQUENCE: 60

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
```

```
                  50                  55                  60
Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 61
<211> LENGTH: 327
<212> TYPE: DNA
<213> ORGANISM: Artificial Sequence
<220> FEATURE:
<223> OTHER INFORMATION: cDNA encoding humanized IF3-3VL antibody
      sequence;

<400> SEQUENCE: 61
caggctgtgg tgactcagga gccctcactg actgtgtccc caggagggac agtcactctc    60
acctgtcgct caagtactgg ggctgttaca actagtaact atgccaactg gtccagcag   120 aaacctggac aagcacccag ggtctgatt ggtggtacca acaagcgagc tccatggacc   180
cctgcccggt tctcaggctc cctccttggg ggcaaagctg ccctgacact gtcaggtgtg   240
cagcctgagg acgaggctga gtattactgc gctctatggt acagcaacct ctgggtgttc   300
ggcggaggga ccaagctgac cgtccta                                      327

<210> SEQ ID NO 62
<211> LENGTH: 109
<212> TYPE: PRT
<213> ORGANISM: Artificial Sequence
<220> FEATURE:
<223> OTHER INFORMATION: Humanized IF3-3VL antibody sequence;

<400> SEQUENCE: 62

Gln Ala Val Val Thr Gln Glu Pro Ser Leu Thr Val Ser Pro Gly Gly
  1               5                  10                  15

Thr Val Thr Leu Thr Cys Arg Ser Ser Thr Gly Ala Val Thr Thr Ser
             20                  25                  30

Asn Tyr Ala Asn Trp Val Gln Gln Lys Pro Gly Gln Ala Pro Arg Gly
         35                  40                  45

Leu Ile Gly Gly Thr Asn Lys Arg Ala Pro Trp Thr Pro Ala Arg Phe
     50                  55                  60

Ser Gly Ser Leu Leu Gly Gly Lys Ala Ala Leu Thr Leu Ser Gly Val
 65                  70                  75                  80
```

Gln Pro Glu Asp Glu Ala Glu Tyr Tyr Cys Ala Leu Trp Tyr Ser Asn
            85                  90                  95

Leu Trp Val Phe Gly Gly Gly Thr Lys Leu Thr Val Leu
            100                 105

<210> SEQ ID NO 63
<211> LENGTH: 649
<212> TYPE: DNA
<213> ORGANISM: Artificial Sequence
<220> FEATURE:
<223> OTHER INFORMATION: cDNA encoding  humanized IF3-3LC antibody
      sequence;

<400> SEQUENCE: 63
caggctgtgg tgactcagga gccctcactg actgtgtccc caggagggac agtcactctc      60
acctgtcgct caagtactgg ggctgttaca actagtaact atgccaactg gtccagcag     120 aaacctggac aagcacccag ggtctgatt ggtggtacca caagcgagc tccatggacc      180 cctgcccggt tctcaggctc cctccttggg ggcaaagctg ccctgacact gtcaggtgtg     240
cagcctgagg acgaggctga gtattactgc gctctatggt acagcaacct ctgggtgttc     300
ggcggaggga ccaagctgac cgtcctaggc caaccgaaag cggcgccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat     540 ctgagcctga cgcctgagca gtggaagtcc acagaagct acagctgcca ggtcacgcat     600
gaagggagca ccgtggagaa agacagtggc ccctacagaa tgttcatag                 649

<210> SEQ ID NO 64
<211> LENGTH: 215
<212> TYPE: PRT
<213> ORGANISM: Artificial Sequence
<220> FEATURE:
<223> OTHER INFORMATION: Humanized IF3-3LC antibody sequence;

<400> SEQUENCE: 64

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
            85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 65
<211> LENGTH: 327
<212> TYPE: DNA
<213> ORGANISM: Artificial Sequence
<220> FEATURE:
<223> OTHER INFORMATION: cDNA encoding humanized IF3-4VL antibody
      sequence;

<400> SEQUENCE: 65
caggctgtgg tgactcagga gccctcactg actgtgtccc caggagggac agtcactctc     60
acctgtcgct caagtactgg ggctgttaca actagtaact atgccaactg gttccagcag    120
aaacctggac aagcacccag gggtctgatt ggtggtacca acaagcgagc tccatggacc    180
cctgcccggt tctcaggctc cctccttggg ggcaaagctg ccctgacact gtcaggtgtg    240
cagcctgagg acgaggctga gtattactgc gctctatggt acagcaacct ctgggtgttc    300
ggcggaggga ccaagctgac cgtccta                                         327

<210> SEQ ID NO 66
<211> LENGTH: 109
<212> TYPE: PRT
<213> ORGANISM: Artificial Sequence
<220> FEATURE:
<223> OTHER INFORMATION: Humanized IF3-4VL antibody sequence;

<400> SEQUENCE: 66

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 67
<211> LENGTH: 648
<212> TYPE: DNA
<213> ORGANISM: Artificial Sequence
<220> FEATURE:
<223> OTHER INFORMATION: cDNA encoding humanized IF3-4LC antibody
      sequence;

<400> SEQUENCE: 67
caggctgtgg tgactcagga gccctcactg actgtgtccc caggagggac agtcactctc     60

```
acctgtcgct caagtactgg ggctgttaca actagtaact atgccaactg gttccagcag    120
aaacctggac aagcacccag gggtctgatt ggtggtacca acaagcgagc tccatggacc    180
cctgcccggt tctcaggctc cctccttggg ggcaaagctg ccctgacact gtcaggtgtg    240
cagcctgagg acgaggctga gtattactgc gctctatggt acagcaacct ctgggtgttc    300
ggcggaggga ccaagctgac cgtcctaggc caaccgaaag cggcgccctc ggtcactctg    360
ttcccgccct cctctgagga gcttcaagcc aacaaggcca cactggtgtg tctcataagt    420
gacttctacc cgggagccgt gacagtggcc tggaaggcag atagcagccc cgtcaaggcg    480
ggagtggaga ccaccacacc ctccaaacaa agcaacaaca gtacgcggc cagcagctat    540 ctgagcctga cgcctgagca gtggaagtcc cacagaagct acagctgcca ggtcacgcat    600
gaagggagca ccgtggagaa gacagtggcc cctacagaat gttcatag              648
```

<210> SEQ ID NO 68
<211> LENGTH: 215
<212> TYPE: PRT
<213> ORGANISM: Artificial Sequence
<220> FEATURE:
<223> OTHER INFORMATION: Humanized IF3-4LC antibody sequence;

<400> SEQUENCE: 68

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 69
<211> LENGTH: 327
<212> TYPE: DNA
<213> ORGANISM: Artificial Sequence
<220> FEATURE:

<223> OTHER INFORMATION: cDNA encoding humanized IF3-5VL antibody
sequence;

<400> SEQUENCE: 69

```
caggctgtgg tgactcagga gccctcactg actgtgtccc caggagggac agtcactctc    60
acctgtcgct caagtactgg ggctgttaca actagtaact atgccaactg gtaccagcag   120
aaacctggac aagcacccag gggtctgatt ggtggtacca acaagcgagc tccatggacc   180
cctgcccggt tctcaggctc cctccttggg ggcaaagctg ccctgacact gtcaggtgtg   240
cagcctgagg acgaggctga gtattactgc gctctatggt acagcaacct ctgggtgttc   300
ggcggaggga ccaagctgac cgtccta                                        327
```

<210> SEQ ID NO 70
<211> LENGTH: 109
<212> TYPE: PRT
<213> ORGANISM: Artificial Sequence
<220> FEATURE:
<223> OTHER INFORMATION: Humanized IF3-5VL antibody sequence;

<400> SEQUENCE: 70

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Tyr Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 71
<211> LENGTH: 648
<212> TYPE: DNA
<213> ORGANISM: Artificial Sequence
<220> FEATURE:
<223> OTHER INFORMATION: cDNA encoding humanized IF3-5LC antibody
sequence;

<400> SEQUENCE: 71

```
caggctgtgg tgactcagga gccctcactg actgtgtccc caggagggac agtcactctc    60
acctgtcgct caagtactgg ggctgttaca actagtaact atgccaactg gtaccagcag   120
aaacctggac aagcacccag gggtctgatt ggtggtacca acaagcgagc tccatggacc   180
cctgcccggt tctcaggctc cctccttggg ggcaaagctg ccctgacact gtcaggtgtg   240
cagcctgagg acgaggctga gtattactgc gctctatggt acagcaacct ctgggtgttc   300
ggcggaggga ccaagctgac cgtcctaggc caaccgaaag cggcgccctc ggtcactctg   360
ttcccgccct cctctgagga gcttcaagcc aacaaggcca cactggtgtg tctcataagt   420
gacttctacc cgggagccgt gacagtggcc tggaaggcag atagcagccc cgtcaaggcg   480
ggagtggaga ccaccacacc ctccaaacaa agcaacaaca gtacgcggc cagcagctat   540 ctgagcctga cgcctgagca gtggaagtcc cacagaagct acagctgcca ggtcacgcat   600
```
gaagggagca ccgtggagaa gacagtggcc cctacagaat gttcatag 648

<210> SEQ ID NO 72
<211> LENGTH: 215
<212> TYPE: PRT
<213> ORGANISM: Artificial Sequence
<220> FEATURE:
<223> OTHER INFORMATION: Humanized IF3-5LC antibody sequence;

<400> SEQUENCE: 72

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Tyr Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 73
<211> LENGTH: 690
<212> TYPE: DNA
<213> ORGANISM: Artificial Sequence
<220> FEATURE:
<223> OTHER INFORMATION: cDNA encoding OKT3Fd monoclonal antibody
      sequence

<400> SEQUENCE: 73
caggtccagc tgcagcagtc tggggctgaa ctggcaagac ctggggcctc agtgaagatg 60
tcctgcaagg cttctggcta cacctttact aggtacacga tgcactgggt aaaacagagg 120
cctggacagg gtctggaatg gattggatac attaatccta gccgtggtta tactaattac 180
aatcagaagt tcaaggacaa ggccacattg actacagaca atcctccag cacagcctac 240 atgcaactga gcagcctgac atctgaggac tctgcagtct attactgtgc aagatattat 300
gatgatcatt actgccttga ctactggggc caaggcacca ctctcacagt ctcctcagct 360
agcaccaagg gcccatcggt cttccccctg gcgccctgct ccaggagcac ctccgagagc 420

```
acagcggccc tgggctgcct ggtcaaggac tacttccccg aaccggtgac ggtgtcgtgg      480
aactcaggcg ctctgaccag cggcgtgcac accttcccag ctgtcctaca gtcctcagga      540
ctctactccc tcagcagcgt ggtgaccgtg ccctccagca acttcggcac ccagacctac      600
acctgcaacg tagatcacaa gcccagcaac accaaggtgg acaagacagt tggtggcggg      660
ggctcccatc atcatcatca tcatcattag                                       690
```

```
<210> SEQ ID NO 74
<211> LENGTH: 229
<212> TYPE: PRT
<213> ORGANISM: Artificial Sequence
<220> FEATURE:
<223> OTHER INFORMATION: OKT3Fd monoclonal antibody sequence;

<400> SEQUENCE: 74
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Gly Gly Gly Ser His His
    210                 215                 220

His His His His His
225

```
<210> SEQ ID NO 75
<211> LENGTH: 642
<212> TYPE: DNA
<213> ORGANISM: Artificial Sequence
<220> FEATURE:
<223> OTHER INFORMATION: cDNA encoding OKT3LC monoclonal antibody
      sequence;

<400> SEQUENCE: 75
caaattgttc tcacccagtc tccagcaatc atgtctgcat ctccagggga gaaggtcacc       60
atgacctgca gtgccagctc aagtgtaagt tacatgaact ggtaccagca gaagtcaggc      120
```

```
acctccccca aaagatggat ttatgacaca tccaaactgg cttctggagt ccctgctcac      180
ttcaggggca gtgggtctgg gacctcttac tctctcacaa tcagcggcat ggaggctgaa      240
gatgctgcca cttattactg ccagcagtgg agtagtaacc cattcacgtt cggctcgggg      300
acaaagttgg aaataaaccg tacggtggct gcaccatctg tcttcatctt cccgccatct      360
gatgagcagt tgaaatctgg aactgcctct gttgtgtgcc tgctgaataa cttctatccc      420
agagaggcca agtacagtgg aaggtggat aacgccctcc aatcgggtaa ctcccaggag       480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642
```

<210> SEQ ID NO 76
<211> LENGTH: 213
<212> TYPE: PRT
<213> ORGANISM: Artificial Sequence
<220> FEATURE:
<223> OTHER INFORMATION: OKT3LC monoclonal antibody sequence

<400> SEQUENCE: 76

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 77
<211> LENGTH: 738
<212> TYPE: DNA
<213> ORGANISM: Artificial Sequence
<220> FEATURE:
<223> OTHER INFORMATION: cDNA encoding EpCAM1.1 single-chain variable
      fragment fusion protein

<400> SEQUENCE: 77

```
caggtacagc tgcagcagtc aggggggaggc ttggtccagc ctgggggatc cctgagactc      60
tcctgtgcag cctctggatt cacctttagt aattattgga tgagctgggt ccgccaggct     120
ccagggaagg ggctggagtg ggtggccaac ataaagcaag atggaagtga gaaattctat     180
gtggactctg tgaagggccg attcaccatc tccagagaca acgccaagaa ctcactgtat     240
ctgcaaatga acagcctgag agccgaagac atggctgtct attactgtgc gagagtgggg     300
ggggcgtggg agctaggcta ctggggccag ggaaccctgg tcactgtctc ggccggtggc     360
ggtggcagcg gcgtggtggg gtccggtggc ggcggatctg gcgcgcagtc tgtactgact     420
caaccgccct cagtgtctgg ggccccaggg cagagggtca ccatctcctg cactgggagc     480
agctccaaca tcgggtctta ttatggtgtg cactggtacc agcagattcc aggaacagcc     540
cccaaactcc tcatctattc tgacactaat cgaccctcag gggtccctga ccgattctct     600
ggctccaagt ctggcacctc ggcctccctg gccatcactg gctccaggc tgaggatgag     660
gctgattatt actgccagtc gtatgacagc agcctgagtg gccgggtgtt cggcggaggg     720
accaaggtca ccgtccta                                                    738
```

<210> SEQ ID NO 78
<211> LENGTH: 246
<212> TYPE: PRT
<213> ORGANISM: Artificial Sequence
<220> FEATURE:
<223> OTHER INFORMATION: EpCAM1.1 single-chain variable fragment fusion protein

<400> SEQUENCE: 78

```
Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Ile
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205
```

Ser Leu Ala Ile Thr Gly Leu Gln Ala Glu Asp Glu Ala Asp Tyr Tyr
    210                 215                 220

Cys Gln Ser Tyr Asp Ser Ser Leu Ser Gly Arg Val Phe Gly Gly Gly
225                 230                 235                 240

Thr Lys Val Thr Val Leu
            245

<210> SEQ ID NO 79
<211> LENGTH: 1485
<212> TYPE: DNA
<213> ORGANISM: Artificial Sequence
<220> FEATURE:
<223> OTHER INFORMATION: cDNA encoding EpCAM1.1 - OKT3Fd fusion
      construct

<400> SEQUENCE: 79

| | | |
|---|---|---|
| caggtacagc tgcagcagtc aggggggaggc ttggtccagc ctgggggatc cctgagactc | 60 |
| tcctgtgcag cctctggatt cacctttagt aattattgga tgagctgggt ccgccaggct | 120 |
| ccagggaagg gctggagtg gtggccaac ataaagcaag atggaagtga gaaattctat | 180 |
| gtggactctg tgaagggccg attcaccatc tccagagaca acgccaagaa ctcactgtat | 240 |
| ctgcaaatga acagcctgag agccgaagac atggctgtct attactgtgc gagagtgggg | 300 |
| ggggcgtggg agctaggcta ctggggccag ggaaccctgg tcactgtctc ggccggtggc | 360 |
| ggtggcagcg gcgtggtgg gtccggtggc ggcggatctg gcgcgcagtc tgtactgact | 420 |
| caaccgccct cagtgtctgg ggccccaggg cagagggtca ccatctcctg cactgggagc | 480 |
| agctccaaca tcgggtctta ttatggtgtg cactggtacc agcagattcc aggaacagcc | 540 |
| cccaaactcc tcatctattc tgacactaat cgaccctcag gggtccctga ccgattctct | 600 |
| ggctccaagt ctggcacctc ggcctccctg gccatcactg gctccaggc tgaggatgag | 660 |
| gctgattatt actgccagtc gtatgacagc agcctgagtg gccgggtgtt cggcggaggg | 720 |
| accaaggtca ccgtcctagg cgcgcgccag gtacagctgc agcagtcagg ggaggcttg | 780 |
| gtccagcctg ggggatccct gagactctcc tgtgcagcct ctggattcac ctttagtaat | 840 |
| tattggatga gctgggtccg ccaggctcca gggaaggggc tggagtgggt ggccaacata | 900 |
| aagcaagatg gaagtgagaa attctatgtg gactctgtga agggccgatt caccatctcc | 960 |
| agagacaacg ccaagaactc actgtatctg caaatgaaca gcctgagagc cgaagacatg | 1020 |
| gctgtctatt actgtgcgag agtggggggg gcgtgggagc taggctactg gggccaggga | 1080 |
| accctggtca ctgtctcggc cggtggcggt ggcagcggcg tggtgggtc cggtggcggc | 1140 |
| ggatctggcg cgcagtctgt actgactcaa ccgccctcag tgtctgggc cccagggcag | 1200 |
| agggtcacca tctcctgcac tgggagcagc tccaacatcg ggtcttatta tggtgtgcac | 1260 |
| tggtaccagc agattccagg aacagccccc aaactcctca tctattctga cactaatcga | 1320 |
| ccctcagggg tccctgaccg attctctggc tccaagtctg gcacctcggc ctccctggcc | 1380 |
| atcactgggc tccaggctga ggatgaggct gattattact gccagtcgta tgacagcagc | 1440 |
| ctgagtggcc gggtgttcgg cggagggacc aaggtcaccg tccta | 1485 |

<210> SEQ ID NO 80
<211> LENGTH: 478
<212> TYPE: PRT
<213> ORGANISM: Artificial Sequence
<220> FEATURE:
<223> OTHER INFORMATION: EpCAM1.1 - OKT3Fd fusion construct

<400> SEQUENCE: 80

-continued

```
Gln Val Gln Leu Gln Gln Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Phe Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Met Ala Val Tyr Tyr Cys
                 85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Ile
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Cys Gln Ser Tyr Asp Ser Ser Leu Ser Gly Arg Val Phe Gly Gly Gly
225                 230                 235                 240

Thr Lys Val Thr Val Leu Gly Arg Ala Gln Val Gln Leu Gln Gln Ser
                245                 250                 255

Gly Ala Glu Leu Ala Arg Pro Gly Ala Ser Val Lys Met Ser Cys Lys
            260                 265                 270

Ala Ser Gly Tyr Thr Phe Thr Arg Tyr Thr Met His Trp Val Lys Gln
        275                 280                 285

Arg Pro Gly Gln Gly Leu Glu Trp Ile Gly Tyr Ile Asn Pro Ser Arg
    290                 295                 300

Gly Tyr Thr Asn Tyr Asn Gln Lys Phe Lys Asp Lys Ala Thr Leu Thr
305                 310                 315                 320

Thr Asp Lys Ser Ser Ser Thr Ala Tyr Met Gln Leu Ser Ser Leu Thr
                325                 330                 335

Ser Glu Asp Ser Ala Val Tyr Tyr Cys Ala Arg Tyr Tyr Asp Asp His
            340                 345                 350

Tyr Cys Leu Asp Tyr Trp Gly Gln Gly Thr Thr Leu Thr Val Ser Ser
        355                 360                 365

Ala Ser Thr Lys Gly Pro Ser Val Phe Pro Leu Ala Pro Cys Ser Arg
    370                 375                 380

Ser Thr Ser Glu Ser Thr Ala Ala Leu Gly Cys Leu Val Lys Asp Tyr
385                 390                 395                 400

Phe Pro Glu Pro Val Thr Val Ser Trp Asn Ser Gly Ala Leu Thr Ser
                405                 410                 415
```

Gly Val His Thr Phe Pro Ala Val Leu Gln Ser Ser Gly Leu Tyr Ser
                420                 425                 430

Leu Ser Ser Val Val Thr Val Pro Ser Ser Asn Phe Gly Thr Gln Thr
            435                 440                 445

Tyr Thr Cys Asn Val Asp His Lys Pro Ser Asn Thr Lys Val Asp Lys
        450                 455                 460

Thr Val Gly Gly Gly Ser His His His His His His
465                 470                 475

<210> SEQ ID NO 81
<211> LENGTH: 1389
<212> TYPE: DNA
<213> ORGANISM: Artificial Sequence
<220> FEATURE:
<223> OTHER INFORMATION: cDNA encoding EpCAM1.1 - OKT3LC fusion
      construct

<400> SEQUENCE: 81
caggtacagc tgcagcagtc aggggaggc ttggtccagc ctgggggatc cctgagactc      60
tcctgtgcag cctctggatt cacctttagt aattattgga tgagctgggt ccgccaggct    120
ccagggaagg ggctggagtg ggtggccaac ataaagcaag atggaagtga gaaattctat    180
gtggactctg tgaagggccg attcaccatc tccagagaca cgccaagaa ctcactgtat     240 ctgcaaatga acagcctgag agccgaagac atggctgtct attactgtgc gagagtgggg    300
ggggcgtggg agctaggcta ctggggccag ggaaccctgg tcactgtctc ggccggtggc    360
ggtggcagcg gcggtggtgg gtccggtggc ggcggatctg gcgcgcagtc tgtactgact    420 caaccgcct cagtgtctgg ggccccaggg cagagggtca ccatctcctg cactgggagc    480
agctccaaca tcgggtctta ttatggtgtg cactggtacc agcagattcc aggaacagcc    540
cccaaactcc tcatctattc tgacactaat cgaccctcag gggtccctga ccgattctct    600
ggctccaagt ctggcaccct ggcctccctg gccatcactg gctccaggc tgaggatgag     660 gctgattatt actgccagtc gtatgacagc agcctgagtg gccgggtgtt cggcggaggg    720
accaaggtca ccgtcctagg cgcgcccaa attgttctca cccagtctcc agcaatcatg     780
tctgcatctc caggggagaa ggtcaccatg acctgcagtg ccagctcaag tgtaagttac    840
atgaactggt accagcagaa gtcaggcacc tcccccaaaa gatggattta tgacacatcc    900
aaactggctt ctggagtccc tgctcacttc aggggcagtg gtctgggac ctcttactct     960 ctcacaatca gcggcatgga ggctgaagat gctgccactt attactgcca gcagtggagt   1020
agtaacccat tcacgttcgg ctcggggaca aagttggaaa taaaccgtac ggtggctgca   1080
ccatctgtct tcatcttccc gccatctgat gagcagttga aatctggaac tgcctctgtt   1140
gtgtgcctgc tgaataactt ctatcccaga gaggccaaag tacagtggaa ggtggataac   1200
gccctccaat cgggtaactc ccaggagagt gtcacagagc aggacagcaa ggacagcacc   1260
tacagcctca gcagcaccct gacgctgagc aaagcagact acgagaaaca caaagtctac   1320
gcctgcgaag tcacccatca gggcctgagc tcgcccgtca caaagagctt caacaggga   1380 gagtgttag                                                           1389

<210> SEQ ID NO 82
<211> LENGTH: 462
<212> TYPE: PRT
<213> ORGANISM: Artificial Sequence
<220> FEATURE:
<223> OTHER INFORMATION: EpCAM1.1 - OKT3LC fusion construct

<400> SEQUENCE: 82

```
Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
            85                  90                  95

Ala Arg Val Gly Gly Ala Trp Glu Leu Gly Tyr Trp Gly Gln Gly Thr
        100                 105                 110

Leu Val Thr Val Ser Ala Gly Gly Gly Ser Gly Gly Gly Gly Ser
    115                 120                 125

Gly Gly Gly Gly Ser Gly Ala Gln Ser Val Leu Thr Gln Pro Pro Ser
130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Ile
            165                 170                 175

Pro Gly Thr Ala Pro Lys Leu Leu Ile Tyr Ser Asp Thr Asn Arg Pro
        180                 185                 190

Ser Gly Val Pro Asp Arg Phe Ser Gly Ser Lys Ser Gly Thr Ser Ala
    195                 200                 205

Ser Leu Ala Ile Thr Gly Leu Gln Ala Glu Asp Glu Ala Asp Tyr Tyr
210                 215                 220

Cys Gln Ser Tyr Asp Ser Ser Leu Ser Gly Arg Val Phe Gly Gly Gly
225                 230                 235                 240

Thr Lys Val Thr Val Leu Gly Arg Ala Gln Ile Val Leu Thr Gln Ser
            245                 250                 255

Pro Ala Ile Met Ser Ala Ser Pro Gly Glu Lys Val Thr Met Thr Cys
        260                 265                 270

Ser Ala Ser Ser Ser Val Ser Tyr Met Asn Trp Tyr Gln Gln Lys Ser
    275                 280                 285

Gly Thr Ser Pro Lys Arg Trp Ile Tyr Asp Thr Ser Lys Leu Ala Ser
290                 295                 300

Gly Val Pro Ala His Phe Arg Gly Ser Gly Ser Gly Thr Ser Tyr Ser
305                 310                 315                 320

Leu Thr Ile Ser Gly Met Glu Ala Glu Asp Ala Ala Thr Tyr Tyr Cys
            325                 330                 335

Gln Gln Trp Ser Ser Asn Pro Phe Thr Phe Gly Ser Gly Thr Lys Leu
        340                 345                 350

Glu Ile Asn Arg Thr Val Ala Ala Pro Ser Val Phe Ile Phe Pro Pro
    355                 360                 365

Ser Asp Glu Gln Leu Lys Ser Gly Thr Ala Ser Val Val Cys Leu Leu
370                 375                 380

Asn Asn Phe Tyr Pro Arg Glu Ala Lys Val Gln Trp Lys Val Asp Asn
385                 390                 395                 400

Ala Leu Gln Ser Gly Asn Ser Gln Glu Ser Val Thr Glu Gln Asp Ser
            405                 410                 415
```

Lys Asp Ser Thr Tyr Ser Leu Ser Ser Thr Leu Thr Leu Ser Lys Ala
                420                 425                 430

Asp Tyr Glu Lys His Lys Val Tyr Ala Cys Glu Val Thr His Gln Gly
            435                 440                 445

Leu Ser Ser Pro Val Thr Lys Ser Phe Asn Arg Gly Glu Cys
        450                 455                 460

<210> SEQ ID NO 83
<211> LENGTH: 1329
<212> TYPE: DNA
<213> ORGANISM: Artificial Sequence
<220> FEATURE:
<223> OTHER INFORMATION: cDNA encoding EpCAM1.1 - humanized 1F3.1Fd
      fusion construct

<400> SEQUENCE: 83

```
caggtacagc tgcagcagtc aggggggaggc ttggtccagc ctgggggatc cctgagactc      60
tcctgtgcag cctctggatt cacctttagt aattattgga tgagctgggt ccgccaggct     120
ccagggaagg ggctggagtg ggtggccaac ataaagcaag atggaagtga aaattctat      180
gtggactctg tgaagggccg attcaccatc tccagagaca cgccaagaa ctcactgtat      240
ctgcaaatga acagcctgag agccgaagac atggctgtct attactgtgc gagagtgggg      300
ggggcgtggg agctaggcta ctggggccag ggaaccctgg tcactgtctc ggccggtggc      360
ggtggcagcg gcggtggtgg gtccggtggc ggcggatctg gcgcgcagtc tgtactgact     420
caaccgccct cagtgtctgg ggccccaggg cagagggtca ccatctcctg cactgggagc      480
agctccaaca tcgggtctta ttatggtgtg cactggtacc agcagattcc aggaacagcc      540
cccaaactcc tcatctattc tgacactaat cgaccctcag gggtccctga ccgattctct      600
ggctccaagt cggggcgcgc cgaggtgcag ctggtggagt ctggggggagg cttggtacag      660
cctgggggggt ccctgagact ctcctgtgca gcctctggat tcacctttag cacctacgcc      720
atgaactggg tccgccaggc tccagggaag gggctggagt gggtctcacg cataagaagt      780
aaatataata attatgcaac atattatgcc gattcagtga agaccggtt caccatctcc      840
agagacgatt ccaagaacac gctgtatctg caaatgaaca gcctgagagc cgaggacacg      900
gccgtatatt actgtgcgag acatgggaac ttcggtaata gctacgtttc ctggtttgct      960
tactggggcc aagggacaat ggtcaccgtc tcttcagcta gcaccaaggg cccatcggtc     1020
ttccccctgg cgccctgctc caggagcacc tccgagagca gcggccct gggctgcctg     1080
gtcaaggact acttccccga accggtgacg gtgtcgtgga actcaggcgc tctgaccagc     1140
ggcgtgcaca ccttcccagc tgtcctacag tcctcaggac tctactccct cagcagcgtg     1200
gtgaccgtgc cctccagcaa cttcggcacc cagacctaca cctgcaacgt agatcacaag     1260
cccagcaaca ccaaggtgga caagacagtt ggtggcgggg gctcccatca tcatcatcat     1320
catcattag                                                             1329
```

<210> SEQ ID NO 84
<211> LENGTH: 484
<212> TYPE: PRT
<213> ORGANISM: Artificial Sequence
<220> FEATURE:
<223> OTHER INFORMATION: EpCAM1.1 - humanized 1F3.1Fd fusion construct

<400> SEQUENCE: 84

Gln Val Gln Leu Gln Gln Ser Gly Gly Gly Leu Val Gln Pro Gly Gly
1               5                   10                  15

```
Ser Leu Arg Leu Ser Cys Ala Ala Ser Gly Phe Thr Phe Ser Asn Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Phe Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Met Ala Val Tyr Tyr Cys
                 85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
            115                 120                 125

Gly Gly Gly Gly Ser Gly Ala Gln Ser Val Leu Thr Gln Pro Pro Ser
130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Ile
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
210                 215                 220

Cys Gln Ser Tyr Asp Ser Ser Leu Ser Gly Arg Val Phe Gly Gly Gly
225                 230                 235                 240

Thr Lys Val Thr Val Leu Gly Arg Ala Glu Val Gln Leu Val Glu Ser
            245                 250                 255

Gly Gly Gly Leu Val Gln Pro Gly Gly Ser Leu Arg Leu Ser Cys Ala
            260                 265                 270

Ala Ser Gly Phe Thr Phe Ser Thr Tyr Ala Met Asn Trp Val Arg Gln
            275                 280                 285

Ala Pro Gly Lys Gly Leu Glu Trp Val Ser Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Leu Tyr Leu Gln Met Asn Ser
                325                 330                 335

Leu Arg Ala Glu Asp Thr Ala Val Tyr Tyr Cys Ala Arg His Gly Asn
            340                 345                 350

Phe Gly Asn Ser Tyr Val Ser Trp Phe Ala Tyr Trp Gly Gln Gly Thr
        355                 360                 365

Met Val Thr Val Ser Ser Ala Ser Thr Lys Gly Pro Ser Val Phe Pro
        370                 375                 380

Leu Ala Pro Cys Ser Arg Ser Thr Ser Glu Ser Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430
```

Ser Ser Gly Leu Tyr Ser Leu Ser Val Val Thr Val Pro Ser Ser
        435                 440                 445

Asn Phe Gly Thr Gln Thr Tyr Thr Cys Asn Val Asp His Lys Pro Ser
450                 455                 460

Asn Thr Lys Val Asp Lys Thr Val Gly Gly Gly Ser His His His
465                 470                 475                 480

His His His His

<210> SEQ ID NO 85
<211> LENGTH: 1395
<212> TYPE: DNA
<213> ORGANISM: Artificial Sequence
<220> FEATURE:
<223> OTHER INFORMATION: cDNA encoding EpCAM1.1 - humanized 1F3.1LC
      fusion construct

<400> SEQUENCE: 85

```
caggtacagc tgcagcagtc aggggggaggc ttggtccagc ctgggggatc cctgagactc    60
tcctgtgcag cctctggatt caccttagt aattattgga tgagctgggt ccgccaggct    120
ccagggaagg gctggagtg gtggccaac ataaagcaag atggaagtga gaaattctat    180
gtggactctg tgaagggccg attcaccatc tccagagaca cgccaagaa ctcactgtat    240 ctgcaaatga acagcctgag agccgaagac atggctgtct attactgtgc gagagtgggg    300
ggggcgtggg agctaggcta ctggggccag ggaaccctgg tcactgtctc ggccggtggc    360
ggtggcagcg gcgtgtggtg gtccggtggc ggcggatctg gcgcgcagtc tgtactgact    420
caaccgccct cagtgtctgg ggccccaggg cagagggtca ccatctcctg cactgggagc    480
agctccaaca tcgggtctta ttatggtgtg cactggtacc agcagattcc aggaacagcc    540
cccaaactcc tcatctattc tgacactaat cgaccctcag gggtccctga ccgattctct    600
ggctccaagt ctggcaccct ggcctccctg gccatcactg gctccaggc tgaggatgag    660 gctgattatt actgccagtc gtatgacagc agcctgagtg gccgggtgtt cggcggaggg    720
accaaggtca ccgtcctagg gcgcgcccag gctgtggtga tcaggagcc ctcactgact    780 gtgtccccag gagggacagt cactctcacc tgtcgctcaa gtactggggc tgttacaact    840
agtaactatg ccaactgggt ccagcagaaa cctggacaag cacccagggg tctgattggt    900
ggtaccaaca gcgagctcc aggtaccct gcccggttct caggctccct ccttgggggc    960
aaagctgccc tgacactgtc aggtgtgcag cctgaggacg aggctgagta ttactgcgct    1020
ctatggtaca gcaacctctg ggtgttcggc ggagggacca agctgaccgt cctaggccaa    1080
ccgaaagcgg cgccctcggt cactctgttc ccgccctcct ctgaggagct tcaagccaac    1140
aaggccacac tggtgtgtct cataagtgac ttctacccgg gagccgtgac agtggcctgg    1200
aaggcagata gcagccccgt caaggcggga gtggagacca cacacccctc caaacaaagc    1260
aacaacaagt acgcggccag cagctatctg agcctgacgc ctgagcagtg gaagtcccac    1320
agaagctaca gctgccaggt cacgcatgaa gggagcaccg tggagaagac agtggcccct    1380
acagaatgtt catag                                                    1395
```

<210> SEQ ID NO 86
<211> LENGTH: 464
<212> TYPE: PRT
<213> ORGANISM: Artificial Sequence
<220> FEATURE:
<223> OTHER INFORMATION: EpCAM1.1 - humanized 1F3.1LC fusion construct

<400> SEQUENCE: 86

```
Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Ser Gly Ala Gln Ser Val Leu Thr Gln Pro Pro Ser
130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Ile
            165                 170                 175

Pro Gly Thr Ala Pro Lys Leu Leu Ile Tyr Ser Asp Thr Asn Arg Pro
        180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
210                 215                 220

Cys Gln Ser Tyr Asp Ser Ser Leu Ser Gly Arg Val Phe Gly Gly Gly
225                 230                 235                 240

Thr Lys Val Thr Val Leu Gly Arg Ala Gln Ala Val Thr Gln Glu
            245                 250                 255

Pro Ser Leu Thr Val Ser Pro Gly Gly Thr Val Thr Leu Thr Cys Arg
        260                 265                 270

Ser Ser Thr Gly Ala Val Thr Thr Ser Asn Tyr Ala Asn Trp Val Gln
        275                 280                 285

Gln Lys Pro Gly Gln Ala Pro Arg Gly Leu Ile Gly Gly Thr Asn Lys
    290                 295                 300

Arg Ala Pro Gly Thr Pro Ala Arg Phe Ser Gly Ser Leu Leu Gly Gly
305                 310                 315                 320

Lys Ala Ala Leu Thr Leu Ser Gly Val Gln Pro Glu Asp Glu Ala Glu
            325                 330                 335

Tyr Tyr Cys Ala Leu Trp Tyr Ser Asn Leu Trp Val Phe Gly Gly Gly
            340                 345                 350

Thr Lys Leu Thr Val Leu Gly Gln Pro Lys Ala Ala Pro Ser Val Thr
        355                 360                 365

Leu Phe Pro Pro Ser Ser Glu Glu Leu Gln Ala Asn Lys Ala Thr Leu
370                 375                 380

Val Cys Leu Ile Ser Asp Phe Tyr Pro Gly Ala Val Thr Val Ala Trp
385                 390                 395                 400

Lys Ala Asp Ser Ser Pro Val Lys Ala Gly Val Glu Thr Thr Pro
            405                 410                 415
```

Ser Lys Gln Ser Asn Asn Lys Tyr Ala Ala Ser Ser Tyr Leu Ser Leu
            420                 425                 430

Thr Pro Glu Gln Trp Lys Ser His Arg Ser Tyr Ser Cys Gln Val Thr
            435                 440                 445

His Glu Gly Ser Thr Val Glu Lys Thr Val Ala Pro Thr Glu Cys Ser
            450                 455                 460

<210> SEQ ID NO 87
<211> LENGTH: 738
<212> TYPE: DNA
<213> ORGANISM: Artificial Sequence
<220> FEATURE:
<223> OTHER INFORMATION: cDNA encoding EpCAM1.2 single-chain variable
      fragment fusion protein

<400> SEQUENCE: 87
gaggtgcagc tggtggagtc agggggaggc ttggtccagc ctggggggatc cctgagactc      60 tcctgtgcag cctctggatt cacctttagt aattattgga tgagctgggt ccgccaggct     120
ccagggaagg ggctggagtg ggtggccaac ataaagcaag atggaagtga aaattctat      180 gtggactctg tgaagggccg attcaccatc tccagagaca acgccaagaa ctcactgtat     240
ctgcaaatga acagcctgag agccgaagac atggctgtct attactgtgc gagagtgggg     300
ggggcgtggg agctaggcta ctggggccag ggaaccctgg tcactgtctc ggccggtggc     360
ggtggcagcg gcggtggtgg gtccggtggc ggcggatctg gcgcgcagtc tgtactgact     420
caaccgccct cagtgtctgg ggccccaggg cagagggtca ccatctcctg cactgggagc     480
agctccaaca tcgggtctta ttatggtgtg cactggtacc agcagcttcc aggaacagcc     540
cccaaactcc tcatctattc tgacactaat cgaccctcag ggtccctga ccgattctct     600 ggctccaagt ctggcacctc ggcctccctg gccatcactg gctccaggc tgaggatgag     660 gctgattatt actgccagtc gtatgacagc agcctgagtg gccgggtgtt cggcggaggg     720
accaagctga ccgtccta                                                    738

<210> SEQ ID NO 88
<211> LENGTH: 246
<212> TYPE: PRT
<213> ORGANISM: Artificial Sequence
<220> FEATURE:
<223> OTHER INFORMATION: EpCAM1.2 single-chain variable fragment fusion
      protein

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Gly Ser Gly Gly Gly Gly Ser

```
            115                 120                 125
Gly Gly Gly Gly Ser Gly Ala Gln Ser Val Leu Thr Gln Pro Pro Ser
            130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
            195                 200                 205

Ser Leu Ala Ile Thr Gly Leu Gln Ala Glu Asp Glu Ala Asp Tyr Tyr
    210                 215                 220

Cys Gln Ser Tyr Asp Ser Ser Leu Ser Gly Arg Val Phe Gly Gly Gly
225                 230                 235                 240

Thr Lys Leu Thr Val Leu
            245

<210> SEQ ID NO 89
<211> LENGTH: 1455
<212> TYPE: DNA
<213> ORGANISM: Artificial Sequence
<220> FEATURE:
<223> OTHER INFORMATION: cDNA encoding EpCAM1.2 - humanized 1F3.1Fd
      fusion construct

<400> SEQUENCE: 89
gaggtgcagc tggtggagtc aggggggaggc ttggtccagc ctgggggatc cctgagactc      60
tcctgtgcag cctctggatt caccttttagt aattattgga tgagctgggt ccgccaggct     120
ccagggaagg ggctggagtg ggtggccaac ataaagcaag atggaagtga aaattctat      180 gtggactctg tgaagggccg attcaccatc tccagagaca acgccaagaa ctcactgtat     240
ctgcaaatga acagcctgag agccgaagac atggctgtct attactgtgc gagagtgggg     300 gggggcgtggg agctaggcta ctggggccag ggaaccctgg tcactgtctc ggccggtggc     360
ggtggcagcg gcggtggtgg gtccggtggc ggcggatctg gcgcgcagtc tgtactgact     420
caaccgccct cagtgtctgg ggccccaggg cagagggtca ccatctcctg cactgggagc     480
agctccaaca tcgggtctta ttatggtgtg cactggtacc agcagcttcc aggaacagcc     540
cccaaactcc tcatctattc tgacactaat cgaccctcag gggtccctga ccgattctct     600
ggctccaagt ctggcaccctc ggcctccctg gccatcactg gctccaggc tgaggatgag     660 gctgattatt actgccagtc gtatgacagc agcctgagtg gccgggtgtt cggcggaggg     720
accaagctga ccgtcctagg cgcgccgag gtgcagctgg tggagtctgg gggaggcttg     780
gtacagcctg gggggtccct gagactctcc tgtgcagcct ctggattcac ctttagcacc     840
tacgccatga ctgggtccg ccaggctcca ggaaggggc tggagtgggt ctcacgcata     900
agaagtaaat ataataatta tgcaacatat tatgccgatt cagtgaaaga ccggttcacc     960
atctccagag acgattccaa gaacacgctg tatctgcaaa tgaacagcct gagagccgag    1020
gacacggccg tatattactg tgcgagacat gggaacttcg gtaatagcta cgtttcctgg    1080
tttgcttact ggggccaagg gacaatggtc accgtctctt cagctagcac caagggccca    1140
tcggtcttcc ccctggcgcc ctgctccagg agcacctccg agagcacagc ggccctgggc    1200
tgcctggtca aggactactt ccccgaaccg gtgacggtgt cgtggaactc aggcgctctg    1260
```

-continued

```
accagcggcg tgcacacctt cccagctgtc ctacagtcct caggactcta ctccctcagc    1320
agcgtggtga ccgtgccctc agcaacttc ggcacccaga cctacacctg caacgtagat     1380
cacaagccca gcaacaccaa ggtggacaag acagttggtg gcgggggctc ccatcatcat    1440
catcatcatc attag                                                      1455

<210> SEQ ID NO 90
<211> LENGTH: 484
<212> TYPE: PRT
<213> ORGANISM: Artificial Sequence
<220> FEATURE:
<223> OTHER INFORMATION: EpCAM1.2 - humanized 1F3.1Fd fusion construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Cys Gln Ser Tyr Asp Ser Ser Leu Ser Gly Arg Val Phe Gly Gly Gly
225                 230                 235                 240

Thr Lys Met Thr Val Leu Gly Arg Ala Glu Val Gln Leu Val Glu Ser
                245                 250                 255

Gly Gly Gly Leu Val Gln Pro Gly Gly Ser Leu Arg Leu Ser Cys Ala
            260                 265                 270

Ala Ser Gly Phe Thr Phe Ser Thr Tyr Ala Met Asn Trp Val Arg Gln
        275                 280                 285

Ala Pro Gly Lys Gly Leu Glu Trp Val Ser Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Leu Tyr Leu Gln Met Asn Ser
```

```
                    325                 330                 335
Leu Arg Ala Glu Asp Thr Ala Val Tyr Tyr Cys Ala Arg His Gly Asn
                340                 345                 350

Phe Gly Asn Ser Tyr Val Ser Trp Phe Ala Tyr Trp Gly Gln Gly Thr
            355                 360                 365

Met Val Thr Val Ser Ser Ala Ser Thr Lys Gly Pro Ser Val Phe Pro
        370                 375                 380

Leu Ala Pro Cys Ser Arg Ser Thr Ser Glu Ser Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Asn Phe Gly Thr Gln Thr Tyr Thr Cys Asn Val Asp His Lys Pro Ser
450                 455                 460

Asn Thr Lys Val Asp Lys Thr Val Gly Gly Gly Ser His His His
465                 470                 475                 480

His His His His
```

<210> SEQ ID NO 91
<211> LENGTH: 1395
<212> TYPE: DNA
<213> ORGANISM: Artificial Sequence
<220> FEATURE:
<223> OTHER INFORMATION: cDNA encoding EpCAM1.2 - humanized 1F3.1LC
      fusion construct

<400> SEQUENCE: 91

```
gaggtgcagc tggtggagtc agggggaggc ttggtccagc ctgggggatc cctgagactc     60
tcctgtgcag cctctggatt caccttagt aattattgga tgagctgggt ccgccaggct    120
ccagggaagg ggctggagtg ggtggccaac ataaagcaag atggaagtga aaattctat    180
gtggactctg tgaagggccg attcaccatc tccagagaca cgccaagaa ctcactgtat    240
ctgcaaatga acagcctgag agccgaagac atggctgtct attactgtgc gagagtgggg    300
ggggcgtggg agctaggcta ctggggccag gaaccctgg tcactgtctc ggccggtggc    360
ggtggcagcg gcggtggtgg gtccggtggc ggcggatctg gcgcgcagtc tgtactgact    420
caaccgccct cagtgtctgg ggccccaggg cagagggtca ccatctcctg cactgggagc    480
agctccaaca tcgggtctta ttatggtgtg cactggtacc agcagcttcc aggaacagcc    540
cccaaactcc tcatctattc tgacactaat cgaccctcag ggtccctga ccgattctct    600
ggctccaagt ctggcaccct ggcctccctg gccatcactg gctccaggc tgaggatgag    660
gctgattatt actgccagtc gtatgacagc agcctgagtg ccgggtgtt cggcggaggg    720
accaagctga ccgtcctagg gcgcgcccag gctgtggtga tcaggagcc ctcactgact    780
gtgtccccag gagggacagt cactctcacc tgtcgctcaa gtactggggc tgttacaact    840
agtaactatg ccaactgggt ccagcagaaa cctggacaag cacccagggg tctgattggt    900
ggtaccaaca gcgagctcc aggtacccct gcccggttct caggctccct ccttggggc    960
aaagctgccc tgacactgtc aggtgtgcag cctgaggacg aggctgagta ttactgcgct   1020
ctatggtaca gcaacctctg ggtgttcggc ggagggacca gctgaccgt cctaggccaa   1080
ccgaaagcgg cgccctcggt cactctgttc ccgccctcct ctgaggagct tcaagccaac   1140
```

-continued

```
aaggccacac tggtgtgtct cataagtgac ttctacccgg gagccgtgac agtggcctgg    1200
aaggcagata gcagcccgt caaggcggga gtggagacca ccacaccctc caaacaaagc     1260
aacaacaagt acgcggccag cagctatctg agcctgacgc ctgagcagtg gaagtcccac    1320
agaagctaca gctgccaggt cacgcatgaa gggagcaccg tggagaagac agtggcccct    1380
acagaatgtt catag                                                     1395
```

<210> SEQ ID NO 92
<211> LENGTH: 464
<212> TYPE: PRT
<213> ORGANISM: Artificial Sequence
<220> FEATURE:
<223> OTHER INFORMATION: EpCAM1.2 - humanized 1F3.1LC fusion construct

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Cys Gln Ser Tyr Asp Ser Ser Leu Ser Gly Arg Val Phe Gly Gly Gly
225                 230                 235                 240

Thr Lys Leu Thr Val Leu Gly Arg Ala Gln Ala Val Thr Gln Glu
                245                 250                 255

Pro Ser Leu Thr Val Ser Pro Gly Gly Thr Val Thr Leu Thr Cys Arg
            260                 265                 270

Ser Ser Thr Gly Ala Val Thr Thr Ser Asn Tyr Ala Asn Trp Val Gln
        275                 280                 285

Gln Lys Pro Gly Gln Ala Pro Arg Gly Leu Ile Gly Gly Thr Asn Lys
    290                 295                 300

Arg Ala Pro Gly Thr Pro Ala Arg Phe Ser Gly Ser Leu Leu Gly Gly
```

```
                305                 310                 315                 320
Lys Ala Ala Leu Thr Leu Ser Gly Val Gln Pro Glu Asp Glu Ala Glu
                    325                 330                 335

Tyr Tyr Cys Ala Leu Trp Tyr Ser Asn Leu Trp Val Phe Gly Gly Gly
                340                 345                 350

Thr Lys Leu Thr Val Leu Gly Gln Pro Lys Ala Ala Pro Ser Val Thr
            355                 360                 365

Leu Phe Pro Pro Ser Ser Glu Glu Leu Gln Ala Asn Lys Ala Thr Leu
        370                 375                 380

Val Cys Leu Ile Ser Asp Phe Tyr Pro Gly Ala Val Thr Val Ala Trp
385                 390                 395                 400

Lys Ala Asp Ser Ser Pro Val Lys Ala Gly Val Glu Thr Thr Thr Pro
                405                 410                 415

Ser Lys Gln Ser Asn Asn Lys Tyr Ala Ala Ser Ser Tyr Leu Ser Leu
                420                 425                 430

Thr Pro Glu Gln Trp Lys Ser His Arg Ser Tyr Ser Cys Gln Val Thr
            435                 440                 445

His Glu Gly Ser Thr Val Glu Lys Thr Val Ala Pro Thr Glu Cys Ser
        450                 455                 460
```

<210> SEQ ID NO 93
<211> LENGTH: 723
<212> TYPE: DNA
<213> ORGANISM: Artificial Sequence
<220> FEATURE:
<223> OTHER INFORMATION: cDNA encoding EpCAM2.2 single-chain variable
      fragment fusion protein

<400> SEQUENCE: 93

```
caggtccagc tgcaggaaag cgggccagga ctggtgaagc ctagcgagac actgacactg      60
acttgtagcg tgagcggggg aagcattagc ggctactatt ggtcctggat cagacagccc     120
cctggcatgg ggctggagtg gattgggagc gtgcaccatt caggaagcac ctcctacaac     180
ccatccctga gagccgggt gactatcagt gtcgacacct caaagaacca gttctctctg     240
aaactgaata gtgtgacagc cgctgacact gctgtctact attgcgcacg gtacagaggc     300
agcggcctgg attattgggg cagggaaccc ctggtgacag tcagctccgg cggaggaggc     360
agcggaggag gagggtccgg aggcggggga tctcagagtg tgctgacaca gccaccatca     420
gtcagcgcag cccctggcca gaaagtgact atctcctgtt ctggcgactc tagtaacatt     480
gggaaaaatt acgtctcttg gtatcagcag ctgcctggaa cagccccaaa gctgctgatc     540
tatgagaaca atgaaaggcc ctctggcgtg cctgatcgct ttagtggatc aaaaagcggc     600
actagcgcca ccctgggcat taccgggctc cagacaggcg acgaagccga ttactattgc     660
gctgcttggg ataccagtct gagtgctcgg gtcttcgggg ggggaacaaa ggtcaccgtg     720
ctg                                                                    723
```

<210> SEQ ID NO 94
<211> LENGTH: 241
<212> TYPE: PRT
<213> ORGANISM: Artificial Sequence
<220> FEATURE:
<223> OTHER INFORMATION: EpCAM2.2 single-chain variable fragment fusion
      protein

<400> SEQUENCE: 94

```
Gln Val Gln Leu Gln Glu Ser Gly Pro Gly Leu Val Lys Pro Ser Glu
1               5                   10                  15
```

```
Thr Leu Thr Leu Thr Cys Ser Val Ser Gly Gly Ser Ile Ser Gly Tyr
         20                  25                  30

Tyr Trp Ser Trp Ile Arg Gln Pro Pro Gly Met Gly Leu Glu Trp Ile
 35                  40                  45

Gly Ser Val His His Ser Gly Ser Thr Ser Tyr Asn Pro Ser Leu Lys
 50                  55                  60

Ser Arg Val Thr Ile Ser Val Asp Thr Ser Lys Asn Gln Phe Ser Leu
65                   70                  75                  80

Lys Leu Asn Ser Val Thr Ala Ala Asp Thr Ala Val Tyr Tyr Cys Ala
                 85                  90                  95

Arg Tyr Arg Gly Ser Gly Leu Asp Tyr Trp Gly Gln Gly Thr Leu Val
             100                 105                 110

Thr Val Ser Ser Gly Gly Gly Ser Gly Gly Gly Ser Gly Gly
         115                 120                 125

Gly Gly Ser Gln Ser Val Leu Thr Gln Pro Pro Ser Val Ser Ala Ala
         130                 135                 140

Pro Gly Gln Lys Val Thr Ile Ser Cys Ser Gly Asp Ser Ser Asn Ile
145                 150                 155                 160

Gly Lys Asn Tyr Val Ser Trp Tyr Gln Gln Leu Pro Gly Thr Ala Pro
                165                 170                 175

Lys Leu Leu Ile Tyr Glu Asn Asn Glu Arg Pro Ser Gly Val Pro Asp
            180                 185                 190

Arg Phe Ser Gly Ser Lys Ser Gly Thr Ser Ala Thr Leu Gly Ile Thr
        195                 200                 205

Gly Leu Gln Thr Gly Asp Glu Ala Asp Tyr Tyr Cys Ala Ala Trp Asp
    210                 215                 220

Thr Ser Leu Ser Ala Arg Val Phe Gly Gly Gly Thr Lys Val Thr Val
225                 230                 235                 240

Leu

<210> SEQ ID NO 95
<211> LENGTH: 1440
<212> TYPE: DNA
<213> ORGANISM: Artificial Sequence
<220> FEATURE:
<223> OTHER INFORMATION: cDNA encoding EpCAM2.2 - humanized 1F3.1Fd
      fusion construct

<400> SEQUENCE: 95
caggtccagc tgcaggaaag cgggccagga ctggtgaagc ctagcgagac actgacactg      60
acttgtagcg tgagcggggg aagcattagc ggctactatt ggtcctggat cagacagccc     120
cctggcatgg gcctggagtg gattgggagc gtgcaccatt caggaagcac ctcctacaac     180
ccatccctga gagccgggt gactatcagt gtcgacacct caaagaacca gttctctctg     240
aaactgaata gtgtgacagc cgctgacact gctgtctact attgcgcacg gtacagaggc     300
agcggcctgg attattgggg gcagggaacc ctggtgacag tcagctccgg cggaggaggc     360
agcggaggag gagggtccgg aggcggggga tctcagagtg tgctgacaca gccaccatca     420
gtcagcgcag cccctggcca gaaagtgact atctcctgtt ctggcgactc tagtaacatt     480
gggaaaaatt acgtctcttg gtatcagcag ctgcctggaa cagccccaaa gctgctgatc     540
tatgagaaca atgaaaggcc ctctggcgtg cctgatcgct ttagtggatc aaaaagcggc     600
actagcgcca ccctgggcat taccggctg cagacaggcg acgaagccga ttactattgc     660
gctgcttggg ataccagtct gagtgctcgg gtcttcgggg ggaacaaa ggtcaccgtg     720
```

```
ctggggcgcg ccgaggtgca gctggtggag tctgggggag gcttggtaca gcctgggggg    780
tccctgagac tctcctgtgc agcctctgga ttcaccttta gcacctacgc catgaactgg    840
gtccgccagg ctccagggaa ggggctggag tgggtctcac gcataagaag taaatataat    900
aattatgcaa catattatgc cgattcagtg aaagaccggt tcaccatctc cagagacgat    960
tccaagaaca cgctgtatct gcaaatgaac agcctgagag ccgaggacac ggccgtatat   1020
tactgtgcga gacatgggaa cttcggtaat agctacgttt cctggtttgc ttactggggc   1080
caagggacaa tggtcaccgt ctcttcagct agcaccaagg gcccatcggt cttccccctg   1140
gcgccctgct ccaggagcac ctccgagagc acagcggccc tgggctgcct ggtcaaggac   1200
tacttccccg aaccggtgac ggtgtcgtgg aactcaggcg ctctgaccag cggcgtgcac   1260
accttcccag ctgtcctaca gtcctcagga ctctactccc tcagcagcgt ggtgaccgtg   1320
ccctccagca acttcggcac ccagacctac acctgcaacg tagatcacaa gcccagcaac   1380
accaaggtgg acaagacagt tggtggcggg ggctcccatc atcatcatca tcatcattag   1440
```

<210> SEQ ID NO 96
<211> LENGTH: 479
<212> TYPE: PRT
<213> ORGANISM: Artificial Sequence
<220> FEATURE:
<223> OTHER INFORMATION: EpCAM2.2 - humanized 1F3.1Fd fusion construct

<400> SEQUENCE: 96

```
Gln Val Gln Leu Gln Glu Ser Gly Pro Gly Leu Val Lys Pro Ser Glu
1               5                   10                  15

Thr Leu Thr Leu Thr Cys Ser Val Ser Gly Gly Ser Ile Ser Gly Tyr
            20                  25                  30

Tyr Trp Ser Trp Ile Arg Gln Pro Pro Gly Met Gly Leu Glu Trp Ile
        35                  40                  45

Gly Ser Val His His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Tyr Arg Gly Ser Gly Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Val Ser Ala Ala
    130                 135                 140

Pro Gly Gln Lys Val Thr Ile Ser Cys Ser Gly Asp Ser Ser Asn Ile
145                 150                 155                 160

Gly Lys Asn Tyr Val Ser Trp Tyr Gln Gln Leu Pro Gly Thr Ala Pro
                165                 170                 175

Lys Leu Leu Ile Tyr Glu Asn Asn Glu Arg Pro Ser Gly Val Pro Asp
            180                 185                 190

Arg Phe Ser Gly Ser Lys Ser Gly Thr Ser Ala Thr Leu Gly Ile Thr
        195                 200                 205

Gly Leu Gln Thr Gly Asp Glu Ala Asp Tyr Tyr Cys Ala Ala Trp Asp
    210                 215                 220

Thr Ser Leu Ser Ala Arg Val Phe Gly Gly Gly Thr Lys Val Thr Val
225                 230                 235                 240
```

Leu Gly Arg Ala Glu Val Gln Leu Val Glu Ser Gly Gly Leu Val
            245                 250                 255

Gln Pro Gly Gly Ser Leu Arg Leu Ser Cys Ala Ala Ser Gly Phe Thr
        260                 265                 270

Phe Ser Thr Tyr Ala Met Asn Trp Val Arg Gln Ala Pro Gly Lys Gly
        275                 280                 285

Leu Glu Trp Val Ser Arg Ile Arg Ser Lys Tyr Asn Asn Tyr Ala Thr
        290                 295                 300

Tyr Tyr Ala Asp Ser Val Lys Asp Arg Phe Thr Ile Ser Arg Asp Asp
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg His Gly Asn Phe Gly Asn Ser Tyr
                340                 345                 350

Val Ser Trp Phe Ala Tyr Trp Gly Gln Gly Thr Met Val Thr Val Ser
            355                 360                 365

Ser Ala Ser Thr Lys Gly Pro Ser Val Phe Pro Leu Ala Pro Cys Ser
        370                 375                 380

Arg Ser Thr Ser Glu Ser Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Asn Phe Gly Thr Gln
        435                 440                 445

Thr Tyr Thr Cys Asn Val Asp His Lys Pro Ser Asn Thr Lys Val Asp
        450                 455                 460

Lys Thr Val Gly Gly Gly Gly Ser His His His His His His
465                 470                 475

<210> SEQ ID NO 97
<211> LENGTH: 1380
<212> TYPE: DNA
<213> ORGANISM: Artificial Sequence
<220> FEATURE:
<223> OTHER INFORMATION: cDNA encoding EpCAM2.2 - humanized 1F3.1LC
      fusion construct

<400> SEQUENCE: 97
caggtccagc tgcaggaaag cgggccagga ctggtgaagc ctagcgagac actgacactg      60
acttgtagcg tgagcggggg aagcattagc ggctactatt ggtcctggat cagacagccc     120
cctggcatgg ggctggagtg gattgggagc gtgaccatt caggaagcac ctcctacaac     180
ccatccctga gagccgggt gactatcagt gtcgacacct caaagaacca gttctctctg     240
aaactgaata gtgtgacagc cgctgacact gctgtctact attgcgcacg gtacagaggc     300
agcggcctgg attattgggg gcagggaacc ctggtgacag tcagctccgg cggaggaggc     360
agcggaggag gagggtccgg aggcggggga tctcagagtg tgctgacaca gccaccatca     420
gtcagcgcag cccctggcca gaaagtgact atctcctgtt ctggcgactc tagtaacatt     480
gggaaaaatt acgtctcttg gtatcagcag ctgcctggaa cagccccaaa gctgctgatc     540
tatgagaaca atgaaaggcc ctctggcgtg cctgatcgct ttagtggatc aaaaagcggc     600
actagcgcca ccctgggcat taccgggctg cagacaggcg acgaagccga ttactattgc     660

-continued

```
gctgcttggg ataccagtct gagtgctcgg gtcttcgggg ggggaacaaa ggtcaccgtg    720
ctggggcgcg cccaggctgt ggtgactcag gagccctcac tgactgtgtc cccaggaggg    780
acagtcactc tcacctgtcg ctcaagtact ggggctgtta caactagtaa ctatgccaac    840
tgggtccagc agaaacctgg acaagcaccc aggggtctga ttggtggtac caacaagcga    900
gctccaggta cccctgcccg gttctcaggc tccctccttg ggggcaaagc tgccctgaca    960
ctgtcaggtg tgcagcctga ggacgaggct gagtattact gcgctctatg gtacagcaac   1020
ctctgggtgt tcggcggagg gaccaagctg accgtcctag gccaaccgaa agcggcgccc   1080
tcggtcactc tgttcccgcc ctcctctgag gagcttcaag ccaacaaggc cacactggtg   1140
tgtctcataa gtgacttcta cccgggagcc gtgacagtgg cctggaaggc agatagcagc   1200
cccgtcaagg cgggagtgga gaccaccaca ccctccaaac aaagcaacaa caagtacgcg   1260
gccagcagct atctgagcct gacgcctgag cagtggaagt cccacagaag ctacagctgc   1320
caggtcacgc atgaagggag caccgtggag aagacagtgg ccctacagaa atgttcatag   1380
```

<210> SEQ ID NO 98
<211> LENGTH: 459
<212> TYPE: PRT
<213> ORGANISM: Artificial Sequence
<220> FEATURE:
<223> OTHER INFORMATION: EpCAM2.2 - humanized 1F3.1LC fusion construct

<400> SEQUENCE: 98

```
Gln Val Gln Leu Gln Glu Ser Gly Pro Gly Leu Val Lys Pro Ser Glu
1               5                  10                  15

Thr Leu Thr Leu Thr Cys Ser Val Ser Gly Gly Ser Ile Ser Gly Tyr
            20                  25                  30

Tyr Trp Ser Trp Ile Arg Gln Pro Pro Gly Met Gly Leu Glu Trp Ile
        35                  40                  45

Gly Ser Val His His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Tyr Arg Gly Ser Gly Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Val Ser Ala Ala
    130                 135                 140

Pro Gly Gln Lys Val Thr Ile Ser Cys Ser Gly Asp Ser Ser Asn Ile
145                 150                 155                 160

Gly Lys Asn Tyr Val Ser Trp Tyr Gln Gln Leu Pro Gly Thr Ala Pro
                165                 170                 175

Lys Leu Leu Ile Tyr Glu Asn Asn Glu Arg Pro Ser Gly Val Pro Asp
            180                 185                 190

Arg Phe Ser Gly Ser Lys Ser Gly Thr Ser Ala Thr Leu Gly Ile Thr
        195                 200                 205

Gly Leu Gln Thr Gly Asp Glu Ala Asp Tyr Tyr Cys Ala Ala Trp Asp
    210                 215                 220

Thr Ser Leu Ser Ala Arg Val Phe Gly Gly Gly Thr Lys Val Thr Val
225                 230                 235                 240
```

```
Leu Gly Arg Ala Gln Ala Val Val Thr Gln Glu Pro Ser Leu Thr Val
                245                 250                 255

Ser Pro Gly Gly Thr Val Thr Leu Thr Cys Arg Ser Ser Thr Gly Ala
            260                 265                 270

Val Thr Thr Ser Asn Tyr Ala Asn Trp Val Gln Gln Lys Pro Gly Gln
        275                 280                 285

Ala Pro Arg Gly Leu Ile Gly Gly Thr Asn Lys Arg Ala Pro Gly Thr
    290                 295                 300

Pro Ala Arg Phe Ser Gly Ser Leu Leu Gly Gly Lys Ala Ala Leu Thr
305                 310                 315                 320

Leu Ser Gly Val Gln Pro Glu Asp Glu Ala Glu Tyr Tyr Cys Ala Leu
                325                 330                 335

Trp Tyr Ser Asn Leu Trp Val Phe Gly Gly Gly Thr Lys Leu Thr Val
            340                 345                 350

Leu Gly Gln Pro Lys Ala Ala Pro Ser Val Thr Leu Phe Pro Pro Ser
        355                 360                 365

Ser Glu Glu Leu Gln Ala Asn Lys Ala Thr Leu Val Cys Leu Ile Ser
    370                 375                 380

Asp Phe Tyr Pro Gly Ala Val Thr Val Ala Trp Lys Ala Asp Ser Ser
385                 390                 395                 400

Pro Val Lys Ala Gly Val Glu Thr Thr Thr Pro Ser Lys Gln Ser Asn
                405                 410                 415

Asn Lys Tyr Ala Ala Ser Ser Tyr Leu Ser Leu Thr Pro Glu Gln Trp
            420                 425                 430

Lys Ser His Arg Ser Tyr Ser Cys Gln Val Thr His Glu Gly Ser Thr
        435                 440                 445

Val Glu Lys Thr Val Ala Pro Thr Glu Cys Ser
    450                 455

<210> SEQ ID NO 99
<211> LENGTH: 1431
<212> TYPE: DNA
<213> ORGANISM: Artificial Sequence
<220> FEATURE:
<223> OTHER INFORMATION: cDNA encoding EpCAM2.2 - delta humanized 1F3.
      1Fd fusion construct

<400> SEQUENCE: 99
caggtccagc tgcaggaaag cgggccagga ctggtgaagc ctagcgagac actgacactg      60
acttgtagcg tgagcggggg aagcattagc ggctactatt ggtcctggat cagacagccc     120
cctggcatgg ggctggagtg gattgggagc gtgaccatt caggaagcac ctcctacaac     180
ccatccctga gagccgggt gactatcagt gtcgacacct caaagaacca gttctctctg     240
aaactgaata gtgtgacagc cgctgacact gctgtctact attgcgcacg gtacagaggc     300
agcggcctgg attattgggg cagggaacc ctggtgacag tcagctccgg cggaggaggc     360
agcggaggag gagggtccgg aggcggggga tctcagagtg tgctgacaca gccaccatca     420
gtcagcgcag cccctggcca gaaagtgact atctcctgtt ctggcgactc tagtaacatt     480
gggaaaaatt acgtctcttg gtatcagcag ctgcctggaa cagccccaaa gctgctgatc     540
tatgagaaca atgaaaggcc ctctggcgtg cctgatcgct ttagtggatc aaaaagcggc     600
actagcgcca ccctgggcat taccgggctg cagacaggcg acgaagccga ttactattgc     660
gctgcttggg ataccagtct gagtgctcgg gtcttcgggg ggggaacaaa ggtcaccgtg     720
ctggaggtgc agctggtgga gtctggggga ggcttggtac agcctggggg gtccctgaga     780
```

```
ctctcctgtg cagcctctgg attcaccttt agcacctacg ccatgaactg ggtccgccag    840
gctccaggga aggggctgga gtgggtctca cgcataagaa gtaaatataa taattatgca    900
acatattatg ccgattcagt gaaagaccgg ttcaccatct ccagagacga ttccaagaac    960
acgctgtatc tgcaaatgaa cagcctgaga gccgaggaca cggccgtata ttactgtgcg   1020
agacatggga acttcggtaa tagctacgtt tcctggtttg cttactgggg ccaagggaca   1080
atggtcaccg tctcttcagc tagcaccaag ggcccatcgg tcttcccect ggcgccctgc   1140 tccaggagca cctccgagag cacagcggcc ctgggctgcc tggtcaagga ctacttcccc   1200
gaaccggtga cggtgtcgtg gaactcaggc gctctgacca gcggcgtgca caccttccca   1260
gctgtcctac agtcctcagg actctactcc ctcagcagcg tggtgaccgt gccctccagc   1320
aacttcggca cccagaccta cacctgcaac gtagatcaca agcccagcaa caccaaggtg   1380
gacaagacag ttggtggcgg gggctcccat catcatcatc atcatcatta g             1431
```

<210> SEQ ID NO 100
<211> LENGTH: 476
<212> TYPE: PRT
<213> ORGANISM: Artificial Sequence
<220> FEATURE:
<223> OTHER INFORMATION: EpCAM2.2 - delta humanized 1F3.1Fd fusion
      construct

<400> SEQUENCE: 100

```
Gln Val Gln Leu Gln Glu Ser Gly Pro Gly Leu Val Lys Pro Ser Glu
1               5                   10                  15

Thr Leu Thr Leu Thr Cys Ser Val Ser Gly Gly Ser Ile Ser Gly Tyr
            20                  25                  30

Tyr Trp Ser Trp Ile Arg Gln Pro Pro Gly Met Gly Leu Glu Trp Ile
        35                  40                  45

Gly Ser Val His His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Tyr Arg Gly Ser Gly Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Val Ser Ala Ala
    130                 135                 140

Pro Gly Gln Lys Val Thr Ile Ser Cys Ser Gly Asp Ser Ser Asn Ile
145                 150                 155                 160

Gly Lys Asn Tyr Val Ser Trp Tyr Gln Gln Leu Pro Gly Thr Ala Pro
                165                 170                 175

Lys Leu Leu Ile Tyr Glu Asn Asn Glu Arg Pro Ser Gly Val Pro Asp
            180                 185                 190

Arg Phe Ser Gly Ser Lys Ser Gly Thr Ser Ala Thr Leu Gly Ile Thr
        195                 200                 205

Gly Leu Gln Thr Gly Asp Glu Ala Asp Tyr Tyr Cys Ala Ala Trp Asp
    210                 215                 220

Thr Ser Leu Ser Ala Arg Val Phe Gly Gly Gly Thr Lys Val Thr Val
225                 230                 235                 240

Leu Glu Val Gln Leu Val Glu Ser Gly Gly Gly Leu Val Gln Pro Gly
```

```
            245                 250                 255
Gly Ser Leu Arg Leu Ser Cys Ala Ala Ser Gly Phe Thr Phe Ser Thr
            260                 265                 270

Tyr Ala Met Asn Trp Val Arg Gln Ala Pro Gly Lys Gly Leu Glu Trp
        275                 280                 285

Val Ser Arg Ile Arg Ser Lys Tyr Asn Asn Tyr Ala Thr Tyr Tyr Ala
    290                 295                 300

Asp Ser Val Lys Asp Arg Phe Thr Ile Ser Arg Asp Asp Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Ala Arg His Gly Asn Phe Gly Asn Ser Tyr Val Ser Trp
            340                 345                 350

Phe Ala Tyr Trp Gly Gln Gly Thr Met Val Thr Val Ser Ser Ala Ser
        355                 360                 365

Thr Lys Gly Pro Ser Val Phe Pro Leu Ala Pro Cys Ser Arg Ser Thr
370                 375                 380

Ser Glu Ser Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
            420                 425                 430

Ser Val Val Thr Val Pro Ser Ser Asn Phe Gly Thr Gln Thr Tyr Thr
        435                 440                 445

Cys Asn Val Asp His Lys Pro Ser Asn Thr Lys Val Asp Lys Thr Val
    450                 455                 460

Gly Gly Gly Gly Ser His His His His His His
465                 470                 475
```

<210> SEQ ID NO 101
<211> LENGTH: 1371
<212> TYPE: DNA
<213> ORGANISM: Artificial Sequence
<220> FEATURE:
<223> OTHER INFORMATION: cDNA encoding EpCAM2.2 - delta humanized 1F3.
      1LC fusion construct

<400> SEQUENCE: 101

```
caggtccagc tgcaggaaag cgggccagga ctggtgaagc ctagcgagac actgacactg      60
acttgtagcg tgagcggggg aagcattagc ggctactatt ggtcctggat cagacagccc     120
cctggcatgg ggctggagtg gattgggagc gtgcaccatt caggaagcac ctcctacaac     180
ccatccctga gagccgggt gactatcagt gtcgaccct caaagaacca gttctctctg       240
aaactgaata gtgtgacagc cgctgacact gctgtctact attgcgcacg gtacagaggc     300
agcggcctgg attattgggg cagggaacc ctggtgacag tcagctccgg cggaggaggc      360
agcggaggag gagggtccgg aggcggggga tctcagagtg tgctgacaca gccaccatca    420
gtcagcgcag cccctggcca gaaagtgact atctcctgtt ctggcgactc tagtaacatt     480
gggaaaaatt acgtctcttg gtatcagcag ctgcctggaa cagccccaaa gctgctgatc     540
tatgagaaca atgaaaggcc ctctggcgtg cctgatcgct ttagtggatc aaaaagcggc     600
actagcgcca ccctgggcat taccgggctg cagacaggcg acgaagccga ttactattgc     660
gctgcttggg ataccagtct gagtgctcgg gtcttcgggg ggggaacaaa ggtcaccgtg     720
```

```
ctgcaggctg tggtgactca ggagccctca ctgactgtgt ccccaggagg acagtcact    780 ctcacctgtc gctcaagtac tggggctgtt acaactagta actatgccaa ctgggtccag    840
cagaaacctg gacaagcacc caggggtctg attggtggta ccaacaagcg agctccaggt    900 accccctgccc ggttctcagg ctccctcctt gggggcaaag ctgccctgac actgtcaggt    960
gtgcagcctg aggacgaggc tgagtattac tgcgctctat ggtacagcaa cctctgggtg   1020
ttcggcggag ggaccaagct gaccgtccta ggccaaccga aagcggcgcc ctcggtcact   1080
ctgttcccgc cctcctctga ggagcttcaa gccaacaagg ccacactggt gtgtctcata   1140
agtgacttct acccgggagc cgtgacagtg gcctggaagg cagatagcag ccccgtcaag   1200
gcgggagtgg agaccaccac accctccaaa caaagcaaca caagtacgc ggccagcagc   1260 tatctgagcc tgacgcctga gcagtggaag tcccacagaa gctacagctg ccaggtcacg   1320
catgaaggga gcaccgtgga agagacagtg gcccctacag aatgttcata g           1371
```

<210> SEQ ID NO 102
<211> LENGTH: 456
<212> TYPE: PRT
<213> ORGANISM: Artificial Sequence
<220> FEATURE:
<223> OTHER INFORMATION: EpCAM2.2 - delta humanized 1F3.1LC fusion
      construct

<400> SEQUENCE: 102

```
Gln Val Gln Leu Gln Glu Ser Gly Pro Gly Leu Val Lys Pro Ser Glu
 1               5                  10                  15

Thr Leu Thr Leu Thr Cys Ser Val Ser Gly Gly Ser Ile Ser Gly Tyr
            20                  25                  30

Tyr Trp Ser Trp Ile Arg Gln Pro Pro Gly Met Gly Leu Glu Trp Ile
        35                  40                  45

Gly Ser Val His His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Tyr Arg Gly Ser Gly Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Val Ser Ala Ala
    130                 135                 140

Pro Gly Gln Lys Val Thr Ile Ser Cys Ser Gly Asp Ser Ser Asn Ile
145                 150                 155                 160

Gly Lys Asn Tyr Val Ser Trp Tyr Gln Gln Leu Pro Gly Thr Ala Pro
                165                 170                 175

Lys Leu Leu Ile Tyr Glu Asn Asn Glu Arg Pro Ser Gly Val Pro Asp
            180                 185                 190

Arg Phe Ser Gly Ser Lys Ser Gly Thr Ser Ala Thr Leu Gly Ile Thr
        195                 200                 205

Gly Leu Gln Thr Gly Asp Glu Ala Asp Tyr Tyr Cys Ala Ala Trp Asp
    210                 215                 220

Thr Ser Leu Ser Ala Arg Val Phe Gly Gly Gly Thr Lys Val Thr Val
225                 230                 235                 240

Leu Gln Ala Val Val Thr Gln Glu Pro Ser Leu Thr Val Ser Pro Gly
```

```
            245                 250                 255
Gly Thr Val Thr Leu Thr Cys Arg Ser Ser Thr Gly Ala Val Thr Thr
            260                 265                 270

Ser Asn Tyr Ala Asn Trp Val Gln Gln Lys Pro Gly Gln Ala Pro Arg
        275                 280                 285

Gly Leu Ile Gly Gly Thr Asn Lys Arg Ala Pro Gly Thr Pro Ala Arg
    290                 295                 300

Phe Ser Gly Ser Leu Leu Gly Gly Lys Ala Ala Leu Thr Leu Ser Gly
305                 310                 315                 320

Val Gln Pro Glu Asp Glu Ala Glu Tyr Tyr Cys Ala Leu Trp Tyr Ser
                325                 330                 335

Asn Leu Trp Val Phe Gly Gly Gly Thr Lys Leu Thr Val Leu Gly Gln
            340                 345                 350

Pro Lys Ala Ala Pro Ser Val Thr Leu Phe Pro Pro Ser Ser Glu Glu
        355                 360                 365

Leu Gln Ala Asn Lys Ala Thr Leu Val Cys Leu Ile Ser Asp Phe Tyr
    370                 375                 380

Pro Gly Ala Val Thr Val Ala Trp Lys Ala Asp Ser Ser Pro Val Lys
385                 390                 395                 400

Ala Gly Val Glu Thr Thr Thr Pro Ser Lys Gln Ser Asn Asn Lys Tyr
                405                 410                 415

Ala Ala Ser Ser Tyr Leu Ser Leu Thr Pro Glu Gln Trp Lys Ser His
            420                 425                 430

Arg Ser Tyr Ser Cys Gln Val Thr His Glu Gly Ser Thr Val Glu Lys
        435                 440                 445

Thr Val Ala Pro Thr Glu Cys Ser
    450                 455

<210> SEQ ID NO 103
<211> LENGTH: 38
<212> TYPE: DNA
<213> ORGANISM: Artificial Sequence
<220> FEATURE:
<223> OTHER INFORMATION: Primer

<400> SEQUENCE: 103
gagacagaat tcgccaccat ggtgttgggg ctgaagtg                          38

<210> SEQ ID NO 104
<211> LENGTH: 36
<212> TYPE: DNA
<213> ORGANISM: Artificial Sequence
<220> FEATURE:
<223> OTHER INFORMATION: Primer

<400> SEQUENCE: 104
gagacagcgg ccgcctattt accaggggag cgagac                            36

<210> SEQ ID NO 105
<211> LENGTH: 40
<212> TYPE: DNA
<213> ORGANISM: Artificial Sequence
<220> FEATURE:
<223> OTHER INFORMATION: Primer

<400> SEQUENCE: 105
gagacagaat tcgccaccat ggcctggatt tcacttatac                        40

<210> SEQ ID NO 106
```

```
<211> LENGTH: 36
<212> TYPE: DNA
<213> ORGANISM: Artificial Sequence
<220> FEATURE:
<223> OTHER INFORMATION: Primer

<400> SEQUENCE: 106
gagacagcgg ccgctcagga acagtcagca cgggac                                    36

<210> SEQ ID NO 107
<211> LENGTH: 30
<212> TYPE: DNA
<213> ORGANISM: Artificial Sequence
<220> FEATURE:
<223> OTHER INFORMATION: Primer

<400> SEQUENCE: 107
gcgtatccat ggatggcgcc cccgcaggtc                                           30

<210> SEQ ID NO 108
<211> LENGTH: 33
<212> TYPE: DNA
<213> ORGANISM: Artificial Sequence
<220> FEATURE:
<223> OTHER INFORMATION: Primer

<400> SEQUENCE: 108
gcgtatgcgg ccgcttttag accctgcatt gag                                       33

<210> SEQ ID NO 109
<211> LENGTH: 10
<212> TYPE: PRT
<213> ORGANISM: Homo sapiens

<400> SEQUENCE: 109

Glu Pro Lys Ser Cys Asp Lys Thr His Thr
1               5                   10

<210> SEQ ID NO 110
<211> LENGTH: 7
<212> TYPE: PRT
<213> ORGANISM: Homo sapiens

<400> SEQUENCE: 110

Glu Arg Lys Cys Cys Val Glu
1               5

<210> SEQ ID NO 111
<211> LENGTH: 12
<212> TYPE: PRT
<213> ORGANISM: Homo sapiens

<400> SEQUENCE: 111

Glu Leu Lys Thr Pro Leu Gly Asp Thr Thr His Thr
1               5                   10

<210> SEQ ID NO 112
<211> LENGTH: 10
<212> TYPE: PRT
<213> ORGANISM: Homo sapiens

<400> SEQUENCE: 112

Glu Pro Lys Ser Cys Asp Thr Pro Pro Pro
1               5                   10
```

-continued

```
<210> SEQ ID NO 113
<211> LENGTH: 7
<212> TYPE: PRT
<213> ORGANISM: Homo sapiens

<400> SEQUENCE: 113

Glu Ser Lys Tyr Gly Pro Pro
1               5

<210> SEQ ID NO 114
<211> LENGTH: 5
<212> TYPE: PRT
<213> ORGANISM: Homo sapiens

<400> SEQUENCE: 114

Cys Pro Pro Cys Pro
1               5

<210> SEQ ID NO 115
<211> LENGTH: 5
<212> TYPE: PRT
<213> ORGANISM: Homo sapiens

<400> SEQUENCE: 115

Cys Pro Arg Cys Pro
1               5

<210> SEQ ID NO 116
<211> LENGTH: 5
<212> TYPE: PRT
<213> ORGANISM: Homo sapiens

<400> SEQUENCE: 116

Cys Pro Ser Cys Pro
1               5

<210> SEQ ID NO 117
<211> LENGTH: 17
<212> TYPE: PRT
<213> ORGANISM: Homo sapiens

<400> SEQUENCE: 117

Glu Leu Lys Thr Pro Leu Gly Asp Thr Thr His Thr Cys Pro Arg Cys
1               5                   10                  15

Pro

<210> SEQ ID NO 118
<211> LENGTH: 15
<212> TYPE: PRT
<213> ORGANISM: Homo sapiens

<400> SEQUENCE: 118

Glu Pro Lys Ser Cys Asp Thr Pro Pro Cys Pro Arg Cys Pro
1               5                   10                  15

<210> SEQ ID NO 119
<211> LENGTH: 34
<212> TYPE: PRT
<213> ORGANISM: Homo sapiens

<400> SEQUENCE: 119

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
```

-continued

```
                 20                  25                  30

Asn Thr

<210> SEQ ID NO 120
<211> LENGTH: 24
<212> TYPE: PRT
<213> ORGANISM: Homo sapiens

<400> SEQUENCE: 120

Gly Arg Gly Gly Glu Glu Lys Lys Glu Lys Glu Lys Glu Glu Gln
1               5                   10                  15

Glu Glu Arg Glu Thr Lys Thr Pro
            20

<210> SEQ ID NO 121
<211> LENGTH: 19
<212> TYPE: PRT
<213> ORGANISM: Homo sapiens

<400> SEQUENCE: 121

Val Pro Ser Thr Pro Pro Thr Pro Ser Pro Ser Thr Pro Pro Thr Pro
1               5                   10                  15

Ser Pro Ser

<210> SEQ ID NO 122
<211> LENGTH: 6
<212> TYPE: PRT
<213> ORGANISM: Homo sapiens

<400> SEQUENCE: 122

Val Pro Pro Pro Pro Pro
1               5

<210> SEQ ID NO 123
<211> LENGTH: 107
<212> TYPE: PRT
<213> ORGANISM: Homo sapiens

<400> SEQUENCE: 123

Val Cys Ser Arg Asp Phe Thr Pro Pro Thr Val Lys Ile Leu Gln Ser
1               5                   10                  15

Ser Ser Asp Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala
            100                 105

<210> SEQ ID NO 124
<211> LENGTH: 112
<212> TYPE: PRT
<213> ORGANISM: Homo sapiens

<400> SEQUENCE: 124
```

-continued

```
Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
                20                  25                  30

Thr Gly Phe Ser Pro Arg Gln Ile Gln Val Ser Trp Leu Arg Glu Gly
            35                  40                  45

Lys Gln Val Gly Ser Gly Val Thr Thr Asp Gln Val Gln Ala Glu Ala
        50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110
```

<210> SEQ ID NO 125
<211> LENGTH: 5
<212> TYPE: PRT
<213> ORGANISM: Artificial Sequence
<220> FEATURE:
<223> OTHER INFORMATION: glycine-serine polymer flexible linker

<400> SEQUENCE: 125

```
Gly Ser Gly Gly Ser
1               5
```

<210> SEQ ID NO 126
<211> LENGTH: 4
<212> TYPE: PRT
<213> ORGANISM: Artificial Sequence
<220> FEATURE:
<223> OTHER INFORMATION: glycine-serine polymer flexible linker

<400> SEQUENCE: 126

```
Gly Gly Gly Ser
1
```

<210> SEQ ID NO 127
<211> LENGTH: 4
<212> TYPE: PRT
<213> ORGANISM: Artificial Sequence
<220> FEATURE:
<223> OTHER INFORMATION: Exemplary glycine-serine polymer flexible
      linker

<400> SEQUENCE: 127

```
Gly Gly Ser Gly
1
```

<210> SEQ ID NO 128
<211> LENGTH: 5
<212> TYPE: PRT
<213> ORGANISM: Artificial Sequence
<220> FEATURE:
<223> OTHER INFORMATION: Exemplary glycine-serine polymer flexible
      linker

<400> SEQUENCE: 128

```
Gly Gly Ser Gly Gly
1               5
```

<210> SEQ ID NO 129
<211> LENGTH: 5
<212> TYPE: PRT

```
<213> ORGANISM: Artificial Sequence
<220> FEATURE:
<223> OTHER INFORMATION: Exemplary glycine-serine polymer flexible
      linker

<400> SEQUENCE: 129

Gly Ser Gly Ser Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Exemplary glycine-serine polymer flexible
      linker

<400> SEQUENCE: 130

Gly Ser Gly Gly Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Exemplary glycine-serine polymer flexible
      linker

<400> SEQUENCE: 131

Gly Gly Gly Ser Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Exemplary glycine-serine polymer flexible
      linker

<400> SEQUENCE: 132

Gly Ser Ser Ser Gly
1               5

<210> SEQ ID NO 133
<211> LENGTH: 6
<212> TYPE: PRT
<213> ORGANISM: Artificial Sequence
<220> FEATURE:
<223> OTHER INFORMATION: Protease substrate cleavage sequence

<400> SEQUENCE: 133

Pro Leu Gly Leu Ala Gly
1               5

<210> SEQ ID NO 134
<211> LENGTH: 8
<212> TYPE: PRT
<213> ORGANISM: Artificial Sequence
<220> FEATURE:
<223> OTHER INFORMATION: Protease substrate cleavage sequence

<400> SEQUENCE: 134

Gly Pro Leu Gly Met Leu Ser Gln
1               5
```

-continued

```
<210> SEQ ID NO 135
<211> LENGTH: 8
<212> TYPE: PRT
<213> ORGANISM: Artificial Sequence
<220> FEATURE:
<223> OTHER INFORMATION: Protease substrate cleavage sequence

<400> SEQUENCE: 135

Gly Pro Leu Gly Leu Trp Ala Gln
1               5

<210> SEQ ID NO 136
<211> LENGTH: 14
<212> TYPE: PRT
<213> ORGANISM: Artificial Sequence
<220> FEATURE:
<223> OTHER INFORMATION: Protease substrate cleavage sequence

<400> SEQUENCE: 136

Glu Gly Lys Ser Ser Gly Ser Gly Ser Glu Ser Lys Val Asp
1               5                   10

<210> SEQ ID NO 137
<211> LENGTH: 18
<212> TYPE: PRT
<213> ORGANISM: Artificial Sequence
<220> FEATURE:
<223> OTHER INFORMATION: Protease substrate cleavage sequence

<400> SEQUENCE: 137

Lys Glu Ser Gly Ser Val Ser Ser Glu Gln Leu Ala Gln Phe Arg Ser
1               5                   10                  15

Leu Asp

<210> SEQ ID NO 138
<211> LENGTH: 5
<212> TYPE: PRT
<213> ORGANISM: Artificial Sequence
<220> FEATURE:
<223> OTHER INFORMATION: Protease substrate cleavage sequence

<400> SEQUENCE: 138

Gly Gly Gly Gly Ser
1               5

<210> SEQ ID NO 139
<211> LENGTH: 5
<212> TYPE: PRT
<213> ORGANISM: Artificial Sequence
<220> FEATURE:
<223> OTHER INFORMATION: EpCAM1.1 and EpCAM1.2 scFv variable heavy chain
      CDR1

<400> SEQUENCE: 139

Asn Tyr Trp Met Ser
1               5

<210> SEQ ID NO 140
<211> LENGTH: 17
<212> TYPE: PRT
<213> ORGANISM: Artificial Sequence
<220> FEATURE:
<223> OTHER INFORMATION: EpCAM1.1 and EpCAM1.2 scFv variable heavy chain
      CDR2

<400> SEQUENCE: 140

Asn Ile Lys Gln Asp Gly Ser Glu Lys Phe Tyr Val Asp Ser Val Lys
```

```
1               5                   10                  15

Gly

<210> SEQ ID NO 141
<211> LENGTH: 9
<212> TYPE: PRT
<213> ORGANISM: Artificial Sequence
<220> FEATURE:
<223> OTHER INFORMATION: EpCAM1.1 and EpCAM1.2 scFv variable heavy chain
      CDR3

<400> SEQUENCE: 141

Val Gly Gly Ala Trp Glu Leu Gly Tyr
1               5

<210> SEQ ID NO 142
<211> LENGTH: 14
<212> TYPE: PRT
<213> ORGANISM: Artificial Sequence
<220> FEATURE:
<223> OTHER INFORMATION: EpCAM1.1 and EpCAM1.2 scFv variable light chain
      CDR1

<400> SEQUENCE: 142

Thr Gly Ser Ser Ser Asn Ile Gly Ser Tyr Tyr Gly Val His
1               5                   10

<210> SEQ ID NO 143
<211> LENGTH: 7
<212> TYPE: PRT
<213> ORGANISM: Artificial Sequence
<220> FEATURE:
<223> OTHER INFORMATION: EpCAM1.1 and EpCAM1.2 scFv variable light chain
      CDR2

<400> SEQUENCE: 143

Ser Asp Thr Asn Arg Pro Ser
1               5

<210> SEQ ID NO 144
<211> LENGTH: 11
<212> TYPE: PRT
<213> ORGANISM: Artificial Sequence
<220> FEATURE:
<223> OTHER INFORMATION: EpCAM1.1 and EpCAM1.2 scFv variable light chain
      CDR3

<400> SEQUENCE: 144

Gln Ser Tyr Asp Ser Ser Leu Ser Gly Arg Val
1               5                   10

<210> SEQ ID NO 145
<211> LENGTH: 5
<212> TYPE: PRT
<213> ORGANISM: Artificial Sequence
<220> FEATURE:
<223> OTHER INFORMATION: EpCAM2.2 scFv variable heavy chain CDR1

<400> SEQUENCE: 145

Gly Tyr Tyr Trp Ser
1               5

<210> SEQ ID NO 146
<211> LENGTH: 16
<212> TYPE: PRT
<213> ORGANISM: Artificial Sequence
<220> FEATURE:
```

```
<223> OTHER INFORMATION: EpCAM2.2 scFv variable heavy chain CDR2

<400> SEQUENCE: 146

Ser Val His His Ser Gly Ser Thr Ser Tyr Asn Pro Ser Leu Lys Ser
1               5                   10                  15

<210> SEQ ID NO 147
<211> LENGTH: 8
<212> TYPE: PRT
<213> ORGANISM: Artificial Sequence
<220> FEATURE:
<223> OTHER INFORMATION: EpCAM2.2 scFv variable heavy chain CDR3

<400> SEQUENCE: 147

Tyr Arg Gly Ser Gly Leu Asp Tyr
1               5

<210> SEQ ID NO 148
<211> LENGTH: 13
<212> TYPE: PRT
<213> ORGANISM: Artificial Sequence
<220> FEATURE:
<223> OTHER INFORMATION: EpCAM2.2 scFv variable light chain CDR1

<400> SEQUENCE: 148

Ser Gly Asp Ser Ser Asn Ile Gly Lys Asn Tyr Val Ser
1               5                   10

<210> SEQ ID NO 149
<211> LENGTH: 7
<212> TYPE: PRT
<213> ORGANISM: Artificial Sequence
<220> FEATURE:
<223> OTHER INFORMATION: EpCAM2.2 scFv variable light chain CDR2

<400> SEQUENCE: 149

Glu Asn Asn Glu Arg Pro Ser
1               5

<210> SEQ ID NO 150
<211> LENGTH: 11
<212> TYPE: PRT
<213> ORGANISM: Artificial Sequence
<220> FEATURE:
<223> OTHER INFORMATION: EpCAM2.2 scFv variable light chain CDR3

<400> SEQUENCE: 150

Ala Ala Trp Asp Thr Ser Leu Ser Ala Arg Val
1               5                   10
```

MULTI-SPECIFIC FAB FUSION PROTEINS AND METHODS OF USE

CROSS REFERENCE TO RELATED APPLICATIONS

This application claims priority to U.S. Provisional Application No. 61/486,690 filed on May 16, 2011, which application is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FABN_001_02US_ST25.txt. The text file is 188 KB, was created on May 16, 2012, and is being submitted electronically via EFS-Web.

BACKGROUND

1. Technical Field

The present disclosure relates generally to multi-specific Fab fusion proteins (MSFP). In particular, the MSFP of the present disclosure comprise an antibody Fab fragment with both N-termini fused to a fusion moiety by a cleavable or non-cleavable linker. The Fab fragment of the MSFP specifically binds to native cell surface target antigens as well as certain soluble forms of the same antigen. One or both fusion moieties bind specifically to target antigens on cell surfaces.

2. Description of the Related Art

Conventional immunoglobulin G (IgG) is a tetrameric molecule comprising two identical immunoglobulin heavy chains and two identical immunoglobulin light chains. IgG heavy chain has a variable region at the N-terminus followed by the first constant region (CH1), a hinge and two additional constant regions (CH2CH3). IgG light chain is comprised of two domains: an N-terminal variable region and a C-terminal constant region. The heavy chain variable region (VH) interacts with the light chain variable region (VL) to constitute the minimal antigen binding region, Fv. The antigen binding region is stabilized by the interaction between the first constant region of heavy chain (CH1) and the light constant (CL) and further by the formation of a disulfide bond between the two constant regions (to form a Fab fragment). The homodimerization of CH2CH3 domains (to form Fc) and consequently the hinge disulfide bond formation stabilize the IgG structure. Thus an IgG has two antigen binding Fab arms which are relatively flexible in orientation with each other and with the Fc domain. In addition, the binding regions (which interact directly with antigen) are located at the N terminus with no further structures beyond. Conceivably, this structure feature facilitates antibody interaction with antigen with minimal interference from steric hindrance. This property is especially important for binding to cell surface antigen that is often located very close to the complex cell membrane.

In recent years, full length monoclonal antibodies have been successfully used to treat cancer, autoimmune and inflammatory diseases and other human diseases (Nelson, Nat. review, Drug Discovery (2010) 9:767-74). Although five different types of immunoglobulins (IgA, IgD, IgG, IgM and IgE) exist naturally, IgG represents the most suitable modality for human therapeutics because of the favorable properties including high binding affinity and specificity, high bioavailability, long serum half life in circulation, potential effector function capability and the industrial-scale manufacturability.

Monoclonal antibodies (non conjugated or naked antibody) currently approved by drug regulatory agencies worldwide for clinical use in oncology setting working generally by one or a combination of the following mechanisms: 1) blocking cell growth signaling, 2) blocking the blood supply to cancer cells, 3) directly mediating cell apoptosis, 4) eliciting immunological effector functions such as antibody dependent cellular cytotoxicity (ADCC), antibody dependent cellular phagocytosis (ADCP) and complement dependent cytotoxicity (CDC), and 5) promoting adaptive immunity towards tumors.

Monoclonal antibody therapies have demonstrated survival benefits in the clinic. However, the overall response rates in cancer patients are low, and the survival benefits are marginal (several months) compared to chemotherapy. Although the underlying reasons for the lack of robust clinical anti-cancer activities are not fully understood, research has suggested that cancer cells often quickly develop compensating signaling pathways to escape cell death. Also, cancer stem cells (CSC), which are considered as potent cancer initiating cells, are less active at cell proliferation therefore they tend to sustain the lack of growth signal better.

In recent years, ADCC was demonstrated to play a significant role in the clinical efficacy of anti cancer antibodies. Antibody Fc binds to Fc gamma receptors of which there are numerous forms: FcγRI, FcγRIIa, FcγRIIb FcγRIIc, FcγRIIIa and FcγRIIIb. The Fc domain has especially high affinity fo FcγRIIIa, which is expressed on natural killing (NK) cells, macrophages, and neutrophils. Binding of Fc to FcγRIIIa activates NK cells which can then destroy nearby cancer cells.

Engineered antibodies with enhanced activating FcγR binding properties via either protein engineering (involving a variety of amino acid mutations in the CH2 region) or production host cell (CHO) line engineering to reduce or eliminate fucosylation in the Asn297 glycan structure have been successfully tested in preclinical studies with improved biological activities. IgG antibodies containing enhanced effector functions are currently in clinical testing with the goal of improved efficacy. The current available clinical data indicate that these antibodies are very promising.

Another anti cancer therapeutic approach is to utilize T cells. T cells provide defense against cancer throughout life by patrolling the body in search for newly arisen cancer cells and eliminating them effectively and promptly. Successful therapeutic approaches harnessing T cell immunity in cancer treatment include: 1) the FDA approved use of PROLEUKIN® (aldesleukin, recombinant IL-2) for metastatic melanoma and metastatic kidney cancer; 2) FDA approved use of PROVENGE® (Sipuleucel-T) for asymptomatic metastatic hormone refractory prostate cancer. PROVENGE® is a dendritic cell vaccine that activates prostate cancer-specific cytotoxic T cells ex vivo, which cells are then reinfused into the patient; 3) FDA approve use of ipilimumab (anti CTLA-4 antibody to activate T cells by inhibiting T cell inhibitory signaling pathway) for advanced melanoma.

Because T cells do not express Fc gamma receptors (FcγR), anti tumor antibodies cannot effectively activate cytotoxic T cells directly. One of the many promising methods aimed to activate T cell for tumor killing purposes is to use bispecific antibodies (bsAb) to directly bring T cells to the proximity of tumor cells, resulting in activation of T cells and the killing the tumor cells. CD28 and CD137 (4-1BB) are two potent T cell co-stimulatory receptors utilized in bispecific targeting approaches. Examples include: CD28×NG2 (Grosse-Hovest et al., Eur J Immunol 33:1334-40, 2003), CD28×CD20 (Otz et al., Leukemia 23:71-7, 2009) and 4-1BB×CD20 (Liu et al., J Immunother 33:500-9, 2010). Other T cell surface targets capable of triggering T activation have also been used for retargeting them to tumor cells using bispecific antibodies. Various bispecific and multispecific antibody formats have been developed in the past and reviewed recently (Muller and Kontermann, Biodrugs 24: 89-98, 2010; Chames and Baty, mAbs 1:539-47, 2009; Deyev and Lebedenko, BioEssays 30:904-918, 2008). These formats fall into the following three large categories: 1) IgG-like bispecific molecules based on Fc heterodimerization or covalent fusion to the heavy or light chain, including quadroma technology (Staerz et al., PNAS 83:1453-7, 1986), knob and hole technology (Nat. Biotechnol. 16: 677-81; J. Biol. Chem. 285:19637-46, 2010), strand-exchange engineered domain "SEED" technology (Davis et al., PEDS 23:195-202, 2010), fusion to the C-terminus of IgG heavy or light chain (Coloma and Morrison, Nat. Biotechnol. 15:159-63, 1997; Shen et al., J. Immunol. Methods 318:65-74, 2007; orcutt et al., PEDS 23:221-8, 2010; Dong et al., J. Biol. Chem., 286:4703-17, 2011, Lazar et al., patent application, US20110054151), fusion to the N-terminus an IgG heavy or light chain (Shen, et al., J. Biol. Chem. 281:10706-17, 2006; Wu et al., Nat. Biotechnol. 25:1290-7, 2007), 2) Fc fusion bispecific antibodies (Mabry et al., PEDS 23:115-127, 2010; Miller et al., PEDS 23:549-557, 2010), 3) antibody variable region only molecules through fusion or nonconvalent association, including diabody (Db) (Holligger et al., PNAS 90:6444-8, 1993), disulfide bond linked diabody (also know as dual affinity re-targeting or DART) (Johnson et al., J. Mol. Biol. 399:436-49, 2010), single chain diabody (scpb) (Alt, et al., FEBS Letters 454:90-4, 1999), tandem diabody (tandAbs) (Kipriyanov, et al., J. Mol. Biol. 293:41-56, 1999), tandem single chain Fv (taFv) (Mack, et al., PNAS 92:7021-5, 1995), and 4) Fab based fusion molecules, including bibody and tribody (Schoonjans et al., J. Immunol. 165:7050-7, 2000; Website of Biotecnol SA, at the world-wide web address biotecnol.com), Fab fusion to single domain antibodies (patent application, US2010/0239582A1), and Fab'2-fusion (U.S. Pat. No. 5,959, 083).

Efforts in the area of the bispecific antibody field over the last two decades started to bear fruits clinically. Cantomaxomab (REMOVAB®, an anti-CD3, anti-EpCAM trifunctional antibody), was approved in Europe for symptomatic malignant ascites in 2009. However, while bispecific antibodies have demonstrated potent tumor cell killing potential, severe side effects, including systemic immune activation, immunogenicity (anti drug antibody response) and general poor manufacturability of these molecules remain and to a large extent, have prevented this class of drugs from broad applications. Recently bispecific antibody technology platform referred to as bi-specific T cell engagers, or BiTEs, employing an anti-CD19 scFv-anti-CD3 scFv fusion (Blinatumomab), attracted a lot of attention because of its outstanding potency demonstrated in preclinical and clinical tests (Bargou et al., Science (2008) 321:974-7). In particular, patients with non-Hodgkin's lymphoma showed tumor regression, and in some cases complete remission during a clinical trial of blinatumomab administration. However, blinatumomab caused severe side effects including central nervous system side effects manifested by the loss of language ability and disorientation. Symptoms were transient and reversible once administration of the drug was stopped. It was hypothesized that the direct binding of the CD3 (on T cells) by the drug causing T partial activation and cell redistribution (patent application, US2010/0150918A1). Some of the redistributed T cells adhere to the brain miscro-vasculature, partially activate the endothelial cells and lead to the enhanced permeability of the micro-vasculature in the brain. It was observed in the clinic trial that the incidence of side effects was lower in patients with high B cell to T cell ratios than those with low ratios. It has also been reported that using different CD3 binding antibody fragments can alleviate or avoid T cell redistribution in Monkeys. These observations strongly suggest that antibody binding to CD3 together with the binding epitope on CD3 and the resultant partial activation of the T cell may be the direct cause of the severe CNS side effects.

Another drawback of the CD19×CD3 bispecific scFv-scFv fusion is that the drug requires daily intravenous infusion (i.v.) drug delivery due to its short half-life and incompatibility with subcutaneous administration. In addition, scFv-scFv fusion proteins have a tendency to aggregate. Therefore, BiTE molecules require highly complicated antibody engineering skills and it is laborious to make them stable and manufacturable.

Anti cancer activities of antibody drugs engaging FcγR or CD3-expressing immune cells demonstrated clinical proof of concept. However, the shortcomings of the current bispecific antibody formats remain a challenge for broad application of these drugs for treating cancer patients with good efficacy and safety profiles. Therefore, there remains an urgent need for new bispecific molecule designs with improved profiles on product efficacy, stability, safety and manufacturability.

References for further background information include: Coloma and Morrison, Nat. Biotechnol. 15:159-63, 1997; Kontermann, Acta Pharmacol. Sin., 26, 1-9. 2005; Marvin and Zhu; Acta Pharmacol. Sin., 26, 649-658.2005; Shen et al., J. Immunol. Methods, 318:65-74, 2007; Shen et al. JBC 281: 10706-10714, 2006; Wu et al., Nat. Biotechnol., 25, 1290-1297, 2007; Orcutt Prot PEDS 23:221-8, 2010; Mabry PEDS vol. 23 no. 3 pp. 115-127, 2010; Schoonjans *The Journal of Immunology*, 2000, 165: 7050-7057; Michaelson, mAbs 1:2, 128-141; 2009; Robinson et al., British Journal of Cancer (2008) 99, 1415-1425.

BRIEF SUMMARY

One aspect of the present disclosure provides a multi-specific Fab fusion protein comprising: a Fab fragment that binds to a target antigen; a first fusion moiety coupled at the N-terminus of the VL of the Fab fragment; and/or a second fusion moiety coupled at the N-terminus of the VH of the Fab fragment. In one embodiment of the multi-specific Fab fusion protein, the binding of the Fab fragment to the Fab target antigen is reduced by between 50% and 90% as compared to the binding of an identical Fab fragment to the Fab target in the absence of the first and second fusion moieties.

One aspect of the present disclosure provides a multi-specific Fab fusion protein comprising a) a Fab fragment that binds to a target antigen, wherein the Fab fragment comprises, i) an immunoglobulin light chain variable region (VL) and an immunoglobulin light chain constant region (CL); and ii) an immunoglobulin heavy chain variable region (VH), and an immunoglobulin heavy chain constant region 1 (CH1); wherein the CL and CH1 regions are optionally connected by a disulfide bond; b) a fusion moiety A wherein the C-terminus of fusion moiety A is covalently linked to the N-terminal end of the VH domain; or c) a fusion moiety B, wherein the C-terminus of fusion moiety B is covalently linked to the N-terminal end of the VL domain; or both b and c; d) optionally, a first linker situated between the fusion moiety A and the VH domain; and e) optionally, a second linker situated between the fusion moiety B and the VL domain. In one embodiment of the MSFP, the fusion moiety A comprises a binding domain and/or the fusion moiety B comprises a binding domain. The fusion moiety A and the fusion moiety B may be identical in sequence or may comprise different sequences.

In yet a further embodiment of the multi-specific Fab fusion protein of the present disclosure, the fusion moiety A comprises a first binding domain and the fusion moiety B comprises a second binding domain, wherein the first and second binding domains bind to the same cell surface antigen. In one embodiment, the fusion moiety A comprises a first binding domain and the fusion moiety B comprises a second binding domain, wherein the first and second binding domains bind to different cell surface antigens. In certain embodiments, the fusion moiety A comprises a first binding domain and the fusion moiety B comprises a second binding domain, wherein the first and second binding domains bind to the same epitope or to different epitopes.

In one embodiment of the multi-specific Fab fusion proteins of present disclosure, the Fab fragment binds to a cell surface target antigen. In one particular embodiment, the fusion moiety A comprises a binding domain and the Fab fragment binds to the same cell surface antigen as the binding domain. In another embodiment, the fusion moiety B comprises a binding domain and the Fab fragment binds to the same cell surface antigen as the binding domain.

In certain embodiments of the multi-specific Fab fusion protein described herein, binding of the Fab fragment to the antigen is inhibited by steric hindrance caused by the fusion moiety A and the fusion moiety B. In some embodiments, the steric hindrance results in no detectable binding of the Fab fragment to the antigen. In other embodiments, the binding of the Fab fragment to its target is reduced by between 50% and 90% as compared to the binding of an identical Fab fragment to its target in the absence of the fusion moiety A and the fusion moiety B.

In one embodiment of the multi-specific Fab fusion proteins described herein, the first and second linkers are cleavable. In further embodiments, binding of the Fab fragment to the antigen is detectable if the first linker is cleaved. In another embodiment, binding of the Fab fragment to the antigen is detectable if the second linker is cleaved. In yet further embodiments, binding of the Fab fragment to the antigen is detectable if the first linker and the second linker are both cleaved.

In another embodiment of the multi-specific Fab fusion proteins described herein, the immunoglobulin heavy chain constant region type is selected from α, δ, ε, γ, and μ. In one embodiment, the immunoglobulin heavy chain is derived from an IgG antibody and in further embodiments, the isotype of the IgG antibody is selected from IgG1, IgG2, IgG3 and IgG4.

In another embodiment of the multi-specific Fab fusion proteins described herein, the immunoglobulin light chain VL and CL are selected from immunoglobulin kappa light chain and the immunoglobulin lambda light chain.

In one embodiment, the fusion moiety A comprises a first binding domain which comprises an scFv antigen-binding domain. In one embodiment of the multi-specific Fab fusion proteins described herein, the fusion protein does not comprise the first linker or the second linker. In this regard, in some embodiments, the fusion moiety A has from 1-3 C-terminal amino acid residues deleted; or wherein the fusion moiety B has from 1-3 C-terminal amino acid residues deleted; or wherein both the fusion moiety A and the fusion moiety B have from 1-3 C-terminal amino acid residues deleted. In further embodiments of the MSFP described herein wherein there is no first or second linker, the N-terminal end of the Fab VH may have from 1-3 amino acid residues deleted; or the N-terminal end of the Fab VL may have from 1-3 amino acid residues deleted; or both the N-terminal end of the VH and the N-terminal end of the VL may have from 1-3 amino acid residues deleted. In further embodiments of the MSFP described herein wherein there is no first or second linker, the fusion moiety A and the fusion moiety B may have from 1-3 C-terminal amino acid residues deleted; and both the N-terminal end of the Fab VH and the N-terminal end of the Fab VL may have from 1-3 amino acid residues deleted. In yet further embodiments, the MSFP described herein contains any combination of a linker and a deletion.

In one embodiment of the multi-specific Fab fusion protein described herein, or a homodimer thereof, the first linker comprises a protease non-cleavable sequence and/or the second linker comprises a protease cleavable sequence. In another embodiment of the multi-specific Fab fusion protein described herein, or a homodimer comprising same, the first linker comprises a protease cleavable sequence and/or the second linker comprises a non-cleavable sequence. In certain embodiments, the first and second linkers comprise protease cleavable sequences cleavable by the same protease. In other embodiments, the first and second linkers comprise protease cleavable sequences cleavable by different proteases. In related embodiments, the protease cleavable sequence comprises a serine protease, a cysteine protease, a aspartate protease, or a matrix metalloprotease (MMP) cleavable sequence. In certain embodiments, the protease cleavable sequence is a MMP cleavable sequence. In this regard, said matrix metalloprotease cleavable sequence may be a matrix metalloprotease 1 (MMP-1), a matrix metalloprotease 2 (MMP-2), a matrix metalloprotease 9 (MMP-9), or a matrix metalloprotease 14 (MMP-14) cleavable sequence.

In another embodiment of the multi-specific Fab fusion proteins described herein, the first linker is 1 to 10 amino acids long or is 1 to 20 amino acids long. In some embodiments, the second linker comprises a protease non-cleavable sequence or comprises a protease cleavable sequence. In this regard, the protease cleavable sequence may be a serine protease, a cysteine protease, a aspartate protease, or a matrix metalloprotease (MMP) cleavable sequence. In certain embodiments, the protease cleavable sequence is a MMP cleavable sequence and in this regard, may be a MMP cleavable sequence selected from a matrix metalloprotease 1 (MMP-1), a matrix metalloprotease 2 (MMP-2), a matrix metalloprotease 9 (MMP-9), or a matrix metalloprotease 14 (MMP-14) cleavable sequence. In certain embodiments, the second linker is 1 to 10 amino acids long or is 1 to 20 amino acids long.

In another aspect of the present disclosure, the multi-specific Fab fusion protein comprising a) a Fab fragment that binds to a target antigen, wherein the Fab fragment comprises, i) an immunoglobulin light chain variable region (VL) and an immunoglobulin light chain constant region (CL); and ii) an immunoglobulin heavy chain variable region (VH), and an immunoglobulin heavy chain constant region 1 (CH1); wherein the CL and CH1 regions are optionally connected by a disulfide bond; b) a fusion moiety A wherein the C-terminus of fusion moiety A is covalently linked to the N-terminal end of the VH domain; c) a fusion moiety B, wherein the C-terminus of fusion moiety B is covalently linked to the N-terminal end of the VL domain; d) optionally, a first linker situated between the fusion moiety A and the VH domain; and e) optionally, a second linker situated between the fusion moiety B and the VL domain; wherein the fusion moiety A comprises a binding domain and/or the fusion moiety B comprises a binding domain and further, either or both of the binding domain binds to a cell surface antigen. In certain embodiments, the cell surface antigen is a tumor antigen. In certain embodiments, one of the binding domains (e.g., of either fusion moiety A or fusion moiety B) binds to human serum albumin.

In another embodiment of the multi-specific Fab fusion proteins described herein, the Fab binds to a target antigen selected from a group of FcγR I, FcγRIIa, FcγRIIb, FcγRIIIa, FcγRIIIa, NKG2D, CD3, CD25, CD28, CTLA-4, FAS, FGFR1, FGFR2, FGFR3, FGFR4, GITR, LTβR, TLR, TRAIL receptor 1, TRAIL receptor 2, EGFR, Her2/neu, ErbB3, CD25, and CD28. In particular embodiments, the Fab binds to CD3. In another embodiment, the Fab binds to T cell receptor. The Fab may be humanized. In certain embodiments, the humanized Fab is derived from OKT3, UCHT-1, or SP34. In one embodiment, the Fab is derived from a fully human antibody which in some embodiments is generated from phage display, yeast display, or human antibody gene transgenic mice.

In one embodiment of the multi-specific Fab fusion proteins described herein, the fusion moiety A comprises a first binding domain and the fusion moiety B comprises a second binding domain, wherein the first and second binding domains bind to the same cell surface antigen, and wherein the first and second binding domains bind to a target selected from a group of: FcγRIIb, CD28, CTLA-4, FAS, FGFR1, FGFR2, FGFR3, FGFR4, GITR, LTβR, TLR, TRAIL receptor 1, TRAIL receptor 2, CD28, CEA, PSMA, BCMA, CAIX, cMet, EGFR1, Her2/neu, ErbB3, EpCAM, Folate receptor, Ephrine receptor, CD19, CD20, CD30, CD33, CD40, CD37, CD38, and CD138.

In a further embodiment of the multi-specific Fab fusion proteins described herein, the fusion moiety A comprises a first binding domain and the fusion moiety B comprises a second binding domain, wherein the first and second binding domains bind to different cell surface antigens and wherein the first and second binding domains bind to a different target selected from a group of: FcγRIIb, CD28, CTLA-4, FAS, FGFR1, FGFR2, FGFR3, FGFR4, GITR, LTβR, TLR, TRAIL receptor 1, TRAIL receptor 2, CD28, CEA, PSMA, BCMA, CAIX, cMet, EGFR1, Her2/neu, ErbB3, EpCAM, Folate receptor, Ephrine receptor, CD19, CD20, CD30, CD33, CD40, CD37, CD38, and CD138.

In certain embodiments, of the multi-specific Fab fusion proteins the first and/or the second binding domain is an antigen-binding fragment of an antibody. In this regard, the antigen-binding fragment may be selected from the group consisting of an scFv, a CDR, a Fv, an immunoglobulin VL domain, an immunoglobulin VH domain, an immunoglobulin VL and a VH domain, a Fab, a camelid VHH, a dAb (domain antibody). In certain embodiments, the antigen-binding fragment is humanized and in other embodiments, the antigen-binding fragment is derived from a mouse, rat, or rabbit monoclonal antibody. In some embodiments, the antigen-binding fragment is derived from a fully human antibody which may be generated from phage display, yeast display, or a human antibody gene transgenic mouse.

In further embodiments, the first and/or the second binding domain of an MSFP described herein is selected from the group consisting of a Fibronectin 3 domain (Fn3), an ankryin repeat, and an Adnectin.

In one embodiment of the multi-specific Fab fusion proteins described herein, the first and/or second linker comprises the amino acid sequence set forth in SEQ ID NO: 133. (PLGLAG).

One aspect of the present disclosure provides isolated polynucleotides encoding the multi-specific Fab fusion proteins described herein, and expression vectors comprising the isolated polynucleotides, and isolated host cells comprising such vectors.

Another aspect of the present disclosure provides a method of expressing a multi-specific Fab fusion protein by culturing a host cell comprising an isolated polynucleotide encoding an a multi-specific Fab fusion protein as described herein under conditions in which the isolated polynucleotide expresses the encoded multi-specific Fab fusion protein.

A further aspect of the disclosure provides a pharmaceutical composition comprising one or more multi-specific Fab fusion proteins as described herein, and a pharmaceutically acceptable carrier.

Another aspect of the disclosure provides a method of treating a condition comprising administering an effective amount of a pharmaceutical composition comprising one or more multi-specific Fab fusion proteins as described herein, and a pharmaceutically acceptable carrier, to a subject in need, wherein the condition is associated with an antigen to which the multi-specific Fab fusion protein can bind.

In a further embodiment of the multi-specific Fab fusion proteins described herein, the fusion moiety A and the fusion moiety B do not dimerize.

Another aspect of the present disclosure provides a multi-specific Fab fusion protein comprising: a Fab fragment that binds to the N-terminus of CD3 epsilon; a fusion moiety A linked to the N-terminus of a VL of the Fab fragment; or a fusion moiety B linked to the N-terminus of a VH of the Fab fragment; or both a fusion moiety A linked to the N-terminus of the VL of the Fab fragment and a fusion moiety B linked to the N-terminus of the VH of the Fab fragment. In one embodiment, the Fab fragment binds to an epitope within amino acids 1-27 of CD3 epsilon. In a further embodiment, the Fab fragment crossreacts with nonhuman primate CD3 epsilon.

In one embodiment of the multi-specific Fab fusion proteins disclosed herein a. the Fab fragment comprises, i. an immunoglobulin light chain variable region (VL) comprising the CDR1, CDR2 and CDR3 amino acid sequences set forth in SEQ ID NOs: 26-28 and an immunoglobulin light chain constant region (CL); and ii. an immunoglobulin heavy chain variable region (VH), comprising the CDR1, CDR2 and CDR3 amino acid sequences set forth in SEQ ID NOs: 23-25, and an immunoglobulin heavy chain constant region 1 (CH1); wherein the CL and CH1 regions are optionally connected by a disulfide bond; b. the C-terminus of the fusion moiety A is covalently linked to the N-terminal end of the VH domain; or c. the C-terminus of the fusion moiety B is covalently linked to the N-terminal end of the VL domain; or d. both b and c; e. optionally, a first linker situated between the fusion moiety A and the VH domain; and f. optionally, a second linker situated between the fusion moiety B and the VL domain. In one embodiment, the VH is selected from any one of the amino acid sequences set forth in SEQ ID NOs: 34, 38, 42, 46, 50, and 54. In another embodiment, VL is selected from any one of the amino acid sequences set forth in SEQ ID NOs: 56, 58, 62, 66, and 70. In another embodiment, the fusion moiety A comprises a binding domain and/or the fusion moiety B comprises a binding domain. In one embodiment, the fusion moiety A and the fusion moiety B are identical in sequence. In yet another embodiment, the fusion moiety A and the fusion moiety B comprise different sequences. In one particular embodiment, the fusion moiety A comprises a first binding domain and the fusion moiety B comprises a second binding domain, wherein the first and second binding domains bind to the same cell surface antigen. In certain embodiments, the fusion moiety A comprises a first binding domain and the fusion moiety B comprises a second binding domain, wherein the first and second binding domains bind to different cell surface antigens. In other embodiments, the fusion moiety A comprises a first binding domain and the fusion moiety B comprises a second binding domain, wherein the first and second binding domains bind to the same epitope. In another embodiment, the fusion moiety A comprises a first binding domain and the fusion moiety B comprises a second binding domain, wherein the first and second binding domains bind to different epitopes.

In one embodiment of the multi-specific Fab fusion proteins disclosed herein, binding of the Fab fragment to CD3 is inhibited by steric hindrance caused by the fusion moiety A and the fusion moiety B. In this regard, the steric hindrance results in no detectable binding of the Fab fragment to CD3 in the absence of binding of the first and second binding domains to the cell surface antigen. In another embodiment, the binding of the Fab fragment to CD3 is reduced by between 50% and 90% in the absence of binding of the first and second binding domains to the cell surface antigen as compared to the binding of the Fab fragment to CD3 in the presence of binding of the first and second binding domains to the cell surface antigen. In a further embodiment, the binding of the Fab fragment to CD3 is reduced by between 50% and 90% as compared to binding of an identical Fab fragment not having the fusion moiety A and the fusion moiety B.

In another embodiment of the multi-specific Fab fusion proteins disclosed herein, the immunoglobulin heavy chain constant region type is selected from α, β, ε, γ, and μ. In one embodiment, the immunoglobulin heavy chain is derived from an IgG antibody. In further embodiments, the isotype of the IgG antibody is selected from IgG1, IgG2, IgG3 and IgG4. In another embodiment, the immunoglobulin light chain VL and CL are selected from immunoglobulin kappa light chain and the immunoglobulin lambda light chain.

In one embodiment of the multi-specific Fab fusion proteins disclosed herein, the fusion moiety A comprises a first binding domain which comprises an scFv antigen-binding domain.

In another embodiment of the multi-specific Fab fusion proteins the first linker and the second linker are 1 to 20 amino acids long. In one particular embodiment, the first and/or second linkers comprise GlyArgAla.

In one embodiment of the multi-specific Fab fusion proteins disclosed herein the Fab is humanized.

In yet another embodiment of the multi-specific Fab fusion proteins disclosed herein, the first and second binding domains bind to a target selected from a group of: FcγRIIb, CD28, CTLA-4, FAS, FGFR1, FGFR2, FGFR3, FGFR4, GITR, LTβR, TLR, TRAIL receptor 1, TRAIL receptor 2, CD28, CEA, PSMA, BCMA, CAIX, cMet, EGFR1, Her2/neu, ErbB3, EpCAM, Folate receptor, Ephrine receptor, TRAIL receptor 2, CD19, CD20, CD30, CD33, CD40, CD37, CD38, and CD138. In one embodiment, the 1st and 2nd binding domains are selected from any one of the amino acid sequences set forth in SEQ ID NOs: 78, 88, and 94.

In another embodiment, the first and second binding domains bind to a different target selected from the group consisting of: FcγRIIb, CD28, CTLA-4, FAS, FGFR1, FGFR2, FGFR3, FGFR4, GITR, LTβR, TLR, TRAIL receptor 1, TRAIL receptor 2, CD28, CEA, PSMA, BCMA, CAIX, cMet, EGFR1, Her2/neu, ErbB3, EpCAM, Folate receptor, Ephrine receptor, TRAIL receptor 2, CD19, CD20, CD30, CD33, CD40, CD37, CD38, and CD138.

In one embodiment, the first and/or the second binding domain is an antigen-binding fragment of an antibody. In another embodiment, the antigen-binding fragment is selected from the group consisting of an scFv, a CDR, a Fv, an immunoglobulin VL domain, an immunoglobulin VH domain, an immunoglobulin VL and a VH domain, a Fab, a camelid VHH, a dAb. In yet a further embodiment, the antigen-binding fragment is humanized. In other embodiments, the antigen-binding fragment is derived from a mouse, rat, or rabbit monoclonal antibody, and the antigen-binding fragment may also be derived from a fully human antibody. In this regard, the fully human antibody is generated from phage display, yeast display, or a human antibody gene transgenic mouse.

In one embodiment, the antigen binding fragment: 1) comprises the VHCDRs and the VLCDRs set forth in SEQ ID NOs: 139-144, respectively; 2) comprises the VHCDRs and the VLCDRs set forth in SEQ ID NOs: 145-150, respectively; 3) comprises the VH present within the scFv as set forth in the amino acid sequence of any one of SEQ ID Nos: 78, 88, and 94; 4) comprises the VL present within the scFv as set forth in the amino acid sequence of any one of SEQ ID Nos: 78, 88, and 94; or 5) comprises an ScFV selected from any one of the amino acid sequences set forth in SEQ ID NOs: 78, 88, and 94.

In certain embodiments, of the multi-specific Fab fusion proteins, the CL region comprises a knob or hole mutation and the CH1 region comprises a corresponding knob or hole mutation such that the CL region and CH1 region stably interact.

In another embodiment, the multi-specific Fab fusion proteins disclosed herein, comprise any one of the amino acid sequences selected from SEQ ID NOs: 84, 90, 96, and 100; and any one of the amino acid sequences selected from SEQ ID NOs: 32, 60, 64, 68, and 72. In a further embodiment, the multi-specific Fab fusion protein of this disclosure comprise any one of the amino acid sequences selected from SEQ ID NOs: 86, 92, 98, and 102; and any one of the amino acid sequences selected from SEQ ID NOs: 30, 36, 40, 44, 48, and 52. In certain embodiments, the CL and CH1 regions are connected by a disulfide bond.

Another aspect of the present disclosure provides an isolated polynucleotide encoding any of the multi-specific Fab fusion proteins disclosed herein, and expression vectors comprising the isolated polynucleotides. This disclosure also provides isolated host cells comprising such vectors. The present disclosure also provides methods of expressing a multi-specific Fab fusion protein by culturing the host cells under conditions in which the isolated polynucleotide expresses the encoded multi-specific Fab fusion protein.

The present disclosure also provides pharmaceutical compositions comprising the multi-specific Fab fusion proteins described herein and a pharmaceutically acceptable carrier.

Another aspect of the present disclosure provides methods for treating a cancer comprising administering an effective amount of a pharmaceutical composition comprising the multi-specific Fab fusion proteins described herein and a pharmaceutically acceptable carrier to a subject having the cancer or suspected of having the cancer, wherein the cancer is associated with an antigen to which the multi-specific Fab fusion protein can bind.

BRIEF DESCRIPTION OF THE DRAWINGS

FIG. 16: ELISA binding assay showed that: A) OKT3 Fab and EpCAM1.1×OKT3 bispecific Fab fusion proteins have no binding activity towards the recombinant cyno CD3epsilon/delta heterodimeric Fc protein; and B) OKT3 Fab and bispecific fusions have no binding activity towards the recombinant human CD3epsilon N-terminal peptide (aa1-27.Fc fusion). Fab and Fab fusion proteins were biotinylated and the -biotinylated antibodies bound to antigens immobilized on 96-well plate were detected using streptavidin-HRP conjugate followed by ABTS substrate for detection.

FIG. 17: ELISA binding assay showed that hu-1F3 Fab and EpCAM1.1×hu-1F3 bispecific Fab fusion proteins (MSFP; Fabe) have positive binding activities A) towards the recombinant cyno CD3epsilon/delta Fc(K+H) heterodimeric protein; and B) towards the recombinant human CD3epsilon N-terminal peptide (aa1-27.Fc fusion). Fab and Fab fusion proteins were biotinylated and the biotin-antibodies bound to 96-well plate immobilized antigens were detected using streptavidin-HRP conjugate followed by ABTS as substrate for detection.

FIG. 18: ELISA binding assay showed that hu-1F3 Fab and EpCAM1.2×hu-1F3.1 MSFP have positive binding activities A) towards the recombinant cyno CD3epsilon/delta Fc(K+H) heterodimeric protein; and B) towards the recombinant human CD3epsilon N-terminal peptide (aa1-27.Fc fusion). Fab and Fab fusion proteins were biotinylated and the labeled fusion proteins bound to 96-well plate immobilized antigens were detected using streptavidin-HRP conjugate followed by ABTS as substrate for detection.

FIG. 19: ELISA binding assay showed that hu-1F3.1 Fab and EpCAM2.2×hu-1F3 MSFP have positive binding activities A) towards the recombinant cyno CD3epsilon/delta Fc(K+H) heterodimeric protein; and B) towards the recombinant human CD3epsilon N-terminal peptide (aa1-27.Fc fusion). Fab and Fab fusion proteins were biotinylated and the biotin-labeled fusion proteins bound to 96-well plate immobilized antigens were detected using streptavidin-HRP conjugate followed by ABTS substrate for detection.

FIG. 20: EpCAM×CD3 MSFP binding to CHO cells stably expressing full length human EpCAM (hu-EpCAM-FL) target on cell surface by FACS analysis. Anti CD3 Fab has no binding to the same CHO cells as expected. EpCAM×CD3 MSFPs show positive binding to EpCAM expressed on CHO cells FIG. 21: FACS based assay to detect PBMC (T cells) mediated cell killing activity redirected by EpCAM×CD3 MSFP in a tumor target dependent manner. In this assay, target cells (CHO cells stably expressing human EpCAM-FL on cell surface (A, B, D) and control cells (CHO only, C) were labeled with PKH-26 fluorescence dye (Sigma, according to product instruction) prior to assay. TO-PRO-3 iodide (TP3, Invitrogen) was used to identify dead cells at the end of the cell killing assay. In this assay, dead target cells were identified from the counts in the upper-right quadrant (PKH-26 positive, TP3 positive) and the live target cells were identified from the upper-left quadrant (PKH-26 positive, TP3 negative). A) EpCAM expressing CHO cells incubated (for 20 hrs) with EpCAM2.2×CD3 MSFP but without PBMCs had ~1.4% dead cells (PKH-26 labelled TP3 positive cells); B) EpCAM-expressing CHO cell incubated (for 20 hrs) with PBMCs but without MSFP had ~14% dead cells among the PKH-26 labelled populations (non specific killing activity of PBMC; C) non EpCAM-expressing CHO cells incubated (for 20 hrs) with PBMCs and EpCAM2.2×CD3 MSFP had a ~14% dead cells (non specific killing activity of PBMCs); and D) EpCAM-expressing CHO cells incubated (for 20 hrs) with PBMCs and examplary EpCAM×CD3 MSFP had ~64% dead cell counts. The tumor cell target dependent % killing activity of EpCAM2.2×CD3 MSFP is ~50% (comparing C and D or B and D)

FIG. 22: The redirected T cell cytolytic activity of MSFPs towards the EpCAM-expressing CHO cells using the FACS assay described in FIG. 18. A) OKT3 Fab and its MSFPs lack significant redirected cytolytic activity; While hu-1F3.1 Fab had no activity towards target cells, B) EpCAM1.1×hu-1F3.1 MSFP had high level activity and the activity level remained high even at 60 pMMSFPs; C) dose dependent activities were detected by EpCAM1.2×hu-1F3.1 MSFP; and D) dose dependent cytolytic activities were detected for EpCAM2.2 scFv single fusions to hu-1F3.1 Fab. For double fusion of EpCAM2.2 scFv to both the HC and LC of hu-1F3.1 Fab, a maximum killing of 50% cell population were observed and the activity level remained high (~40%) when its concentration was at as low as 60 pM. Percentage killing activities were calculated by subtracting percentage of dead cells in the control assay (EpCAM-CHO+PBMC+no MSFP) from the percentage of dead cells in the sample assay.

FIG. 23: T cell activation (in PBMC) by EpCAM2.2-(H+L)-hu-1F3.1 MSFP is tumor target dependent. A) PBMCs incubated with EpCAM2.2-(H+L)-hu-1F3.1 (30 nM) in the presence of non EpCAM-expressing CHO resulted in basal level T cell activation measured by CD69 expression by FACS analysis; B) PBMCs incubated with EpCAM2.2-(H+L)-hu-1F3.1 (30 nM, 16 hrs) in the presence of non EpCAM-expressing CHO resulted in significant increase of T cell activation measured by CD69 expression detected by FACS assay.

DETAILED DESCRIPTION

Figure 1:
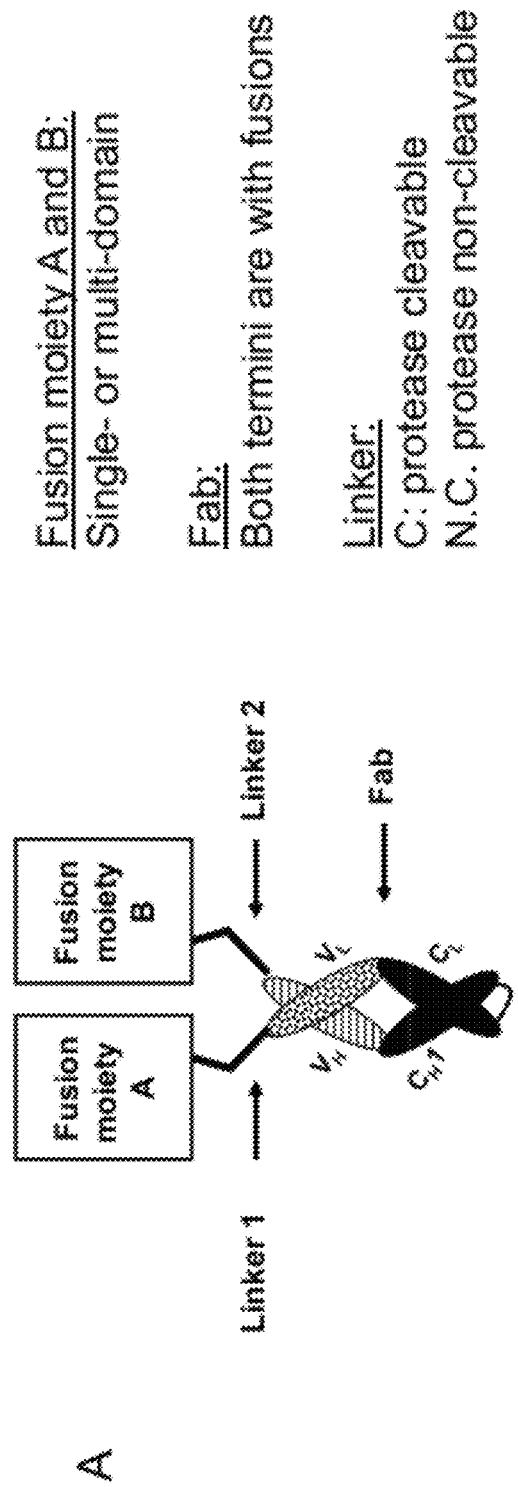
FIG. 1. Schematic diagram depicting a multi-specific Fab fusion protein (MSFP). Fusion moiety A and fusion moiety B, single-domain or multi-domain proteins, are covalently fused to the N-terminal ends of a Fab fragment through linker sequences that are either cleavable or non-cleavable by proteases. Fusion moiety A and fusion moiety B can have antigen-specific binding capability or have no antigen specific binding capability.
Figure 2:
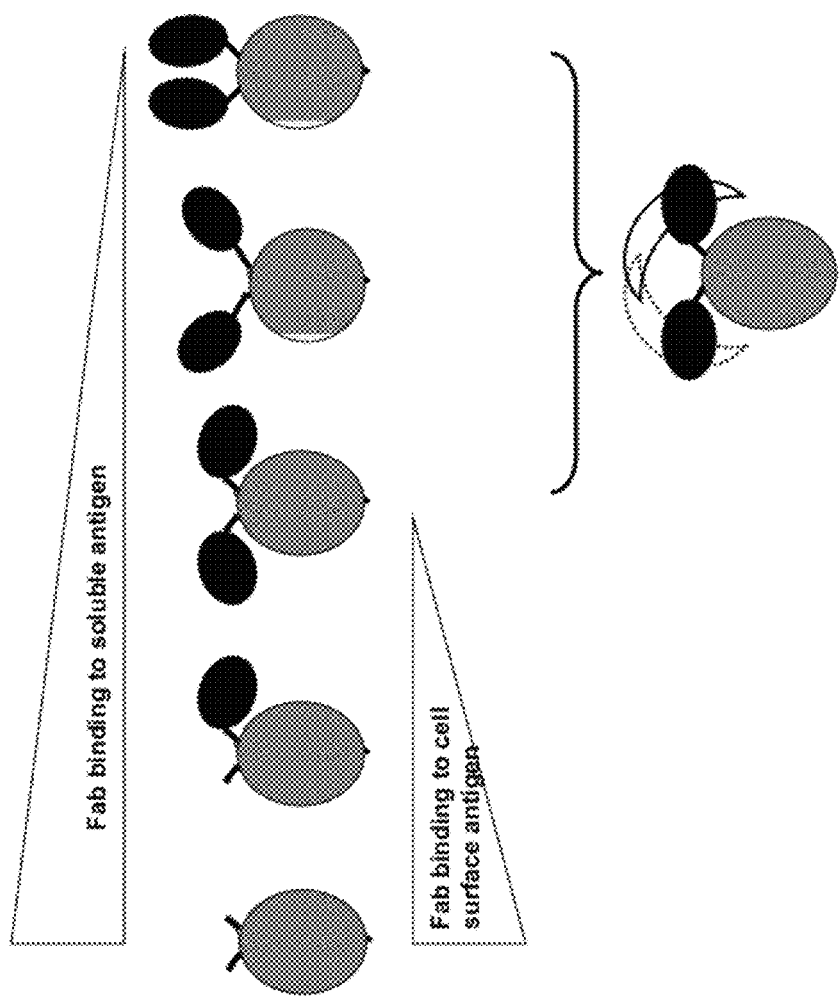
FIG. 2. Schematic diagram depicting different conformations of the fusion moieties in MSFP and the relative strength of Fab binding affinities to cell surface target or soluble form of the target. The lower panel of the figure shows the conformational flexibility of the fusion moieties in MSFP.
Figure 3:
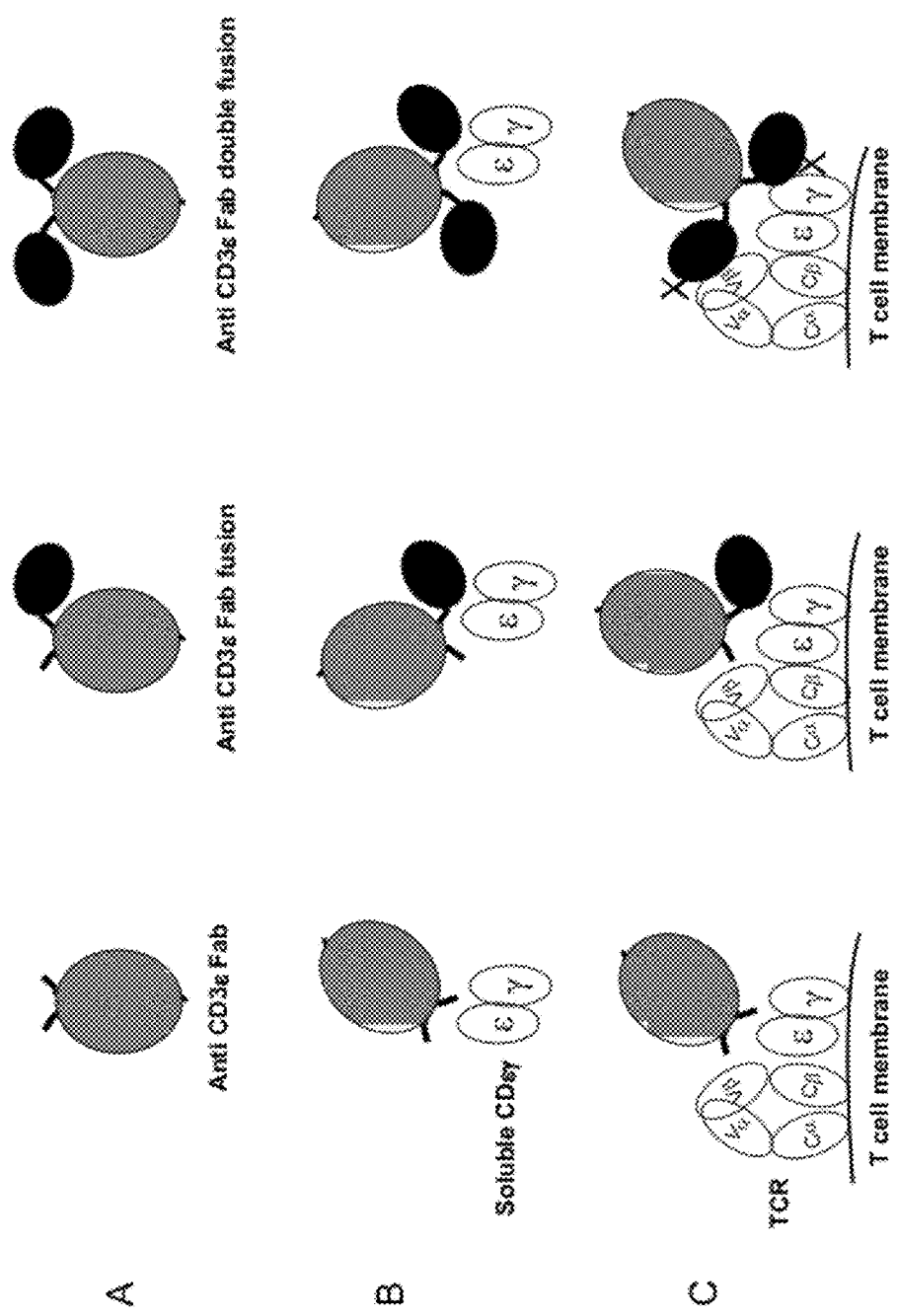
FIG. 3. Schematic diagrams illustrating the binding properties of Fab in different fusion formats to soluble and cell surface targets. A, the structures of a Fab, a fusion protein of Fab with a single fusion moiety at one of the N-termini, and a fusion protein of Fab with fusion moieties at both N-termini of the Fab; B. Schematic diagrams depicting the Fab in all three Fab fusion formats capable of binding to its soluble target; C. Schematic diagrams depicting the Fab domain without fusion and with single fusion moiety at the N-terminus of Fab can bind to its target on cell surface, However, a Fab domain with fusions at the N-termini of both H- and L-chain can no longer bind to its target presented on cell surface due to steric hindrance.
Figure 4:
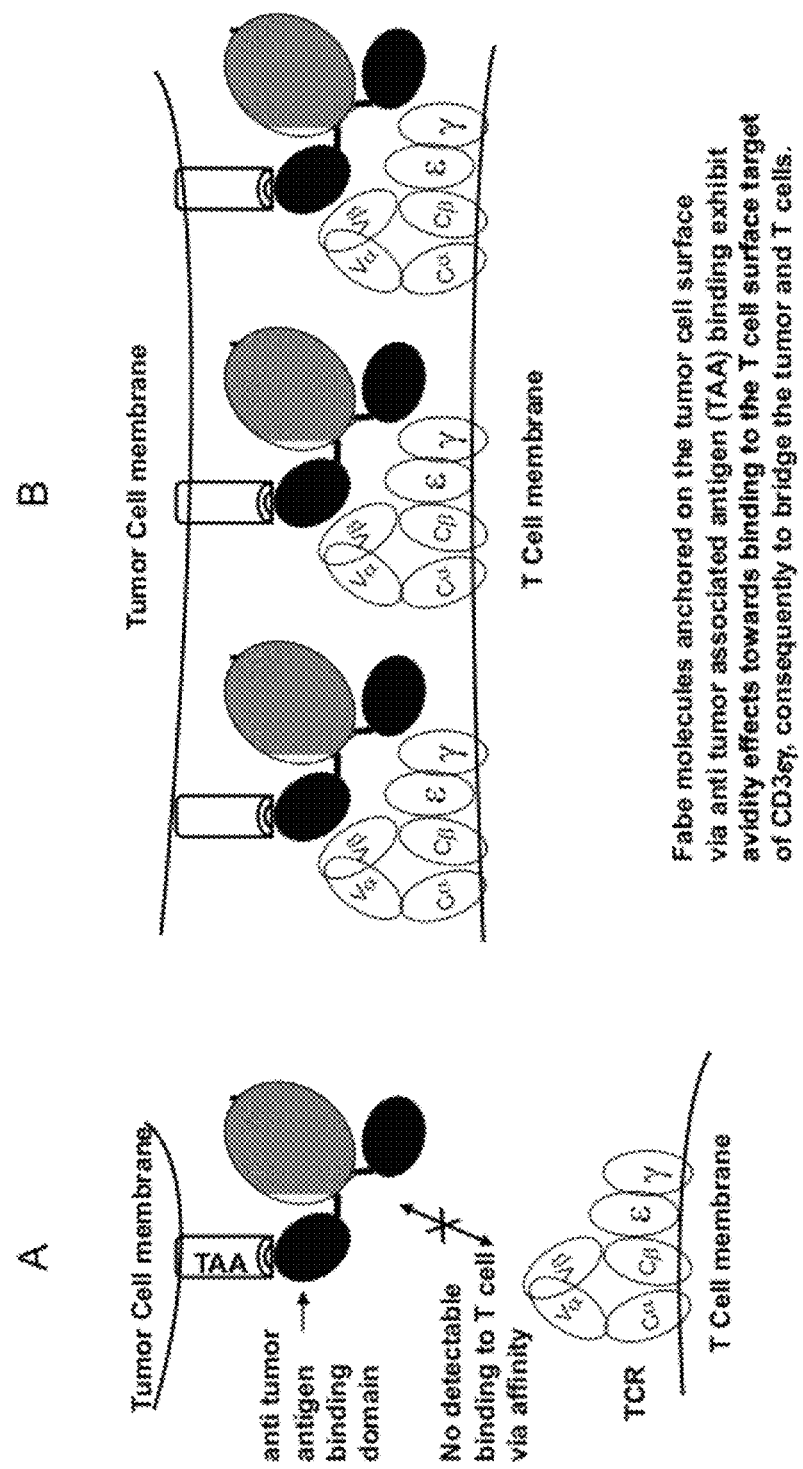
FIG. 4. Schematic diagram depicting the necessary condition for a MSFP binding to T cells: A, MSFP with anti tumor cell surface target binding moieties at the N-termini of both H- and L-chain can bind to a tumor cell through tumor associated antigen (TAA) but does not bind to CD3 on a T cell (because of the dramatically reduced affinity, see FIG. 3C), B. When MSFP molecules with low affinity binding to CD3 on T cells can effectively engage tumor and T cells by avidity effects. Representative MSFP molecules are clustered on tumor cell through TAA binding, the CD3 binding arms will bind to a T cell via avidity, resulting in bridging a tumor cell and a T cell.
Figure 5:
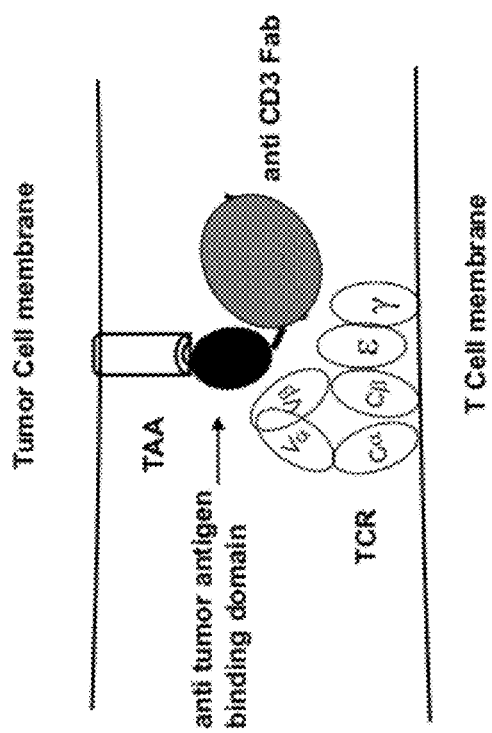
FIG. 5. Schematic diagram depicting a Fab fusion with single anti-tumor cell surface target moiety (or a single arm cleavage product from a Fab fusion at both H- and L-chain) can bind to targets both on tumor and T cell resulting in bridging the two cell types.
Figure 6:
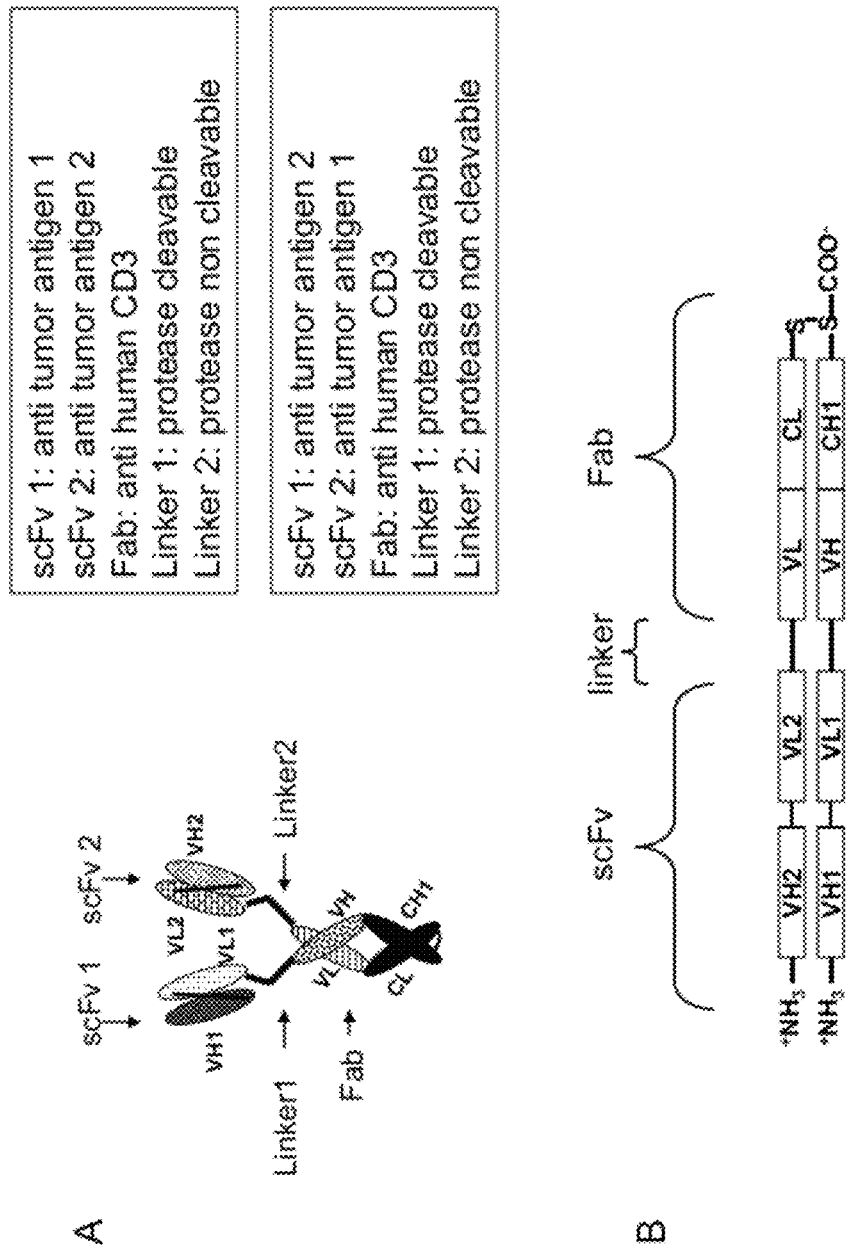
FIG. 6. A, Schematic diagram of Fabe showing two single chain Fv (scFv) domains as fusion moieties. A Fabe refers to a MSFP wherein the Fab binding target is an immune cell surface effector molecules, such as CD3 epsilon chain or T cell receptor on T cells, NKG2D on NK cells, or Fc gamma receptor on NK, monocytic cells and macrophage. The two scFv domains can have the same specificity or different specificities; B, schematic diagram of protein domains and the inter-chain disulfide bond in primary sequences. The inter chain disulfide bond between the CH and CL is optional. The configuration of the scFv can be in either VH-VL or VL-VH and the VH and VL configuration in scFv1 and scFv2 can be the same or different.
Figure 7:
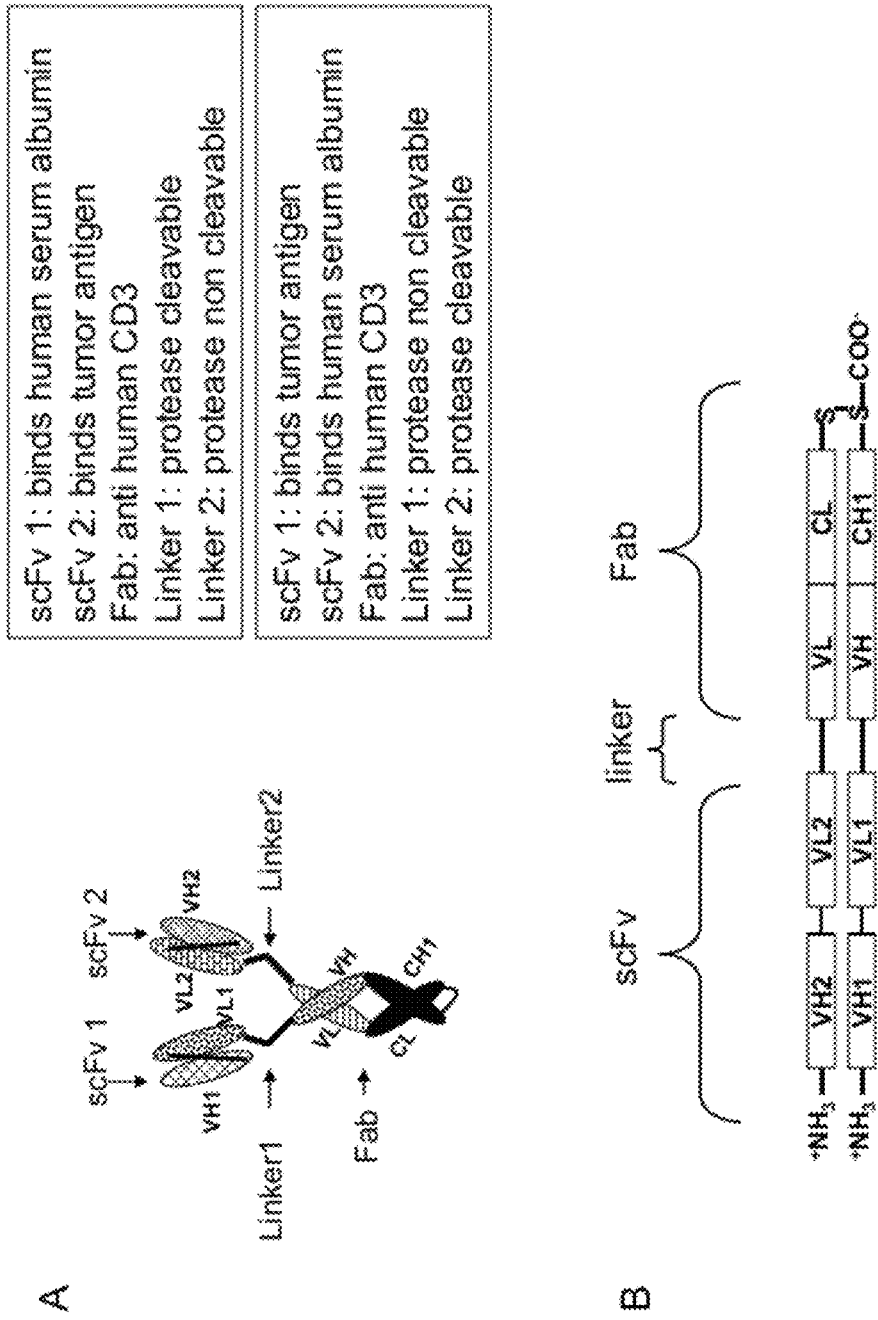
FIG. 7. A, Schematic diagram of Fabe-albu showing two single chain Fv (scFv) domains as fusion moieties. A Fabe-albu is a specific type of Fabe where one scFv has binding specificity to human albumin and the second scFv has binding specificity to tumor cell surface antigen (TAA); B, schematic diagram of protein domains and inter-chain disulfide bond in primary sequences. The configuration of the scFv can be in either VH-VL or VL-VH and the VH and VL configuration in scFv1 and scFv2 can be the same or different.
Figure 8:
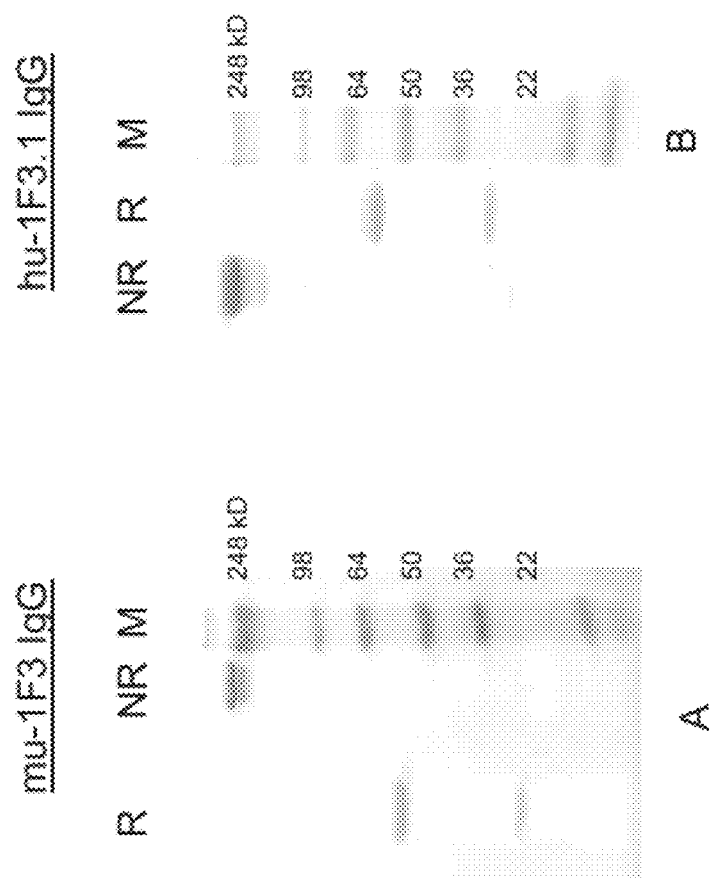
FIG. 8. 4-20% tris glycine SDS-PAGE (polyacrylamide gel analysis) (Invitrogen) of mouse anti human CD3 antibody 1F3 and a humanized 1F3 antibody, hu-1F3. Gel was stained using simply blue reagent (Invitrogen). "NR" is under non reducing and "R" is under reducing condition with 5% mercaptoethanol. Protein bands indicate both antibodies have normal sizes of intact IgG, IgGHC and IgGLC.

The present disclosure relates to multi-specific Fab fusion proteins (MSFP). In particular, the MSFP of the present disclosure comprise a Fab fragment which binds a particular target antigen of interest (e.g., CD3, T cell receptor, NKG2D, or FcγR) and has one or two fusion moieties which bind to one or, in some embodiments, two additional target antigens (e.g., a serum albumin protein, a tumor antigen or other disease-associate antigen).

It is envisioned that the effectiveness of cancer treatment including the efficacy, safety, costs related to the manufacturing of drug substance and route of drug administration can be dramatically improved by developing innovative drugs possessing most or all of the following attributes:

1. Enhanced selectivity for targeting tumor cells over normal cells using bivalent tumor associated antigen (TAA) binding molecules. The energetics of antibody and antigen interaction is usually expressed by the terms of affinity and avidity. Avidity is distinct from affinity, which is a term used to describe the strength of a single site interaction between an antibody binding domain and an antigen. As such, avidity is the combined synergistic strength of affinities. Antibody binding to tumor cells is dependent on the intrinsic binding affinity, the number of binding sites present on an antibody (valency) and the density of the target antigen on cells (Reynolds, *Biochemistry* 18:264-9, 1979). When a monovalent antibody is used, the measured binding strength is related to affinity. When a bivalent or multivalent antibody is used for cell binding, avidity is usually measured. Higher antigen concentration usually leads to higher avidity. It is known that many tumor cells overexpress TAA on the tumor cell surface. MSFP with two anti tumor target binding domains can have selectively higher binding to tumor cells over-expressing TAA than normal tissue cells also expressing the same target. Based on the avidity principle, Adams et al. successfully demonstrated that using a bivalent anti her2/neu antibody fragment improved the accumulation in tumor mass 3 times better than using a corresponding monovalent version of the same antibody fragment (Adams et al., *Clin Cancer Res* 12:1599-1605, 2006). In terms of tumor targeting, high affinity of antibody usually results in the accumulation at the periphery of the tumor mass while high avidity effect leads to deeper penetration of the antibody into the tumors.

2. Enhanced selectivity at targeting tumor over normal cells using bispecific antibodies. Bispecific reagents can be designed for their goals to bind and kill tumor cells more selectively over normal cells and ultimately to increase the efficacy and safety over a monospecific reagent (Chang et al., Mol Cancer Ther 1:553, 2002; Kipriyanov and Le Gall, Curr Opin Drug Discov Devel 7:233, 2004). Requirement for the presence of both antigens on tumor cells and careful design of proper affinities of each antigen binding arm are critical aspects of this approach. For example, MM-111 is an anti Her2 and Her3 bispecific fusion protein designed to use her2 arm to target the drug to cancer cells and to use anti her3 arm to inhibit the her3 receptor heterodimerization and signaling in cancer cells (Robinson et al., British Journal of Cancer 99, 1415-1425, 2008). Important aspects considered for the design of MM-111 include: 1) relatively restricted tissue expression pattern and cancer cell overexpression of Her2, 2) broad tissue expression of Her3 and critical importance of Her3 signalling in cancer cell growth and survival, 3) high affinity binding to Her2 (1.1 nM) and low affinity binding to Her3 (160 nM). In an in vitro binding assay, MM-111 demonstrated up to 9.7 fold high binding to Her2/Her3 doubly positive cells than Her2 single positive cells while there was no detectable binding to Her3 single positive cells at a concentration as high as 1 µM (Robinson et al., British Journal of Cancer 99, 1415-1425, 2008).

Thus, the present disclosure provides these and other advantages as described further herein. In particular, the MSFP of the present disclosure provide distinct advantages, including but not limited to the following: 1) The MSFP do not bind or have reduced binding to the primary Fab target when the Fab is bound to fusion moieties. E.g., an MSFP comprising an anti-CD3 Fab does not bind to or has significantly reduced binding to CD3 when the Fab is bound to fusion moiety A and fusion moiety B, particularly when the fusion moieties are not engaged with their target. This lowers unwanted side-effects (e.g., unwanted general activation of T cells prior to binding tumor cells) or other cells expressing Fab target antigen). 2) Bivalent binding or bispecific binding enhances the selectivity of the MSFP for tumor versus normal cells. 3) The MSFP is relatively large (~75-100 kD) thereby avoiding fast renal clearance (filtration threshold size for renal clearance is 70 kD) but is smaller than a regular antibody (150 kD) which allows improved tumor tissue penetration. 5) The ability of some MSFP to bind serum albumin dramatically enhances the circulation half-life. 6) The MSFP structure tends to be more stable than fusion proteins having only scFv.

In certain embodiments, the MSFPs of the present disclosure are bivalent with respect to binding a specific target antigen (e.g., tumor antigen) and are bispecific in that it binds a target tumor antigen via the fusion moieties and a second target antigen via the Fab binding domain (e.g., CD3, T cell receptor, NKG2D, or FcγR) which enhances its efficacy though activation of, for example, the immune system against cells expressing a particular target antigen.

The illustrative MSFP of the present disclosure comprises an anti-CD3 Fab. However, other Fab targets are specifically contemplated herein. Concerning the anti-CD3 Fab, to date, protein molecules directed against the TCR complex either, together with T cell activation, also induce a T cell signal resulting in a cytokine storm, which can result in severe side effects, or have little effect on cells in the absence of cross-linking. The present MSFP provides the advantage of inhibiting TCR (CD3) binding and activation unless the MSFP first binds to a secondary target antigen, e.g., a tumor antigen, thus activating T cells. This greatly reduces unwanted cytokine storm and unwanted activation of T cells in the absence of the desired target cell (e.g., a tumor cell target).

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); Oligonucleotide Synthesis (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

"C-terminal" of a polypeptide as used herein refers to the last amino acid residue of the polypeptide which donates its amine group to form a peptide bond with the carboxyl group of its adjacent amino acid residue. "N-terminal" of a polypeptide as used herein refers to the first amino acid of the polypeptide which donates its carboxyl group to form a peptide bond with the amine group of its adjacent amino acid residue.

The term "covalently link" as used herein refers to direct linking through one or more chemical bonds or indirect linking through one or more linkers.

Any suitable chemical bonds can be used to make a direct link, including without limitation, covalent bonds such as peptide bond and disulfide bond, non-covalent bonds such as hydrogen bond, hydrophobic bond, ionic bond, and Van der Waals bond.

A "covalent bond" refers herein to a stable association between two atoms which share one or more electrons. Examples of the covalent bonds include, without limitation, a peptide bond and a disulfide bond. "Peptide bond" as used herein refers to the covalent bond formed between the carboxyl group of an amino acid and the amine group of the adjacent amino acid. "Disulfide bond" as used herein refers to a covalent bond formed between two sulfur atoms. A disulfide bond can be formed from oxidation of two thiol groups. In certain embodiments, the covalently link is direct link through a covalent bond. In certain embodiments, the covalently link is direct link through a peptide bond or a disulfide bond.

A "non-covalent bond" refers herein to an attractive interaction between two molecules or two chemical groups that does not involve sharing of electrons. Examples of non-covalent bonds include, without limitation, a hydrogen bond, a hydrophobic bond, an ionic bond, and a Van der Waals bond. A "hydrogen bond" refers herein to attractive force between a hydrogen atom of a first molecule/group and an electronegative atom of a second molecule/group. A "hydrophobic bond" refers herein to a force that causes hydrophobic or non-polar molecules/groups to aggregate or associate together in an aqueous environment. An "ionic bond" refers herein to an attraction between a positive ion and a negative ion. A "Van der Waals bond" refers herein to a non-specific attraction force between two adjacent molecules/groups which have momentary random fluctuations in the distribution of electrons. In certain embodiments, the covalently link is direct link through a non-covalent bond. In certain embodiments, the covalently link is direct link through a hydrogen bond, a hydrophobic bond, an ionic bond, or a Van der Waals bond.

A binding domain (or a fusion protein thereof) "specifically binds" to a target molecule if it binds to or associates with a target molecule with an affinity or Ka (i.e., an equilibrium association constant of a particular binding interaction with units of 1/M) of, for example, greater than or equal to about $10^5$ M$^{-1}$. In certain embodiments, a binding domain (or a fusion protein thereof) binds to a target with a Ka greater than or equal to about $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. "High affinity" binding domains (or single chain fusion proteins thereof) refers to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, at least $10^{13}$ M$^{-1}$, or greater. Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides and fusion proteins according to the present disclosure can be readily determined using conventional techniques (see, e.g., Scatchard et al. (1949) Ann. N.Y. Acad. Sci. 51:660; and U.S. Pat. Nos. 5,283,173; 5,468,614, or the equivalent).

"Derivative" as used herein refers to a chemically or biologically modified version of a compound (e.g., a protein) that is structurally similar to a parent compound and (actually or theoretically) derivable from that parent compound.

The term "steric hindrance" refers to the prevention or retardation of a binding interaction between molecules, resulting from their sizes or spatial disposition.

The term "avidity" is a term used to describe the combined strength of multiple bond interactions. Avidity is distinct from affinity, which is a term used to describe the strength of a single bond. With regard to antibodies, avidity refers to antibody interactions in which multiple antigen binding sites simultaneously interact with targets. Individually, each binding interaction may be readily broken, however, when many binding interactions are present at the same time, transient unbinding of a single site does not allow the molecule to diffuse away, and binding of that site is likely to be reinstated. The overall effect is synergistic, strong binding of antigen to antibody.

Multi-Specific Fab Fusion Proteins

The present disclosure provides multi-specific Fab fusion proteins (MSFP; also referred to in the figures as Fabe where the Fab binds to an immune effector molecule, such as CD3 epsilon chain, T cell receptor, NKG2D, or FcγR) that comprise a Fab fragment (e.g., of the basic structure NH$_2$-VL-CL-S-S-CH1-VH-NH$_2$) having attached thereto a first fusion moiety at the N-terminal end of the VL and/or a second fusion moiety attached at the N-terminal end of the VH. Between the fusion moities and the VH and VL there may be a linker which is optionally protease cleavable. This general format is the basic structure that can be built upon to construct more complex homodimer multi-specific Fab fusion protein complexes depending on the fusion moieties used as described further below.

Prior to the present application, there has been no description for a Fab-based fusion having fusion moieties at the N-terminal end of both the heavy chain and the light chain of the Fab. As would be understood by the skilled person, such fusions would severely cripple Fab binding affinity thus to render them practically non-useful. This general notion of reduced binding upon fusion of binding domain(s) to the N-terminus of a Fab was observed in MSFP. For example, fusion to the N-terminus of the OKT3 anti-CD3 Fab significantly reduced the binding to the Fab target and resulted in almost complete loss of biological activity of the bispecific Fab fusion proteins. However it is surprising that fusion of antigen binding domains to the N-terminus of the hu-1F3.1 humanized anti-CD3 Fab, in some cases did not result in significant loss of binding to the Fab target. In some cases, loss of binding to cell surface target was more significant than to the soluble protein target. In some other cases, loss of binding did not result in loss of biological activity. On the contrary, MSFP with lower binding affinity to CD3 on T cells can have higher biological activity. While this is surprising, it underscores the importance of at least, but not limited to, two factors: 1) upon high binding to tumor cells (using the binding domains of fusion moieties A and B), MSFP exhibit high avidity to overcome the low affinity of the Fab portion for binding to T cells, thus inducing killing; 2) It is highly antibody-, therefore epitope-dependent because OKT3 Fab fusion proteins behaved completely differently than the anti CD3 antibody, 1F3 derived MSFPs. The MSFP in this disclosure made with Fab fragments derived from antibodies binding to the CD3 epsilon epitope recognized by 1F3 and its humanized variants, possesses many uniques features and these features can be utilized to develop human therapeutics with desirable attributes in drug safety, efficacy and manufacturability. As described herein, this property is used advantageously in the MSFP of the present disclosure to mask Fab binding until the MSFP are in an appropriate environment (e.g., in the vicinity of a tumor).

The specific structural components of the MSFP are described in more detail in the sections below. The function of the MSFP is described in more detail in the section below entitled "Function of the Multi-Specific Fab Fusion Proteins".

Fab Fragment

As noted above, the multi-specific Fab fusion proteins disclosed herein comprise at their core, a Fab fragment. As would be understood by the skilled person, a Fab fragment is the antigen-binding fragment of an antibody. The Fab is composed of one constant and one variable region of an immunoglobulin heavy and an immunoglobulin light chain. The heavy chain constant and variable regions heterodimerize with the light chain variable and constant regions and are usually covalently linked by a disulfide bond between the heavy and light chain constant regions (see e.g., diagram in FIG. 1). Thus, as used herein, "Fab" with regard to an antibody generally refers to that portion of the antibody consisting of a single light chain (both variable and constant regions) bound to the variable region and first constant region of a single heavy chain by a disulfide bond.

As would be recognized by the skilled person, a disulfide bond between the heavy and light chain is preferable, but not essential for function (Orcutt, et al. (2010), PEDS, 23:221-228). Thus, in certain embodiments the Fab fragment of the present invention may not comprise a disulfide bond. In this regard, the heavy and light chains may be engineered in such a way so as to stably interact without the need for disulfide bond. For example, in certain embodiments, the heavy or light chain can be engineered to remove a cysteine residue and wherein the heavy and light chains still stably interact and function as a Fab. In one embodiment, mutations are made to facilitate stable interaction between the heavy and light chains. For example, a "knobs into holes" engineering strategy can be used to facilitate dimerization between the heavy and light chains of a Fab (see e.g., 1996 Protein Engineering, 9:617-621). Using this strategy, "knobs" are created by replacing small amino acid side chains at the interface between interacting domains with larger ones. Corresponding "holes" are made at the interface between interacting molecules by replacing large side chains with smaller ones. Thus, also contemplated for use herein are variant Fab fragments designed for a particular purpose, for example, amino acid changes in the constant domains of CH1 and or CL, and removal of a disulfide bond or addition of tags for purification, etc.

In another embodiment, the configuration of the variable and constant regions within the Fab fragment may be different from what is found in a native Fab. In other words, in one embodiment, the orientation of the variable and constant regions may be VH-CL in one chain and in another VL-CH1 (Shaefer et al. (2011), PNAS, 108:111870-92). Such modified Fab fragments still function to bind their particular target antigen and are contemplated for use in the MSFPs of the present invention. Thus, in this regard the variable regions and constant regions that make up the Fab are considered modular.

In certain embodiments, the Fab fragments of this disclosure are derived from monoclonal antibodies and may be derived from antibodies of any type, including IgA, IgM, IgD, IgG, IgE and subtypes thereof, such as IgG1, IgG2, IgG3, and IgG4. The light chain domains may be derived from the kappa or lambda chain. The Fab fragments for use herein may be made recombinantly.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also humanized antibodies, chimeric antibodies, and any other modified configuration of the immunoglobulin molecule that comprises an antigen-binding site or fragment (epitope recognition site) of the required specificity.

The Fab fragment as disclosed herein comprises an antigen-binding portion comprised of an immunoglobulin heavy chain variable region and an immunoglobulin light chain variable region (VH and VL). More specifically, the term "antigen-binding portion" as used herein refers to a polypeptide fragment that contains at least one CDR of an immunoglobulin heavy and/or light chains that binds to the target antigen of interest, such as the CD3 molecule. In this regard, an antigen-binding portion of the herein described multi-specific Fab fusion proteins may comprise 1, 2, 3, 4, 5, or all 6 CDRs of a VH and VL sequence of a parent antibody that binds to a target antigen of interest. In certain embodiments, the antigen-binding portion of the Fab fragment of an MSFP binds to CD3.

In certain embodiments, a specific VH and/or VL of the MSFP described herein may be used to screen a library of the complementary variable region to identify VH/VL with desirable properties, such as increased affinity for a target antigen of interest. Such methods are described, for example, in Portolano et al., J. Immunol. (1993) 150:880-887; Clarkson et al., Nature (1991) 352:624-628.

Other methods may also be used to mix and match CDRs to identify Fab having desired binding activity (such as binding to CD3, or other target antigen of interest as described herein for other binding domains present in the fusion moieties of the MSFP). For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antigen-binding fragments of antibodies according to several embodiments of the disclosure described herein, using routine methodology in the art.

Also disclosed herein is a method for obtaining an antibody antigen binding domain specific for a target antigen (e.g., CD3 or any target antigen described elsewhere herein for targets of fusion moiety binding domains), the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for a target antigen of interest (e.g., CD3) and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody, or Fab or scFv thereof, "specifically binds" or "preferentially binds" to a target if it binds with greater affinity, avidity, more readily, and/or with greater duration than it binds to other substances. For example, an antibody that specifically or preferentially binds to a CD3 epitope is an antibody that binds one CD3 epitope with greater affinity, avidity, more readily, and/ or with greater duration than it binds to other CD3 epitopes or non-CD3 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/ or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_D$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) can be determined by calculation of the concentrations and the actual rates of association and the "off rate constant" ($k_{off}$) and can be determined by the actual rates of dissociation. The ratio of $k_{off}/k_{on}$ is thus equal to the dissociation constant $K_D$. See, generally, Davies et al. (1990) *Annual Rev. Biochem.* 59:439-473.

The term "antigen" refers to a molecule or a portion of a molecule capable of being bound by a selective binding agent, such as an antigen-binding portion of a Fab fragment, and additionally capable of being used in an animal to produce antibodies capable of binding to an epitope of that antigen. An antigen may have one or more epitopes.

The term "epitope" includes any determinant, in certain embodiments, a polypeptide determinant, capable of specific binding to an immunoglobulin or T-cell receptor. An epitope is a region of an antigen that is bound by an antibody or an antigen-binding fragment thereof. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an MSFP is said to specifically bind an antigen when it preferentially recognizes its target antigen in a complex mixture of proteins and/or macromolecules. An MSFP is said to specifically bind an antigen when the equilibrium dissociation constant is $\leq 10^{-5}$, $10^{-6}$ or $10^{-7}$ M. In some embodiments, the equilibrium dissociation constant may be $\leq 10^{-8}$ M or $\leq 10^{-9}$ M. In some further embodiments, the equilibrium dissociation constant may be $\leq 10^{-10}$ M or $\leq 10^{-11}$ M In certain embodiments, antigen-binding portions of the Fab fragment as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable regions may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In one particular embodiment of the present disclosure, the Fab fragment binds to CD3. "T cell receptor" (TCR) is a molecule found on the surface of T cells that, along with CD3, is generally responsible for recognizing antigens bound to major histocompatibility complex (MHC) molecules. It consists of a disulfide-linked heterodimer of the highly variable (alpha) and (beta) chains in most T cells. In other T cells, an alternative receptor made up of variable Y and (delta) chains is expressed. Each chain of the TCR is a member of the immunoglobulin superfamily and possesses one N-terminal immunoglobulin variable region, one immunoglobulin constant region, a transmembrane region, and a short cytoplasmic tail at the C-terminal end (see, Abbas and Lichtman, Cellular and Molecular Immunology (5th Ed.), Editor: Saunders, Philadelphia, 2003; Janeway et ai, Immunobiology: The Immune System in Health and Disease, 4th Ed., Current Biology Publications, p 148, 149, and 172, 1999). TCR as used in the present disclosure may be from various animal species, including human, mouse, rat, or other mammals.

"Anti-TCR Fab" or "Anti-TCR Fabe", refers to a Fab or an MSFP comprising such a Fab that specifically binds to a TCR molecule or one of its individual chains (e.g., TCR(alpha), TCR(beta), TCRY or TCR(delta) chain). In certain embodiments, an anti-TCR Fab binds to a TCR(alpha), a TCR(beta), or both.

"CD3" is known in the art as a multi-protein complex of six chains (see, Abbas and Lichtman, 2003; Janeway et al., p 172 and 178, 1999). In mammals, the complex comprises a CD3 (gamma) chain, a CD3(delta) chain, two CD3(epsilon) chains, and a homodimer of CD3(zeta) chains. The CD3 (gamma), CD3(delta), and CD3(epsilon) chains are highly related cell surface proteins of the immunoglobulin super-family containing a single immunoglobulin domain. The transmembrane regions of the CD3(gamma), CD3(delta), and CD3(epsilon) chains are negatively charged, which is a characteristic that allows these chains to associate with the positively charged T cell receptor chains. The intracellular tails of the CD3(gamma), CD3(delta), and CD3(epsilon) chains each contain a single conserved motif known as an immunoreceptor tyrosine-based activation motif or ITAM, whereas each CD3(zeta) chain has three. Without wishing to be bound by theory, it is believed the ITAMs are important for the signaling capacity of a TCR complex. CD3 as used in the present disclosure may be from various animal species, including human, mouse, rat, or other mammals.

"Anti-CD3 Fab" as used herein, refers to a Fab that specifically binds to individual CD3 chains (e.g., CD3(gamma) chain, CD3(delta) chain, CD3(epsilon) chain) or a complex formed from two or more individual CD3 chains (e.g., a complex of more than one CD3(epsilon) chains, a complex of a CD3(gamma) and CD3(epsilon) chain, a complex of a CD3 (delta) and CD3(epsilon) chain). In certain embodiments, an anti-CD3 Fab specifically binds to a CD3(gamma), a CD3 (delta), a CD3(epsilon), or any combination thereof, and in certain embodiments, a CD3(epsilon). In one embodiment, an anti-CD3 Fab binds to the N-terminus of CD3 epsilon. In one particular embodiment, the anti-CD3 Fab binds to amino acids 1-27 of CD3 epsilon.

"TCR complex," as used herein, refers to a complex formed by the association of CD3 with TCR. For example, a TCR complex can be composed of a CD3(gamma) chain, a CD3(delta) chain, two CD3(epsilon) chains, a homodimer of CD3(zeta) chains, a TCR(alpha) chain, and a TCR(beta) chain. Alternatively, a TCR complex can be composed of a CD3(gamma) chain, a CD3(delta) chain, two CD3(epsilon) chains, a homodimer of CD3(zeta) chains, a TCRY chain, and a TCR(delta) chain.

"A component of a TCR complex," as used herein, refers to a TCR chain (i.e., TCR(alpha), TCR(beta), TCRY or TCR (delta)), a CD3 chain (i.e., CD3(gamma), CD3(delta), CD3 (epsilon) or CD3(zeta)), or a complex formed by two or more TCR chains or CD3 chains (e.g., a complex of TCR(alpha) and TCR(beta), a complex of TCRY and TCR(delta), a complex of CD3(epsilon) and CD3(delta), a complex of CD3

(gamma) and CD3(epsilon), or a sub-TCR complex of TCR (alpha), TCR(beta), CD3(gamma), CD3(delta), and two CD3 (epsilon) chains).

By way of background, the TCR complex is generally responsible for initiating a T cell response to antigen bound to MHC molecules. It is believed that binding of a peptide:MHC ligand to the TCR and a co-receptor (i.e., CD4 or CD8) brings together the TCR complex, the co-receptor, and CD45 tyrosine phosphatase. This allows CD45 to remove inhibitory phosphate groups and thereby activate Lck and Fyn protein kinases. Activation of these protein kinases leads to phosphorylation of the ITAM on the CD3(zeta) chains, which in turn renders these chains capable of binding the cytosolic tyrosine kinase ZAP-70. The subsequent activation of bound ZAP-70 by phosphorylation triggers three signaling pathways, two of which are initiated by the phosphorylation and activation of PLC-(gamma), which then cleaves phosphatidylinositol phosphates (PIPs) into diacylglycerol (DAG) and inositol trisphosphate (IP3). Activation of protein kinase C by DAG leads to activation of the transcription factor NFKB. The sudden increase in intracellular free $Ca^{2+}$ as a result of IP3 action activates a cytoplasmic phosphatase, calcineurin, which enables the transcription factor NFAT (nuclear factor of activated T cells) to translocate form the cytoplasm to the nucleus. Full transcriptional activity of NFAT also requires a member of the AP-1 family of transcription factors; dimers of members of the Fos and Jun families of transcription regulators.

A third signaling pathway initiated by activated ZAP-70 is the activation of Ras and subsequent activation of a MAP kinase cascade. This culminates in the activation of Fos and hence of the AP-1 transcription factors. Together, NFKB, NFAT, and AP-1 act on the T cell chromosomes, initiating new gene transcription that results in the differentiation, proliferation and effector actions of T cells. See, Janeway et al., p 178, 1999.

In certain embodiments, the Fab specifically binds to an individual human CD3 chain (e.g., human CD3(gamma) chain, human CD3(delta) chain, and human CD3(epsilon) chain) or a combination of two or more of the individual human CD3 chains (e.g., a complex of human CD3(gamma) and human CD3(epsilon) or a complex of human CD3(delta) and human CD3(epsilon)). In certain preferred embodiments, the Fab specifically binds to a human CD3(epsilon) chain.

In certain other embodiments, a Fab of the present disclosure specifically binds to TCR(alpha), TCR(beta), or a heterodimer formed from TCR(alpha) and TCR(beta). In certain embodiments, a Fab specifically binds to one or more of human TCR(alpha), human TCR(beta), or a heterodimer formed from human TCR(alpha) and human TCR(beta).

In certain embodiments, a Fab of the present disclosure binds to a complex formed from one or more CD3 chains with one or more TCR chains, such as a complex formed from a CD3(gamma) chain, a CD3(delta) chain, a CD3(epsilon) chain, a TCR(alpha) chain, or a TCR(beta) chain, or any combination thereof. In other embodiments, a Fab of the present disclosure binds to a complex formed from one CD3 (gamma) chain, one CD3(delta) chain, two CD3(epsilon) chains, one TCR(alpha) chain, and one TCR(beta) chain. In further embodiments, a Fab of the present disclosure binds to a complex formed from one or more human CD3 chains with one or more human TCR chains, such as a complex formed from a human CD3(gamma) chain, a human CD3(delta) chain, a human CD3(epsilon) chain, a human TCR(alpha) chain, or a human TCR(beta) chain, or any combination thereof. In certain embodiments, a Fab of the present disclosure binds to a complex formed from one human CD3(gamma) chain, one human CD3(delta) chain, two human CD3(epsilon) chains, one human TCR(alpha) chain, and one human TCR(beta) chain.

Fabs of this disclosure can be generated as described herein or by a variety of methods known in the art (see, e.g., U.S. Pat. Nos. 6,291,161; 6,291,158). Sources of Fabs include monoclonal antibody nucleic acid sequences from various species (which can be formatted as antibodies, Fvs, scFvs or Fabs, such as in a phage library), including human, camelid (from camels, dromedaries, or llamas; Hamers-Casterman et al. (1993) Nature, 363:446 and Nguyen et al. (1998) J. Mol. Biol., 275:413), shark (Roux et al. (1998) Proc. Nat'l. Acad. Sci. (USA) 95:11804), fish (Nguyen et al. (2002) Immunogenetics, 54:39), rodent, avian, or ovine.

An anti human CD3 antibody with cross reactivity to monkey CD3 is particularly desirable, such as the SP34 mouse monoclonal antibody, which binds specifically to human CD3 in denatured form (western blot or dot blot) and in native form (on T cells) (Pressano, S. The EMBO J. 4:337-344, 1985; Alarcon, B. EMBO J. 10:903-912, 1991). SP34 mouse monoclonal antibody also binds to CD3ε singly transfected COS cells as well as CD3ε/γ or CD3ε/δ double transfectants (Salmeron A. et al., J. Immunol. 147:3047-52, 1991). SP34 antibody also cross reacts non-human primates (Yoshino N. et al., Exp. Anim 49:97-110, 2000; Conrad M L. et al., Cytometry 71A:925-33, 2007). In addition, SP34 activates T cell when cross-linked (Yang et al., J. Immunol. 137:1097-1100, 1986). Cross-reactivity to monkey CD3 is important as this allows toxicity studies to be carried out in non-human primates using the clinical candidate directly, rather than in chimpanzee or using a surrogate molecule. Thus, toxicity studies using such cross-reactive anti-CD3 Fab in an MSFP of the present disclosure provide more relevant safety assessments.

Other illustrative anti-CD3 antibodies include the Cris-7 monoclonal antibody (Reinherz, E. L. et al. (eds.), Leukocyte typing II., Springer Verlag, New York, (1986)), BC3 monoclonal antibody (Anasetti et al. (1990) J. Exp. Med. 172: 1691), OKT3 (Ortho multicenter Transplant Study Group (1985) N. Engl. J. Med. 313:337) and derivatives thereof such as OKT3 ala-ala (Herold et al. (2003) J. Clin. Invest. 11:409), visilizumab (Carpenter et al. (2002) Blood 99:2712), and 145-2C11 monoclonal antibody (Hirsch et al. (1988) J. Immunol. 140: 3766). Further CD3 binding molecules contemplated for use herein include UCHT-1 (Beverley, P C and Callard, R. E. (1981) Eur. J. Immunol. 11: 329-334) and CD3 binding molecules described in WO2004/106380; WO2010/ 037838; WO2008/119567; WO2007/042261; WO2010/ 0150918.

An exemplary anti-TCR antibody is H57 monoclonal antibody (Lavasani et al. (2007) Scandinavian Journal of Immunology 65:39-47).

In certain embodiments, the Fab binds to other cell surface targets, including but not limited to, FcγRI, FcγRIIa, FcγRIIb, FcγRIIIa, FcγRIIIa, NKG2D, CD25, CD28, CD137, CTLA-4, FAS, FGFR1, FGFR2, FGFR3, FGFR4, GITR, LTβR, TLR, TRAIL receptor 1, TRAIL receptor 2, EGFR, Her2/ neu, and ErbB3.

Antigen binding fragment sequences (e.g., heavy and light chain variable region sequences) for Fab fragments may be available in public databases or using traditional strategies for hybridoma development using a CD3 chain, TCR component, or other Fab binding target as an immunogen in convenient systems (e.g., mice, HUMAB MOUSE®, TC MOUSE®, KM MOUSE®, llamas, chicken, rats, hamsters, rabbits, etc.) can be used to develop Fabs for use herein. As would be understood by the skilled person, Fab fragments may be generated using various technologies known in the art, including antibody display technologies such as phage, yeast, ribosome and mRNA display technologies; B cell culture technology such as SLAM technology; or using high throughput gene sequencing technologies on B cells or plasma B cells isolated from an immunized animal subject or immunized human subject.

Illustrative Fabs for use in the MSFPs of the present disclosure include the VH, Fd, HC, VL, and LC amino acid sequences, and the polynucleotides encoding them, as set forth in SEQ ID NOs: 29-76, including CDRs thereof, such as those set forth in SEQ ID NOs: 23-28.

Fusion Moieties

The fusion moieties of the MSFP as described herein not only provide additional binding specificities and/or functional attributes to the MSFP (e.g., increased serum half-life, activation of ADCC or other immune activation cascades), but also create steric hindrance to significantly reduce the binding of the Fab to its target antigen, except where/when intended (e.g. in the presence of tumor cells), particularly binding of the Fab to a target on a cell surface, especially Fab target antigens that are close to the cell membrane (such as CD3) and therefore have restricted accessibility. This is in direct contrast to other Fab fusion proteins, such as TRIBODIES™, which fuse additional binding domains at the C terminus of the Fab fragment (see e.g., *Journal of Immunology,* 2000, 165: 7050-7057).

Further, within a single MSFP, the first and second fusion moieties are not intended to dimerize. This distinguishes the MSFP of the present disclosure from other known fusion proteins such as those described in WO2008/024188 and WO2009/149185. The constructs described in the '188 and '185 publications differ by having the general format of VH1-VH2-CH1-hinge-CH2-CH3 and VL1-VL2-CL. In this construct, the VH1 and VL1 dimerizes to form an additional antigen combining site. This differs from the format of the MSFP described herein, for example as shown in FIG. 7B. In the MSFP of the present disclosure, the first and second fusion moieties do not associate to form a single antigen combining site. A further distinguishing characteristic of the MSFP, as described elsewhere herein, is that the fusion moeities reduce the binding affinity of the Fab to its target when the MSFP is not clustered on a target such as a cell surface target. On the contrary, the proteins described in WO2008/024188 and WO2009/149185 do not exhibit reduced binding affinities for the antibody binding target.

The fusion moieties of the MSFP of the present disclosure may comprise a binding domain, one or more functional domains, or a combination thereof. As depicted in FIG. 1, in one embodiment, the MSFP of the present disclosure comprise two fusion moieties, shown as Fusion moiety A and Fusion moiety B in FIG. 1. The fusion moieties may also be referred to herein as a first fusion moiety and a second fusion moiety, or similar language to distinguish one from the other. Illustrative fusion moieties comprise the amino acid sequences set forth in SEQ ID NOs: 78, 88, and 94, encoded by the polynucleotide set forth in SEQ ID NOs: 77, 87, and 93; or a CDR, VH or VL thereof (see e.g. SEQ ID Nos: 139-150).

In certain embodiments, the first and second fusion moieties are identical. In further embodiments, both fusion moieties comprise identical binding domains but may differ in other respects by having or lacking functional domains. In another embodiment, the first fusion moiety comprises a first binding domain that binds a first target antigen and the second fusion moiety comprises a second binding domain that binds a second target antigen.

In certain embodiments, the first and second fusion moieties each comprise a binding domain and these may be referred to as the first and second binding domains, respectively. In certain embodiments, the first binding domain binds to the same target as the second binding domain. In this regard, the first binding domain may, in certain embodiments, bind to the same target as the second binding domain in the sense that the targets share at least one similarity, for example without limitation, the targets comprise both protein, polynucleotide, or lipid, the targets are the same protein though may be different splice forms; or in certain embodiments, the targets have the same amino acid sequence though may have different modifications, such as glycosylation. In certain embodiments, the first binding domain binds to the same target as the second binding domain but on different epitopes of the same target. In certain embodiments, the first and second binding domains bind to different targets.

In another embodiment, the first fusion moiety comprises a first binding domain and the second fusion moiety comprises a second binding domain wherein the first and second binding domains bind the same target molecule but are of different formats (e.g., the first binding domain is an scFv that binds to a cell surface receptor and the second binding domain is a ligand for the receptor; or similarly, the first binding domain is an scFv that binds to a ligand, the second binding domain is an extracellular domain of the receptor for the ligand).

Binding Domains

As noted above, in certain embodiments, the first and/or second fusion moieties comprise a binding domain. A "binding domain" or "binding region" according to the present disclosure may be, for example, any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable region regions, or the light and heavy chain variable region regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE™ analysis).

Illustrative binding domains are described further herein below. In certain embodiments, the target molecule may be a cell surface expressed protein, such as a receptor or a tumor antigen. In another embodiment, the target molecule bound by a binding domain useful herein is a soluble antigen such as a cytokine, albumin, or other serum protein. Illustrative binding domains include immunoglobulin antigen-binding domains such as scFv, scTCR, extracellular domains of receptors, ligands for cell surface molecules/receptors, or receptor binding domains thereof, and tumor binding proteins. In certain embodiments, the antigen binding domains can be an scFv, a VH, a VL, a domain antibody variant (dAb), a camelid antibody (VHH), a fibronectin 3 domain variant, an ankyrin repeat variant and other antigen-specific binding domain derived from other protein scaffolds.

Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

Examples include, without limitation, a complementarity determining region (CDR), a variable region (Fv), a heavy chain variable region (VH), a light chain variable region (VL), a heavy chain, a light chain, a single chain variable region (scFv), a Fab, a single domain camel antibody (camelid VHH), and single domain antibodies (dAb).

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as λ or κ. Immunoglobins comprising the α, δ, ε, γ, and μ heavy chains are classified as immunoglobin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

"Complementarity determining region" or "CDR" with regard to an antibody refers to a highly variable loop in the variable region of the heavy chain or the light chain of an antibody. CDRs can interact with the antigen conformation and largely determine binding to the antigen (although some framework regions are known to be involved in binding). The heavy chain variable region and the light chain variable region each contain 3 CDRs. The CDRs can be defined or identified by conventional methods, such as by sequence according to Kabat et al (Wu, T T and Kabat, E. A., J Exp Med. 132(2):211-50, (1970); Borden, P. and Kabat E. A., PNAS, 84: 2440-2443 (1987); Kabat, E. A. et al, Sequences of proteins of immunological interest, Published by DIANE Publishing, 1992), or by structure according to Chothia et al (Choithia, C. and Lesk, A. M., J. Mol. Biol., 196(4): 901-917 (1987), Choithia, C. et al, Nature, 342: 877-883 (1989)).

"Heavy chain variable region" or "VH" with regard to an antibody refers to the fragment of the heavy chain that contains three CDRs interposed between flanking stretches known as framework regions, which are more highly conserved than the CDRs and form a scaffold to support the CDRs.

"Light chain variable region" or "VL" with regard to an antibody refers to the fragment of the light chain that contains three CDRs interposed between framework regions.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" with regard to an antibody refers to an engineered antibody consisting of a light chain variable region and a heavy chain variable region connected to one another directly or via a peptide linker sequence.

"Single domain camel antibody" or "camelid VHH" as used herein refers to the smallest known antigen-binding unit of a heavy chain antibody (Koch-Nolte, et al, FASEB J., 21: 3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"Single domain antibody" or "dAb" refers to an antibody fragment that consists of the variable region of an antibody heavy chain (VH domain) or the variable region of an antibody light chain (VL domain) (Holt, L., et al, Trends in Biotechnology, 21(11): 484-490).

The term "disulfide bond" as used herein refers to the binding of a heavy chain fragment and a light chain fragment through one or more disulfide bonds. The one or more disulfide bonds can be formed between the two fragments by linking the thiol groups in the two fragments. In certain embodiments, the one or more disulfide bonds can be formed between one or more cysteine residues in the heavy chain fragment and the light chain fragment, respectively.

A "variable region linking sequence" is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In certain embodiments, a hinge useful for linking a binding domain to an immunoglobulin CH2 or CH3 region polypeptide may be used as a variable region linking sequence (see further discussion of hinges elsewhere herein).

In certain embodiments, a binding domain comprises a non-antibody component. The non-antibody component which binds to an antigen can be any suitable protein domain or components that can recognize and bind to a target antigen of interest, such as for example, protein domains that involve in protein-protein interactions, in protein-lipid interactions, in protein-polynucleotide interactions, in protein-sugar interactions, or in ligand binding. Examples of suitable non-antibody component include, without limitation, Fibronectin 3 domain (Fn3), an ankryin repeat, and an Adnectin.

An alternative source of binding domains of this disclosure includes sequences that encode random peptide libraries or sequences that encode an engineered diversity of amino acids in loop regions of alternative non-antibody scaffolds, such as fibrinogen domains (see, e.g., Weisel et al. (1985) Science 230:1388), Kunitz domains (see, e.g., U.S. Pat. No. 6,423, 498), lipocalin domains (see, e.g., WO 2006/095164), V-like domains (see, e.g., US Patent Application Publication No. 2007/0065431), C-type lectin domains (Zelensky and Gready (2005) FEBS J. 272:6179), or Fcab™ (see, e.g., PCT Patent Application Publication Nos. WO 2007/098934; WO 2006/072620), or the like.

In certain embodiments, a binding domain comprises an Fn3 domain. "Fibronectin 3 domain" or "Fn3" as used herein refers to an autonomous folding unit in fibronectin which is involved in binding to biological molecules (Calaycay, J. et al, J. Biol. Chem., 260(22): 12136-41 (1985); Koide, A. et al, J. Mol. Biol., 284(4): 1141-1151 (1998); Bloom, L. et al, Drug Discovery Today, 14(19-20): 949-955 (2009)). The Fn3 domain can be found in a variety of proteins and different repeats of Fn3 domain are found to contain binding sites for biological molecules such as DNA and proteins.

In certain embodiments, a binding domain comprises adnectin. "Adnectin" as used herein refers to a genetically engineered protein that is based on an Fn3 domain (Koide, A. et al, Methods Mol. Biol., 352: 95-109 (2007)). The Fn3 domain in Adnectin contains three loops that mimics the three CDRs of the variable region of an antibody, and can be genetically tailored for specific binding to different target molecules.

In certain embodiments, a binding domain comprises an ankyrin repeat. "Ankyrin repeat" as used herein refers to a protein component containing repeats of a 33-amino acid residue found in erythrocyte ankyrin (Davis, L. H. et al, J. Biol. Chem., 266(17): 11163-11169 (1991)). Ankyrin repeat is known as one of the most common protein-protein interaction structure that occurs in a large number of proteins with different functions.

As depicted in the Figures, scFv are particularly illustrative binding domains. The scFv as used as a binding domain of a fusion moiety may bind to any of a variety of target molecules, including but not limited to FcγRI, FcγRIIa FcγRIIb FcγRIIIa FcγRIIIb, CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1) and TRAIL receptor 2, carcinoembryonic antigen (CEA), prostate-specific membrane antigen (PSMA) protein, prostate stem cell antigen (PSCA) protein, B cell maturation antigen (BCMA; also known as human tumor necrosis factor receptor superfamily member 17 (TNFRSF17) and CD269), tumour-associated protein carbonic anhydrase IX (CAIX), hepatocyte growth factor receptor (HGFR), epidermal growth factor receptor 1 (EGFR1), human epidermal growth factor receptor 2 (Her2/neu; Erb2), ErbB3, epithelial cell adhesion molecule (EpCAM), Folate receptor, ephrin receptors, CD19, CD20, CD30, CD33, CD40, CD37, CD38, and CD138.

In certain embodiments, the binding domain binds to a tumor antigen. Illustrative tumor antigen target molecules include, without limitation, p53, cMet, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, BRCA1, BRCA2, MART-1, MC1R, Gp100, PSA, PSM, Tyrosinase, Wilms' tumor antigen (WT1), TRP-1, TRP-2, ART-4, CAMEL, CEA, Cyp-B, Her2/neu, hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, and TEL/AML1. These and other tumor proteins are known to the skilled artisan.

Other binding domains useful in the fusion moieties of the MSFP of the present disclosure include ligands which bind to cell surface receptors. Illustrative ligands include, but are not limited to, ligands for cell surface receptors such as CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1) and TRAIL receptor 2, carcino-embryonic antigen (CEA), prostate-specific membrane antigen (PSMA) protein, prostate stem cell antigen (PSMA) protein, B cell maturation antigen (BCMA; also known as human tumor necrosis factor receptor superfamily member 17 (TNFRSF17) and CD269), tumour-associated protein carbonic anhydrase IX (CAIX), hepatocyte growth factor receptor (HGFR), epidermal growth factor receptor 1 (EGFR1), human epidermal growth factor receptor 2 (Her2/neu; Erb2), ErbB3, epithelial cell adhesion molecule (EpCAM), Folate receptor, ephrin receptor, CD19, CD20, CD30, CD33, CD40, CD37, CD38, and CD138.

In one embodiment, a binding domain binds to serum albumin. Binding to human serum albumin offers the potential to extend the half life ($t_{1/2}$) of a protein drug to several days or even longer. It is known in the prior art that serum albumin binding or fusion to serum albumin can significantly extend the half life of a therapeutic molecule. In certain embodiments, the binding domain which binds to human serum albumin can cross react with the non human primate orthologue, permitting estimation of the half life of the drug in preclinical animal toxicological studies that may be more relevant to treatment in humans.

In certain embodiments, the binding domain specifically binds to an antigen target that is associated with a disease condition. The disease condition may include a physiological condition, a pathological condition and a cosmetic condition. Examples of illustrative conditions include, without limitation, cancer, inflammatory disorders, allograft transplantation, type I diabetes, type II diabetes, and multiple sclerosis.

In certain embodiments, the antigen target is negatively associated with the condition. In certain embodiments, the binding of the antigen target by an MSFP comprising a binding domain can inactivate or antagonize the biological function of the antigen target, and thereby improve the condition. In certain embodiments, the binding of the antigen target by an MSFP comprising a binding domain will activate or antagonize the biological function of the antigen target, and thereby improve the condition. As such the MSFPs described herein may be agonist or antagonist molecules with respect to the fusion moiety target antigens.

Illustrative binding domains are provided in SEQ ID NOs: 78, 88, 94 (amino acid) and SEQ ID NOs: 77, 87, 93 (polynucleotide) and include CDRs, VH, and VL thereof (see e.g. SEQ ID Nos: 139-150).

Thus, the binding domains as described herein can specifically bind to any suitable antigen targets. As noted, examples of suitable antigen targets include, without limitation, TNF receptor (Shen H. M. et al, FASEB J. 20(10):1589-98 (2006)), cMet (Bottaro, D. P. et al, Science, 251 (4995): 802-804 (1991)), CD3 (Chetty R. et al, J. Pathol., 173(4): 303-7 (1994)), CD40 (Chatzigeorgiou A. et al, Biofactors., 35(6): 474-83 (2009)), DR3 (Meylan F. et al, Immunity., 29(1):79-89 (2008)), FcγR (Torkildsen O. et al, Acta Neurol Scand Suppl. 183:61-3 (2006)), NKG2D (Obeidy P. et al, Int J Biochem Cell Biol., 41(12):2364-7 (2009)), and any derivative thereof.

In certain embodiments, the binding domains bind specifically to a single target antigen. In another embodiment, the binding domains are cross-reactive with more than one antigen target. "Cross-reactivity" as used herein refers to that a binding domain can specifically bind to more than one antigen target. In certain embodiments, the first binding domain and/or the second binding domain can have cross-reactivity to completely different antigen targets, such as for example, hepatitis C core protein and host-derived GOR protein. In certain embodiments, the first binding domain and/or the second binding domain can have cross-reactivity to an antigen target from a different species, such as for example, an antigen derived from a protein from human, mouse or non-human primates.

Junction Between Fusion Moiety A, B and Fab

In certain embodiments, fusion moiety A and/or fusion moiety B are linked directly to the N-terminus of the VH or VL of the Fab (i.e., with no additional amino acids added between). In other embodiments, fusion moiety A and/or fusion moiety B are linked to the N-terminus of the VH or VL of the Fab using a linker (with additional amino acids as described below). In some embodiments, it may be necessary to delete several amino acids (e.g., from 1-3 amino acids or from 1-10 amino acids; e.g., 1, 2, 3, 4, 5, 6, 7, 8, 9, or 10 amino acids) from the C-terminus of a given fusion moiety A and/or B, depending on the Fab target and the surrounding space of the Fab target on the cell surface (accessability of the Fab target on the cell surface).

In other embodiments, it may be necessary to delete several amino acids (e.g., from 1-3 amino acids or from 1-10 amino acids; e.g., 1, 2, 3, 4, 5, 6, 7, 8, 9, or 10 amino acids) from the N-terminus of the heavy and/or light chain of the Fab. In yet further embodiments, it may be necessary to delete several amino acids (e.g., from 1-3 amino acids or from 1-10 amino acids; e.g., 1, 2, 3, 4, 5, 6, 7, 8, 9, or 10 amino acids) from the C-terminus of the fusion moiety and at the same time, to delete several amino acids (e.g., from 1-3 amino acids or from 1-10 amino acids; e.g., 1, 2, 3, 4, 5, 6, 7, 8, 9, or 10 amino acids) from the N-terminus of the Fab chain. The length and the sequence of the junction between fusion moiety A, fusion moiety B and the Fab fragment can be the same or different.

The junction between the fusion moieties and the Fab fragment may make use of a combination of deletions and linkers as needed. As would be understood by the skilled artisan, the junction between the Fab and the fusion moieties can be adjusted accordingly and tested for desired functionality (e.g., binding affinity) using methods known in the art and described herein.

Linkers

The MSFP of the present disclosure may also comprise a linker situated between the VH and the VL of the Fab fragment and the fusion moieties A and B. (See e.g., FIG. 1). And illustrative linker comprises the sequence GlyArgAla. A In one embodiment, the linker between a fusion moiety and the Fab VH or VL is 1-10 amino acids long. In other embodiments, the linker between a fusion moiety and the Fab VH or VL is 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long.

In certain embodiments, linkers suitable for use in the MSFP described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO: 125) and $(GGGS)_n$ (SEQ ID NO: 126), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 127), Gly-Gly-Ser-Gly-Gly (SEQ ID NO: 128), Gly-Ser-Gly-Ser-Gly (SEQ ID NO: 129), Gly-Ser-Gly-Gly-Gly (SEQ ID NO: 130), Gly-Gly-Gly-Ser-Gly (SEQ ID NO: 131), Gly-Ser-Ser-Ser-Gly (SEQ ID NO: 132), and the like. The ordinarily skilled artisan will recognize that design of an MSFP can include linkers that are all or partially flexible, such that the linker can include a flexible linker as well as one or more portions that confer less flexible structure to provide for a desired MSFP structure.

In certain embodiments, the linker between the Fab and the fusion moieties is a stable linker (not cleavable by protease, especially MMPs). In certain embodiments, the linker is a peptide linker. In certain embodiments, the MSFP comprises a stable peptide linker, and the N-terminal of the peptide linker is covalently linked to the C-terminus of the fusion moiety, and the C terminal of the peptide linker is covalently linked to the N-terminal of the antigen-binding domain.

In one embodiment, the linker is a cleavable linker. In particular, the linker between the Fab VH or VL and a fusion moiety comprises a protease substrate cleavage sequence, for example, an MMP substrate cleavage sequence. A well known peptide sequence of PLGLAG (SEQ ID NO: 133) in a substrate can be cleaved by most MMPs. Substrate sequences that can be cleaved by MMPs have been extensively studied. For example, the sequence of PLGLAG (SEQ ID NO: 133) can be cleaved by most MMPs. A protease substrate cleavage sequence refers to a peptide sequence that can be cleaved by protease treatment. An MMP substrate sequence refers to a peptide sequence that can be cleaved by incubation with a MMP. PLGLAG (SEQ ID NO: 133) is a commonly used MMP substrate cleavage sequence (see e.g., Jiang, PNAS (2004) 101:17867-72; Olson, PNAS (2010) 107:4311-6). In another embodiment, the protease cleavage site is recognized by MMP-2, MMP-9 or a combination thereof. In yet another embodiment, the protease site comprises the sequence selected from the group consisting of GPLGMLSQ (SEQ ID NO: 134) and GPLGLWAQ (SEQ ID NO: 135). A stable linker or a protease non cleavable linker refers to a linker peptide sequence that does not belong to the known protease substrate sequences and thus does not lead to significant cleavage product formation upon incubation with a protease.

In some embodiments, the cleavage substrate (or cleavage sequence) of the linker may include an amino acid sequence that can serve as a substrate for a protease, usually an extracellular protease. In other embodiments, the cleavage sequence comprises a cysteine-cysteine pair capable of forming a disulfide bond, which can be cleaved by action of a reducing agent. In other embodiments the cleavage sequence comprises a substrate capable of being cleaved upon photolysis.

The cleavage substrate is positioned in the linker such that when the cleavage substrate is cleaved by a cleaving agent (e.g., a cleavage substrate of a linker is cleaved by the protease and/or the cysteine-cysteine disulfide bond is disrupted via reduction by exposure to a reducing agent) or by light-induced photolysis, in the presence of a target, resulting in cleavage products having various functional properties as described herein.

The cleavage substrate of a linker may be selected based on a protease that is co-localized in the diseased tissue, or on the surface of the cell that expresses the target antigen of interest of a binding domain of a fusion moiety. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-limiting examples of disease include: all types of cancers (breast, lung, colorectal, prostate, head and neck, pancreatic, etc), rheumatoid arthritis, Crohn's disease, melanomas, SLE, cardiovascular damage, ischemia, etc. Furthermore, anti-angiogenic targets, such as VEGF, are known. As such, where the binding domain of a fusion moiety of the MSFP of the present disclosure is selected such that it is capable of binding a tumor antigen, a suitable cleavage substrate sequence for the linker will be one which comprises a peptide substrate that is cleavable by a protease that is present at the cancerous treatment site, particularly that is present at elevated levels at the cancer treatment site as compared to non-cancerous tissues. In one exemplary embodiment, the binding domain of an MSFP can bind, e.g., Her2 and the cleavage substrate sequence can be a matrix metalloprotease (MMP) substrate, and thus is cleavable by an MMP. In other embodiments, the binding domain of a fusion moiety in the MSFP can bind a target of interest and the cleavage substrate present in the linker can be, for example, legumain, plasmin, TMPRSS-3/4, MMP-9, MT1-MMP, cathepsin, caspase, human neutrophil elastase, beta-secretase, uPA, or PSA. In other embodiments, the cleave substrate is cleaved by other disease-specific proteases, in diseases other than cancer such as multiple sclerosis or rheumatoid arthritis.

The unmodified or uncleaved linker can allow for tethering the Fab fragment to the fusion moiety. When the linker is cleaved, multiple cleavage products with various functions may result as described further herein for example, in the Figures.

The linkers of the MSFP (e.g., the linker between the VH of the Fab and a first fusion moiety and the linker between the VL of the Fab and a second fusion moiety) can comprise the same cleavage substrate or may comprise different cleavage substrates, e.g., the first linker may comprise a first cleavage substrate and the second linker may comprise a second cleavage substrate. The first and second cleavage substrates can be different substrates for the same enzyme (for example exhibiting different binding affinities to the enzyme), or different substrates for different enzymes, or the first cleavage substrate can be an enzyme substrate and the second cleavage substrate can be a photolysis substrate, or the first cleavage substrate can be an enzyme substrate and the second cleavage substrate can be a substrate for reduction, and the like.

For specific cleavage by an enzyme, contact between the enzyme and the cleavage substrate is made. When the MSFP comprising a Fab coupled to a first and a second fusion moiety by first and second linkers having cleavage substrates in the presence sufficient enzyme activity, the cleavage substrate can be cleaved. Sufficient enzyme activity can refer to the ability of the enzyme to make contact with the linker having the cleavage substrate and effect cleavage. It can readily be envisioned that an enzyme may be in the vicinity of the MSFP but unable to cleave because of other cellular factors or protein modification of the enzyme.

Exemplary substrates can include but are not limited to substrates cleavable by one or more of the following enzymes or proteases: ADAM10; Caspase 8, Cathepsin S, MMP 8, ADAM12, Caspase 9, FAP, MMP 9, ADAM17, Caspase 10, Granzyme B, MMP-13, ADAMTS, Caspase 11, Guanidinobenzotase (GB), MMP 14, ADAMTS5. Caspase 12, Hepsin, MT-SP1, BACE, Caspase 13, Human Neutrophil Elastase Neprilysin (HNE), Caspases, Caspase 14, Legumain, NS3/4A, Caspase 1, Cathepsins, Matriptase 2, Plasmin, Caspase 2, Cathepsin A, Meprin, PSA, Caspase 3, Cathepsin B, MMP 1, PSMA, Caspase 4, Cathepsin D, MMP 2, TACE, Caspase 5, Cathepsin E, MMP 3, TMPRSS ¾, Caspase 6, Cathepsin K, MMP 7, uPA, Caspase 7, MT1-MMP.

In another embodiment, the cleavage substrate can involve a disulfide bond of a cysteine pair, which is thus cleavable by a reducing agent such as, for example, but not limited to a cellular reducing agent such as glutathione (GSH), thioredoxins, NADPH, flavins, ascorbate, and the like, which can be present in large amounts in tissue of or surrounding a solid tumor.

Other appropriate protease cleavage sites for use in the cleavable linkers herein are known in the art or may be identified using methods such as those described by Turk et al., 2001 Nature Biotechnology 19, 661-667.

In certain embodiments, the linker can be a peptide linker, a thiol residue-containing peptide linker, such as a cystein residue, a polymer linker or a chemical linker. In certain embodiments, the MSFP comprises a linker where one end of the linker is covalently linked to the C-terminal of the fusion moiety, and the other end of the linker is covalently linked to the N-terminal of the VH or VL of the Fab fragment.

Junctional Amino Acids

In certain embodiments, there may be one or a few amino acid residues between two domains of a MSFP, such as between a binding domain and a linker polypeptide, such as amino acid residues resulting from construct design of the fusion protein (e.g., amino acid residues resulting from the use of a restriction enzyme site during the construction of a nucleic acid molecule encoding a single chain polypeptide). As described herein, such amino acid residues may be referred to "junction amino acids" or "junction amino acid residues", or "peptide spacers".

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide spacer comprises about 1, 5, 10, 15, 20, 25, 30, 35, 40, 45, 50 or more amino acids in length.

Such junctional amino acids link any of the domains of the MSFP In certain embodiments, the junctional amino acid(s) is a hinge or a part of a hinge as defined herein. In certain embodiments, a variable region linking sequence useful for connecting a heavy chain variable region to a light chain variable region may be used as a peptide spacer.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (SEQ ID NO:136) (Chaudhary et al., 1990, *Proc. Natl. Acad. Sci. U.S.A.* 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:137) (Bird et al., 1988, Science 242:423-426).

In some embodiments, spacer sequences are not required when the first and second polypeptides have non-essential N-terminal amino acid regions that can be used to separate the functional domains and prevent steric interference. Two coding sequences or domains of the MSFP of the present disclosure can be fused directly without any junctional amino acids or by using a flexible polylinker composed, for example, of the pentamer Gly-Gly-Gly-Gly-Ser (SEQ ID NO:138) repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

Any suitable linkers can be used to make an indirect link, such as without limitation, peptide linker, polymer linker, and chemical linker. In certain embodiments, the covalent link is an indirect link through a peptide linker.

It should be noted that, within a single MSFP, the first and second fusion moieties do not dimerize. This distinguishes the MSFP of the present disclosure from other known fusion proteins such as those described in WO2008/024188 and WO2009/149185. These constructs differ by having the general format of VH1-VH2-CH1-hinge-CH2-CH3 and VL1-VL2-CL. In this construct, the VH1 and VL1 dimerizes to form an additional antigen combining site. In the MSFP of the present disclosure, the first and second fusion moieties do not associate to form a single antigen combining site. A further distinguishing characteristic of the MSFP, as described elsewhere herein, is that the fusion moeities reduce the binding affinity of the Fab to its target when the MSFP is not clustered. On the contrary, the proteins described in WO2008/024188 and WO2009/149185 do not exhibit reduced binding affinities for the antibody binding target.

Illustrative MSFP of the present disclosure comprise any one of the amino acid sequences selected from SEQ ID NOs: 84, 90, 96, and 100; and any one of the amino acid sequences selected from SEQ ID NOs: 32, 60, 64, 68, and 72. Additional illustrative MSFP of the present disclosure comprise any one of the amino acid sequences selected from SEQ ID NOs: 86, 92, 98, and 102; and any one of the amino acid sequences selected from SEQ ID NOs: 30, 36, 40, 44, 48, and 52.

Function of the Multi-Specific Fab Fusion Proteins

The MSFP of the present disclosure functions to enhance drug stability, specificity, selectivity, potency, and safety and the convenience of drug administration. In certain embodiments, the Fab, when expressed without the fusion moieties fused to its N-terminus, is able to bind to its target antigen in soluble recombinant form (usually the extracellular domain of a receptor protein, e.g., a T cell receptor component such as CD3) as well as on the cell surface. In certain embodiments, the Fab antigen-binding fragment, when expressed with fusion moieties fused to its N-termini of both heavy and light chains and in a monomeric form (non aggregated or not multimeric form), has no binding or has reduced binding or similar level of binding as Fab alone to its specific antigen presented on cell surface at pharmacological concentrations of the drug (concentration of the polypeptide in treated patients) in the absence of target antigen binding by a fusion moiety binding domain. Lack of binding or greatly reduced binding to cell surface antigen in the absence of the target antigen binding by a fusion moiety binding domain may be explained by the dramatically reduced affinity resulting from the designed steric hindrance around the antigen binding site.

Lack of binding or greatly reduced binding to cell surface antigen in the absence of the target antigen binding by a fusion moiety binding domain may be viewed as desirable for MSFP as a human therapeutic. It is important to note that lack of binding or significantly reduced binding of MSFP alone (in the absence of tumor target cells) to, e.g., T cell can, 1) dramatically improve the undesirable systematic T cell activation, therefore to dramatically improve the drug safety profile; 2) dramatically improves the feasibility of subcutaneous route of drug administration; and 3) dramatically increase the drug tolerability of high drug concentration in blood circulation.

It is important to note that T cell binding by antibodies such as OKT3 or UCHT-1 via conformational epitopes may transduce partial signaling, leading either to unwanted T cell activation (causing cytokine storm) or T cell anergy (resulting in T cells unable to kill tumor cells). Mu-1F3, hu-1F3 and its variants binding to a linear epitope of CD3 is conceivably less likely to induce T cell signaling in the absence of cross linking of the CD3. This property may be advantageous for reducing systemic side effects that occur when using OKT3 and UCHT-1 like antibodies.

It is also important to note that once a fusion moiety in a MSFP is cleaved by protease, it functions such that the steric hindrance around the Fab antigen-binding site is removed so that it can then bind to its (Fab) target with high affinity, particularly target antigen expressed on the cell surface. Therefore, following cleavage at the cleavage substrate sequence in a linker (thereby releasing a fusion moiety) the MSFP is converted into a more potent cross linker between tumor and T cells.

Furthermore, it is important to note that once a fusion moiety binding domain binds to its target antigen, the MSFP molecules become highly concentrated on tumor cell surface to create high avidity based binding toward the Fab target (e.g. CD3) on T cells. Therefore, only in the presence of the fusion moiety binding is the Fab antigen-binding fragment able to bind its target thus for MSFP to function as a cross-linker between tumor and T cells.

The properties of the MSFP of the present disclosure allow for relatively high dose of the MSFP in circulation without unwanted side-effects (e.g., the MSFP does not bind to the Fab fragment target antigen (e.g., CD3) when in circulation. This also allows for reduced dosing frequency and promotes tissue penetration by diffusion driven by concentration gradient.

The properties of the MSFP of the present disclosure also allow the potential for the subcutaneous administration which can enhance access to the target. Further, although in certain embodiments the MSFP are permissive for cross linking without protease treatment, in certain particular embodiments, the binding activity and the tumor killing potency increase dramatically after protease treatment.

In one embodiment, the antigen binding domain (Fv) formed by VH and VL is stabilized by the CH1 and CL heterdimerizing domain, and is further stabilized by the disulfide bond, or other stabilizing interaction (e.g., knobs/hole interaction), between CH1 and CL.

In one embodiment, the Fab in the MSFP is sterically hindered by the fusion moieties at its N-termini such that binding to the Fab target antigen (especially when cell surface target antigens are concerned) is reduced in a statistically significant manner (i.e., relative to an appropriate control as will be known to those skilled in the art; e.g., as compared to the same Fab in a format without fusion moieties at its N-termini (both VH and VL)). In a further embodiment, the Fab in the MSFP is sterically hindered by the fusion moieties at its N-termini so the binding to the desirable antigen (especially when cell surface target antigens are concerned) is reduced by at least 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold, or 100 fold, or 1000 fold, or 10,000 fold as compared to the same Fab in a format without fusion moieties at its N-termini (both VH and VL).

In certain embodiments, the affinity of the Fab antigen-binding domain in the fusion protein format for the Fab cell surface target antigen is below 500 nM. In further embodiments, the affinity of the Fab antigen binding domain in the fusion protein format (i.e., the MSFP) demonstrates no significant detectible binding as measured using FACS or other binding measurement method (e.g., cell binding ELISA) at concentration ranges of the therapeutics used in humans. In one embodiment, less than 1% of a population of Fab target cells (e.g., CD3+ cells) will be bound by the Fab fusion protein at a therapeutic concentration (this is in the absence of cells expressing a fusion moiety binding domain target antigen). In one embodiment, less than 5% population of the Fab target cells will be bound by the MSFP at a therapeutic concentration. In yet another embodiment, less than 10% population of the Fab target cells will be bound by the MSFP at a therapeutic concentration.

The elevated level of proteases, especially MMPs, present in tumor tissues will generate cleavage products at the MMP substrate cleavage site of a linker. Because the cleavage of the protease substrate sequence of a linker results in the relief of the steric hindrance at the Fab antigen-binding region, the binding to the Fab cell surface target will be fully restored or at least partially restored. The restored binding can be demonstrated using techniques of FACS, cell-based ELISA) or other cell binding techniques known to the skilled person.

The term "dramatically reduced affinity" refers to at least 30% reduction in the binding of the Fab antigen-binding domain, as compared to the binding when the N-termini of the VH and VL of the Fab are free of fusion moieties. The percentage of reduction can be, for example without limitation, 30%, about 40%, about 50%, about 60%, about 70%, about 80%, about 90%, or about 99% or greater. Methods for detecting binding are known to the skilled person and can be performed using FACS, cell binding ELISA or cell binding using radioisotype labeled antibodies.

The illustrative Fab for use in the MSFP of the present disclosure as described herein is an anti-CD3 Fab. In this regard, the MSFP functions such that, when the fusion moiety binding domain binds to a tumor cell antigen, the Fab is able bind to CD3 of passing T cells, thereby redirecting the T cells and activating them to kill the tumor cell. In another embodiment, the MSFP (also referred to herein as Fabe where the Fab fragment binds to an immune effect or molecule, such as CD3) can exhibit an avidity effect when clustered on tumor cell surface via tumor antigen binding by fusion moiety binding domain(s). As such, the apparent binding to immune cells by the sterically hindered Fab can increase due to avidity. As such, the Fabe/MSFP becomes capable of bridging immune and tumor cells thereby mediating anti tumor activity.

In certain embodiments, separate binding of the Fab to its target antigen or a fusion moiety binding agent binding to its target antigen does not lead to target activation. However, when simultaneously bound, the Fab antigen target and the fusion moiety binding domain antigen target can generate signal transduction. For example, an MSFP can bind to a Fab antigen target which is, e.g., CD3, and a fusion moiety binding domain antigen target which is a tumor surface antigen. When the MSFP is separately bound to either CD3 or tumor surface antigen, the T cells will not be activated, however, when the CD3 and tumor surface antigen are simultaneously bound to the MSFP and when multiple copies of the bound complexes are anchored and clustered on tumor cell surface, the T cells are activated in the vicinity of cancer cells bearing the tumor surface antigen, and therefore significantly enhance the tumor killing efficiency of T cells locally and avoid the side effects due to cytokine storm.

In certain embodiments, the combination of the Fab antigen target and the fusion moiety binding domain antigen target can be CD3 and tumor surface antigen, which combination can enhance tumor killing effects by T cells. In certain embodiments, the combination of the Fab antigen target and the fusion moiety antigen target can be FcγR and tumor surface antigen, which combination can induce FcγR-expressing immune cells to kill tumor cells. In certain embodiments, the combination of the Fab antigen target and the fusion moiety antigen target can be NKG2D and a tumor cell surface antigen, which combination can induce natural killer (NK) cell to kill tumor cells.

In certain embodiments, the first and second fusion moieties comprise binding domains that bind a first and second target antigen. In this way, the MSFP binds three different target antigens (i.e., the Fab target plus two different fusion moiety targets). Thus, in certain embodiments, the Fab antigen target is selected from the group consisting of CD3, TCR, FcγR and NKG2D, and the first and second binding domains of the first and second fusion moieties are two different antigens preferentially expressed on cancer cells. Such an MSFP having three different target antigens may enhance the targeting specificity for tumor cells and prevent killing of normal cells that may express one of the fusion moiety binding domain target antigens or that may express low levels of both fusion moiety binding domain target antigens.

Thus, in an illustrative embodiment, the MSFP of the present disclosure comprises a Fab antigen-binding fragment that binds to the TCR or a component thereof, such as a CD3 polypeptide. As noted above, the MSFP of the present disclosure does not bind to the Fab target antigen except when fusion moiety binding domains engage their target antigen or following a linker cleavage event.

Thus, in certain embodiments, an MSFP of the present disclosure does not or minimally activates T cells in the absence of fusion moiety binding domain target antigen engagement. An MSFP "does not or minimally or nominally activates T cells" if the MSFP does not cause a statistically significant increase in the percentage of activated T cells as compared to activation of T cells in the presence of cells expressing fusion moiety binding domain target antigens (e.g., an appropriate tumor cell/cell line), as measured in at least one in vitro or in vivo assay. Such assays are known in the art and include, without limitation, proliferation assays, CTL chromium release assays (see e.g., Lavie et al., (2000) International Immunology 12(4):479-486), ELISPOT assays, intracellular cytokine staining assays, and others as described, for example, in Current Protocols in Immunology, John Wiley & Sons, New York, N.Y. (2009). In certain embodiments, T cell activation is measured using and in vitro primed T cell activation assay. See also assays as described in the examples herein.

In a related aspect, therefore, the present disclosure provides a method for detecting T cell activation induced by the MSFP that comprises a Fab that specifically bindings to a TCR complex or a component thereof, comprising: (a) providing antigen or mitogen-primed T cells, (b) treating the primed T cells of step (a) with the MSFP that comprises a Fab that specifically binds to a TCR complex or a component thereof, and (c) detecting activation of the primed T cells that have been treated in step (b).

The term "mitogen" as used herein refers to a chemical substance that induces mitosis in lymphocytes of different specificities or clonal origins. Exemplary mitogens that may be used to prime T cells include phytohaemagglutinin (PHA), concanavalin A (ConA), lipopolysaccharide (LPS), pokeweed mitogen (PWM), and phorbol myristate acetate (PMA). Antigen-loaded beads or PBMC can also be used to prime T cells.

In certain embodiments of methods for detecting T cell activation provided herein, the MSFP comprising a Fab that specifically binds to a TCR complex or a component thereof comprises one or more fusion moieties comprising one or more binding domains that bind to tumor antigens.

T cell activation may be detected by measuring the expression of activation markers known in the art, such as CD25, CD40 ligand, and CD69. Activated T cells may also be detected by cell proliferation assays, such as CFSE labeling and thymidine uptake assays (Adams (1969) Exp. Cell Res. 56:55). T cell effector function (e.g., cell killing) can be measured, for example, by chromium release assays or FACS based assays using fluorescent dyes (e.g. TP3). In a related aspect, T cell activation and cytolytic activity can be measured by lytic synapse formation between T cell and tumor cell. Effector molecules such as Granzymes and porforin can be detected in the cytolytic synapse.

In another related aspect, T cell activation may be measured by cytokine release. A method for detecting cytokine release induced by an MSFP that comprises a Fab that specifically binds to a TCR complex or a component thereof, may comprise: (a) providing primed T cells, (b) treating the primed T cells of step (a) with the MSFP that comprises a Fab that specifically binds to a TCR complex or a component thereof, and (c) detecting release of a cytokine from the primed T cells that have been treated in step (b). In particular embodiments, experiments are carried out in the presence or absence of appropriate cancer cells or cell lines expressing target tumor antigens bound by binding domains present in the first and/or second fusion moieties of the MSFP.

In certain embodiments of methods for detecting cytokine release provided herein, the MSFP that comprises a Fab that specifically binds to a TCR complex or a component thereof is an MSFP that further comprises fusion moieties that comprise binding domains that bind to a tumor target antigen.

In further preferred embodiments, the MSFP of the present disclosure do not induce a cytokine storm or do not induce a cytokine release sufficient to induce toxic side-effects. An MSFP "does not induce a cytokine storm" (also referred to as "inducing an undetectable, nominal, or minimal cytokine release" or "does not induce or induces a minimally detectable cytokine release") if, in the absence of secondary target cells (e.g., tumor cells expressing antigens bound by binding domain of the fusion moieties) or appropriate linker cleavage agents (such as proteases), it does not cause a statistically significant increase in the amount of at least one cytokine including IFNγ; In certain embodiments at least two cytokines including IFNγ and TNFα or IL-6 and TNFα; in one embodiment three cytokines including IL-6, IFNγ, and TNFα; in another embodiment four cytokines including IL-2, IL-6, IFNγ, and TNFα; and in yet a further embodiment at least five cytokines including IL-2, IL-6, IL-10, IFNγ, and TNFα; released from treated cells in the absence of secondary target cells (e.g., an appropriate cancer cell line) or appropriate linker cleavage agents, as compared to from treated cells in the presence of appropriate secondary target cells or linker cleavage agents, in at least one in vitro or in vivo assay known in the art or provided herein. Clinically, cytokine-release syndrome is characterized by fever, chills, rash, nausea, and sometimes dyspnea and tachycardia, which is in parallel with maximal release of certain cytokines, such as IFNγ, as well as IL-2, IL-6, and TNFα. Cytokines that may be tested for release in an in vitro assay or in vivo include G-CSF, GM-CSF, IL-2, IL-4, IL-5, IL-6, IL-10, IL-13, IL-17, IP-10, KC, MCP1, IFNγ, and TNFα; and in another embodiment include IL-2, IL-6, IL-10, IFNγ, and TNFα.

In further embodiments, an MSFP of the present disclosure causes an increase in calcium flux in cells, such as T cells. An MSFP causes an "increase in calcium" if, when used to activate T cells in the presence of an appropriate secondary target cell (e.g., cancer cell) or linker cleavage agents, it causes a statistically significant, rapid increase in calcium flux of the treated cells (preferably within 300 seconds, more preferably within 200 seconds, and most preferably within 100 seconds of treatment) as compared to cells treated in the absence of an appropriate secondary target cell or linker cleavage agents, as measured in an in vitro assay known in the art or provided herein.

In further embodiments, an MSFP of the present disclosure induces phosphorylation of a molecule in the TCR signal transduction pathway. The "TCR signal transduction pathway" refers to the signal transduction pathway initiated via the binding of a peptide:MHC ligand to the TCR and its co-receptor (CD4 or CD8). A "molecule in the TCR signal transduction pathway" refers to a molecule that is directly involved in the TCR signal transduction pathway, such as a molecule whose phosphorylation state (e.g., whether the molecule is phosphorylated or not), whose binding affinity to another molecule, or whose enzymatic activity, has been changed in response to the signal from the binding of a peptide:MHC ligand to the TCR and its co-receptor. Exemplary molecules in the TCR signal transduction pathway include the TCR complex or its components (e.g., CD3ζ chains), ZAP-70, Fyn, Lck, phospholipase c-γ, protein kinase C, transcription factor NFκB, phasphatase calcineurin, transcription factor NFAT, guanine nucleotide exchange factor (GEF), Ras, MAP kinase kinase kinase (MAPKKK), MAP kinase kinase (MAPKK), MAP kinase (ERK1/2), and Fos.

An MSFP of this disclosure "induces phosphorylation of a molecule in the TCR signal transduction pathway" if it causes a statistically significant increase in phosphorylation of a molecule in the TCR signal transduction pathway (e.g., CD3ζ chains, ZAP-70, and ERK1/2) only in the presence of appropriate secondary target antigens, or cells expressing such antigen (e.g., cancer cells expressing tumor antigens bound by fusion moiety binding domains) or linker cleavage agents, in an in vitro or in vivo assay or receptor signaling assays known in the art. Results from most receptor signaling assays known in the art are determined using immunohistochemical methods, such as western blots or fluorescence microscopy.

Similarly, the MSFP of the present disclosure induce killing of secondary target cell, such as tumor cells expressing fusion moiety binding domain target antigens, by T cells. Such cell killing can be measured using a variety of assays known in the art, including chromium release assays.

The specificity and function of an MSFP of the present disclosure may be tested by contacting the MSFP with appropriate test sample and, in certain embodiments, treating the MSFP with an appropriate protease which is thought to be specific for the cleavage recognition site in the linker and assaying for cleavage products. Proteases may be isolated, for example from cancer cells or they may be prepared recombinantly, for example following the procedures in Darket et al. (J. Biol. Chem. 254:2307-2312 (1988)). The cleavage products may be identified for example based on size, antigenicity or activity. The toxicity of the MSFP may be investigated by subjecting the MSFP and cleavage products thereof to in vitro cytotoxicity, proliferation, binding, or other appropriate assays known to the skilled person. Toxicity of the cleavage products may be determined using a ribosomal inactivation assay (Westby et al., Bioconjugate Chem. 3:377-382 (1992)). The effect of the cleavage products on protein synthesis may be measured in standardized assays of in vitro translation utilizing partially defined cell free systems composed for example of a reticulocyte lysate preparation as a source of ribosomes and various essential cofactors, such as mRNA template and amino acids. Use of radiolabeled amino acids in the mixture allows quantitation of incorporation of free amino acid precursors into trichloroacetic acid precipitable proteins. Rabbit reticulocyte lysates may be conveniently used (O'Hare, FEBS Lett. 273:200-204 (1990)).

The ability of the MSFP of the invention to destroy cancer cells and/or activate T cells may be readily tested in vitro using cancer cell lines, T cell lines or isolated PBMC or T cells. The effects of the MSFP of the present disclosure may be determined, for example, by demonstrating by selective lysis of cancer cells. In addition, the protease specificity can be tested by comparing the inhibition of cellular proliferation using an MSFP of the present disclosure alone or in the presence of protease-specific inhibitors. Such protease inhibitors may include MMP-2/MMP-9 inhibitors GM1489, GM6001 and GI-I to GI-IV.

Toxicity may also be measured based on cell viability, for example the viability of normal and cancerous cell cultures exposed to the MSFP may be compared. Cell viability may be assessed by known techniques, such as trypan blue exclusion assays. Toxicity may also be measured based on cell lysis, for example the lysis of normal and cancerous cell cultures exposed to the MSFP may be compared. Cell lysis may be assessed by known techniques, such as Chromium (Cr) release assays or dead cell indicator dyes (propidium Iodide, TO-PRO-3 Iodide).

Polypeptides

The present disclosure provides MSFP polypeptides, and fragments thereof. Illustrative polypeptides, and the polynucleotides encoding them, are provided in SEQ ID NOs: 23-102 and 109-150. He The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the MSFP and dimers thereof of the present disclosure, or sequences that have deletions from, additions to, and/or substitutions of one or more amino acid of an MSFP as disclosed herein. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-CD3, or other antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

Amino acid sequence modification(s) of the MSFPs described herein are contemplated. For example, it may be desirable to improve the binding affinity and/or other biological properties of the MSFP. For example, amino acid sequence variants of an MSF, or binding domain or Fab thereof may be prepared by introducing appropriate nucleotide changes into a polynucleotide that encodes the MSFP, or a domain thereof, or by peptide synthesis. Such modifications include, for example, deletions from, and/or insertions into and/or substitutions of, residues within the amino acid sequences of the MSFP. Any combination of deletion, insertion, and substitution may be made to arrive at the final MSFP, provided that the final construct possesses the desired characteristics, such as specific binding to a target antigen of interest by a binding domain or Fab. The amino acid changes also may alter post-translational processes of the MSFP, such as changing the number or position of glycosylation sites. Any of the variations and modifications described above for polypeptides of the present invention may be included in antibodies of the present invention.

The present disclosure provides variants of the MSFP disclosed herein. In certain embodiments, such variant MSFP comprise variant binding domains or Fab fragments thereof, or antigen-binding fragments, or CDRs thereof, bind to a target of interest at least about 50%, at least about 70%, and in certain embodiments, at least about 90% as well as a given reference or wild-type sequence, including any such sequences specifically set forth herein. In further embodiments, such variants bind to a target antigen with greater affinity the reference or wild-type sequence set forth herein, for example, that bind quantitatively at least about 105%, 106%, 107%, 108%, 109%, or 110% as well as a reference sequence specifically set forth herein.

In certain embodiments, the present disclosure provides variants of the MSFPs disclosed herein where such variants comprise Fabs that have been modified with regard to the disulfide bond between the VH and VL. As would be recognized by the skilled person, in certain embodiments the Fab fragment used in the MSFP of the present invention may not comprise a disulfide bond. In this regard, the heavy and light chains may be engineered in such a way so as to stably interact without the need for disulfide bond. For example, in certain embodiments, the heavy or light chain can be engineered to remove a cysteine residue and wherein the heavy and light chains still stably interact and function as a Fab. In one embodiment, mutations are made to facilitate stable interaction between the heavy and light chains. For example, a "knobs into holes" engineering strategy can be used to facilitate dimerization between the heavy and light chains of a Fab (see e.g., 1996 Protein Engineering, 9:617-621). Thus, also contemplated for use herein are variant Fab fragments designed for a particular purpose, for example, removal of a disulfide bond addition of tax for purification, etc.

In particular embodiments, a subject MSFP may have: an amino acid sequence that is at least 80% identical, at least 95% identical, at least 90%, at least 95% or at least 98% or 99% identical, to the MSFP described herein.

Determination of the three-dimensional structures of representative polypeptides may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450: 176 (2007); Qian et al., *Nature* 450:259 (2007); Raman et al. *Science* 327:1014-1018 (2010). Some additional non-limiting examples of computer algorithms that may be used for these and related embodiments, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

Polynucleotides Encoding the Multi-Specific Fab Fusion Proteins/Vectors/Host Cells/ and Methods of Making Multi-Specific Fab Fusion Proteins The present disclosure further provides in certain embodiments an isolated nucleic acid encoding the polypeptide MSFP as described herein. Illustrative polynucleotides, and the polypeptides encoded thereby, an and fragments thereof, are provided in SEQ ID NOs: 23-102 and 109-150. Nucleic acids include DNA and RNA. These and related embodiments may include polynucleotides encoding the MSFP as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

In other related embodiments, polynucleotide variants may have substantial identity to a polynucleotide sequence encoding an MSFP, or domain thereof as described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an MSFP or domain thereof described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of a binding domain, or binding affinity of a Fab, or function of the MSFP encoded by the variant polynucleotide is not substantially diminished relative to the unmodified reference protein encoded by a polynucleotide sequence specifically set forth herein.

In certain other related embodiments, polynucleotide fragments may comprise or consist essentially of various lengths of contiguous stretches of sequence identical to or complementary to a sequence encoding an MSFP or domain thereof as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an MSFP or domain thereof, such as a binding domain or Fab antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an MSFP or domain thereof described herein or at both ends of a polynucleotide encoding an MSFP or domain thereof described herein.

In another embodiment, polynucleotides are provided that are capable of hybridizing under moderate to high stringency conditions to a polynucleotide sequence an MSFP or domain thereof, such as a binding domain or a Fab antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode an MSFP or domain thereof, such as a binding domain or a Fab, e.g., a Fab that binds CD3 or a binding domain that binds a tumor antigen target. In other embodiments, such polynucleotides encode MSFP that bind to CD3 and/or a tumor antigen at least about 50%, at least about 70%, and in certain embodiments, at least about 90% as well as an MSFP sequence specifically set forth herein. In further embodiments, such polynucleotides encode an MSFP or domain thereof, that, e.g., bind to CD3 and/or a target antigen with greater affinity than the MSFP, or domain thereof, set forth herein, for example, that bind quantitatively at least about 105%, 106%, 107%, 108%, 109%, or 110% as well as an MSFP, or domain thereof, sequence specifically set forth herein.

As described elsewhere herein, determination of the three-dimensional structures of representative polypeptides (e.g., variant MSFP as provided herein, for instance, an MSFP having a binding domain and a Fab as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within, for example, an antibody or antigen-binding fragment thereof, such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an MSFP as described herein. Some of these polynucleotides bear minimal sequence identity to the nucleotide sequence of the native or original polynucleotide sequence that encode MSFP, for example an MSFP that binds to CD3 and or a tumor target antigen. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the MSFP described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an MSFP disclosed herein, or a domain thereof, to alter one or more properties of the encoded polypeptide, such as the binding affinity of a binding domain or the Fab antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In certain embodiments, the isolated polynucleotide is inserted into a vector. The term "vector" as used herein refers to a vehicle into which a polynucleotide encoding a protein may be covalently inserted so as to bring about the expression of that protein and/or the cloning of the polynucleotide. The isolated polynucleotide may be inserted into a vector using any suitable methods known in the art, for example, without limitation, the vector may be digested using appropriate restriction enzymes and then may be ligated with the isolated polynucleotide having matching restriction ends.

Examples of suitable vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

For expression of the polypeptide, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

A vector may also include materials to aid in its entry into the cell, including but not limited to a viral particle, a liposome, or a protein coating.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector.

Suitable host cells can include, without limitation, prokaryotic cells, fungal cells, yeast cells, or higher eukaryotic cells such as mammalian cells.

Suitable prokaryotic cells for this purpose include, without limitation, eubacteria, such as Gram-negative or Gram-positive organisms, for example, Enterobactehaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis, Pseudomonas such as P. aeruginosa, and Streptomyces.

The expression of antibodies and antigen-binding fragments in prokaryotic cells such as E. coli is well established in the art. For a review, see for example Pluckthun, A. Bio/ Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable fungal cells for this purpose include, without limitation, filamentous fungi and yeast. Illustrative examples of fungal cells include, *Saccharomyces cerevisiae*, common baker's yeast, *Schizosaccharomyces pombe, Kluyveromyces* hosts such as, eg., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Higher eukaryotic cells, in particular, those derived from multicellular organisms can be used for expression of glycosylated polypeptide provided herein. Suitable higher eukaryotic cells include, without limitation, invertebrate cells and insect cells, and vertebrate cells. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the K-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts. Examples of vertebrate cells include, mammalian host cell lines such as monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRK-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art.

In certain embodiments, the host cells comprise a first vector encoding a first polypeptide and a second vector encoding a second polypeptide. In certain embodiments, the first vector and the second vector may be the same or not the same. In certain embodiments, the first polypeptide and the second polypeptide may be the same or not the same.

In certain embodiments, the first vector and the second vector may or may not be introduced simultaneously. In certain embodiments, the first vector and the second vector may be introduced together into the host cell. In certain embodiments, the first vector may be introduced first into the host cell, and then the second vector may be introduced. In certain embodiments, the first vector may be introduced into the host cell which is then established into a stable cell line expressing the first polypeptide, and then the second vector may be introduced into the stable cell line.

In certain embodiments, the host cells comprise a vector encoding for a first polypeptide and a second polypeptide. In certain embodiments, the first polypeptide and the second polypeptide may be the same or not the same.

In certain embodiments, the present disclosure provides methods of expressing the polypeptide provided herein, comprising culturing the host cell containing the vector under conditions in which the inserted polynucleotide in the vector is expressed.

Suitable conditions for expression of the polynucleotide may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

In certain embodiments, the polypeptide expressed in the host cell can form a dimer and thus produce an MSFP dimer or polypeptide complex provided herein. In certain embodiments, the polypeptide expressed in the host cell can form a polypeptide complex which is a homodimer. In certain embodiments, where the host cells express a first polynucleotide and a second polynucleotide, the first polynucleotide and the second polynucleotide can form a polypeptide complex which is a heterodimer.

In certain embodiments, the polypeptide complex may be formed inside the host cell. For example, the dimer may be formed inside the host cell with the aid of relevant enzymes and/or cofactors. In certain embodiments, the polypeptide complex may be secreted out of the cell. In certain embodiments, the first polypeptide and the second polypeptide may be secreted out of the host cell and form a dimer outside of the host cell.

In certain embodiments, the first polypeptide and the second polypeptide may be separately expressed and allowed to dimerize under suitable conditions. For example, the first polypeptide and the second polypeptide may be combined in a suitable buffer and allow the first protein monomer and the second protein monomer to dimerize through appropriate interactions such as hydrophobic interactions. For another example, the first polypeptide and the second polypeptide may be combined in a suitable buffer containing an enzyme and/or a cofactor which can promote the dimerization of the first polypeptide and the second polypeptide. For another example, the first polypeptide and the second polypeptide may be combined in a suitable vehicle and allow them to react with each other in the presence of a suitable reagent and/or catalyst.

The expressed polypeptide and/or the polypeptide complex can be collected using any suitable methods. The polypeptide and/or the polypeptide complex can be expressed intracellularly, in the periplasmic space or be secreted outside of the cell into the medium. If the polypeptide and/or the polypeptide complex is expressed intracellularly, the host cells containing the polypeptide and/or the polypeptide complex may be lysed and polypeptide and/or the polypeptide complex may be isolated from the lysate by removing the unwanted debris by centrifugation or ultrafiltration. If the polypeptide and/or the polypeptide complex is secreted into periplasmic space of *E. coli*, the cell paste may be thawed in the presence of agents such as sodium acetate (pH 3.5), EDTA, and phenylmethylsulfonylfluoride (PMSF) over about 30 min, and cell debris can be removed by centrifugation (Carter et al., BioTechnology 10:163-167 (1992)). If the polypeptide and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or a antibiotics may be included in the collection and concentration steps to inhibit protein degradation and/or growth of contaminated microorganisms.

The expressed polypeptide and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis, 2007; Janson, J. C., et al, Protein purification: principles, high resolution methods and applications, published by Wiley-VCH, 1998).

In certain embodiments, the polypeptides and/or polypeptide dimer complexes can be purified by affinity chromatography. In certain embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol. Meth. 62:1-13 (1983)); Zettlit, K. A., Antibody Engineering, Part V, 531-535, 2010). In certain embodiments, protein G chromatography can be useful for purification of polypeptides and/or polypeptide complexes comprising IgG γ3 heavy chain (Guss et al., EMBO J. 5:1567 1575 (1986)). In certain embodiments, protein L chromatography can be useful for purification of polypeptides and/or polypeptide complexes comprising K light chain (Sudhir, P., Antigen engineering protocols, Chapter 26, published by Humana Press, 1995; Nilson, B. H. K. et al, J. Biol. Chem., 267, 2234-2239 (1992)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX resin (J. T. Baker, Phillipsburg, N.J.) is useful for purification.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Compositions and Methods of Use

The present disclosure provides compositions comprising the MSFP as described herein and administration of such composition in a variety of therapeutic settings.

Administration of the MSFP described herein, in pure form or in an appropriate pharmaceutical composition, can be carried out via any of the accepted modes of administration of agents for serving similar utilities. The pharmaceutical compositions can be prepared by combining an MSFP or an MSFP-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in disease symptoms as would be known to the skilled clinician.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The MSFP-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described MSFP in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an MSFP of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an MSFP as herein disclosed such that a suitable dosage will be obtained. Typically, this amount is at least 0.01% of the MSFP in the composition. When intended for oral administration, this amount may be varied to be between 0.1 and about 70% of the weight of the composition. Certain oral pharmaceutical compositions contain between about 4% and about 75% of the MSFP. In certain embodiments, pharmaceutical compositions and preparations according to the present invention are prepared so that a parenteral dosage unit contains between 0.01 to 10% by weight of the MSFP prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an MSFP as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the MSFP composition so as to facilitate dissolution or homogeneous suspension of the MSFP in the aqueous delivery system.

The compositions may be administered in a therapeutically effective amount, which will vary depending upon a variety of factors including the activity of the specific compound (e.g., MSFP) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the MSFP of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising MSFP of the invention and each active agent in its own separate pharmaceutical dosage formulation. For example, an MSFP as described herein and the other active agent can be administered to the patient together in a single oral dosage composition such as a tablet or capsule, or each agent administered in separate oral dosage formulations. Similarly, an MSFP as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising MSFP and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of MSFP compositions of this disclosure in combination with one or more other therapeutic agents. Such therapeutic agents may be accepted in the art as a standard treatment for a particular disease state as described herein, such as cancer, inflammatory disorders, allograft transplantation, type I diabetes, and multiple sclerosis. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the MSFP disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K (PSK); razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as TARGRETIN™ (bexarotene), PARETIN™ (alitretinoin); ONTAKT™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onaprestone, and toremifene (FARESTON®); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the MSFP described herein. In one embodiment, the MSFP is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

The compositions comprising herein described MSFP may be administered to an individual afflicted with a disease as described herein, including, but not limited to cancer and autoimmune and inflammatory diseases. For in vivo use for the treatment of human disease, the MSFP described herein are generally incorporated into a pharmaceutical composition prior to administration. A pharmaceutical composition comprises one or more of the MSFP described herein in combination with a physiologically acceptable carrier or excipient as described elsewhere herein. To prepare a pharmaceutical composition, an effective amount of one or more of the MSFPs is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens, phenols or cresols, mercurials, chlorobutanol, methyl and propyl p-hydroxybenzoic acid esters, thimerosal, benzalkonium chloride and benzethonium chloride); antioxidants (such as ascorbic acid and sodium bisulfite; methionine, sodium thiosulfate, platinum, catalase, citric acid, cysteine, thioglycerol, thioglycolic acid, thiosorbitol, butylated hydroxyanisol, butylated hydroxytoluene, and/or propyl gallate) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising MSFP as described herein may be prepared with carriers that protect the MSFP against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The present MSFP are useful for the treatment of a variety of cancers. For example, one embodiment of the invention provides a method for the treatment of a cancer including, but not limited to, melanoma, non-Hodgkin's lymphoma, Hodgkin's disease, leukemia, plasmocytoma, sarcoma, glioma, thymoma, breast cancer, prostate cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers, by administering to a cancer patient a therapeutically effective amount of a herein disclosed MSFP. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for preventing metastasis of a cancer including, but not limited to, melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers, by administering to a cancer patient a therapeutically effective amount of a herein disclosed MSFP (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to, melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers, by administering to a cancer patient a therapeutically effective amount of a herein disclosed MSFP.

Another embodiment provides a method for treating, inhibiting the progression of or prevention of melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers, by administering to a patient afflicted by one or more of these diseases a therapeutically effective amount of a herein disclosed MSFP.

In one aspect, the present disclosure provides a method for directing T cell activation, comprising administering to a patient in need thereof an effective amount of an MSFP that comprises a Fab that specifically binds TCRα, TCRβ, CD3γ, CD3δ, CD3ε or a combination thereof, and a fusion moiety the comprises a binding domain that specifically binds a different target, for instance, a tumor-specific antigen or other antigen of choice at a site or cell where T cell activation is desired.

EXAMPLES

Example 1

Generation of Humanized Anti-CD3 Antibodies

The heavy and light chain antibody genes were cloned from an established anti-CD3 hybridoma by steps 1) isolation of total RNA from hybridoma cells, 2) reverse transcription (RT) of the hybridoma total RNA and 3) PCR amplification of HC and LC using specific antibody gene primers. RT PCR was performed using M-muLV reverse transcriptase (New England Biolabs) with oligo-dT$_{16}$ primer for 2 hrs at 37° C. The antibody heavy chain and light chain genes were PCR amplified from the oligo-dT$_{16}$ primed first strand cDNA using primer pairs of HC5': GAG ACA GAATTC GCCACC ATG GTG TTG GGG CTG AAG TG (SEQ ID NO: 103), HC3': GAG ACA GCGGCCGC CTA TTT ACC AGG GGA GCG AGA C (SEQ ID NO: 104) and LC5': GAG ACA GAATTC GCCACC ATG GCC TGG ATT TCA CTT ATA C (SEQ ID NO: 105), LC3': GAG ACA GCGGCCGC TCA GGA ACA GTC AGC ACG GGA C (SEQ ID NO: 106). The 5' primers were designed to anneal to the antibody secretion signal and the 3' primers were designed to anneal to the 3' end of the mouse antibody constant region. PCR products were cleaned and restriction digested with EcoRI and NotI and subsequently cloned into pcDNA3.3 vector for DNA sequence determination and recombinant expression of IgG in a 293F transient mammalian system. The cloned antiCD3 antibody is referred to as 1F3. The amino acid sequences for the 1F3

VHCDR1, CDR2 and CDR3 are provided in SEQ ID NOs: 23-25. The amino acid sequences for the 1F3 VLCDR1, CDR2 and CDR3 are provided in SEQ ID NOs: 26-28.

Conventional CDR grafting technique was used for humanization of the 1F3 mouse antibody. In particular, the amino acid sequences of the mouse 1F3 were aligned with human germline sequences (VBASE2, at the world-wide web address vbase2.org). Mouse 1F3VH matched best to the human germline segments subclass 3 (VH3). Two representative germline segments, namely VH3-23 and VH3-73 were chosen as the acceptor on to which the mouse 1F3 CDRs were grafted. VH3-23 is known to be the most frequent V domain found in human antibodies and it has relatively high stability. VH3-73 has the most similar HCDR2 sequence suggesting similar HCDR2 structure and conformation. For VL, the best matched human germline, VLλ7a was chosen as the acceptor for mouse 1F3 light chain CDRs. The genes for the initial humanized constructs were synthesized by gblock technology (Integrated DNA Technologies). Further variation of amino acids in the initial humanization constructs were generated using oligonucleotide based site-directed mutagenesis (Strategene).

Table 1 below summarizes the nucleotide and amino acid sequences for the various heavy and light chain variable regions generated.

TABLE 1

1F3 and Variant Sequences

| Construct Name | Nucleotide SEQ ID NO | Amino acid SEQ ID NO |
| --- | --- | --- |
| mu-1F3 VHCDR1 | | 23 |
| mu-1F3 VHCDR2 | | 24 |
| mu-1F3 VHCDR3 | | 25 |
| mu-1F3 VLCDR1 | | 26 |
| mu-1F3 VLCDR2 | | 27 |
| mu-1F3 VLCDR3 | | 28 |
| hu-1F3-IgGHC | 29 | 30 |
| hu-1F3LC | 31 | 32 |
| hu-1F3-1VH | 33 | 34 |
| hu-1F3-1Fd | 35 | 36 |
| hu-1F3-2VH | 37 | 38 |
| hu-1F3-2Fd | 39 | 40 |
| hu-1F3-3VH | 41 | 42 |
| hu-1F3-3Fd | 43 | 44 |
| hu-1F3-4VH | 45 | 46 |
| hu-1F3-4Fd | 47 | 48 |
| hu-1F3-5VH | 49 | 50 |
| hu-1F3-5Fd | 51 | 52 |
| hu-1F3-11VH | 53 | 54 |
| hu-1F3-1VL | 55 | 56 |
| hu-1F3-2VL | 57 | 58 |
| hu-1F3-2LC | 59 | 60 |
| hu-1F3-3VL | 61 | 62 |
| hu-1F3-3LC | 63 | 64 |
| hu-1F3-4VL | 65 | 66 |
| hu-1F3-4LC | 67 | 68 |
| hu-1F3-5VL | 69 | 70 |
| hu-1F3-5LC | 71 | 72 |
| OKT3Fd | 73 | 74 |
| OKT3LC | 75 | 76 |

A variety of humanized antibodies/Fabs were generated using different humanized 1F3 VL and VH pairs as summarized in Table 2 below.

TABLE 2 hu-1F3 IgG and Fab variants

| Humanized VH | Humanized VL | |
| --- | --- | --- |
| | hu-1F3-1VL | hu-1F3-2VL |
| hu-1F3-1VH | hu-1F3.1, hu-1F3 IgG | hu-1F3.6 |
| hu-1F3-2VH | hu-1F3.2 | hu-1F3.7 |
| hu-1F3-3VH | hu-1F3.3 | hu-1F3.8 |
| hu-1F3-4VH | hu-1F3.4 | hu-1F3.9 |
| hu-1F3-5VH | hu-1F3.5 | hu-1F3.10 |
| hu-1F3-11VH | | |

Example 2

Tumor Antigen EpCAM Protein Generation

The genes corresponding to the extracellular domain of human and cynomolgus EpCAM (epithelial cell adhesion molecules) was PCR amplified from human and monkey cDNA libraries using primers with restriction sites (SEQ ID NO: 107: N-term primer: GCGTAT CCATGG ATG GCG CCC CCG CAG GTC, SEQ ID NO: 108: C-term primer: GCGTAT GCGGCCGC TTT TAG ACC CTG CAT TGA G) with Phusion polymerase (New England Biolabs) (98° C., 1 min; 30 cycles of 98° C. for 15 s, 50° C. for 20 s and 72° C. for 20 s; 72° C., 5 min). Cleaned PCR products (Fermentas life sciences) were restriction digested (NcoI and NotI) and cloned into the N-terminus of a human Fc gene in a pcDNA3.3 vector. Human EpCAM ECD and full-length polynucleotide sequences are provided in SEQ ID NOs: 1 and 5; encoding the amino acid sequences provided in SEQ ID NOs: 2 and 6. Cynomolgus EpCAM ECD and full-length polynucleotide sequences are provided in SEQ ID NOs: 3 and 7; encoding the amino acid sequences provided in SEQ ID NOs: 4 and 8. Human and cynomolgus CD3 epsilon ECD.Fc knob mutant sequences were also generated and are provided in SEQ ID NOs: 9 and 11 respectively (polynucleotide) and 10 and 12, respectively (amino acid). Human and cynomolgus CD3 epsilon ECD.Fc hole mutant sequences were generated and are provided in SEQ ID NOs: 13 and 15, respectively (polynucleotide) and SEQ ID NOs: 14 and 16, respectively (amino acid). As is known in the art, the knob and whole mutants can be used for forming heterodimerization (see e.g., Ridgeway et al. (1996), protein Engineering 9:617-621).

Example 3

Generation of Anti-EpCAM Antibodies Using Human scFv Phage Display

General protocols are referenced in Phage display technology—a laboratory manual (Eds Carlos F. Barbas III; Dennis R. Burton; Jamie K. Scott; Gregg J. Silverman, 2001 Cold Spring Harbor Laboratory Press). A naïve human scFv phage display library was used for isolation of EpCAM specific antibodies (Viva Biotech, Shanghai, China). The following steps were employed for round 1 phage selection: 1) 50 ul of human naïve ScFv library was blocked with 500 ul 3% non-fat dry milk/PBS (MPBS); 2) Incubate milk blocked phage with immunotube pre coated with 5 ug/ml Fc for 30 minutes at room temperature, repeated 2 times; 3) add Fc protein to the above depleted phage at the final concentration of 500 ug/ml and incubated at room temperature to further capture phage displaying anti-Fc ScFv; 4) incubate the above phage solution with huEpCAM.Fc coated immuno-tube (coated with a 5 ug/ml conc and blocked with MPBS) at room temperature 1 hr; 5) the tube was washed 3 times with PBST (PBS containing 0.1% Tween-20) followed by 3 washes with PBS; 6) The bound phage was eluted with 500 ul of freshly prepared solution of 100 mM triethylamine for 10 minutes at room temperature; 7) The eluted phage was used to infect 5 ml of mid log phase TG1 cells at 37° C. for 30 min stationary and 30 min with shaking at 200 rpm; 8) TG1 cells reinfected with eluted phage were grown at 30° C. overnight on large square Nunc plates of 2×YT agar supplemented with 4% glucose and 100 ug/ml ampcillin; 9) overnight grown TG1 cells were scraped off the plate and inoculated to 25 ml of 2×YT media (plus 100 ug/ml ampcillin and 2% glucose and grown at 37° C. till OD600; 10) helper phage KO7 was added to the TG1 culture to rescue the phage (30 min stationary, 30 minutes shaking at 37° C.); 11) Superinfected TG1 cells were gently pelleted and resuspended into 2× YT media supplemented with 100 ug/ml ampicillin and 100 ug/ml kanamycin to shake at 37° C. overnight; 12) Overnight culture was centrifuged and ⅕ volume of 20% PEG8000 was added to the cleared supernatant containing phage and incubated at room temperature for 30 min; 13) the precipitated phage was pelleted by centrifugation in 50 ml conical tubes at 3000 rpm for 20 minutes; 14) pelleted phage was resuspended into PBS buffer and is ready for use in next round of selection.

Round 2 selection was done on cynoEpCAM.Fc using the same steps described above. The eluted phage from round 2 selection was reintroduced into TG1 cells and plated for single colonies on 2×YT (100 ug/ml ampcillin and 2% glucose) plates. Single colonies were picked into 96-well plates and duplicate plates were made as master plates for samples. Individual clonal phage in 96 well plates was grown using similar step described above adjusted for smaller volume. Cleared phage supernatant (cleared by centrifugation of 96 well plates at 3000 rpm for 5 minutes) was used for ELISA binding assay on human and cyno EpCAM.Fc antigens using the following steps: 1) phage solution was diluted at 1:5 in 5% MPBS incubated at room temperature for 1 hr; 2) phage MPBS solution was transferred to 96 well maxisorp plates pre-coated with huEpCAM.Fc or cyno EpCAM.Fc with blocking using MPBS; 3) plates were incubated at room temperature for 1 hr and followed by 3 washes using PBST; 4) 100 ul of 1/1000 diluted anti M13/HRP conjugate was added to the plates and incubated at room temperature for 1 hr; 5) after 3 washes with PBST, 100 ul of TMB peroxidase substrate solution was added to plates and incubated in dark for 20 minutes; 6) 50 ul of 0.25 M sulphuric acid was added to each well on the plate to stop substrate development; 7) absorbance were read at 450 nm on a microplate reader. The EpCAM positive binders were DNA sequenced using *E. coli* stock from the master plates.

Example 4

Optimization of Fully Human AntiEpCAM Antibodies

The VH and VL genes of anti EpCAM antibodies were synthesized using gblock technology (Integrated DNA Technologies). The V gene gblocks were either identical to those isolated form phage display technology or contained mutations designed to improve the expression and/or stability of the V gene products. The design of mutations is primarily based on the sequence comparison with the best matched germline sequence or consensus of the germlines (VBASE2 at the world-wide web address vbase2.org) or by examining the homologous V domain structures. The VH and VL gblocks were assembled into the scFv format using PCR methology. For example, EpCAM1.1 contains amino acid changes of VL residue 1-3 (Kabat numbering, Kabat et al. (1991), sequences of proteins of immunological interest, 5th edition) from "HVI" in EpCAM1.0 to "QSV". The latter is common according to human germline sequences (VBASE2, at the world-wide web address vbase2.org). EpCAM1.2 contains mutations at position 1, 5, 6 in VH and position 39 in VL (Kabat numbering) in comparison to EpCAM1.1. EpCAM2.2 contains multiple mutations compared to the parental clone at position 5, 6, 13, 40, 76, 77, 81, 82 in VH and positions 2, 8, 39, 58 in VL (Kabat numbering). The anti EpCAM antibody nucleotide and amino acid sequences are summarized in Table 3 below

TABLE 3 anti EpCAM antibody constructs

| Construct Name | Nucleotide SEQ ID NO | Amino acid SEQ ID NO |
|---|---|---|
| EpCAM1.1scFv | 77 | 78 |
| EpCAM1.1-OKT3Fd | 79 | 80 |
| EpCAM1.1-OKT3LC | 81 | 82 |
| EpCAM1.1-hu-1F3.1Fd | 83 | 84 |
| EpCAM1.1-hu-1F3.1LC | 85 | 86 |
| EpCAM1.2scFv | 87 | 88 |
| EpCAM1.2-hu-1F3Fd | 89 | 90 |
| EPCAM1.2-hu-1F3.1LC | 91 | 92 |
| EpCAM2.2scFv | 93 | 94 |
| EpCAM2.2-hu-1F3Fd | 95 | 96 |
| EpCAM2.2-hu-1F3.1LC | 97 | 98 |
| EpCAM2.2-Δ-hu-1F3.1Fd* | 99 | 100 |
| EpCAM2.2-Δ-hu-1F3.1LC* | 101 | 102 |
| EpCAM1.1 VHCDR1 |  | 139 |
| EpCAM1.1 VHCDR2 |  | 140 |
| EpCAM1.1 VHCDR3 |  | 141 |
| EpCAM1.1 VLCDR1 |  | 142 |
| EpCAM1.1 VLCDR2 |  | 143 |
| EpCAM1.1 VLCDR3 |  | 144 |
| EpCAM1.2 VHCDR1 |  | 139 |
| EpCAM1.2 VHCDR2 |  | 140 |
| EpCAM1.2 VHCDR3 |  | 141 |
| EpCAM1.2 VLCDR1 |  | 142 |
| EpCAM1.2 VLCDR2 |  | 143 |
| EpCAM1.2 VLCDR3 |  | 144 |
| EpCAM2.2 VHCDR1 |  | 145 |
| EpCAM2.2 VHCDR2 |  | 146 |
| EpCAM2.2 VHCDR3 |  | 147 |
| EpCAM2.2 VLCDR1 |  | 148 |
| EpCAM2.2 VLCDR2 |  | 149 |
| EpCAM2.2 VLCDR3 |  | 150 |

*Δ indicates no linker

A variety of MSFP proteins were generated using the anti EpCAM and hu-1F3.1 constructs, as summarized below. scFv in the summary below refers to an anti-EpCAM scFv. His-tag is attached to the C-terminus of the Fd chain in each Fab and is not shown in the illustration.

scFv-D(H)-hu-1F3.1 Fab
    scFv-hu-1F3.1VH-CH1
    hu-1F3.1-LC
scFv-(H)-hu-1F3.1 Fab
    scFv-GlyArgAla-hu-1F3.1VH-CH1
    hu-1F3.1-LC

-continued

```
scFv-D(L)-hu-1F3.1 Fab
    hu-1F3.1VH-CH1
    scFv-hu-1F3.1-LC
scFv-(L)-hu-1F3.1 Fab
    hu-1F3.1VH-CH1
    scFv-GlyArgAla-hu-1F3.1-LC
scFv-D(H + L)-hu-1F3.1 Fab
    scFv-hu-1F3.1VH-CH1
    scFvhu-1F3.1-LC
scFv-(H + L)-hu-1F3.1 Fab
    scFv-GlyArgAla-hu-1F3.1VH-CH1
    scFv-GlyArgAla-hu-1F3.1-LC
```

Example 5

Recombinant IgG, Fc Fusion Protein, Fab, and Fab Fusion Protein Expression and Purification Fab fusion proteins were expressed in a transient mammalian expression system employing pcDNA and HEK293F suspension cell (Invitrogen). The expression constructs were transfected into HEK293F cells (Invitrogen) adding preformed DNA and 25 kd polyethylenimine (PEI) complex (DNA to linear 25 kD PEI at 1:3 ratio by weight) in 1/10 of cell culture volume of F-17 synthetic medium (Invitrogen). Transfected cells grown in 5% moisturized CO2 incubator with shaking were fed with 25 ml of 20% TN1 (Organotechnie SA, France) 24 hr post transfection. Culture supernatants were usually harvested 5 days posttransfection and proteins were purified using affinity chromatography by either protein A (for human IgG and Fc proteins), protein G (for mouse IgG), or HisTrap columns (for his-tagged Fab and his-tagged Fab fusions) (GE Healthcare). After buffer exchange using 10 kD MW cut off spin tubes, proteins were stored in PBS buffer at 4° C. Proteins were usually analyzed by 4-20% SDS-PAGE (polyacrylamide gel electrophoresis, Novex mini gel) under nonreducing and/or reducing condition (5% mercaptoethanol).

Example 6

Mouse 1F3 and Humanized 1F3 IgG and Fab Binding to CD3 Epsilon Related Proteins

Western blot, ELISA and flow cytometric analysis were used to study binding of mouse and human IF3 antibodies and Fabs. In particular, the following four protein samples were prepared in an SDS-PAGE sample buffer with 5% mercaptoethanol (samples 1. human CD3epsilon/delta.Fc(K–H); 2. cyno CD3epsilon/delta.Fc(K–H); 3). human CD3epsilonAA1-27.Fc; and 4) control peptide.Fc fusion (reverse amino acid sequence of the first 16 residues in CD3epsilonAA1-27.Fc. "Fc(K–H)" denotes "knob and hole" Fc mutants (Ridgeway et al. (1996), protein Engineering 9:617-621). 100 ng of protein for each sample was loaded to each lane on a 4-20% tris-glycine gel (Novex) and samples were run in 1×SDS running buffer (25 mM Tris, 192 mM Glycine, 0.1% SDS, pH8.3) at 125V for 1 hr. Protein bands were transferred to a nitrocellulose (NC) membrane in 1×SDS running buffer with 20% methanol using a Novex transfer module. NC Membranes were blocked with 5% dry milk TBS-T followed by incubation with 1 ug/ml of biotinylated mouse 1F3 IgG or biotinylated hu-1F3 IgG for 1 hr at rt. After 3×5 min washes, the membranes were incubated with 1:3000 diluted streptavidin-HRP conjugate for 1 hr. After 3×10 minute washes, the membrane was developed ECL reagent and signals exposed to Kodak films.

Figure 9:
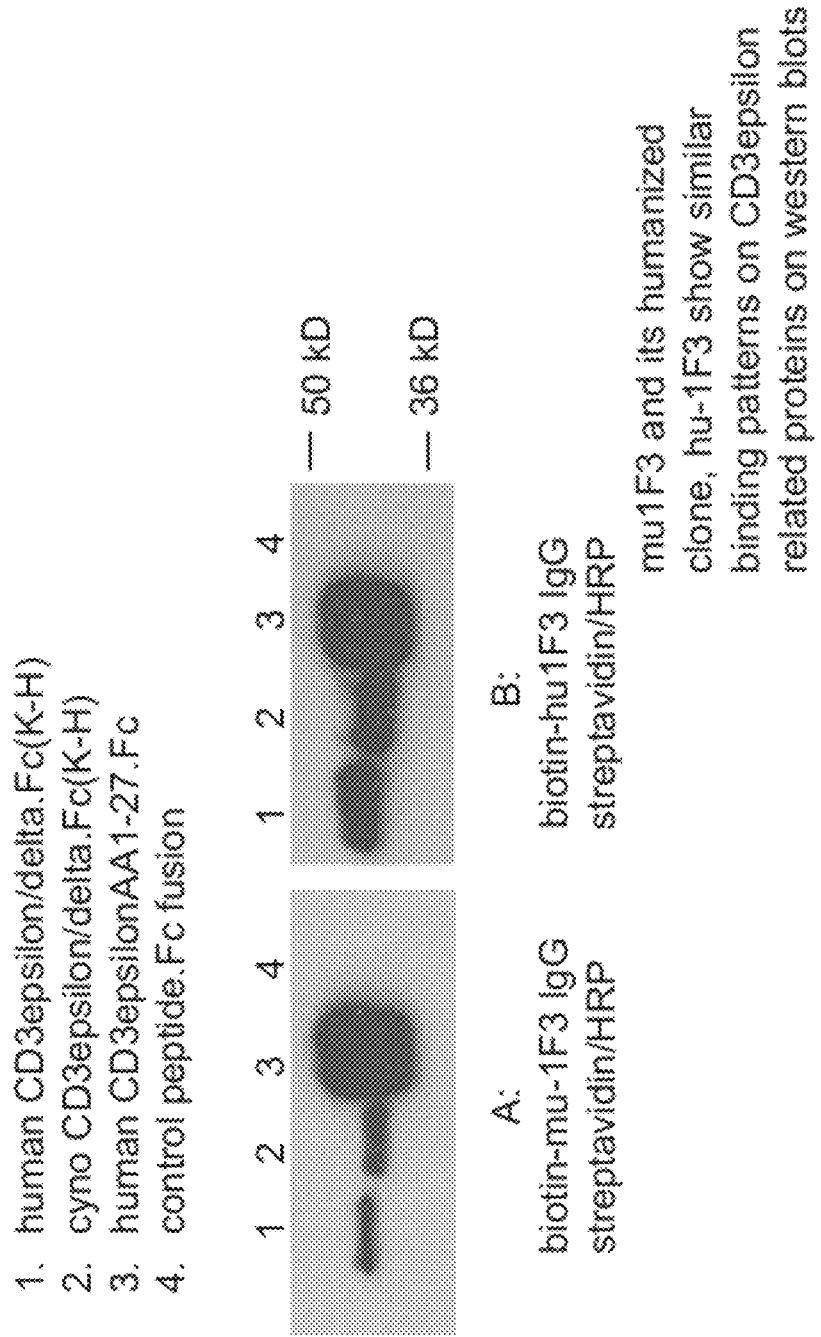
FIG. 9. Detection of reduced and denatured recombinant CD3 related proteins by mouse anti CD3 antibody, mu-1F3 and the humanized anti CD3 antibody, hu-1F3. 100 ng of indicated antigens were run on a 4-20% tris glycine gel and transferred to a nitrocellulose membrane. 1 ug/ml of biotinylated mu-1F3 IgG (A) and biotinylated hu-1F3 IgG was used to incubate with the membrane followed by streptavidin/HRP incubation. Detection was by ECL reagent. Fc(K–H) represents "knob and hole" heterodimerizing Fc mutants. CD3epsilonAA1-27.Fc is a CD3epsilon N-terminal peptide fusion with human Fc (see SEQ ID NO:18). The control peptide has the same amino acid composition as the CD3epsilonAA1-27 but with reverse sequence order of the first 16 aa (see SEQ ID NO:20). The mouse anti CD3 IgG was able to recognize the denature CD3epsilon chain of human and cynomolgus species as well as the N-terminal amino acid 1-27 of human CD3epsilon. A peptide with reverse order of amino acid sequence for the first 16 residues was not recognized by mouse 1F3 IgG suggesting the positive bands are specific. Humanized 1F3 antibody, hu-1F3 IgG, showed very similar pattern of recognition of the same panel of antigens indicating that this antibody has similar specificity and epitope as the parental mouse 1F3 antibody.
Figure 10:
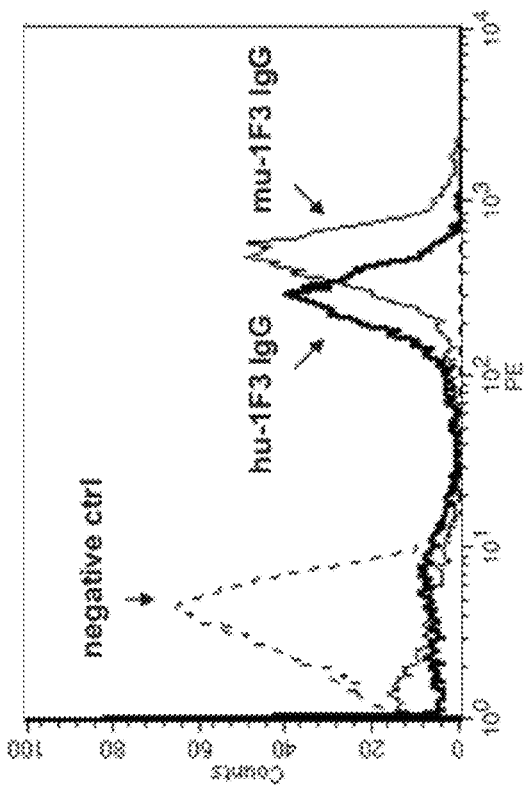
FIG. 10: Flow cytometric analysis of the binding to human PBMCs by mouse anti human CD3 antibody, mu-1F3 and its humanized version, hu-1F3. FACS staining was done using biotinylated IgGs followed by a second step using streptavidin-PE conjugate. The mu-1F3 and the hu-1F3 IgG generated similar cell staining pattern: large shift for T cells (2-3 logs), the majority of cells in human PBMCs. It is known that mouse Fc (in mu-1F3) lacks human Fcgamma receptor binding activity. Accordingly, the slight difference in the low shifting cell population (0-1 log) is likely due to the low affinity binding of hu-1F3 IgG (human IgG2 Fc) to the Fcgamma receptor expressing cells in the PBMC preparation. FACS was done using a FACScalibur instrument (BD Bioscience).

As shown in FIG. 9, the mouse 1F3 IgG and the humanized version of 1F3 recognized this panel of antigen in a very similar manner. Specifically, 1) both mouse 1F3 and the hu-1F3 IgG are able to bind denatured human CD3epsilon/delta and the cynomolgus CD3epsilon/delta; 2) both antibodies are able to bind denatured Fc fusion protein containing the peptide sequence corresponding to the N-terminal amino acid 1 to 27 of CD3epsilon (SEQ ID NO: 18); and 3) neither mouse 1F3 nor hu-1F3 IgG binds to a Fc fusion protein with a control peptide (SEQ ID NO: 20). Results from this experiment strongly suggest that 1F3 is specific to CD3epsilon and the epitope is within the N-terminal part of the epsilon subunit. Flow cytometric analysis also showed a similar binding pattern on human PBMCs for the human and mouse 1F3 antibodies (see FIG. 10). Of note, a small shift in the MFI of the low fluorescent cell populations was observed. It is well known that mouse Fc has much reduced binding to human Fc gamma receptors compared to the human Fc. Thus, the results shown in FIG. 10 suggest that human Fc in the hu-1F3 IgG binds to the Fcgamma receptors on this population of immune cells (non T cells) in the PBMC prep and caused the small MFI shift.

Maxisorp plates were used for ELISA binding assays. 50 ul of 1 ug/ml of antigens in 50 mM NaHCO3 were used to coat the plates at 4° C. overnight followed by incubation with 200 ul of 5% dry milk/TBS-0.05% tween20 (MTBS-T)/well. Antibodies were usually diluted in 5% MTBS-T and transferred to antigen coated plates and incubated for 1 hr with gentle shaking at room temperature. Bound antibodies were detected either by streptavidin-HRP (for detecting biotinylated antibodies) or anti-his tag-HRP conjugate (for his tagged antibodies). ABTS solution in 50 mM citrate buffer was used for detection with OD405 measurement on using a microplate reader (Biotek).

Figure 11:
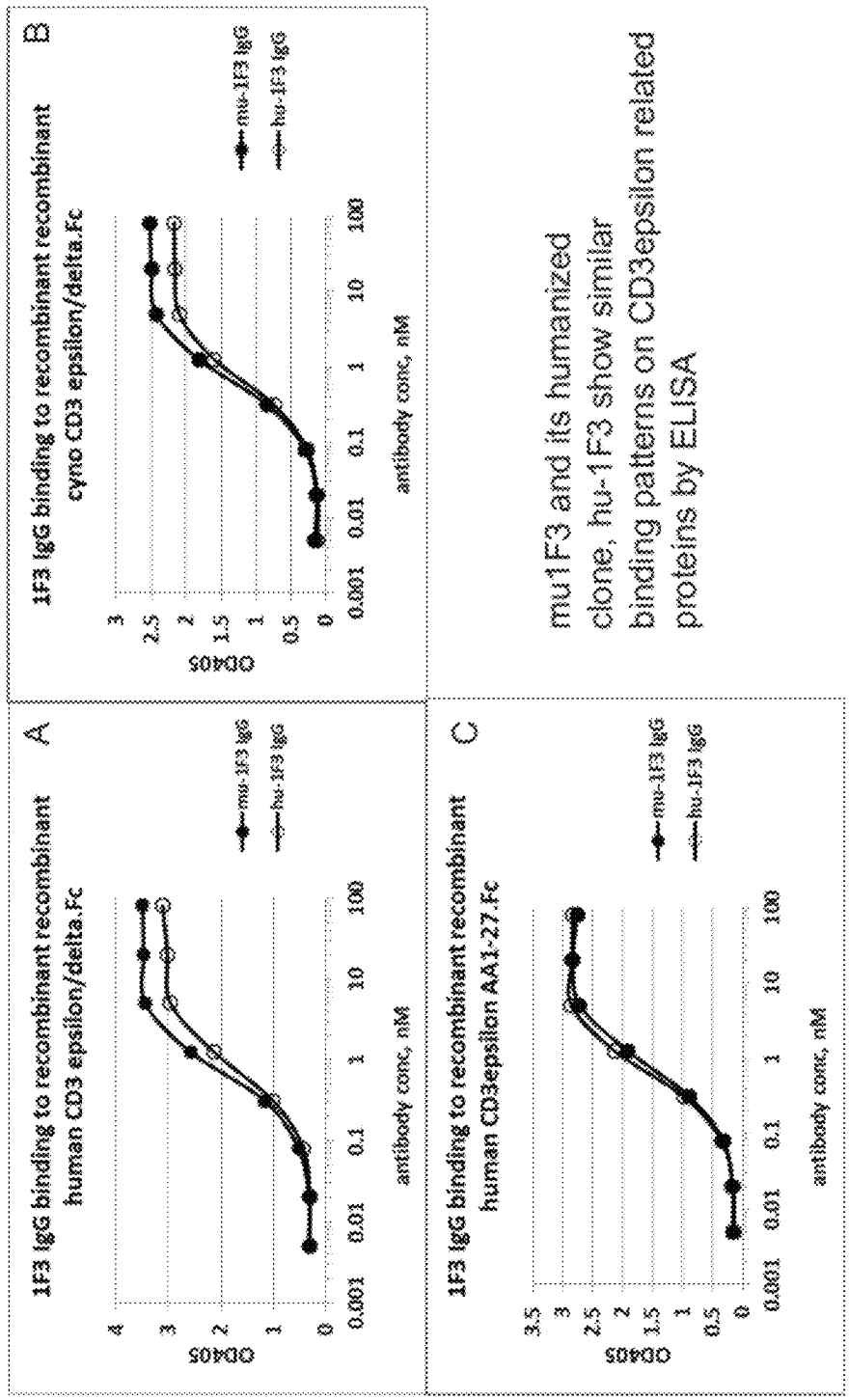
FIG. 11: ELISA binding studies of mu-1F3 and hu-1F3 IgG to recombinant CD3epsilon related proteins. 50 ul of 1 ug/ml of indicated protein antigens were coated on maxisorp ELISA plates (per well). Biotinylated mu-1F3 IgG and hu-1F3 IgG (0.5 ug/ml in 4% milk TBS-0.05% Tween 20) were added to bind the immobilized antigens followed by streptavidin/HRP conjugate. ABTS was used for color development and absorbance measured at 405 nm. ELISA on a control peptide Fc fusion (see SEQ ID NO: 20) are negative for both antibodies (data not shown). The results indicated very similar binding patterns towards different antigen forms by the parental mouse antibody, mu-1F3 and the humanized version, hu-1F3 suggesting the specificity and the epitope for the humanized antibody are retained.

FIG. 11 shows the binding activities of biotinylated mouse antiCD3 antibody 1F3 and biotinylated hu-1F3 IgG. The two antibodies demonstrated very similar pattern of positive binding to human CD3epsilon/delta "knob and hole" Fc heterodimer (Ridgeway et al. (1996), protein Engineering 9:617-621), to cynomolgus CD3epsilon/delta "knob and hole" Fc heterodimer and to the human CD3epsilon N-terminal peptide (AA1-27) Fc fusion protein.

Figure 13:
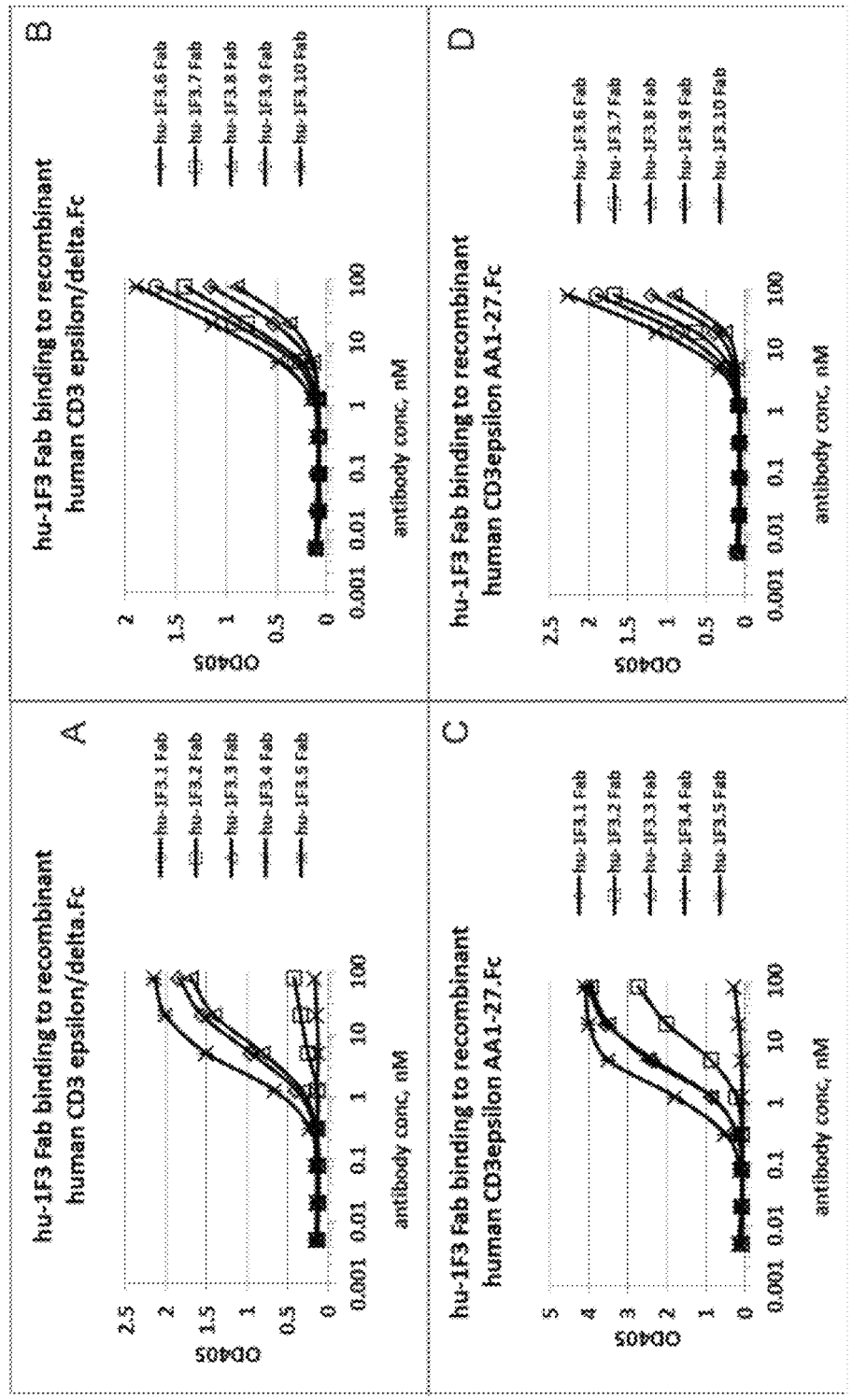
FIG. 13: ELISA binding of humanized antiCD3 antibodies to recombinant human CD3epsilon/delta Fc(K–H) heterodimer (panel A and B); recombinant human CD3epsilon N-terminal amino acid 1-27 peptide Fc fusion (panel C and D); recombinant cyno CD3epsilon/delta Fc(K+L) heterodimer (panel E and F). Humanized Fab proteins are his 6 tagged at the C-terminus of Fd and the Fabs bound to the 96-well plate immobilized antigens were detected using anti his6 tag mouse antibody conjugated with HRP. ABTS was used as substrate and absorptions were measured at 405 nm.
Figure 13:
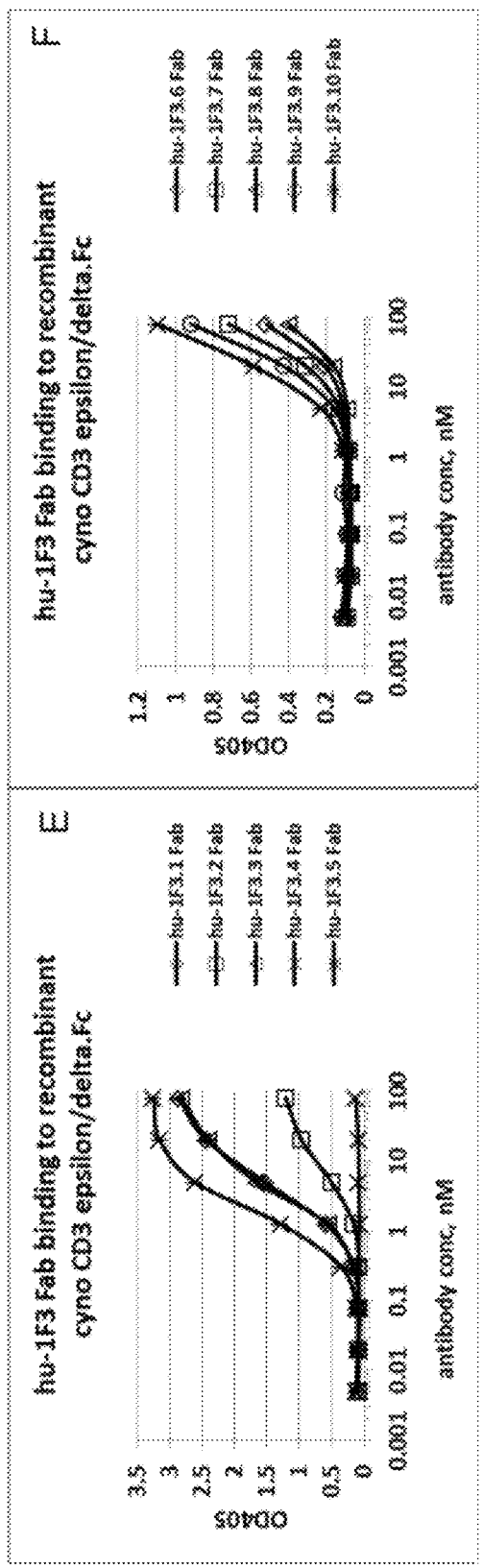

FIG. 13 shows binding to the same panel of antigens described in FIG. 11 by ten representative humanized Fab proteins detected with anti his tag/HRP conjugate and ABTS substrate. Dose dependent binding was observed for hu-1F3.1, hu-1F3.2, hu-1F3.3 and hu-1F3.5 through hu-1F3.10 Fabs. Hu-1F3.4 Fab binding is very low even in the concentration range tested (5-8,000 pM). Slightly lower affinities for the Fab binding to all three antigens were noticed as compared to the IgG (FIG. 11). Monovalent binding of Fab may explain the lower binding affinity compared to that of the hu-1F3 full IgG (in FIG. 11).

Figure 12:
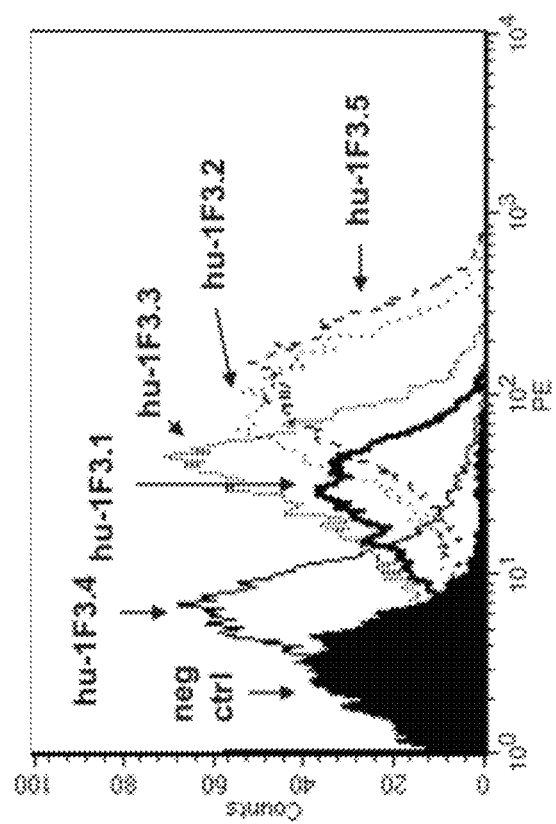
FIG. 12: Humanized 1F3 antibodies in Fab format recognize CD3 on Jurkat cells. His-tagged Fab proteins at concentration of 2 ug/ml were incubated with Jurkat cells followed by mouse anti his-tag antibody followed by anti mouse-PE conjugate. FACS was run on a FACScalibur instrument (BD biosciences).

Five of the ten representative humanized Fab proteins (hu-IF3.1-huIF3.5) were tested for binding to the Jurkat human T-cell line expressing CD3. As shown in FIG. 12, the humanized 1F3 Fabs bind to Jurkat cells.

Example 7

Characterization of the EpCAM×CD3 Bispecific Fab Fusion Proteins

Flow cytometric analysis and ELISA were used to characterize the EpCAM×CD3 Fab fusion proteins. Detailed materials and methods are described at the end of this example.

Figure 14:
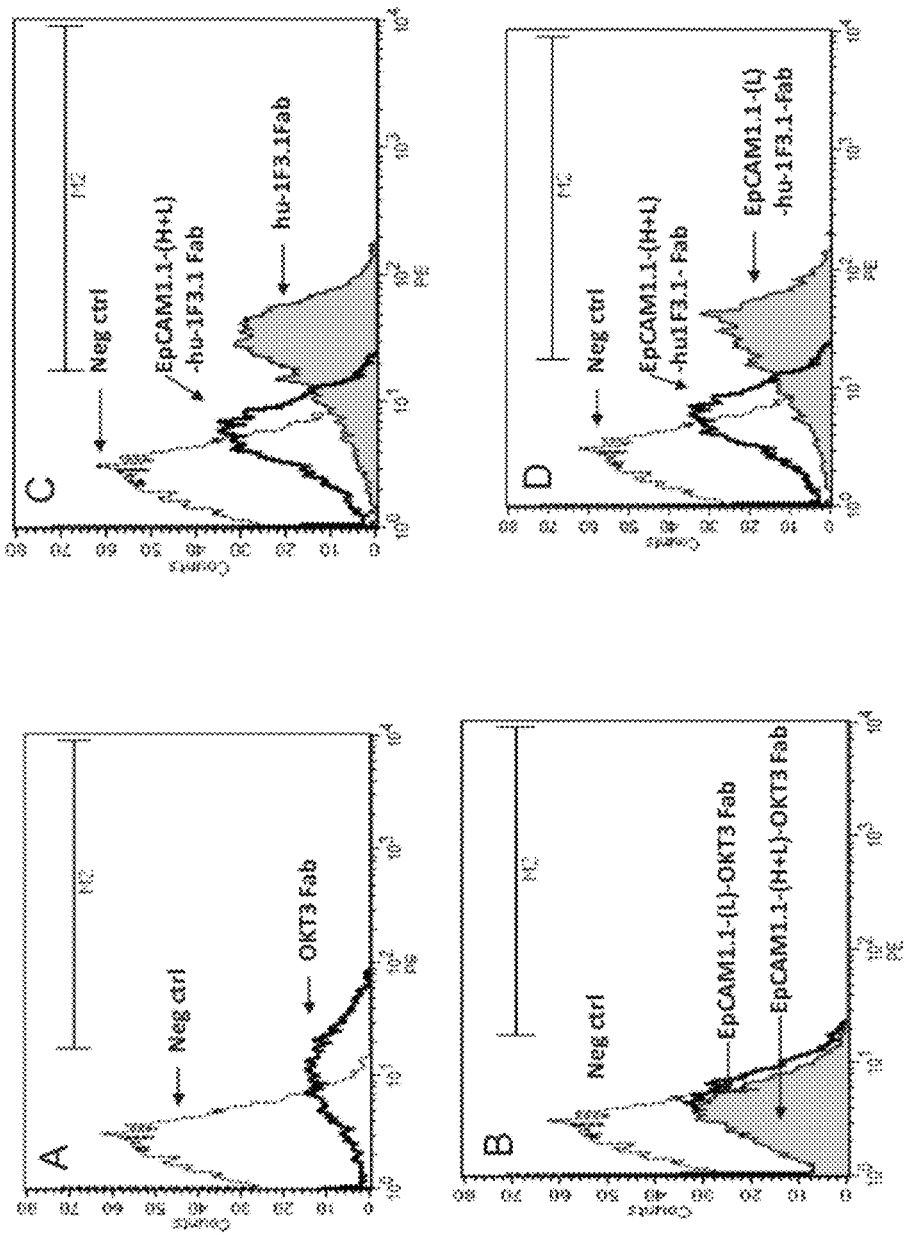
FIG. 14: EpCAM×CD3 Fab fusion proteins (MSFP) binding to Jurkat cells expressing human CD3 using FACS analysis. Biotinylated Fab and Fab fusions bound to Jurkats were detected by streptavidin-PE conjugate. OKT3 Fab showed binding to CD3 on Jurkats but the anti EpCAM scFv fusion to either the LC alone or to both HC and LCcompletely abolished the CD3 binding ability of OKT3 Fab moiety. Humanized anti CD3 antibody Fab, hu-1F3 is able to bind CD3 on Jurkat cells. Contrary to OKT3 Fab fusion proteins, anti EpCAM scFv fused to the N-terminal of hu-1F3 LC retained the binding activity at similar level as the hu-1F3 Fab; simultaneous fusion of anti EpCAM scFv fusion to the LC and HC of hu-1F3 Fab showed positive binding to CD3 on Jurkat cells but at a reduced level.

As shown in FIG. 14, EpCAM×CD3 Fab fusion proteins (MSFP) bind to Jurkat cells expressing human CD3 using FACS. In this experiment, biotinylated Fab and Fab fusions bound to Jurkat cells were detected by streptavidin-PE conjugate. OKT3 Fab showed binding to CD3 on Jurkat cells but the anti EpCAM scFv fusion to either the LC alone or to both HC and LC completely abolished the CD3 binding ability of OKT3 Fab moiety. Humanized antiCD3 antibody Fab, hu-1F3 was able to bind CD3 on Jurkat cells. Contrary to OKT3 Fab fusion proteins, anti EpCAM scFv fused to the N-terminal of hu-1F3 LC retained the binding activity at similar level as the hu-1F3 Fab; simultaneous fusion of anti EpCAM scFv to the LC and HC of hu-1F3 Fab also showed positive binding to CD3 on Jurkat cells, though at a reduced level.

Figure 15:
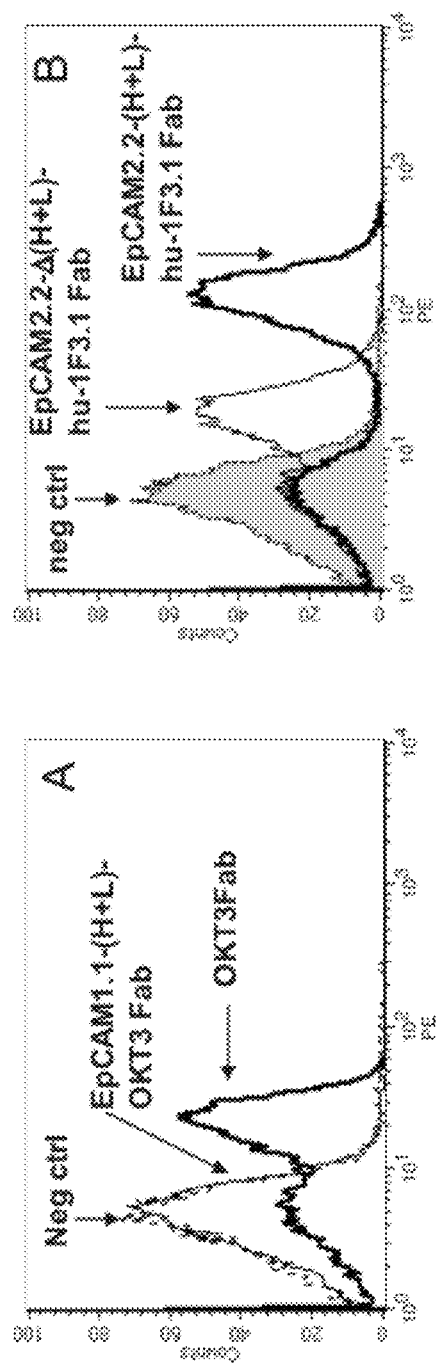
FIG. 15: EpCAM×CD3 MSFP binding to human PBMCs using FACS analysis. Biotinylated Fab and Fab fusions bound to Jurkat cells were detected by streptavidin-PE conjugate. A) OKT3 Fab bound to PBMCs expressing CD3 (T cells); the anti EpCAM scFv fused to both HC and LC completely abolished the CD3 binding ability of OKT3 Fab moiety. B) Humanized antiCD3 antibody Fab, hu-1F3.1 is able to bind CD3 on T cells in PBMC preparation; unlike the OKT3 Fab fusion protein, anti EpCAM×hu-1F3.1 Fab with simultaneous fusions to the LC and HC of Fab showed positive binding to CD3 on Jurkat cells and the level of binding is at a reduced level.

FIG. 15 shows EpCAM×CD3 MSFP binding to human PBMCs as shown by FACS. Biotinylated Fab and Fab fusions bound to Jurkat cells were detected by streptavidin-PE conjugate. Panel A shows OKT3 Fab bound to PBMCs expressing CD3 (T cells); the anti EpCAM scFv to both HC and LC completely abolished the CD3 binding ability of OKT3 Fab moiety. Panel B shows humanized antiCD3 antibody Fab, hu-1F3.1 is able to bind CD3 on T cells in PBMC preparation; unlike the OKT3 Fab fusion protein, anti EpCAM×hu-1F3.1 Fab with simultaneous fusions to the LC and HC of Fab showed positive binding to CD3 on Jurkat cells and the level of binding is at a reduced level.

As shown in FIG. 16, ELISA binding assays showed that: OKT3 Fab and EpCAM1.1×OKT3 bispecific Fab fusion proteins have no binding activity towards the recombinant cyno CD3epsilon/delta heterodimeric Fc protein; and OKT3 Fab and bispecific fusions have no binding activity towards the recombinant human CD3epsilon N-terminal peptide (aa1-27.Fc fusion). It is expected that OKT3 does not bind to monkey CD3 or the N-terminus of human CD3 epsilon. Fab and Fab fusion proteins were biotinylated and the biotin-antibodies bound to 96-well plate immobilized antigens were detected using streptavidin-HRP conjugate followed by ABTS substrate for detection.

FIG. 17 shows ELISA binding results demonstrating that hu-1F3 Fab and EpCAM1.1×hu-1F3.1 bispecific Fab fusion proteins (MSFP; Fabe) bind the recombinant cyno CD3epsilon/delta heterodimeric Fc protein (panel A); and the recombinant human CD3epsilon N-terminal peptide (aa1-27.Fc fusion) (panel B). Fab and Fab fusion proteins were biotinylated and the biotin-antibodies bound to 96-well plate immobilized antigens were detected using streptavidin-HRP conjugate followed by ABTS substrate for detection.

As shown in FIG. 18, ELISA binding assays showed that hu-1F3 Fab and EpCAM1.2×hu-1F3.1 MSFP bind the recombinant cyno CD3epsilon/delta heterodimeric Fc protein (panel A); and towards the recombinant human CD3epsilon N-terminal peptide (aa1-27.Fc fusion) (panel B). Fab and Fab fusion proteins were biotinylated and the labeled fusion proteins bound to 96-well plate immobilized antigens were detected using streptavidin-HRP conjugate followed by ABTS substrate for detection.

As shown in FIG. 19, ELISA binding assays showed that hu-1F3.1 Fab and EpCAM2.2×hu-1F3 MSFP bind the recombinant cyno CD3epsilon/delta heterodimeric Fc protein (panel A); and towards the recombinant human CD3epsilon N-terminal peptide (aa1-27.Fc fusion) (panel B). Fab and Fab fusion proteins were biotinylated and the biotin-labeled fusion proteins bound to 96-well plate immobilized antigens were detected using streptavidin-HRP conjugate followed by ABTS substrate for detection.

As shown in FIG. 20, flow cytometric analysis showed EpCAM×CD3 MSFP binding to CHO cells stably expressing full length human EpCAM target on the cell surface. Anti CD3 Fab showed no binding to the same CHO cells.

Materials and Methods:

Flow cytometric analysis (Fluorescence activated cell sorting; FACS) was used to characterize the cell binding of IF3-based Fab fusion proteins (also referred to herein as a Fabe; Fab fusion proteins are also generically referred to as MSFP). In general, cells were blocked in 1% BSA/PBS for 1 hr at 4 C and antibodies of interest were diluted into 1% BSA/PBS were added to blocked cells for incubation at 4° C. for 1 hr. after one wash with 1% BSA/PBS, staining procedures vary depending on the availability of antibodies or fluorescent antibody conjugate. In some case, direct fluorescence conjugates were used. In other cases, anti affinity tag antibodies (secondary antibody) were used to incubate with the cells followed by anti species antibody conjugated with a particular fluorophore. In some other experiments, antibody (or other affinity reagent such as streptavidin) with fluorescence conjugate was used directly as secondary antibody (secondary reagent). In FIGS. 10, 14, 16, 17, 20A and 20B biotinylated antibodies were used to incubate with cells and in FIGS. 12, 15, 18, 19, and 20C and 20D, $his_6$ tagged antibodies were used for incubation with cells followed by anti his tag antibody and final detection is by anti mouse-PE conjugate.

Example 8

EpCAM×CD3 Bispecific Fab Fusion Proteins Redirect T-Cell Mediated Cell Killing Activity A cell killing assay was used to test the ability of the EpCAM×CD3 bispecific Fab fusion proteins to redirect T-cell mediated killing of target cells.

As shown in FIG. 21, a FACS based assay (described in detail at the end of the Example) demonstrated that the EpCAM×CD3 bispecific Fab fusion proteins redirect T cell-mediated target cell killing activity in a tumor target dependent manner. In this assay, target cells (CHO cells stably expressing human EpCAM-FL on cell surface (FIG. 21, panels A, B, D) and control cells (CHO only, FIG. 21 panel C) were labeled with PKH-26 fluorescence dye prior to the assay. TP3 (Invitrogen) was used to identify dead cells upon completion of the assay. In this assay, dead target cells were identified from the counts in the upper-right quadrant and the live target cells were identified from the upper-left quadrant. EpCAM expressing CHO cells incubated (for 20 hrs) without PBMC and bispecific antibody showed ~1.4% dead cells among the PKH-26 labelled populations (TP3 positive) (FIG. 21, panel A); EpCAM-expressing CHO cell incubated (for 20 hrs) with PBMCs but without bispecific antibody had ~14% dead cells among the PKH-26 labelled populations (FIG. 21 Panel B); non EpCAM-expressing CHO cells incubated (for 20 hrs) with PBMCs and bispecific antibody had ~14% dead cells (FIG. 21 Panel C); and EpCAM-expressing CHO cells incubated (for 20 hrs) with PBMCs and exemplary bispecific Fab fusions had ~64% dead cell counts (FIG. 21, panel D).

FIG. 22 plots the killing data as described above in FIG. 21, Panel D, for various concentrations of EpCAM×CD3 bispecific Fab fusions. OKT3 Fab and fusion proteins lack significant redirected cytolytic activity (FIG. 22, panel A); EpCAM1.1×hu-1F3.1 MSFP had high level activity and the activity level remained high even at 60 pM fusion protein concentration, while hu-1F3.1 Fab had no activity towards target cells (FIG. 22, panel B); dose dependent activities were detected by EpCAM1.2×hu-1F3.1 MSFP (FIG. 22, Panel C);

and dose dependent cytolytic activities were detected for EpCAM2.2 scFv single fusions to hu-1F3.1 Fab (FIG. 22, Panel D); for double fusion of EpCAM2.2 scFv to both the HC and LC of hu-1F3.1 Fab, a maximum killing of 50% cell population were observed and the activity level remained high (~40%) for concentrations as low as 60 pM. Percentage killing activities were calculated by subtracting percentage of dead cells in the control assay (EpCAM-CHO+PBMC) from the percentage of dead cells in the sample assay.

FIG. 23 shows that T cell activation by EpCAM2.2-(H+L)-hu-1F3.1 MSFP is tumor target dependent. Panel A) PBMCs incubated with EpCAM2.2-(H+L)-hu-1F3.1 (30 nM) in the presence of non EpCAM-expressing CHO resulted in basal level T cell activation measured by CD69 expression detected by FACS assay; Panel B) PBMCs incubated with EpCAM2.2-(H+L)-hu-1F3.1 (30 nM, 16 hrs) in the presence of non EpCAM-expressing CHO resulted in significant increase of T cell activation measured by CD69 expression detected by FACS assay.

Materials and Methods:

Target cells were labeled with PKH-26 (Sigma) dye (Sigma) (signal detection in FL2) prior to the assay and killed target cells in the assay were identified by addition of TO-PRO-3 (TP3) dye (Invitrogen) (signal detection in FL4). PKH-26 labelling of target cells was performed according to manufacturer's instructions. In particular, 2 million target cells washed with serum free complete medium were resuspended in 0.5 ml of Diluent C (provided in the product kit). 2 ul of 1 mM PKH-26 dye was also diluted in 0.5 ml of Diluent C. The diluted dye was then added to the target cell preparation and incubated at room temperature for 5 min. 2 ml of fetal bovine serum was added to the mixture and incubated for 2 minutes to stop the labeling reaction. Labeled cells were washed with complete media for three times and resuspended in complete media for use. Labeled cells were counted and checked for viability. For cell killing assay, 100 ul mixture of target cells and PBMCs in complete media were added to FACS tubes followed by addition of 100 ul of antibody solution in complete cell culture media and incubated for 20 hrs in a CO2 incubator. At the end of the assay, 5 ul of 10 uM TO-PRO-3 (TP3) was added cells immediately before the FACS assay on a FACScalibur flow cytometer. PKH-26 labelled cells were put in 2-3$^{rd}$ log region (FL2). Cells with FL2 signal greater than log 20 were considered as target cells. Cells with FL4 signal (TP3) greater than log 30 were considered as dead cells. Killed target cells were counted from the upper right quadrant and live target cells were counted from the upper left quadrant (see FIG. 21). A total of 5,000 target cell events were collected for each sample. Activity of cell lysis was calculated by subtracting the dead cell counts of the control assay (EpCAM-expressing target cells plus PBMCs) from the dead cell counts of the sample assay (EpCAM-expressing target cells plus PBMCs plus antibody drug) divided by total target cell counts of 5,000 Percentage of cell lysis activity was calculated by multiplying the above activity by 100.

In summary, the above Examples demonstrate that the MSFP of the present disclosure comprising the 1F3 anti-CD3 Fab, function to redirect T-cell killing only in the presence of the appropriate tumor target cell (e.g., EpCAM expressing cells). Surprisingly, anti-EpCAM-OKT3 Fab fusion proteins were not able to bind to Jurkat T cells expressing CD3. This suggests that the CD3 epsilon epitope recognized by the 1F3 Fab is important for the function of the 1F3 Fab fusion proteins. The data described in the above examples supports the use of the MSFPs of the present disclosure in a variety of therapeutic settings including in the treatment of a number of cancers via the recruitment of T cells.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A multi-specific Fab fusion protein comprising: a Fab fragment that binds to the N-terminus of CD3 epsilon; a fusion moiety A linked to the N-terminus of the VL of the Fab fragment and a fusion moiety B linked to the N-terminus of the VH of the Fab fragment, wherein the Fab fragment binds to an epitope within amino acids 1-27 of CD3 epsilon, wherein the fusion moiety A comprises a binding domain and wherein the fusion moiety B comprises a binding domain, and wherein:
   a. the Fab fragment comprises,
      i. an immunoglobulin light chain variable region (VL) comprising the CDR1, CDR2, and CDR3 amino acids sequences set forth in SEQ ID NOs: 26-28 respectively, immunoglobulin light chain constant region (CL), an immunoglobulin heavy chain variable region (VH) comprising the amino acid sequence set forth in SEQ ID NO: 34, and an immunoglobulin heavy chain constant region 1 (CH1); or
      ii. a VH comprising the CDR1, CDR2, and CDR3 amino acid sequences set forth in SEQ ID NOs: 23-25, respectively, a CH1, a VL comprising the amino acid sequence set forth in SEQ ID NO: 56, and a CL; wherein the CL and CH1 regions are optionally connected by a disulfide bond; and
   b. the C-terminus of the fusion moiety A is covalently linked to the N-terminal end of the VL domain of the Fab fragment; and
   c. the C-terminus of the fusion moiety B is covalently linked to the N-terminal end of the VH domain of the Fab fragment; and
   d. optionally, a first linker situated between the fusion moiety A and the VL domain of the Fab fragment; and e. optionally, a second linker situated between the fusion moiety B and the VH domain of the Fab fragment.

2. The multi-specific Fab fusion protein of claim 1, comprising the amino acid sequence of SEQ ID NOs: 96 and 98.

3. A multi-specific Fab fusion protein comprising: a Fab fragment that binds to the N-terminus of CD3 epsilon; a fusion moiety A linked to the N-terminus of the VL of the Fab fragment and a fusion moiety B linked to the N-terminus of the VH of the Fab fragment, wherein the Fab fragment binds to an epitope within amino acids 1-27 of CD3 epsilon, wherein the fusion moiety A comprises a first binding domain, and wherein the fusion moiety B comprises a second binding domain, wherein the first and second binding domains bind to the same cell surface antigen, and wherein the first and second binding domains comprise the amino acid sequence set forth in SEQ ID NO:94, and wherein:
 a. the Fab fragment comprises,
  i. an immunoglobulin light chain variable region (VL) comprising the CDR1, CDR2, and CDR3 amino acids sequences set forth in SEQ ID NOs: 26-28 respectively and an immunoglobulin light chain constant region (CL); and
  ii. an immunoglobulin heavy chain variable region (VH), comprising the CDR1, CDR2, and CDR3 amino acid sequences set forth in SEQ ID NOs: 23-25, respectively, and an immunoglobulin heavy chain constant region 1 (CH1);
  wherein the CL and CH1 regions are optionally connected by a disulfide bond; and
 b. the C-terminus of the fusion moiety A is covalently linked to the N-terminal end of the VL domain of the Fab fragment; and
 c. the C-terminus of the fusion moiety B is covalently linked to the N-terminal end of the VH domain of the Fab fragment; and
 d. optionally, a first linker situated between the fusion moiety A and the VL domain of the Fab fragment; and
 e. optionally, a second linker situated between the fusion moiety B and the VH domain of the Fab fragment.

4. A multi-specific Fab fusion protein comprising: a Fab fragment that binds to the N-terminus of CD3 epsilon; a fusion moiety A linked to the N-terminus of the VL of the Fab fragment and a fusion moiety B linked to the N-terminus of the VH of the Fab fragment, wherein the Fab fragment binds to an epitope within amino acids 1-27 of CD3 epsilon, wherein the fusion moiety A comprises a first binding domain, and wherein the fusion moiety B comprises a second binding domain, wherein the first and second binding domains bind to the same cell surface antigen, and wherein the first and second binding domains comprise an antigen-binding fragment of an antibody that comprises the VH CDRs 1-3 and the VL CDRS 1-3 set forth in SEQ ID NOs: 145-150, respectively, and wherein:
 a. the Fab fragment comprises,
  i. an immunoglobulin light chain variable region (VL) comprising the CDR1, CDR2, and CDR3 amino acids sequences set forth in SEQ ID NOs: 26-28 respectively and an immunoglobulin light chain constant region (CL); and
  ii. an immunoglobulin heavy chain variable region (VH), comprising the CDR1, CDR2, and CDR3 amino acid sequences set forth in SEQ ID NOs: 23-25, respectively, and an immunoglobulin heavy chain constant region 1 (CH1);
  wherein the CL and CH1 regions are optionally connected by a disulfide bond; and
 b. the C-terminus of the fusion moiety A is covalently linked to the N-terminal end of the VL domain of the Fab fragment; and
 c. the C-terminus of the fusion moiety B is covalently linked to the N-terminal end of the VH domain of the Fab fragment; and
 d. optionally, a first linker situated between the fusion moiety A and the VL domain of the Fab fragment; and
 e. optionally, a second linker situated between the fusion moiety B and the VH domain of the Fab fragment.

\* \* \* \* \*